US011090383B2

(12) United States Patent
McNagny et al.

(10) Patent No.: US 11,090,383 B2
(45) Date of Patent: Aug. 17, 2021

(54) ANTI-PODOCALYXIN ANTIBODIES AND METHODS OF USING THE SAME

(71) Applicants: CENTRE FOR DRUG RESEARCH AND DEVELOPMENT, Vancouver (CA); THE UNIVERSITY OF BRITISH COLUMBIA, Vancouver (CA)

(72) Inventors: Kelly Marshall McNagny, Vancouver (CA); Calvin D. Roskelley, Vancouver (CA); Michael R. Hughes, Vancouver (CA); Diana Canals Hernaez, Vancouver (CA); Klas Ola Blixt, Vintrie (SE); John Stephen Babcook, Vancouver (CA); Christopher John Bond, Mercer Island, WA (US); Ismael Samudio, Vancouver (CA); Jan Peter Bergqvist, Vancouver (CA); Katherine Grace MacDonald, Vancouver (CA); Anna Von Rossum, Vancouver (CA); Bradley John Hedberg, Sooke (CA); Pamela Megan Dean, Vancouver (CA)

(*) Notice: Subject to any disclaimer, the term of this patent is extended or adjusted under 35 U.S.C. 154(b) by 72 days.

(21) Appl. No.: 15/765,233

(22) PCT Filed: Sep. 30, 2016

(86) PCT No.: PCT/CA2016/051145
§ 371 (c)(1),
(2) Date: Mar. 30, 2018

(87) PCT Pub. No.: WO2017/054089
PCT Pub. Date: Apr. 6, 2017

(65) Prior Publication Data
US 2018/0296673 A1  Oct. 18, 2018

Related U.S. Application Data

(60) Provisional application No. 62/236,130, filed on Oct. 1, 2015, provisional application No. 62/244,644, filed on Oct. 21, 2015, provisional application No. 62/291,262, filed on Feb. 4, 2016.

(51) Int. Cl.
| | |
|---|---|
| *A61K 39/00* | (2006.01) |
| *A61K 39/395* | (2006.01) |
| *A61K 35/17* | (2015.01) |
| *C07K 16/30* | (2006.01) |
| *C07K 16/28* | (2006.01) |
| *A61K 47/68* | (2017.01) |
| *C07K 14/705* | (2006.01) |
| *C07K 14/725* | (2006.01) |
| *A61P 35/00* | (2006.01) |
| *C12N 5/10* | (2006.01) |

(52) U.S. Cl.
CPC ........ *A61K 39/39558* (2013.01); *A61K 35/17* (2013.01); *A61K 47/6803* (2017.08); *A61K 47/6809* (2017.08); *A61K 47/6817* (2017.08); *A61K 47/6849* (2017.08); *A61K 47/6851* (2017.08); *A61P 35/00* (2018.01); *C07K 14/705* (2013.01); *C07K 14/7051* (2013.01); *C07K 14/70517* (2013.01); *C07K 14/70521* (2013.01); *C07K 16/28* (2013.01); *C07K 16/30* (2013.01); *C07K 16/3076* (2013.01); *C12N 5/10* (2013.01); *A61K 2039/505* (2013.01); *A61K 2039/5156* (2013.01); *A61K 2039/5158* (2013.01); *C07K 2317/24* (2013.01); *C07K 2317/33* (2013.01); *C07K 2317/622* (2013.01); *C07K 2317/732* (2013.01); *C07K 2317/92* (2013.01); *C07K 2319/03* (2013.01); *C07K 2319/33* (2013.01); *C07K 2319/41* (2013.01)

(58) Field of Classification Search
CPC .......... A61K 39/39558; A61K 47/6851; A61K 2039/505; C07K 16/28; C07K 16/30; A61P 35/00
See application file for complete search history.

(56) References Cited

U.S. PATENT DOCUMENTS

| | | | |
|---|---|---|---|
| 7,807,794 B2 | 10/2010 | Lazarides et al. | |
| 7,833,733 B2 | 11/2010 | McNagny et al. | |
| 8,828,387 B2 * | 9/2014 | Kajikawa .......... | C07K 16/3046 424/133.1 |
| 2009/0123461 A1 | 5/2009 | Fitzhugh et al. | |
| 2010/0061978 A1 | 3/2010 | Huntsman et al. | |
| 2013/0287783 A1 | 10/2013 | Frank et al. | |

FOREIGN PATENT DOCUMENTS

| | | |
|---|---|---|
| EP | 2452950 A1 | 5/2012 |
| WO | WO 2007/102787 A1 | 9/2007 |
| WO | WO 2012/011876 A1 | 1/2012 |
| WO | WO 2014/031476 A1 | 2/2014 |
| WO | WO 2015/058301 A1 | 4/2015 |

OTHER PUBLICATIONS

Strome et al., The Oncologist, 2007; 12:1084-95 (Year: 2007).*
Brand et al., Anticancer Res. 2006; 26:463-70, (Year: 2006).*
George et al. (Circulation. 1998; 97: 900-906) (Year: 1998).*
U.S. Appl. No. 16/538,744 (U.S. Publication No. 2019-0367606), entitled, "Anti-Podocalyxin Antibodies and Methods of Using the Same", filed Aug. 12, 2019, of Babcook, et al.
U.S. Appl. No. 15/031,244 (U.S. Publication No. 2016-0264663), entitled, "Anti-Podocalyxin Antibodies and Methods of Using the Same", filed Apr. 21, 2016, of Babcook, et al. (Abandoned).
(Continued)

*Primary Examiner* — Sheela J. Huff
(74) *Attorney, Agent, or Firm* — Todd A. Lorenz

(57) ABSTRACT

The present invention is directed to anti-podocalyxin antibodies, compositions comprising the same, and methods of using such antibodies and compositions for the prevention, diagnosis and treatment of cancer.

18 Claims, 35 Drawing Sheets

Specification includes a Sequence Listing.

(56) References Cited

OTHER PUBLICATIONS

Binder et al., "Podocalyxin-Like Protein Is Expressed in Glioblastoma Multiforme Stem-Like Cells and Is Associated with Poor Outcome", PLOS ONE, vol. 8:(10), pp. e75945, pp. 1-15 (2013).

Blixt et al., "Printed covalent glycan array for liand profiling of divers glycan binding proteins", PNAS, vol. 101, No. 49, pp. 17033-13038 (2004).

Boman et al., "Membranous expression of podocalyxinplike protein is an independent facttor ofpoor prognosis in urothelial bladder cancer", Br J Cancer, vol. 108(11), pp. 2321-2328 (2013).

Bovin et al., "Repertoire of human natural anti-glycan immunoglobulins. Do we have auto-antibodies?", Biochimica et Biophisica Acta 1820, pp. 1373-1382 (2012).

Casset et al., "A peptide mimetic of an anti-CD4 monoclonal antibody by rational design", BBRC, vol. 307, pp. 198-205 (2003).

Choo A.B. et al., "Selection against undifferentiated human embryonic stem cells by a cytotoxic antibody recognizing podocalyxin-like protein-1" Stem Cells, vol. 26(6), pp. 1454-1463 (2008).

Cipollone et al., "The Anti-adhesive mucin podocalyxin may help initiate the transperiotoneal metastasis of high grade werous ovarian carcinoma", Clin Exp Metasatasis, vol. 29(3), pp. 239-252 (2012).

Dallas et al., "Sialofucosylated podocalyxin is a function E- and L-selctin ligand expressed by metastatic pancreatic cancer cells", Am J Phsiol Cell Phsiol, vol. 303: C616-C624 (2012).

Doyonnas et al.,"Anuria, Omphalocele, and Preintal Lethality in Mice Lacking the CD34-related Protein Podocalyxin", J Exp Med, vol. 194 (1), pp. 13-27 (2001).

Heukamp et al., "Podocalyxin-like protein 1 expression in primary hepatic tumours and tumour-like lesions", Histopathology, vol. 49(3), pp. 242-247 (2006).

Hsu et al., "Podocalyxin EBP50 Ezrin Molecular Complex Enhances the Metastatic Potential of Renal Cell Carcinoma Though Recruiting Rac1 Guanine Nucleotide Exchange Factor ARHGEF7", Am J Pathology, vol. 176(6), pp. 3050-3061 (2010).

Jacob et al., "The clycosphingolipid P1 is an ovarian cancer-associated carbohydrate antigen involved in migration", Britsh J of Cancer, vol. 111, pp. 1634-1645 (2014).

Kaprio et al., "Podocalyxin is a marker of poor prognosis in colerectal cancer", BMC Cancer, vol. 14:493, pp. 1-7 (2014).

Konstantopoulos et al., "Cancer Cells in Transit: The Vascular Interactions of Tumor Cells", Annu Rev Biomed Eng, vol. 11, pp. 177-202 (2009).

Larsson et al. "Overexpression of podocalyxin-like protein is an independent factor of poor prognosis in colorectal cancer", British Journal of Cancer, vol. 105(5), pp. 666-672 (2011).

Natunen et al., "The binding specificity of the marker antibodies Tra-1-60 and Tra-1-81 reveals a novel pluripotency-associated type 1 lactosamine epitope", Glycobiology, vol. 21, No. 9, pp. 1125-1130 (2011).

Nielsen et al., "Novel functions of the CD34 family", Journal of Cell Science, vol. 121, No. 22, pp. 3683-3692 (2008).

Nielsen et al, "The Role of Pdocalyxin in Health and Disease", J Am Soc Nephrol, vol. 20, pp. 1669-1676 (2009).

Oh et al., "Live dynamic imaging of caveolae pumping targeted antibody rapidly and specifically across endothelium in the lung : Abstract : Nature Biotechnology", Nature Biotechnology: Abstract (2007).

Ono et al., "Glycosylation defining cancer cell motility and invasiveness" Glycoconjugate Journal, vol. 20, pp. 71-78 (2004).

Pascalis et al., "Grafting of "Abbreviated" Complementarity-Determining Regions Containing Specificity-Determining Residues Essential for Ligand Contact to Engineer a Less Immunogenic Humanized Monoclonal Antibody" J of Immunology, vol. 169, pp. 3076-3084 (2002).

Paul et al., Fundamental Immunology, 3rd Edition, pp. 292-295 (1993).

Rudikoff et al, "Single amino acid substitution altering antigen-binding specificity", Proc. Natl. Acad. Sci., vol. 79, p. 1979-1983 (1982).

Snyder et al, "Podocalyxin enhances breast tumor growth and metastasis and is a target for monoclonal antibody therapy", Breast Cancer Research, Current Medicine Group Ltd, GB, vol. 17, No. 1, pp. 1-14 (2015).

Somasiri et al.,"Overexpressioin of the Anti-Adhesin Podocalyxin Is an Independent Predictor of Breast Cancer Progression", Cancer Research, vol. 64 (15): 5068-5073 (2004).

Thomas et al., "Identification , characterization and utilization of tumor cell selectin ligands in the design of colon cancer diagnostics", Biorheology, vol. 46 (3), pp. 207-225 (2009).

Thomas et al., "Podocalyxin-like protein is an E-/L-selectin ligand on colon carcinoma cells: comparative biochemical properties of selectin ligands in host and tumor cells", Am J Physiol Cell Physiol, vol. 296 (3), pp. C505-C513 (2009).

Tuccillo et al., "Aberrant glycosylation as biomarker for cancer: focus on CD43", Biomed Reaserach International, United States, pp. 2314-6141 (2014).

3rd Party Observations filed Sep. 18, 2019 in EP3060580.

* cited by examiner

FIG. 1

Amino acid sequence of podocalyxin isoform 1 (SEQ ID NO:31)

```
  1 mrcalalsal lllstppll psspspspsp sqnatgtttd ssnktaptpa ssvtimatdt
 61 aggstvptsk aneilasvka ttlgvssdsp gtttlaqqvs gpvnttvarg ggsgnptttí
121 espkstksad tttvatstat akpnttssqn gaedttnsgg ksshsvttdl tstkaehltt
181 phptsplspr qptsthpvat ptssghdhlm kissssstva ipgytftspg mttlletvf
241 hhvsqagle1 ltsgdlptla sgsagitass visqrtgqts sqmpasstap ssqetvqpts
301 patalrtptl petmsssspta astthrypkt psptvahesn wakcedletq tqsekqlvln
361 ltgntlcagg asdeklisli cravkatfnp aqdkcgirla svpgsqtvvv keitihtklp
421 akdvyerlkd kwdelkeagv sdmklgdqgp peeaedrfsm pliitivcma sfllivaaly
481 gcchqrlsqr kdqqrlteel gtvengyhdn ptlevmetss emqekkvvsl ngelgdswiv
541 pldnltkddl deeedthl
```

Amino acid sequence of podocalyxin isoform 2 (SEQ ID NO:32)

```
  1 mrcalalsal lllstppll psspspspsp sqnatgtttd ssnktaptpa ssvtimatdt
 61 aggstvptsk aneilasvka ttlgvssdsp gtttlaqqvs gpvnttvarg ggsgnptttí
121 espkstksad tttvatstat akpnttssqn gaedttnsgg ksshsvttdl tstkaehltt
181 phptsplspr qptsthpvat ptssghdhlm kissssstva ipgytftspg mttlpssvi
241 sqrtgqtssq mpasstapss getvqptspa talrtptlpe tmsssptaas tthrypktps
301 ptvahesrwa kcedletqtq sekqlvlnlt gntlcaggas deklislicr avkatfnpaq
361 dkcgirlasv pgsqtvvvke itihtklpak dvyerlkdkw delkeagvsd mklgdqgppe
421 eaedrfsmpl iitivcmasf llivaalygc chqrlsqrkd qqrlteelgt vengyhdnpt
481 levmetssem qekkvvslng elgdswivpl dnltkddlde eedthl
```

FIG. 2

A.) Nucleic acid sequence for the heavy chain variable region (underlined; rabbit) of the Podo447 antibody <u>ATGGAGACTGGGCTGCGCTGGCTGCTTCCTCGTGGCTGTGCTCAAAGGTGTCAGTGCTGCTGGAGGAGTCCGGGGGTCGCCTGGTCAC
GCCTGGGACACCCCTGACACTGACCTGCACAGCCTCTGGATTCTCCCTCAGTGGCTACTACAGATGAACTGGGTCCGCCAGGCTCCAGGGAAGGG
GCTGGAGTGGATCGGATATATTTGGAGTGATGGTACAGATACGCGAGCTGGGCGAAAGGCCGATTCACCATCTCCAAAACCTCGTGAC
CACGGTGGATCTGAAAATGACCAGTCTGACAACCGAGGACACGGCCACCTATTTCTGTGCCAGGGAGGGATACTGGCTTGGTGCTTTGATCC
CTGGGGCCCAGGACTGGTCACCGTCTCTTCAG</u>GCACCAAGGGCCCATCAGTCTTCCCCTTGGCACCCTCCTCCAAGAGCACCTCTGGG
GGCACAGCGGCCCTGGGCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACCGTGCCCTCCAGCAGCTTGGGCACCCAGACCTACATCTGC
AACGTGAATCACAAGCCCAGCAACACCAAGGTGGACAAGAGAGTTGAGCACAAATCTTGTGACAAAACTCACACATGCCCACCGTGCCCAGCA
CCTGAACTCCTGGGGGACCGTCAGTCTTCCTCTTCCCCCCAAAACCCAAGGACACCCTCATGATCTCCGACCCCTGAGGTCACATGCGTGGT
GGTGGACGTGAGCCACGAAGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGAGAACCACAGGTGTACACCCTGCCCCATCCCGGG
ATGAGCTGACCAAGAACCAAGGTCAGCTGACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTACAGCAAGCTCACCGTGGACAAGAGCAGGTGGCA
GCAGGGGAACGTCTTCTCATGCTCCGTGATGCATGAGGCTCTGCACAACCACTACACGCAGAAGAGCCTCTCCCTGTCTCCGGGTAAA (SEQ ID NO:12)

Amino acid sequence for the heavy chain variable region of the Podo447 antibody

METGLRWLLLVAVLKGVQCQSLEESGGRLVTPGTPLTLTCTASGFSLSGYQMNWVRQAPGKGLEWIGYIWSDGGTDYASWAKGRFTISKT SSTTVDLKMTSLTTEDTATYFCAREGYWLGAFDPWGPGTLVTVSS (SEQ ID NO:27)

Nucleic acid sequence for the light chain variable region of the Podo447 antibody ATGGACACGAGGGCCCCACTCAGTCTGTGGGCTCCTGCTCTGGCTCTCCAGGTGCCACATTTGCCGCCGT
GCTGACCCAGACTCCAGACTCCATCTCCGTGTCTGCAGTCGTGGGAGCCACAGTCAGTGTCCAGTCCAGTCAGA
GTGTCCATCATAAGAACGACTTAGCCTGGTTTCAGCAGAAACCAGGTCAGCCTCCCAAGCTCCTGATCTATTATAC
ATCCACTCTGGCATCTGGGGTCCCATCACGGTTCAAGGGCAGTGGATCTGGGACACAGTTCACTCTCACCATCAG
CGACCTGGAGTGTGACGATGCTGCCACTTACTACTGTCAGGCGTTTATGAGGTAGTAGTGATAATAGGCTTT
CGGGGAGGGACCGAGGTGGTGGTCAAA
(SEQ ID NO:14)

Amino acid sequence for the light chain variable region of the Podo447 antibody

MDTRAPTQLLGLLLLWLPGATFAAVLTQTPSPVSAAVGATVSVSCQSSQSVHHKNDLAWFQQKPGQPPKLLIYYTST
LASGVPSRFKGSGSGTQFTLTISDLECDDAATYYCAGVYEGSSDNRAFGGGTEVVVK
(SEQ ID NO:29)

FIG. 3

| | Selectivity Cell Line Panel (Live cell GeoMean FL) | | | | | | | | | Primary Human Ascites | | % Shifting (FL4) Live Cells | | |
|---|---|---|---|---|---|---|---|---|---|---|---|---|---|---|
| | A172 | HUVEC | 293 | MDA-MB-231 | MCF7 | T47-D | CaOV3 | OVCAR3 | OVCAR10 | SKOV3 | Sample 1 | Sample 2 | cPodo/CHO | mPodo/CHO | Mock/CHO |
| Podo-83 | 223501 | 24482 | 28225 | 88890 | 28437 | 1126 | 23357 | 28603 | 1532 | 59773 | 35892 | 3205 | 0% | 1% | 2% |
| Podo-447 | 326788 | 3968 | 6706 | 14362 | 4290 | 2166 | 5623 | 25280 | 4031 | 47738 | ND | ND | 22% | 2% | 1% |
| Control Rb/HuIgG1 | 644 | 489 | 446 | 477 | 657 | 667 | 767 | 629 | 653 | ND | 22850 | 2338 | 0% | 3% | 2% |
| RnD anti-hPodo | 94247 | 3594 | 13289 | 17350 | 17193 | 1987 | 17108 | 12974 | 2164 | 35583 | 4775 | 8213 | 1% | 1% | 1% |
| MsIgG2a | 797 | 484 | 556 | 478 | 1126 | 787 | 892 | 708 | 618 | 485 | 2374 | 5843 | 1% | 2% | 2% |

FIG. 4
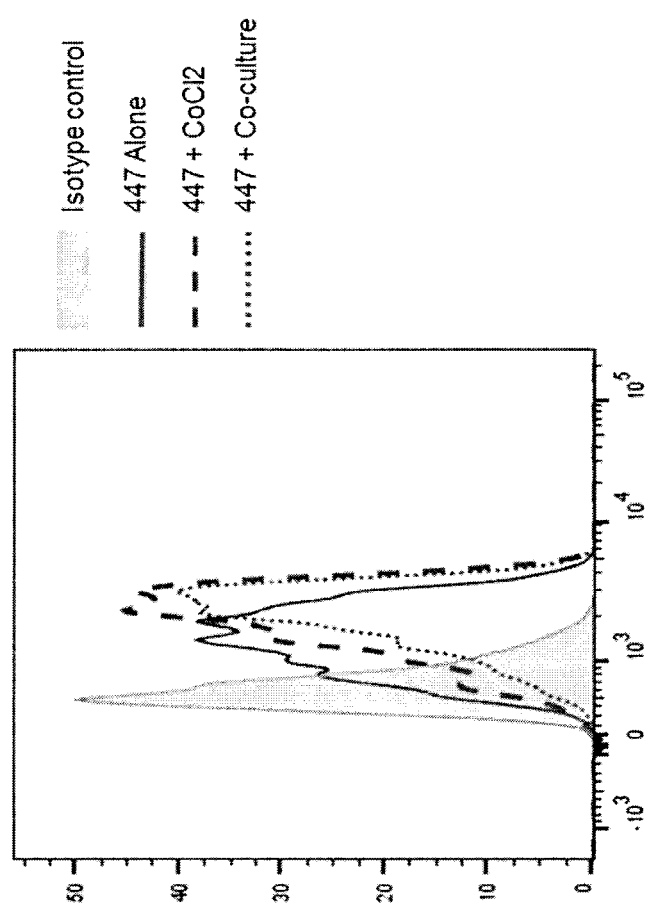
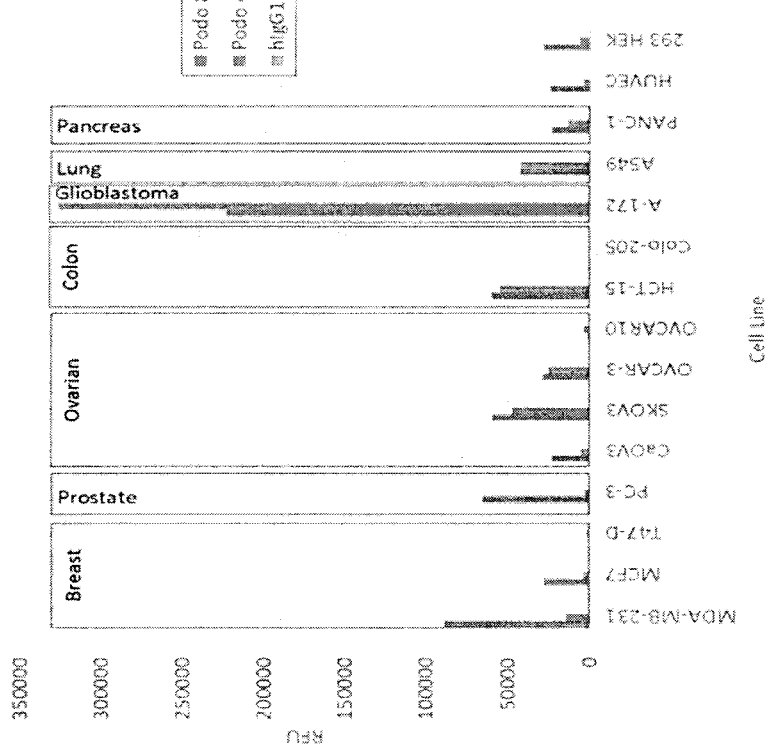

| Antibody | Antigen | Kd | Kd Low | Kd High | Epitopes/Cell |
|---|---|---|---|---|---|
| Podo 447 Rb/hIgG1 Chimeric | MDA-MB-231 Cells | 189.3pM | 42.54pM | 52.4nM | ~64,000 |
| Podo 447 Rb/hIgG1 Chimeric | A172 Cells | 7.57pM | 2.30pM | 24.88pM | ~420,000 |

FIG. 5

FIG. 6
A.)
Human Kidney      Macaque Kidney
Podo-83
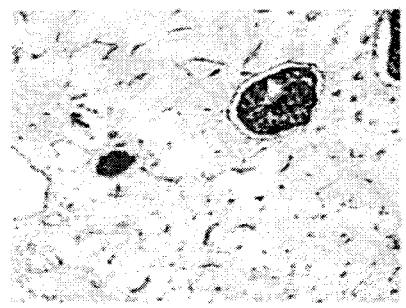 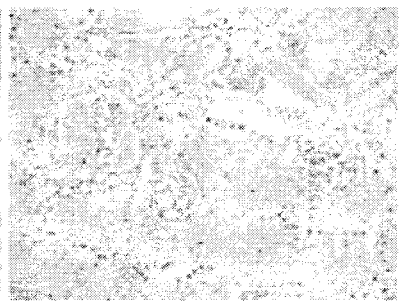
Podo447
 
B.)
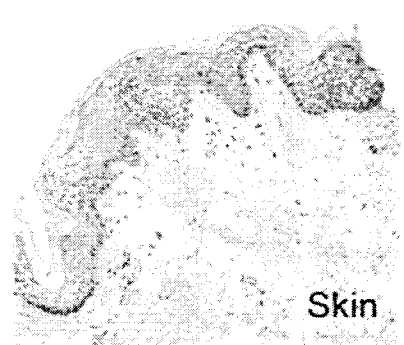 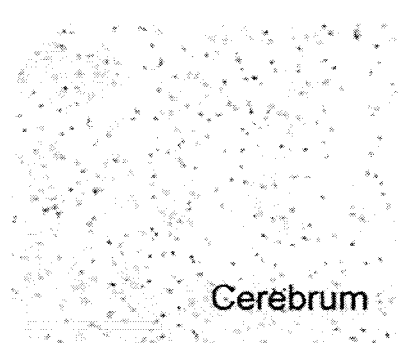
Skin      Cerebrum
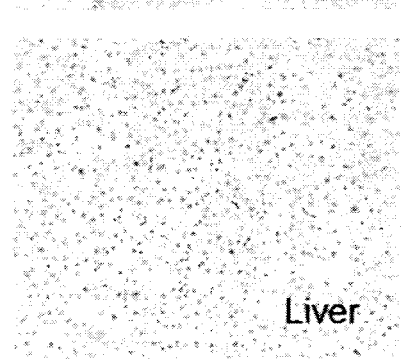 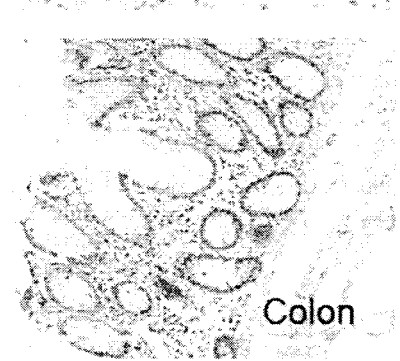
Liver      Colon

FIG. 7

| Tissue Type | Negative | Weak | Strong |
|---|---|---|---|
| Normal Kidney | 99/101 (98%) | 2/101 (1.9%) | - |
| Normal Cerebellum | 0/10 | - | - |
| Glioblastoma multiforme (grade 3-4) | 33/60(55%) | 14/60 (23%) | 13/60(22%) |
| Melanoma | | | |
| Benign | 4/17(24%) | 8/17(47%) | 5/17(29%) |
| Stage I | 10/27(37%) | 7/27(26%) | 10/27(37%) |
| Stage II | 5/23(22%) | 5/23(22%) | 13/23(57%) |
| Stage III | 3/10(30%) | 3/10(30%) | 4/10(40%) |
| Metastatic Melanoma | 4/19(21%) | 5/19(26%) | 10/19(53%) |

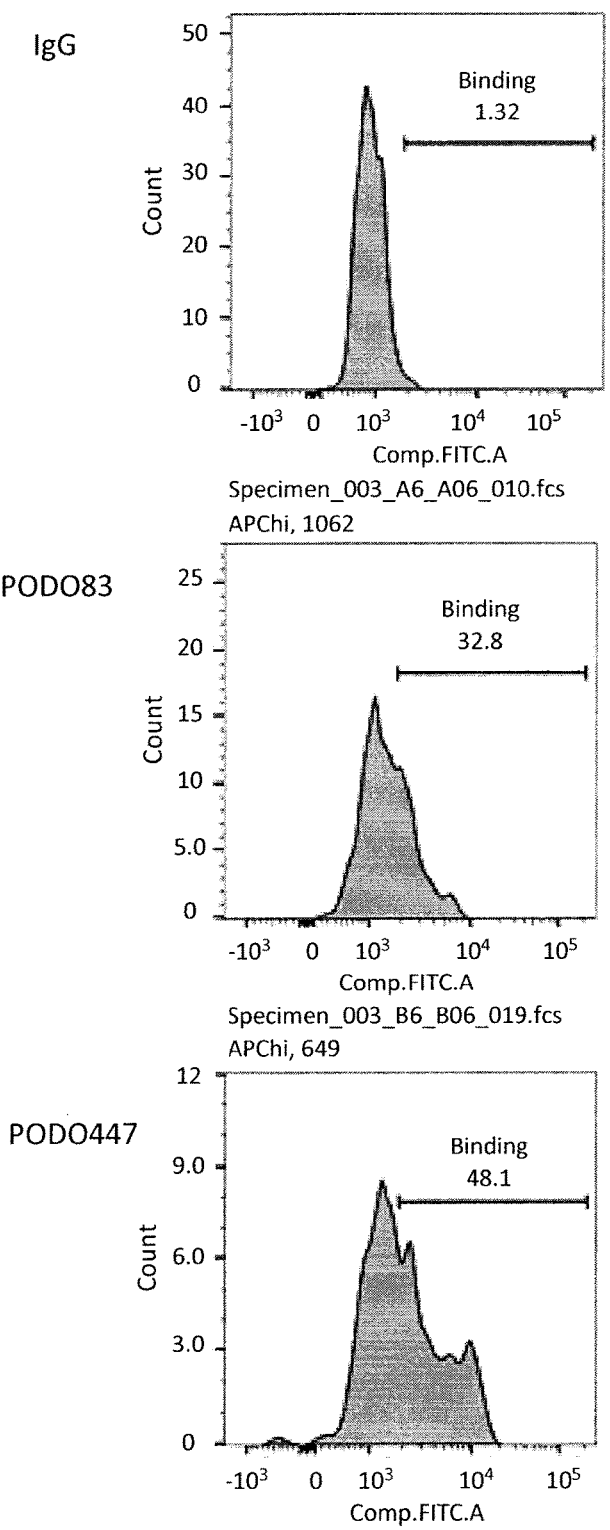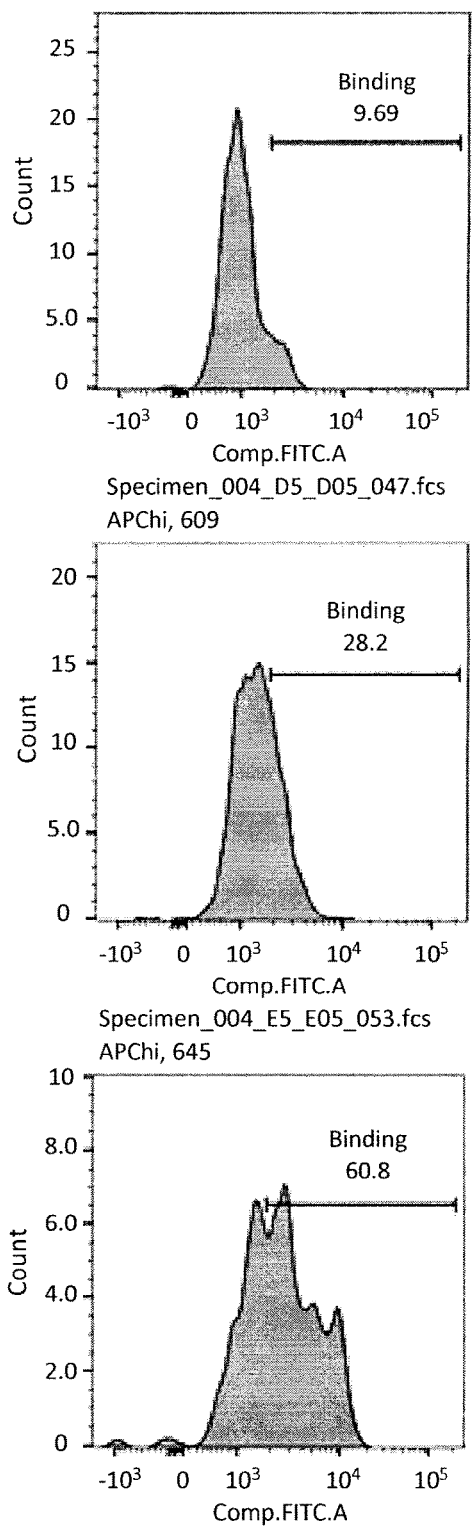
FIGURE 11

FIG. 23

Summary of anti-PODO 447 binding

| | Anti-PODO 447 binding | Anti-PODO 83 binding |
|---|---|---|
| 4T1 | ✗ | ✗ |
| PC3 | ✗ | ✓ |
| MIA PaCa-2 | ✓ | ✓ |
| B16 | ✗ | ✗ |
| BxPC-3 | ✗ | ✓ |
| MDA.MB.231 Scr | ✓ | ✓ |
| MDA.MB.231 Podo KD | → 2.5 X (similar to level of siRNA KD) | → 2.5 X (similar to level of siRNA KD) |
| MDA.MB.231 ATCC | ✓ | ✓ |
| MDA.MB.231 ATCC PODXL KO | ✗ | ✗ |
| MIA PaCa-2 neg. cntrl | ✓ | ✓ |
| MIA PaCa-2 PODXL siRNA | → 10 X | → 10 X |
| PANC-1 | ✓ | ✓ |
| CFPAC-1 | 27% + population | ✓ |

FIG. 29 cont.

SEQUENCE LISTING

<160> NUMBER OF SEQ ID NOS: 84

<210> SEQ ID NO 1
<211> LENGTH: 1593
<212> TYPE: DNA
<213> ORGANISM: Artificial sequence
<220> FEATURE:
<223> OTHER INFORMATION: scFv_VH_GGGGS_VL_CAR

<400> SEQUENCE: 1

```
atggagacgg gactcaggtg gctgcttctt gtcgccgtcc tgaaggggt  gcagtgccag      60 agccttgaag aaagcggcgg aagactggtc acgcctggga ctccgctgac  actgacttgc     120
acggcttccg gattttcact cagtggatac caaatgaact gggttaggca  agccccaggg    180
aagggtctcg aatggatcgg ctatatatgg agtgatggag gcaccgatta  tgcctcctgg    240
gctaagggac gcttcactat atccaagacc tccagtacta cagtggactt  gaaaatgaca    300
tctcttacga cagaggacac cgccacctac ttctgcgcaa gagagggta  ctggctgggc     360 gcctttgacc catgggcc cggaccctt gtgaccgtga gttccgggg  aggtgggtcc         420 ggcggggcg gcagtggagg cggcggtct gccgtcctta ctcaaacacc  aagccccgtg     480
```

```
tccgccgcag ttggcgctac tgttagcgtc agctgccaga gttcccagtc agtgcatcac      540
aagaacgacc ttgcatggtt tcagcagaag cccgggcaac acccaagct cctcatttat       600 tatacaagta ctctggccag tggggtgcca tcccgcttca aggggtcagg gtctgggacc      660
caatttacac tcactattag cgacctcgag tgtgacgacg ccgccacgta ttattgcgcc     720
ggagtgtacg aaggcagctc tgataaccgc gccttcggcg gtgggactga agtggttgtt     780
aaagagcaga agctgatcag cgaggaggac ctgaaccgga tccgtggggt caccgtctct    840
tcagcgctga gcaactccat catgtacttc agccacttcg tgccggtctt cctgccagcg    900
aagcccacca cgacgccagc gccgcgacca ccaacaccgg cgcccaccat cgcgtcgcag   960
cccctgtccc tgcgcccaga ggcgtgccgg ccagcggcgg ggggcgcagt gcacacgagg  1020
gggctggacc cctttgggtt ttgggtgctg gtggtggttg gtggagtcct ggcttgctat   1080
agcttgctag taacagtggc ctttattatt ttctgggtga ggagtaagag gagcaggctc   1140
ctgcacagtg actacatgaa catgactccc cgccgcccg ggcccacccg caagcattac   1200
cagccctatg ccccaccacg cgacttcgca gcctatcgct ccctcgagag agtgagagtg   1260
aagttcagca ggagcgcaga cgcccccgcg taccagcagg gccagaacca gctctataac  1320
gagctcaatc taggacgaag agaggagtac gatgttttgg acaagagacg tggccgggac  1380
cctgagatgg ggggaaagcc gagaaggaag aaccctcagg aaggcctgta caatgaactg    1440
cagaaagata agatggcgga ggcctacagt gagattggga tgaaaggcga gcgccggagg  1500
ggcaaggggc acgatggcct ttaccagggt ctcagtacag ccaccaagga cacctacgac  1560
gcccttcaca tgcaggccct gccccctcgc taa                                    1593

<210> SEQ ID NO 2
<211> LENGTH: 1605
<212> TYPE: DNA
<213> ORGANISM: Artificial sequence
<220> FEATURE:
<223> OTHER INFORMATION: scFv_VL_GGGGS_VH_CAR

<400> SEQUENCE: 2
atggataccc gcgcacccac tcaactgctc gggctgctcc tgctgtggct ccctggggca      60
acatttgctg ccgtccttac tcaaacacca gccccgtgt ccgccgcagt tggcgctact     120
gttagcgtca gctgccagag ttcccagtca gtgcatcaca agaacgacct tgcatggttt    180
cagcagaagc ccgggcaacc acccaagctc ctcatttatt atacaagtac tctggccagt    240
ggggtgccat cccgcttcaa ggggtcaggg tctgggaccc aatttacact cactattagc   300
gacctcgagt gtgacgacgc cgccacgtat tattgcgccg gagtgtacga aggcagctct   360
gataaccgcg ccttcggcgg tgggactgaa gtggttgtta aaggggagg tgggtccggc   420 ggggcggca gtggaggcgg cgggtctcag tcccttgagg agtctggggg tagacttgtg     480
accccgggaa caccactgac tctgacgtgt accgcgtctg gcttctccct gagtggctac   540
caaatgaact gggtgaggca ggctcctgga aaaggactcg agtggattgg ctatatctgg   600
tccgacggtg gcaccgacta tgccagctgg gctaagggaa gatttacaat ctcaaaaacc   660
agcagcacca cagtggacct caaaatgacc agcctcacta cagaagatac cgccacgtat     720
ttctgtgcca gagagggata ttggcttggg gcttttgacc catgggggcc tgggaccctc   780
gtcaccgtga gttcagagca gaagctgatc agcgaggagg acctgaaccg gatccgtggg   840
gtcaccgtct cttcagcgct gagcaactcc atcatgtact tcagccactt cgtgccggtc   900
```

```
ttcctgccag cgaagcccac cacgacgcca gcgccgcgac caccaacacc ggcgcccacc    960
atcgcgtcgc agcccctgtc cctgcgccca gaggcgtgcc ggccagcggc gggggcgca   1020 gtgcacacga gggggctgga ccccttggg ttttgggtgc tggtggtggt tggtggagtc   1080
ctggcttgct atagcttgct agtaacagtg gcctttatta ttttctgggt gaggagtaag   1140
aggagcaggc tcctgcacag tgactacatg aacatgactc ccgccgccc cgggcccacc   1200 cgcaagcatt accagcccta tgccccacca cgcgacttcg cagcctatcg ctccctcgag   1260
agagtgagag tgaagttcag caggagcgca gacgccccg cgtaccagca gggccagaac   1320
cagctctata cgagctcaa tctaggacga agagaggagt acgatgtttt ggacaagaga   1380
cgtggccggg accctgagat gggggaaag ccgagaagga agaaccctca ggaaggcctg   1440
tacaatgaac tgcagaaaga taagatggcg gaggcctaca gtgagattgg gatgaaaggc   1500
gagcgccgga ggggcaaggg gcacgatggc ctttaccagg gtctcagtac agccaccaag   1560
gacacctacg acgcccttca catgcaggcc ctgccccctc gctaa              1605

<210> SEQ ID NO 3
<211> LENGTH: 2220
<212> TYPE: DNA
<213> ORGANISM: Artificial sequence
<220> FEATURE:
<223> OTHER INFORMATION: scFab_VL_CL_GGGGS_VH_CH1_CAR

<400> SEQUENCE: 3 atggatacccc gcgcacccac tcaactgctc gggctgctcc tgctgtggct ccctggggca    60
acatttgctg ccgtccttac tcaaacacca agccccgtgt ccgccgcagt tggcgctact   120
gttagcgtca gctgccagag ttcccagtca gtgcatcaca agaacgacct tgcatggttt   180
cagcagaagc ccgggcaacc acccaagctc ctcatttatt atacaagtac tctggccagt   240
ggggtgccat cccgcttcaa ggggtcaggg tctggaccc aatttacact cactattagc   300
gacctcgagt gtgacgacgc cgccacgtat tattgcgccg gagtgtacga aggcagctct   360
gataaccgcg ccttcggcgg tgggactgaa gtggttgtta acgcacagt cgcagccccc   420 tccgtgtta tcttccctcc tagcgacgaa caactgaaga gcggaacagc cagcgtcgta   480
tgtttgctca ataacttcta tccaagggaa gccaaagtgc agtggaaagt cgataatgca   540
ctccagagcg gcaatagcca ggaaagtgta actgagcagg acagcaaaga tagcacctat   600
agcctgagct caaccctgac actgtcaaaa gcagattacg agaaacacaa ggtttacgcg   660
tgcgaagtga ctcatcaagg gttgtccagt cccgtgacaa aaagcttcaa tcgaggcgag   720
tgtggcgggg gcggtagcgg cggaggtggc agtggtggtg gcggctcaca gtctctggag   780
gaaagcggag gcaggctggt gaccccaggt acaccctga ccctcacctg taccgccagc   840
ggctttagcc tttctgggta ccagatgaat tgggtacgac aggcccctgg gaagggtctg   900
gagtggatag ttatatctg gtctgatggg ggcaccgatt acgcaagctg ggcgaagggc   960
agattcacta tcagcaaaac ttccagcacc accgtagatc tgaaaatgac cagtctgaca   1020
acagaagata ctgccactta tttttgcgcc agggaaggat actggctggg cgccttcgat   1080
ccttggggcc ccgtacgct ggtaactgtc tcatccgcat ccacgaaggg accttctgtg   1140
ttccctttgg ctccaagctc caaaagcaca agcggaggaa ccgcagcgct ggctgtttg   1200 gttaaggatt acttccccga acctgtgact gtgtcatgga actctggggc gcttaccagc   1260
ggcgtccaca catttccagc agttctgcag tctagtgggc tttacagtct gtcatctgta   1320
gtgactgtgc cttcttccag cctcgggacc cagacctaca tctgcaatgt caatcacaag   1380
```

```
ccatccaaca ctaaagtgga taagagagtg gagcagaagc tgatcagcga ggaggacctg    1440
aaccggatcc gtggggtcac cgtctcttca gcgctgagca actccatcat gtacttcagc    1500
cacttcgtgc cggtcttcct gccagcgaag cccaccacga cgccagcgcc gcgaccacca    1560
acaccggcgc ccaccatcgc gtcgcagccc ctgtccctgc cccagaggc gtgccggcca     1620 gcggcggggg gcgcagtgca cacgaggggg ctggaccct ttgggttttg ggtgctggtg     1680
gtggttggtg gagtcctggc ttgctatagc ttgctagtaa cagtggcctt tattattttc    1740
tgggtgagga gtaagaggag caggctcctg cacagtgact acatgaacat gactccccgc    1800
cgcccccggc ccacccgcaa gcattaccag ccctatgccc caccacgcga cttcgcagcc    1860
tatcgctccc tcgagagagt gagagtgaag ttcagcagga gcgcagacgc ccccgcgtac    1920
cagcagggcc agaaccagct ctataacgag ctcaatctag gacgaagaga ggagtacgat    1980
gttttggaca agagacgtgg ccgggaccct gagatggggg gaaagccgag aaggaagaac    2040
cctcaggaag gcctgtacaa tgaactgcag aaagataaga tggcggaggc ctacagtgag    2100
attgggatga aggcgagcg ccggaggggc aaggggcacg atggccttta ccagggtctc     2160
agtacagcca ccaaggacac ctacgacgcc cttcacatgc aggccctgcc ccctcgctaa    2220

<210> SEQ ID NO 4
<211> LENGTH: 783
<212> TYPE: DNA
<213> ORGANISM: Artificial sequence
<220> FEATURE:
<223> OTHER INFORMATION: Podo447_scFv_VH_GGGGS_VL

<400> SEQUENCE: 4
atggagacgg gactcaggtg gctgcttctt gtcgccgtcc tgaaggggt gcagtgccag      60 agccttgaag aaagcggcgg aagactggtc acgcctggga ctccgctgac actgacttgc    120
acggcttccg gattttcact cagtggatac caaatgaact gggttaggca agccccaggg    180
aagggtctcg aatggatcgg ctatatatgg agtgatggag gcaccgatta tgcctcctgg    240
gctaagggac gcttcactat atccaagacc tccagtacta cagtggactt gaaaatgaca    300
tctcttacga cagaggacac cgccacctac ttctgcgcaa gagagggta ctggctgggc     360 gcctttgacc catggggccc cgggacccct gtgaccgtga gttccggggg aggtgggtcc    420 ggcggggcg gcagtggagg cggcgggtct gccgtcctta ctcaaacacc aagcccgtg     480 tccgccgcag ttggcgctac tgttagcgtc agctgccaga gttcccagtc agtgcatcac    540
aagaacgacc ttgcatggtt tcagcagaag cccgggcaac cacccaagct cctcatttat    600
tatacaagta ctctggccag tggggtgcca tcccgcttca ggggtcagg gtctgggacc    660 caatttacac tcactattag cgacctcgag tgtgacgacg ccgccacgta ttattgcgcc    720
ggagtgtacg aaggcagctc tgataaccgc gccttcggcg gtgggactga agtggttgtt    780
aaa                                                                 783

<210> SEQ ID NO 5
<211> LENGTH: 795
<212> TYPE: DNA
<213> ORGANISM: Artificial sequence
<220> FEATURE:
<223> OTHER INFORMATION: Podo447_scFv_VL_GGGGS_VH

<400> SEQUENCE: 5 atggatacc gcgcacccac tcaactgctc gggctgctcc tgctgtggct ccctgggggca     60
```

| | |
|---|---|
| acatttgctg ccgtccttac tcaaacacca agccccgtgt ccgccgcagt tggcgctact | 120 |
| gttagcgtca gctgccagag ttcccagtca gtgcatcaca agaacgacct tgcatggttt | 180 |
| cagcagaagc ccgggcaacc acccaagctc ctcatttatt atacaagtac tctggccagt | 240 |
| ggggtgccat cccgcttcaa ggggtcaggg tctgggaccc aatttacact cactattagc | 300 |
| gacctcgagt gtgacgacgc cgccacgtat tattgcgccg gagtgtacga aggcagctct | 360 |
| gataaccgcg ccttcggcgg tgggactgaa gtggttgtta aggggggagg tgggtccggc | 420 |
| gggggcggca gtggaggcgg cgggtctcag tcccttgagg agtctggggg tagacttgtg | 480 |
| accccgggaa caccactgac tctgacgtgt accgcgtctg gcttctccct gagtggctac | 540 |
| caaatgaact gggtgaggca ggctcctgga aaaggactcg agtggattgg ctatatctgg | 600 |
| tccgacggtg gcaccgacta tgccagctgg gctaagggaa gatttacaat ctcaaaaacc | 660 |
| agcagcacca cagtggacct caaaatgacc agcctcacta cagaagatac cgccacgtat | 720 |
| ttctgtgcca gagagggata ttggcttggg gcttttgacc catgggggcc tgggaccctc | 780 |
| gtcaccgtga gttca | 795 |

<210> SEQ ID NO 6
<211> LENGTH: 1410
<212> TYPE: DNA
<213> ORGANISM: Artificial sequence
<220> FEATURE:
<223> OTHER INFORMATION: Podo447_scFab_VL_CL_GGGGS_VH_CH1

<400> SEQUENCE: 6

| | |
|---|---|
| atggataccc gcgcacccac tcaactgctc gggctgctcc tgctgtggct ccctggggca | 60 |
| acatttgctg ccgtccttac tcaaacacca agccccgtgt ccgccgcagt tggcgctact | 120 |
| gttagcgtca gctgccagag ttcccagtca gtgcatcaca agaacgacct tgcatggttt | 180 |
| cagcagaagc ccgggcaacc acccaagctc ctcatttatt atacaagtac tctggccagt | 240 |
| ggggtgccat cccgcttcaa ggggtcaggg tctgggaccc aatttacact cactattagc | 300 |
| gacctcgagt gtgacgacgc cgccacgtat tattgcgccg gagtgtacga aggcagctct | 360 |
| gataaccgcg ccttcggcgg tgggactgaa gtggttgtta aacgcacagt cgcagccccc | 420 |
| tccgtgttta tcttccctcc tagcgacgaa caactgaaga gcggaacagc cagcgtcgta | 480 |
| tgtttgctca ataacttcta tccaaggaa gccaaagtgc agtggaaagt cgataatgca | 540 |
| ctccagagcg gcaatagcca ggaaagtgta actgagcagg acagcaaaga tagcacctat | 600 |
| agcctgagct caaccctgac actgtcaaaa gcagattacg agaaacacaa ggtttacgcg | 660 |
| tgcgaagtga ctcatcaagg ttgtccagt cccgtgacaa aaagcttcaa tcgaggcgag | 720 |
| tgtggcgggg gcgtagcgg cggaggtggc agtggtggtg gcggctcaca gtctctggag | 780 |
| gaaagcggag caggctggt gaccccaggt acacccctga ccctcacctg taccgccagc | 840 |
| ggctttagcc tttctgggta ccagatgaat tgggtacgac aggcccctgg aagggtctg | 900 |
| gagtggatag ttatatctg gtctgatggg ggcaccgatt acgcaagctg gcgaagggc | 960 |
| agattcacta tcagcaaaac ttccagcacc accgtagatc tgaaaatgac cagtctgaca | 1020 |
| acagaagata ctgccactta tttttgcgcc agggaaggat actggctggg cgccttcgat | 1080 |
| ccttggggcc ccggtacgct ggtaactgtc tcatccgcat ccacgaaggg accttctgtg | 1140 |
| ttcccttgg ctccaagctc caaaagcaca gcggaggaa ccgcagcgct ggctgtttg | 1200 |
| gttaaggatt acttccccga acctgtgact gtgtcatgga actctggggc cttaccagc | 1260 |
| ggcgtccaca catttccagc agttctgcag tctagtgggc tttacagtct gtcatctgta | 1320 |

```
gtgactgtgc cttcttccag cctcgggacc cagacctaca tctgcaatgt caatcacaag    1380
ccatccaaca ctaaagtgga taagagagtg                                      1410

<210> SEQ ID NO 7
<211> LENGTH: 30
<212> TYPE: DNA
<213> ORGANISM: Artificial sequence
<220> FEATURE:
<223> OTHER INFORMATION: MYC tag

<400> SEQUENCE: 7
gagcagaagc tgatcagcga ggaggacctg                                      30

<210> SEQ ID NO 8
<211> LENGTH: 189
<212> TYPE: DNA
<213> ORGANISM: Artificial sequence
<220> FEATURE:
<223> OTHER INFORMATION: CD8 hinge

<400> SEQUENCE: 8
tcagcgctga gcaactccat catgtacttc agccacttcg tgccggtctt cctgccagcg    60
aagcccacca cgacgccagc gccgcgacca ccaacaccgg cgcccaccat cgcgtcgcag    120
cccctgtccc tgcgcccaga ggcgtgccgg ccagcggcgg ggggcgcagt gcacacgagg    180
gggctggac                                                             189

<210> SEQ ID NO 9
<211> LENGTH: 81
<212> TYPE: DNA
<213> ORGANISM: Artificial sequence
<220> FEATURE:
<223> OTHER INFORMATION: CD28 TM

<400> SEQUENCE: 9
ttttgggtgc tggtggtggt tggtggagtc ctggcttgct atagcttgct agtaacagtg    60
gcctttatta ttttctgggt g                                               81

<210> SEQ ID NO 10
<211> LENGTH: 123
<212> TYPE: DNA
<213> ORGANISM: Artificial sequence
<220> FEATURE:
<223> OTHER INFORMATION: CD28 IC

<400> SEQUENCE: 10
aggagtaaga ggagcaggct cctgcacagt gactacatga acatgactcc ccgccgcccc    60
gggcccaccc gcaagcatta ccagccctat gccccaccac gcgacttcgc agcctatcgc    120
tcc                                                                   123

<210> SEQ ID NO 11
<211> LENGTH: 339
<212> TYPE: DNA
<213> ORGANISM: Artificial sequence
<220> FEATURE:
<223> OTHER INFORMATION: CD3z

<400> SEQUENCE: 11
agagtgaagt tcagcaggag cgcagacgcc cccgcgtacc agcagggcca gaaccagctc    60
tataacgagc tcaatctagg acgaagagag gagtacgatg ttttggacaa gagacgtggc    120
```

| | |
|---|---|
| cgggaccctg agatggggggg aaagccgaga aggaagaacc ctcaggaagg cctgtacaat | 180 |
| gaactgcaga aagataagat ggcggaggcc tacagtgaga ttgggatgaa aggcgagcgc | 240 |
| cggaggggca aggggcacga tggcctttac cagggtctca gtacagccac caaggacacc | 300 |
| tacgacgccc ttcacatgca ggccctgccc cctcgctaa | 339 |

<210> SEQ ID NO 12
<211> LENGTH: 1395
<212> TYPE: DNA
<213> ORGANISM: Artificial sequence
<220> FEATURE:
<223> OTHER INFORMATION: podo447VH

<400> SEQUENCE: 12

| | |
|---|---|
| atggagactg ggctgcgctg gcttctcctg gtcgctgtgc tcaaaggtgt ccagtgtcag | 60 |
| tcgctggagg agtccggggg tcgcctggtc acgcctggga caccctgac actcacctgc | 120 |
| acagcctctg gattctccct cagtggctac cagatgaact gggtccgcca ggctccaggg | 180 |
| aaggggctgg agtggatcgg atatatttgg agtgatggtg gtacagacta cgcgagctgg | 240 |
| gcgaaaggcc gattcaccat ctccaaaacc tcgtcgacca cggtggatct gaaaatgacc | 300 |
| agtctgacaa ccgaggacac ggccacctat ttctgtgcca gggagggata ctggcttggt | 360 |
| gcttttgatc cctggggccc aggcaccctg gtcaccgtct cttcagctag caccaagggc | 420 |
| ccatcggtct tcccctggc accctcctcc aagagcacct ctgggggcac agcggccctg | 480 |
| ggctgcctgg tcaaggacta cttccccgaa ccggtgacgg tgtcgtggaa ctcaggcgcc | 540 |
| ctgaccagcg gcgtgcacac cttcccggct gtcctacagt cctcaggact ctactccctc | 600 |
| agcagcgtgg tgaccgtgcc ctccagcagc ttgggcaccc agacctacat ctgcaacgtg | 660 |
| aatcacaagc ccagcaacac caaggtggac aagagagttg agcccaaatc ttgtgacaaa | 720 |
| actcacacat gcccaccgtg cccagcacct gaactcctgg ggggaccgtc agtcttcctc | 780 |
| ttccccccaa aacccaagga caccctcatg atctcccgga cccctgaggt cacatgcgtg | 840 |
| gtggtggacg tgagccacga agaccctgag gtcaagttca actggtacgt ggacggcgtg | 900 |
| gaggtgcata atgccaagac aaagccgcgg gaggagcagt acaacagcac gtaccgtgtg | 960 |
| gtcagcgtcc tcaccgtcct gcaccaggac tggctgaatg gcaaggagta caagtgcaag | 1020 |
| gtctccaaca aagccctccc agcccccatc gagaaaacca tctccaaagc caagggcag | 1080 |
| ccccgagaac acaggtgta caccctgccc ccatcccggg atgagctgac caagaaccag | 1140 |
| gtcagcctga cctgcctggt caaaggcttc tatcccagcg acatcgccgt ggagtgggag | 1200 |
| agcaatgggc agccggagaa caactacaag accacgcctc ccgtgctgga ctccgacggc | 1260 |
| tccttcttcc tctacagcaa gctcaccgtg gacaagagca ggtggcagca ggggaacgtc | 1320 |
| ttctcatgct ccgtgatgca tgaggctctg cacaaccact acacgcagaa gagcctctcc | 1380 |
| ctgtctccgg gtaaa | 1395 |

<210> SEQ ID NO 13
<211> LENGTH: 2388
<212> TYPE: DNA
<213> ORGANISM: Artificial sequence
<220> FEATURE:
<223> OTHER INFORMATION: podo447VH_hIgG1C_chimeric

<400> SEQUENCE: 13

| | |
|---|---|
| atggagactg ggctgcgctg gcttctcctg gtcgctgtgc tcaaaggtgt ccagtgtcag | 60 |
| tcgctggagg agtccggggg tcgcctggtc acgcctggga caccctgac actcacctgc | 120 |

-continued

```
acagcctctg gattctccct cagtggctac cagatgaact gggtccgcca ggctccaggg      180
aaggggctgg agtggatcgg atatatttgg agtgatggtg gtacagacta cgcgagctgg      240
gcgaaaggcc gattcaccat ctccaaaacc tcgtcgacca cggtggatct gaaaatgacc      300
agtctgacaa ccgaggacac ggccacctat ttctgtgcca gggagggata ctggcttggt      360
gcttttgatc cctggggccc aggcaccctg gtcaccgtct cttcagctag caccaagggc      420
ccatcggtct tccccctggc accctcctcc aagagcacct ctgggggcac agcggccctg      480
ggctgcctgg tcaaggacta cttccccgaa ccggtgacgg tgtcgtggaa ctcaggcgcc      540
ctgaccagcg gcgtgcacac cttcccggct gtcctacagt cctcaggact ctactccctc      600
agcagcgtgg tgaccgtgcc ctccagcagc ttgggcaccc agacctacat ctgcaacgtg      660
aatcacaagc ccagcaacac caaggtggac aagagagttg agcccaaatc ttgtgacaaa      720
actcacacat gcccaccgtg cccagcacct gaactcctgg ggggaccgtc agtcttcctc      780
ttccccccaa aacccaagga caccctcatg atctcccgga cccctgaggt cacatgcgtg      840
gtggtggacg tgagccacga agaccctgag gtcaagttca actggtacgt ggacggcgtg      900
gaggtgcata atgccaagac aaagccgcgg gaggagcagt acaacagcac gtaccgtgtg      960
gtcagcgtcc tcaccgtcct gcaccaggac tggctgaatg gcaaggagta caagtgcaag     1020
gtctccaaca agccctccc agccccatc gagaaaacca tctccaaagc caagggcag     1080
ccccgagaac cacaggtgta caccctgccc ccatcccggg atgagctgac caagaaccag     1140
gtcagcctga cctgcctggt caaaggcttc tatcccagcg acatcgccgt ggagtgggag     1200
agcaatgggc agccggagaa caactacaag accacgcctc ccgtgctgga ctccgacggc     1260
tccttcttcc tctacagcaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gtaaagctag caccaagggc ccatcggtct tccccctggc accctcctcc     1440
aagagcacct ctgggggcac agcggccctg ggctgcctgg tcaaggacta cttccccgaa     1500
ccggtgacgg tgtcgtggaa ctcaggcgcc ctgaccagcg gcgtgcacac cttcccggct     1560
gtcctacagt cctcaggact ctactccctc agcagcgtgg tgaccgtgcc ctccagcagc     1620
ttgggcaccc agacctacat ctgcaacgtg aatcacaagc ccagcaacac caaggtggac     1680
aagagagttg agcccaaatc ttgtgacaaa actcacacat gcccaccgtg cccagcacct     1740
gaactcctgg ggggaccgtc agtcttcctc ttccccccaa aacccaagga caccctcatg     1800
atctcccgga cccctgaggt cacatgcgtg gtggtggacg tgagccacga agaccctgag     1860
gtcaagttca actggtacgt ggacggcgtg gaggtgcata atgccaagac aaagccgcgg     1920
gaggagcagt acaacagcac gtaccgtgtg gtcagcgtcc tcaccgtcct gcaccaggac     1980
tggctgaatg gcaaggagta caagtgcaag gtctccaaca agccctccc agccccatc     2040
gagaaaacca tctccaaagc caagggcag ccccgagaac cacaggtgta caccctgccc     2100
ccatcccggg atgagctgac caagaaccag gtcagcctga cctgcctggt caaaggcttc     2160
tatcccagcg acatcgccgt ggagtgggag agcaatgggc agccggagaa caactacaag     2220
accacgcctc ccgtgctgga ctccgacggc tccttcttcc tctacagcaa gctcaccgtg     2280
gacaagagca ggtggcagca ggggaacgtc ttctcatgct ccgtgatgca tgaggctctg     2340
cacaaccact acacgcagaa gagcctctcc ctgtctccgg gtaaatga                  2388
```

<210> SEQ ID NO 14

<211> LENGTH: 402
<212> TYPE: DNA
<213> ORGANISM: Artificial sequence
<220> FEATURE:
<223> OTHER INFORMATION: podo447VL

<400> SEQUENCE: 14

| | | | | | |
|---|---|---|---|---|---|
| atggacacga | gggcccccac | tcagctgctg | gggctcctgc | tgctctggct | cccaggtgcc | 60 |
| acatttgccg | ccgtgctgac | ccagactcca | tctcccgtgt | ctgcagctgt | gggagccaca | 120 |
| gtcagcgtca | gttgccagtc | cagtcagagt | gtccatcata | gaacgactt | agcctggttt | 180 |
| cagcagaaac | aggtcagcc | tcccaagctc | ctgatctatt | atacatccac | tctggcatct | 240 |
| ggggtcccat | cacggttcaa | gggcagtgga | tctgggacac | agttcactct | caccatcagc | 300 |
| gacctggagt | gtgacgatgc | tgccacttac | tactgtgcag | gcgtttatga | gggtagtagt | 360 |
| gataataggg | ctttcggcgg | agggaccgag | gtggtggtca | aa | | 402 |

<210> SEQ ID NO 15
<211> LENGTH: 726
<212> TYPE: DNA
<213> ORGANISM: Artificial sequence
<220> FEATURE:
<223> OTHER INFORMATION: podo447VL_hIgkC_chimeric

<400> SEQUENCE: 15

| | | | | | |
|---|---|---|---|---|---|
| atggacacga | gggcccccac | tcagctgctg | gggctcctgc | tgctctggct | cccaggtgcc | 60 |
| acatttgccg | ccgtgctgac | ccagactcca | tctcccgtgt | ctgcagctgt | gggagccaca | 120 |
| gtcagcgtca | gttgccagtc | cagtcagagt | gtccatcata | gaacgactt | agcctggttt | 180 |
| cagcagaaac | aggtcagcc | tcccaagctc | ctgatctatt | atacatccac | tctggcatct | 240 |
| ggggtcccat | cacggttcaa | gggcagtgga | tctgggacac | agttcactct | caccatcagc | 300 |
| gacctggagt | gtgacgatgc | tgccacttac | tactgtgcag | gcgtttatga | gggtagtagt | 360 |
| gataataggg | ctttcggcgg | agggaccgag | gtggtggtca | aacgtacggt | ggctgcacca | 420 |
| tctgtcttca | tcttcccgcc | atctgatgag | cagttgaaat | ctggaactgc | ctctgttgtg | 480 |
| tgcctgctga | taacttcta | tcccagagag | gccaaagtac | agtggaaggt | ggataacgcc | 540 |
| ctccaatcgg | gtaactccca | ggagagtgtc | acagagcagg | acagcaagga | cagcacctac | 600 |
| agcctcagca | gcaccctgac | gctgagcaaa | gcagactacg | agaaacacaa | agtctacgcc | 660 |
| tgcgaagtca | cccatcaggg | cctgagctcg | cccgtcacaa | agagcttcaa | caggggagag | 720 |
| tgttag | | | | | | 726 |

<210> SEQ ID NO 16
<211> LENGTH: 530
<212> TYPE: PRT
<213> ORGANISM: Artificial sequence
<220> FEATURE:
<223> OTHER INFORMATION: scFv_VH_GGGGS_VL_CAR

<400> SEQUENCE: 16

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Gly Tyr Gln Met Asn Trp Val Arg Gln Ala Pro Gly Lys Gly Leu Glu
    50                  55                  60

```
Trp Ile Gly Tyr Ile Trp Ser Asp Gly Gly Thr Asp Tyr Ala Ser Trp
 65                  70                  75                  80

Ala Lys Gly Arg Phe Thr Ile Ser Lys Thr Ser Ser Thr Val Asp
                 85                  90                  95

Leu Lys Met Thr Ser Leu Thr Thr Glu Asp Thr Ala Thr Tyr Phe Cys
            100                 105                 110

Ala Arg Glu Gly Tyr Trp Leu Gly Ala Phe Asp Pro Trp Gly Pro Gly
                115                 120                 125

Thr Leu Val Thr Val Ser Ser Gly Gly Gly Ser Gly Gly Gly Gly
130             135                 140

Ser Gly Gly Gly Gly Ser Ala Val Leu Thr Gln Thr Pro Ser Pro Val
145                 150                 155                 160

Ser Ala Ala Val Gly Ala Thr Val Ser Val Ser Cys Gln Ser Ser Gln
                165                 170                 175

Ser Val His His Lys Asn Asp Leu Ala Trp Phe Gln Gln Lys Pro Gly
            180                 185                 190

Gln Pro Pro Lys Leu Leu Ile Tyr Tyr Thr Ser Thr Leu Ala Ser Gly
                195                 200                 205

Val Pro Ser Arg Phe Lys Gly Ser Gly Ser Gly Thr Gln Phe Thr Leu
210                 215                 220

Thr Ile Ser Asp Leu Glu Cys Asp Asp Ala Ala Thr Tyr Tyr Cys Ala
225                 230                 235                 240

Gly Val Tyr Glu Gly Ser Ser Asp Asn Arg Ala Phe Gly Gly Gly Thr
                245                 250                 255

Glu Val Val Val Lys Glu Gln Lys Leu Ile Ser Glu Glu Asp Leu Asn
                260                 265                 270

Arg Ile Arg Gly Val Thr Val Ser Ser Ala Leu Ser Asn Ser Ile Met
            275                 280                 285

Tyr Phe Ser His Phe Val Pro Val Phe Leu Pro Ala Lys Pro Thr Thr
            290                 295                 300

Thr Pro Ala Pro Arg Pro Pro Thr Pro Ala Pro Thr Ile Ala Ser Gln
305                 310                 315                 320

Pro Leu Ser Leu Arg Pro Glu Ala Cys Arg Pro Ala Ala Gly Gly Ala
                325                 330                 335

Val His Thr Arg Gly Leu Asp Pro Phe Gly Phe Trp Val Leu Val Val
            340                 345                 350

Val Gly Gly Val Leu Ala Cys Tyr Ser Leu Leu Val Thr Val Ala Phe
            355                 360                 365

Ile Ile Phe Trp Val Arg Ser Lys Arg Ser Arg Leu Leu His Ser Asp
            370                 375                 380

Tyr Met Asn Met Thr Pro Arg Arg Pro Gly Pro Thr Arg Lys His Tyr
385                 390                 395                 400

Gln Pro Tyr Ala Pro Pro Arg Asp Phe Ala Ala Tyr Arg Ser Leu Glu
                405                 410                 415

Arg Val Arg Val Lys Phe Ser Arg Ser Ala Asp Ala Pro Ala Tyr Gln
                420                 425                 430

Gln Gly Gln Asn Gln Leu Tyr Asn Glu Leu Asn Leu Gly Arg Arg Glu
            435                 440                 445

Glu Tyr Asp Val Leu Asp Lys Arg Arg Gly Arg Asp Pro Glu Met Gly
            450                 455                 460

Gly Lys Pro Arg Arg Lys Asn Pro Gln Glu Gly Leu Tyr Asn Glu Leu
465                 470                 475                 480
```

```
Gln Lys Asp Lys Met Ala Glu Ala Tyr Ser Glu Ile Gly Met Lys Gly
                485                 490                 495

Glu Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
        515                 520                 525

Pro Arg
    530

<210> SEQ ID NO 17
<211> LENGTH: 534
<212> TYPE: PRT
<213> ORGANISM: Artificial sequence
<220> FEATURE:
<223> OTHER INFORMATION: scFv_VL_GGGGS_VH_CAR

<400> SEQUENCE: 17

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Ala Ala Val Gly Ala Thr Val Ser Val Ser Cys Gln Ser Ser
            35                  40                  45

Gln Ser Val His His Lys Asn Asp Leu Ala Trp Phe Gln Gln Lys Pro
        50                  55                  60

Gly Gln Pro Pro Lys Leu Leu Ile Tyr Tyr Thr Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
                100                 105                 110

Ala Gly Val Tyr Glu Gly Ser Ser Asp Asn Arg Ala Phe Gly Gly Gly
            115                 120                 125

Thr Glu Val Val Val Lys Gly Gly Gly Ser Gly Gly Gly Gly Ser
        130                 135                 140

Gly Gly Gly Gly Ser Gln Ser Leu Glu Glu Ser Gly Gly Arg Leu Val
145                 150                 155                 160

Thr Pro Gly Thr Pro Leu Thr Leu Thr Cys Thr Ala Ser Gly Phe Ser
                165                 170                 175

Leu Ser Gly Tyr Gln Met Asn Trp Val Arg Gln Ala Pro Gly Lys Gly
            180                 185                 190

Leu Glu Trp Ile Gly Tyr Ile Trp Ser Asp Gly Gly Thr Asp Tyr Ala
        195                 200                 205

Ser Trp Ala Lys Gly Arg Phe Thr Ile Ser Lys Thr Ser Ser Thr Thr
    210                 215                 220

Val Asp Leu Lys Met Thr Ser Leu Thr Thr Glu Asp Thr Ala Thr Tyr
225                 230                 235                 240

Phe Cys Ala Arg Glu Gly Tyr Trp Leu Gly Ala Phe Asp Pro Trp Gly
                245                 250                 255

Pro Gly Thr Leu Val Thr Val Ser Ser Glu Gln Lys Leu Ile Ser Glu
            260                 265                 270

Glu Asp Leu Asn Arg Ile Arg Gly Val Thr Val Ser Ser Ala Leu Ser
        275                 280                 285

Asn Ser Ile Met Tyr Phe Ser His Phe Val Pro Val Phe Leu Pro Ala
    290                 295                 300
```

```
Lys Pro Thr Thr Thr Pro Ala Pro Arg Pro Pro Thr Pro Ala Pro Thr
305                 310                 315                 320

Ile Ala Ser Gln Pro Leu Ser Leu Arg Pro Glu Ala Cys Arg Pro Ala
                325                 330                 335

Ala Gly Gly Ala Val His Thr Arg Gly Leu Asp Pro Phe Gly Phe Trp
            340                 345                 350

Val Leu Val Val Val Gly Gly Val Leu Ala Cys Tyr Ser Leu Leu Val
        355                 360                 365

Thr Val Ala Phe Ile Ile Phe Trp Val Arg Ser Lys Arg Ser Arg Leu
    370                 375                 380

Leu His Ser Asp Tyr Met Asn Met Thr Pro Arg Arg Pro Gly Pro Thr
385                 390                 395                 400

Arg Lys His Tyr Gln Pro Tyr Ala Pro Pro Arg Asp Phe Ala Ala Tyr
                405                 410                 415

Arg Ser Leu Glu Arg Val Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
        435                 440                 445

Gly Arg Arg Glu Glu Tyr Asp Val Leu Asp Lys Arg Arg Gly Arg Asp
450                 455                 460

Pro Glu Met Gly Gly Lys Pro Arg Arg Lys Asn Pro Gln Glu Gly Leu
465                 470                 475                 480

Tyr Asn Glu Leu Gln Lys Asp Lys Met Ala Glu Ala Tyr Ser Glu Ile
                485                 490                 495

Gly Met Lys Gly Glu Arg Arg Arg Gly Lys Gly His Asp Gly Leu Tyr
            500                 505                 510

Gln Gly Leu Ser Thr Ala Thr Lys Asp Thr Tyr Asp Ala Leu His Met
        515                 520                 525

Gln Ala Leu Pro Pro Arg
        530

<210> SEQ ID NO 18
<211> LENGTH: 739
<212> TYPE: PRT
<213> ORGANISM: Artificial sequence
<220> FEATURE:
<223> OTHER INFORMATION: scFab_VL_CL_GGGGS_VH_CH1_CAR

<400> SEQUENCE: 18

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
                20                  25                  30

Val Ser Ala Ala Val Gly Ala Thr Val Ser Val Ser Cys Gln Ser Ser
            35                  40                  45

Gln Ser Val His His Lys Asn Asp Leu Ala Trp Phe Gln Gln Lys Pro
        50                  55                  60

Gly Gln Pro Pro Lys Leu Leu Ile Tyr Tyr Thr Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Val Tyr Glu Gly Ser Ser Asp Asn Arg Ala Phe Gly Gly Gly
        115                 120                 125
```

-continued

Thr Glu Val Val Val Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys Gly Gly Gly Gly Ser Gly Gly Gly Gly Ser Gly Gly Gly Gly Ser
                245                 250                 255

Gln Ser Leu Glu Glu Ser Gly Gly Arg Leu Val Thr Pro Gly Thr Pro
            260                 265                 270

Leu Thr Leu Thr Cys Thr Ala Ser Gly Phe Ser Leu Ser Gly Tyr Gln
        275                 280                 285

Met Asn Trp Val Arg Gln Ala Pro Gly Lys Gly Leu Glu Trp Ile Gly
290                 295                 300

Tyr Ile Trp Ser Asp Gly Thr Asp Tyr Ala Ser Trp Ala Lys Gly
305                 310                 315                 320

Arg Phe Thr Ile Ser Lys Thr Ser Ser Thr Thr Val Asp Leu Lys Met
                325                 330                 335

Thr Ser Leu Thr Thr Glu Asp Thr Ala Thr Tyr Phe Cys Ala Arg Glu
            340                 345                 350

Gly Tyr Trp Leu Gly Ala Phe Asp Pro Trp Gly Pro Gly Thr Leu Val
        355                 360                 365

Thr Val Ser Ser Ala Ser Thr Lys Gly Pro Ser Val Phe Pro Leu Ala
370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
450                 455                 460

Lys Val Asp Lys Arg Val Glu Gln Lys Leu Ile Ser Glu Glu Asp Leu
465                 470                 475                 480

Asn Arg Ile Arg Gly Val Thr Val Ser Ser Ala Leu Ser Asn Ser Ile
                485                 490                 495

Met Tyr Phe Ser His Phe Val Pro Val Phe Leu Pro Ala Lys Pro Thr
            500                 505                 510

Thr Thr Pro Ala Pro Arg Pro Pro Thr Pro Ala Pro Thr Ile Ala Ser
        515                 520                 525

Gln Pro Leu Ser Leu Arg Pro Glu Ala Cys Arg Pro Ala Ala Gly Gly
530                 535                 540

Ala Val His Thr Arg Gly Leu Asp Pro Phe Gly Phe Trp Val Leu Val

```
            545                 550                 555                 560
Val Val Gly Gly Val Leu Ala Cys Tyr Ser Leu Leu Val Thr Val Ala
                    565                 570                 575
Phe Ile Ile Phe Trp Val Arg Ser Lys Arg Ser Arg Leu Leu His Ser
                580                 585                 590
Asp Tyr Met Asn Met Thr Pro Arg Pro Gly Pro Thr Arg Lys His
            595                 600                 605
Tyr Gln Pro Tyr Ala Pro Pro Arg Asp Phe Ala Ala Tyr Arg Ser Leu
        610                 615                 620
Glu Arg Val Arg Val Lys Phe Ser Arg Ser Ala Asp Ala Pro Ala Tyr
625                 630                 635                 640
Gln Gln Gly Gln Asn Gln Leu Tyr Asn Glu Leu Asn Leu Gly Arg Arg
                    645                 650                 655
Glu Glu Tyr Asp Val Leu Asp Lys Arg Arg Gly Arg Asp Pro Glu Met
                660                 665                 670
Gly Gly Lys Pro Arg Arg Lys Asn Pro Gln Glu Gly Leu Tyr Asn Glu
            675                 680                 685
Leu Gln Lys Asp Lys Met Ala Glu Ala Tyr Ser Glu Ile Gly Met Lys
        690                 695                 700
Gly Glu Arg Arg Arg Gly Lys Gly His Asp Gly Leu Tyr Gln Gly Leu
705                 710                 715                 720
Ser Thr Ala Thr Lys Asp Thr Tyr Asp Ala Leu His Met Gln Ala Leu
                    725                 730                 735
Pro Pro Arg

<210> SEQ ID NO 19
<211> LENGTH: 261
<212> TYPE: PRT
<213> ORGANISM: Artificial sequence
<220> FEATURE:
<223> OTHER INFORMATION: Podo447_scFv_VH_GGGGS_VL

<400> SEQUENCE: 19

Met Glu Thr Gly Leu Arg Trp Leu Leu Leu Val Ala Val Leu Lys Gly
1               5                   10                  15
Val Gln Cys Gln Ser Leu Glu Glu Ser Gly Gly Arg Leu Val Thr Pro
                20                  25                  30
Gly Thr Pro Leu Thr Leu Thr Cys Thr Ala Ser Gly Phe Ser Leu Ser
            35                  40                  45
Gly Tyr Gln Met Asn Trp Val Arg Gln Ala Pro Gly Lys Gly Leu Glu
        50                  55                  60
Trp Ile Gly Tyr Ile Trp Ser Asp Gly Gly Thr Asp Tyr Ala Ser Trp
65                  70                  75                  80
Ala Lys Gly Arg Phe Thr Ile Ser Lys Thr Ser Thr Thr Val Asp
                85                  90                  95
Leu Lys Met Thr Ser Leu Thr Thr Glu Asp Thr Ala Thr Tyr Phe Cys
                100                 105                 110
Ala Arg Glu Gly Tyr Trp Leu Gly Ala Phe Asp Pro Trp Gly Pro Gly
            115                 120                 125
Thr Leu Val Thr Val Ser Ser Gly Gly Gly Gly Ser Gly Gly Gly Gly
        130                 135                 140
Ser Gly Gly Gly Gly Ser Ala Val Leu Thr Gln Thr Pro Ser Pro Val
145                 150                 155                 160
Ser Ala Ala Val Gly Ala Thr Val Ser Val Ser Cys Gln Ser Ser Gln
                165                 170                 175
```

```
Ser Val His His Lys Asn Asp Leu Ala Trp Phe Gln Gln Lys Pro Gly
            180                 185                 190

Gln Pro Pro Lys Leu Leu Ile Tyr Tyr Thr Ser Thr Leu Ala Ser Gly
        195                 200                 205

Val Pro Ser Arg Phe Lys Gly Ser Gly Ser Gly Thr Gln Phe Thr Leu
    210                 215                 220

Thr Ile Ser Asp Leu Glu Cys Asp Asp Ala Ala Thr Tyr Tyr Cys Ala
225                 230                 235                 240

Gly Val Tyr Glu Gly Ser Ser Asp Asn Arg Ala Phe Gly Gly Gly Thr
                245                 250                 255

Glu Val Val Val Lys
            260
```

```
<210> SEQ ID NO 20
<211> LENGTH: 265
<212> TYPE: PRT
<213> ORGANISM: Artificial sequence
<220> FEATURE:
<223> OTHER INFORMATION: Podo447_scFv_VL_GGGGS_VH

<400> SEQUENCE: 20

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Ala Thr Val Ser Val Ser Cys Gln Ser Ser
        35                  40                  45

Gln Ser Val His His Lys Asn Asp Leu Ala Trp Phe Gln Gln Lys Pro
    50                  55                  60

Gly Gln Pro Pro Lys Leu Leu Ile Tyr Tyr Thr Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Val Tyr Glu Gly Ser Ser Asp Asn Arg Ala Phe Gly Gly Gly
        115                 120                 125

Thr Glu Val Val Val Lys Gly Gly Gly Ser Gly Gly Gly Gly Ser
    130                 135                 140

Gly Gly Gly Gly Ser Gln Ser Leu Glu Glu Ser Gly Gly Arg Leu Val
145                 150                 155                 160

Thr Pro Gly Thr Pro Leu Thr Leu Thr Cys Thr Ala Ser Gly Phe Ser
                165                 170                 175

Leu Ser Gly Tyr Gln Met Asn Trp Val Arg Gln Ala Pro Gly Lys Gly
            180                 185                 190

Leu Glu Trp Ile Gly Tyr Ile Trp Ser Asp Gly Thr Asp Tyr Ala
        195                 200                 205

Ser Trp Ala Lys Gly Arg Phe Thr Ile Ser Lys Thr Ser Ser Thr Thr
    210                 215                 220

Val Asp Leu Lys Met Thr Ser Leu Thr Thr Glu Asp Thr Ala Thr Tyr
225                 230                 235                 240

Phe Cys Ala Arg Glu Gly Tyr Trp Leu Gly Ala Phe Asp Pro Trp Gly
                245                 250                 255

Pro Gly Thr Leu Val Thr Val Ser Ser
            260                 265
```

<210> SEQ ID NO 21
<211> LENGTH: 470
<212> TYPE: PRT
<213> ORGANISM: Artificial sequence
<220> FEATURE:
<223> OTHER INFORMATION: Podo447_scFab_VL_CL_GGGGS_VH_CH1

<400> SEQUENCE: 21

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Ala Thr Val Ser Val Ser Cys Gln Ser Ser
        35                  40                  45

Gln Ser Val His His Lys Asn Asp Leu Ala Trp Phe Gln Gln Lys Pro
    50                  55                  60

Gly Gln Pro Pro Lys Leu Leu Ile Tyr Tyr Thr Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Val Tyr Glu Gly Ser Ser Asp Asn Arg Ala Phe Gly Gly Gly
        115                 120                 125

Thr Glu Val Val Val Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys Gly Gly Gly Gly Ser Gly Gly Gly Ser Gly Gly Gly Gly Ser
                245                 250                 255

Gln Ser Leu Glu Glu Ser Gly Gly Arg Leu Val Thr Pro Gly Thr Pro
            260                 265                 270

Leu Thr Leu Thr Cys Thr Ala Ser Gly Phe Ser Leu Ser Gly Tyr Gln
        275                 280                 285

Met Asn Trp Val Arg Gln Ala Pro Gly Lys Gly Leu Glu Trp Ile Gly
    290                 295                 300

Tyr Ile Trp Ser Asp Gly Thr Asp Tyr Ala Ser Trp Ala Lys Gly
305                 310                 315                 320

Arg Phe Thr Ile Ser Lys Thr Ser Thr Thr Val Asp Leu Lys Met
                325                 330                 335

Thr Ser Leu Thr Thr Glu Asp Thr Ala Thr Tyr Phe Cys Ala Arg Glu
            340                 345                 350

Gly Tyr Trp Leu Gly Ala Phe Asp Pro Trp Gly Pro Gly Thr Leu Val
        355                 360                 365
```

```
Thr Val Ser Ser Ala Ser Thr Lys Gly Pro Ser Val Phe Pro Leu Ala
        370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
            435                 440                 445

Gly Thr Gln Thr Tyr Ile Cys Asn Val Asn His Lys Pro Ser Asn Thr
        450                 455                 460

Lys Val Asp Lys Arg Val
465                 470
```

<210> SEQ ID NO 22
<211> LENGTH: 10
<212> TYPE: PRT
<213> ORGANISM: Artificial sequence
<220> FEATURE:
<223> OTHER INFORMATION: MYC tag

<400> SEQUENCE: 22

```
Glu Gln Lys Leu Ile Ser Glu Glu Asp Leu
1               5                   10
```

<210> SEQ ID NO 23
<211> LENGTH: 63
<212> TYPE: PRT
<213> ORGANISM: Artificial sequence
<220> FEATURE:
<223> OTHER INFORMATION: CD8 hinge

<400> SEQUENCE: 23

```
Ser Ala Leu Ser Asn Ser Ile Met Tyr Phe Ser His Phe Val Pro Val
1               5                   10                  15

Phe Leu Pro Ala Lys Pro Thr Thr Thr Pro Ala Pro Arg Pro Pro Thr
            20                  25                  30

Pro Ala Pro Thr Ile Ala Ser Gln Pro Leu Ser Leu Arg Pro Glu Ala
        35                  40                  45

Cys Arg Pro Ala Ala Gly Gly Ala Val His Thr Arg Gly Leu Asp
    50                  55                  60
```

<210> SEQ ID NO 24
<211> LENGTH: 27
<212> TYPE: PRT
<213> ORGANISM: Artificial sequence
<220> FEATURE:
<223> OTHER INFORMATION: CD28 TM

<400> SEQUENCE: 24

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 25
<211> LENGTH: 41
<212> TYPE: PRT
<213> ORGANISM: Artificial sequence
<220> FEATURE:

```
<223> OTHER INFORMATION: CD28 IC

<400> SEQUENCE: 25

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 26
<211> LENGTH: 112
<212> TYPE: PRT
<213> ORGANISM: Artificial sequence
<220> FEATURE:
<223> OTHER INFORMATION: CD3z

<400> SEQUENCE: 26

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 27
<211> LENGTH: 135
<212> TYPE: PRT
<213> ORGANISM: Artificial sequence
<220> FEATURE:
<223> OTHER INFORMATION: podo447VH

<400> SEQUENCE: 27

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Gly Tyr Gln Met Asn Trp Val Arg Gln Ala Pro Gly Lys Gly Leu Glu
    50                  55                  60

Trp Ile Gly Tyr Ile Trp Ser Asp Gly Thr Asp Tyr Ala Ser Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Ala Arg Glu Gly Tyr Trp Leu Gly Ala Phe Asp Pro Trp Gly Pro Gly
        115                 120                 125

Thr Leu Val Thr Val Ser Ser
```

<210> SEQ ID NO 28
<211> LENGTH: 465
<212> TYPE: PRT
<213> ORGANISM: Artificial sequence
<220> FEATURE:
<223> OTHER INFORMATION: podo447VH_hIgG1C_chimeric

<400> SEQUENCE: 28

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Gly Tyr Gln Met Asn Trp Val Arg Gln Ala Pro Gly Lys Gly Leu Glu
    50                  55                  60

Trp Ile Gly Tyr Ile Trp Ser Asp Gly Gly Thr Asp Tyr Ala Ser Trp
65                  70                  75                  80

Ala Lys Gly Arg Phe Thr Ile Ser Lys Thr Ser Ser Thr Thr Val Asp
                85                  90                  95

Leu Lys Met Thr Ser Leu Thr Thr Glu Asp Thr Ala Thr Tyr Phe Cys
            100                 105                 110

Ala Arg Glu Gly Tyr Trp Leu Gly Ala Phe Asp Pro Trp Gly Pro Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr

```
                        355                 360                 365
Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 29
<211> LENGTH: 134
<212> TYPE: PRT
<213> ORGANISM: Artificial sequence
<220> FEATURE:
<223> OTHER INFORMATION: podo447VL

<400> SEQUENCE: 29

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Ala Thr Val Ser Val Ser Cys Gln Ser Ser
        35                  40                  45

Gln Ser Val His His Lys Asn Asp Leu Ala Trp Phe Gln Gln Lys Pro
    50                  55                  60

Gly Gln Pro Pro Lys Leu Leu Ile Tyr Tyr Thr Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Val Tyr Glu Gly Ser Ser Asp Asn Arg Ala Phe Gly Gly Gly
        115                 120                 125

Thr Glu Val Val Val Lys
    130

<210> SEQ ID NO 30
<211> LENGTH: 241
<212> TYPE: PRT
<213> ORGANISM: Artificial sequence
<220> FEATURE:
<223> OTHER INFORMATION: podo447VL_hIgkC_chimeric

<400> SEQUENCE: 30

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Ala Thr Val Ser Val Ser Cys Gln Ser Ser
        35                  40                  45
```

```
Gln Ser Val His His Lys Asn Asp Leu Ala Trp Phe Gln Gln Lys Pro
    50                  55                  60
Gly Gln Pro Pro Lys Leu Leu Ile Tyr Tyr Thr Ser Thr Leu Ala Ser
 65                  70                  75                  80
Gly Val Pro Ser Arg Phe Lys Gly Ser Gly Ser Gly Thr Gln Phe Thr
                 85                  90                  95
Leu Thr Ile Ser Asp Leu Glu Cys Asp Asp Ala Ala Thr Tyr Tyr Cys
            100                 105                 110
Ala Gly Val Tyr Glu Gly Ser Ser Asp Asn Arg Ala Phe Gly Gly Gly
                115                 120                 125
Thr Glu Val Val Val Lys Arg Thr Val Ala Ala Pro Ser Val Phe Ile
130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
Gln Asp Ser Lys Asp Ser Thr Tyr Ser Leu Ser Ser Thr Leu Thr Leu
        195                 200                 205
Ser Lys Ala Asp Tyr Glu Lys His Lys Val Tyr Ala Cys Glu Val Thr
210                 215                 220
His Gln Gly Leu Ser Ser Pro Val Thr Lys Ser Phe Asn Arg Gly Glu
225                 230                 235                 240
Cys

<210> SEQ ID NO 31
<211> LENGTH: 557
<212> TYPE: PRT
<213> ORGANISM: Homo sapiens

<400> SEQUENCE: 31

Met Arg Cys Ala Leu Ala Leu Ser Ala Leu Leu Leu Leu Leu Ser Thr
1                5                  10                  15
Pro Pro Leu Leu Pro Ser Ser Pro Ser Pro Ser Pro Ser Pro Ser Gln
                20                  25                  30
Asn Ala Thr Gln Thr Thr Thr Asp Ser Ser Asn Lys Thr Ala Pro Thr
            35                  40                  45
Pro Ala Ser Ser Val Thr Ile Met Ala Thr Asp Thr Ala Gln Gln Ser
        50                  55                  60
Thr Val Pro Thr Ser Lys Ala Asn Glu Ile Leu Ala Ser Val Lys Ala
65                  70                  75                  80
Thr Thr Leu Gly Val Ser Ser Asp Ser Pro Gly Thr Thr Thr Leu Ala
                85                  90                  95
Gln Gln Val Ser Gly Pro Val Asn Thr Thr Val Ala Arg Gly Gly Gly
            100                 105                 110
Ser Gly Asn Pro Thr Thr Thr Ile Glu Ser Pro Lys Ser Thr Lys Ser
        115                 120                 125
Ala Asp Thr Thr Thr Val Ala Thr Ser Thr Ala Thr Ala Lys Pro Asn
130                 135                 140
Thr Thr Ser Ser Gln Asn Gly Ala Glu Asp Thr Thr Asn Ser Gly Gly
145                 150                 155                 160
Lys Ser Ser His Ser Val Thr Thr Asp Leu Thr Ser Thr Lys Ala Glu
                165                 170                 175
```

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
            195                 200             205

Leu Met Lys Ile Ser Ser Ser Ser Thr Val Ala Ile Pro Gly Tyr
            210                 215                 220

Thr Phe Thr Ser Pro Gly Met Thr Thr Leu Leu Glu Thr Val Phe
225                 230                 235                 240

His His Val Ser Gly Ala Gly Leu Glu Leu Thr Ser Gly Asp Leu
                245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
            275                 280                 285

Ala Pro Ser Ser Gly Glu Thr Val Gln Pro Thr Ser Pro Ala Thr Ala
            290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
            340                 345                 350

Ser Glu Lys Gln Leu Val Ile Asn Leu Thr Gly Asn Thr Ile Cys Ala
            355                 360                 365

Gly Gly Ala Ser Asp Glu Lys Leu Ile Ser Leu Ile Cys Arg Ala Val
370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
            405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Gly Asp Gln Gly
            435                 440                 445

Pro Pro Glu Glu Ala Glu Asp Arg Phe Ser Met Pro Leu Ile Ile Thr
450                 455                 460

Ile Val Cys Met Ala Ser Phe Leu Leu Leu Val Ala Ala Leu Tyr Gly
465                 470                 475                 480

Cys Cys His Gln Arg Leu Ser Gln Arg Lys Asp Gln Gln Arg Leu Thr
                485                 490                 495

Glu Glu Leu Gln Thr Val Glu Asn Gly Tyr His Asp Asn Pro Thr Leu
            500                 505                 510

Glu Val Met Glu Thr Ser Ser Glu Met Gly Glu Lys Lys Val Val Ser
            515                 520                 525

Leu Asn Gly Glu Leu Gly Asp Ser Trp Ile Val Pro Leu Asp Asn Ile
            530                 535                 540

Thr Lys Asp Asp Leu Asp Glu Glu Glu Asp Thr His Leu
545                 550                 555

<210> SEQ ID NO 32
<211> LENGTH: 526
<212> TYPE: PRT
<213> ORGANISM: Homo sapiens

<400> SEQUENCE: 32

```
Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Gln
                20              25              30

Asn Ala Thr Gln Thr Thr Thr Asp Ser Ser Asn Lys Thr Ala Pro Thr
        35              40                  45

Pro Ala Ser Ser Val Thr Ile Met Ala Thr Asp Thr Ala Gln Gln Ser
    50              55                  60

Thr Val Pro Thr Ser Lys Ala Asn Glu Ile Leu Ala Ser Val Lys Ala
65              70                  75                  80

Thr Thr Leu Gly Val Ser Ser Asp Ser Pro Gly Thr Thr Thr Leu Ala
            85                  90                  95

Gln Gln Val Ser Gly Pro Val Asn Thr Thr Val Ala Arg Gly Gly Gly
                100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
    130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
    210                 215                 220

Thr Phe Thr Ser Pro Gly Met Thr Thr Thr Leu Pro Ser Ser Val Ile
225                 230                 235                 240

Ser Gln Arg Thr Gln Gln Thr Ser Ser Gln Met Pro Ala Ser Ser Thr
                245                 250                 255

Ala Pro Ser Ser Gln Glu Thr Val Gln Pro Thr Ser Pro Ala Thr Ala
                260                 265                 270

Leu Arg Thr Pro Thr Leu Pro Glu Thr Met Ser Ser Ser Pro Thr Ala
            275                 280                 285

Ala Ser Thr Thr His Arg Tyr Pro Lys Thr Pro Ser Pro Thr Val Ala
    290                 295                 300

His Glu Ser Asn Trp Ala Lys Cys Glu Asp Leu Glu Thr Gln Thr Gln
305                 310                 315                 320

Ser Glu Lys Gln Leu Val Ile Asn Ile Thr Gly Asn Thr Ile Cys Ala
                325                 330                 335

Gly Gly Ala Ser Asp Glu Lys Leu Ile Ser Leu Ile Cys Arg Ala Val
            340                 345                 350

Lys Ala Thr Phe Asn Pro Ala Gln Asp Lys Cys Gly Ile Arg Leu Ala
                355                 360                 365

Ser Val Pro Gly Ser Gln Thr Val Val Lys Glu Ile Thr Ile His
    370                 375                 380

Thr Lys Leu Pro Ala Lys Asp Val Tyr Glu Arg Leu Lys Asp Lys Trp
385                 390                 395                 400

Asp Glu Leu Lys Glu Ala Gly Val Ser Asp Met Lys Leu Gly Asp Gln
                405                 410                 415
```

Gly Pro Pro Glu Ala Glu Asp Arg Phe Ser Met Pro Leu Ile Ile
            420                 425                 430

Thr Ile Val Cys Met Ala Ser Phe Leu Leu Val Ala Ala Leu Tyr
            435                 440                 445

Gly Cys Cys His Gln Arg Leu Ser Gln Arg Lys Asp Gln Gln Arg Leu
            450                 455                 460

Thr Glu Glu Leu Gln Thr Val Glu Asn Gly Tyr His Asp Asn Pro Thr
465                 470                 475                 480

Leu Glu Val Met Glu Thr Ser Ser Glu Met Gln Glu Lys Lys Val Val
                    485                 490                 495

Ser Leu Asn Gly Glu Leu Gly Asp Ser Trp Ile Val Pro Leu Asp Asn
                500                 505                 510

Ile Thr Lys Asp Asp Leu Asp Glu Glu Glu Asp Thr His Leu
            515                 520                 525

<210> SEQ ID NO 33
<211> LENGTH: 8
<212> TYPE: PRT
<213> ORGANISM: Artificial sequence
<220> FEATURE:
<223> OTHER INFORMATION: Podo447_VH_CDR1_ IMGT

<400> SEQUENCE: 33

Gly Phe Ser Leu Ser Gly Tyr Gln
1               5

<210> SEQ ID NO 34
<211> LENGTH: 7
<212> TYPE: PRT
<213> ORGANISM: Artificial sequence
<220> FEATURE:
<223> OTHER INFORMATION: Podo447_VH_CDR1_ Chotia

<400> SEQUENCE: 34

Gly Phe Ser Leu Ser Gly Tyr
1               5

<210> SEQ ID NO 35
<211> LENGTH: 5
<212> TYPE: PRT
<213> ORGANISM: Artificial sequence
<220> FEATURE:
<223> OTHER INFORMATION: Podo447_VH_CDR1_ Kabat

<400> SEQUENCE: 35

Gly Tyr Gln Met Asn
1               5

<210> SEQ ID NO 36
<211> LENGTH: 7
<212> TYPE: PRT
<213> ORGANISM: Artificial sequence
<220> FEATURE:
<223> OTHER INFORMATION: Podo447_VH_CDR2_ IMGT

<400> SEQUENCE: 36

Ile Trp Ser Asp Gly Gly Thr
1               5

<210> SEQ ID NO 37
<211> LENGTH: 5
<212> TYPE: PRT
<213> ORGANISM: Artificial sequence
<220> FEATURE:

```
<223> OTHER INFORMATION: Podo447_VH_CDR2_ Chotia

<400> SEQUENCE: 37

Trp Ser Asp Gly Gly
1               5

<210> SEQ ID NO 38
<211> LENGTH: 16
<212> TYPE: PRT
<213> ORGANISM: Artificial sequence
<220> FEATURE:
<223> OTHER INFORMATION: Podo447_VH_CDR2_ Kabat

<400> SEQUENCE: 38

Tyr Ile Trp Ser Asp Gly Gly Thr Asp Tyr Ala Ser Trp Ala Lys Gly
1               5                   10                  15

<210> SEQ ID NO 39
<211> LENGTH: 12
<212> TYPE: PRT
<213> ORGANISM: Artificial sequence
<220> FEATURE:
<223> OTHER INFORMATION: Podo447_VH_CDR3_ IMGT

<400> SEQUENCE: 39

Ala Arg Glu Gly Tyr Trp Leu Gly Ala Phe Asp Pro
1               5                   10

<210> SEQ ID NO 40
<211> LENGTH: 10
<212> TYPE: PRT
<213> ORGANISM: Artificial sequence
<220> FEATURE:
<223> OTHER INFORMATION: Podo447_VH_CDR3_ Chotia

<400> SEQUENCE: 40

Glu Gly Tyr Trp Leu Gly Ala Phe Asp Pro
1               5                   10

<210> SEQ ID NO 41
<211> LENGTH: 10
<212> TYPE: PRT
<213> ORGANISM: Artificial sequence
<220> FEATURE:
<223> OTHER INFORMATION: Podo447_VH_CDR3_ Kabat

<400> SEQUENCE: 41

Glu Gly Tyr Trp Leu Gly Ala Phe Asp Pro
1               5                   10

<210> SEQ ID NO 42
<211> LENGTH: 8
<212> TYPE: PRT
<213> ORGANISM: Artificial sequence
<220> FEATURE:
<223> OTHER INFORMATION: Podo447_Vk_CDR1_ IMGT

<400> SEQUENCE: 42

Gln Ser Val His His Lys Asn Asp
1               5

<210> SEQ ID NO 43
<211> LENGTH: 10
<212> TYPE: PRT
<213> ORGANISM: Artificial sequence
<220> FEATURE:
<223> OTHER INFORMATION: Podo447_Vk_CDR1_ Chotia
```

<400> SEQUENCE: 43

Gln Ser Val His His Lys Asn Asp Leu Ala
1               5                   10

<210> SEQ ID NO 44
<211> LENGTH: 13
<212> TYPE: PRT
<213> ORGANISM: Artificial sequence
<220> FEATURE:
<223> OTHER INFORMATION: Podo447_Vk_CDR1_ Kabat

<400> SEQUENCE: 44

Gln Ser Ser Gln Ser Val His His Lys Asn Asp Leu Ala
1               5                   10

<210> SEQ ID NO 45
<211> LENGTH: 3
<212> TYPE: PRT
<213> ORGANISM: Artificial sequence
<220> FEATURE:
<223> OTHER INFORMATION: Podo447_Vk_CDR2_ IMGT

<400> SEQUENCE: 45

Tyr Thr Ser
1

<210> SEQ ID NO 46
<211> LENGTH: 6
<212> TYPE: PRT
<213> ORGANISM: Artificial sequence
<220> FEATURE:
<223> OTHER INFORMATION: Podo447_Vk_CDR2_ Chotia

<400> SEQUENCE: 46

Tyr Thr Ser Leu Ala Ser
1               5

<210> SEQ ID NO 47
<211> LENGTH: 6
<212> TYPE: PRT
<213> ORGANISM: Artificial sequence
<220> FEATURE:
<223> OTHER INFORMATION: Podo447_Vk_CDR2_ Kabat

<400> SEQUENCE: 47

Tyr Thr Ser Leu Ala Ser
1               5

<210> SEQ ID NO 48
<211> LENGTH: 12
<212> TYPE: PRT
<213> ORGANISM: Artificial sequence
<220> FEATURE:
<223> OTHER INFORMATION: Podo447_Vk_CDR3_ IMGT

<400> SEQUENCE: 48

Ala Gly Val Tyr Glu Gly Ser Ser Asp Asn Arg Ala
1               5                   10

<210> SEQ ID NO 49
<211> LENGTH: 12
<212> TYPE: PRT
<213> ORGANISM: Artificial sequence
<220> FEATURE:
<223> OTHER INFORMATION: Podo447_Vk_CDR3_ Chotia

<400> SEQUENCE: 49

Ala Gly Val Tyr Glu Gly Ser Ser Asp Asn Arg Ala
1               5                   10

<210> SEQ ID NO 50
<211> LENGTH: 12
<212> TYPE: PRT
<213> ORGANISM: Artificial sequence
<220> FEATURE:
<223> OTHER INFORMATION: Podo447_Vk_CDR3_ Kabat

<400> SEQUENCE: 50

Ala Gly Val Tyr Glu Gly Ser Ser Asp Asn Arg Ala
1               5                   10

<210> SEQ ID NO 51
<211> LENGTH: 24
<212> TYPE: DNA
<213> ORGANISM: Artificial sequence
<220> FEATURE:
<223> OTHER INFORMATION: Podo447_VH_CDR1_ IMGT

<400> SEQUENCE: 51
ggattctccc tcagtggcta ccag                                          24

<210> SEQ ID NO 52
<211> LENGTH: 21
<212> TYPE: DNA
<213> ORGANISM: Artificial sequence
<220> FEATURE:
<223> OTHER INFORMATION: Podo447_VH_CDR1_ Chotia

<400> SEQUENCE: 52
ggattctccc tcagtggcta c                                             21

<210> SEQ ID NO 53
<211> LENGTH: 9
<212> TYPE: DNA
<213> ORGANISM: Artificial sequence
<220> FEATURE:
<223> OTHER INFORMATION: Podo447_VH_CDR1_ Kabat

<400> SEQUENCE: 53 ggctaccag                                                            9

<210> SEQ ID NO 54
<211> LENGTH: 21
<212> TYPE: DNA
<213> ORGANISM: Artificial sequence
<220> FEATURE:
<223> OTHER INFORMATION: Podo447_VH_CDR2_ IMGT

<400> SEQUENCE: 54
atttggagtg atggtggtac a                                             21

<210> SEQ ID NO 55
<211> LENGTH: 15
<212> TYPE: DNA
<213> ORGANISM: Artificial sequence
<220> FEATURE:
<223> OTHER INFORMATION: Podo447_VH_CDR2_ Chotia

<400> SEQUENCE: 55
tggagtgatg gtggt                                                    15

<210> SEQ ID NO 56
<211> LENGTH: 48
<212> TYPE: DNA
<213> ORGANISM: Artificial sequence
<220> FEATURE:
<223> OTHER INFORMATION: Podo447_VH_CDR2_ Kabat

<400> SEQUENCE: 56
tatatttgga gtgatggtgg tacagactac gcgagctggg cgaaaggc                    48

<210> SEQ ID NO 57
<211> LENGTH: 36
<212> TYPE: DNA
<213> ORGANISM: Artificial sequence
<220> FEATURE:
<223> OTHER INFORMATION: Podo447_VH_CDR3_ IMGT

<400> SEQUENCE: 57
gccagggagg gatactggct tggtgctttt gatccc                                 36

<210> SEQ ID NO 58
<211> LENGTH: 30
<212> TYPE: DNA
<213> ORGANISM: Artificial sequence
<220> FEATURE:
<223> OTHER INFORMATION: Podo447_VH_CDR3_ Chotia

<400> SEQUENCE: 58
gagggatact ggcttggtgc ttttgatccc                                        30

<210> SEQ ID NO 59
<211> LENGTH: 30
<212> TYPE: DNA
<213> ORGANISM: Artificial sequence
<220> FEATURE:
<223> OTHER INFORMATION: Podo447_VH_CDR3_ Kabat

<400> SEQUENCE: 59
gagggatact ggcttggtgc ttttgatccc                                        30

<210> SEQ ID NO 60
<211> LENGTH: 24
<212> TYPE: DNA
<213> ORGANISM: Artificial sequence
<220> FEATURE:
<223> OTHER INFORMATION: Podo447_Vk_CDR1_ IMGT

<400> SEQUENCE: 60
cagagtgtcc atcataagaa cgac                                              24

<210> SEQ ID NO 61
<211> LENGTH: 39
<212> TYPE: DNA
<213> ORGANISM: Artificial sequence
<220> FEATURE:
<223> OTHER INFORMATION: Podo447_Vk_CDR1_ Chotia

<400> SEQUENCE: 61
cagtccagtc agagtgtcca tcataagaac gacttagcc                              39

<210> SEQ ID NO 62
<211> LENGTH: 39
<212> TYPE: DNA
<213> ORGANISM: Artificial sequence
<220> FEATURE:
<223> OTHER INFORMATION: Podo447_Vk_CDR1_ Kabat

```
<400> SEQUENCE: 62
cagtccagtc agagtgtcca tcataagaac gacttagcc                              39

<210> SEQ ID NO 63
<211> LENGTH: 9
<212> TYPE: DNA
<213> ORGANISM: Artificial sequence
<220> FEATURE:
<223> OTHER INFORMATION: Podo447_Vk_CDR2_ IMGT

<400> SEQUENCE: 63 tatacatcc                                                               9

<210> SEQ ID NO 64
<211> LENGTH: 18
<212> TYPE: DNA
<213> ORGANISM: Artificial sequence
<220> FEATURE:
<223> OTHER INFORMATION: Podo447_Vk_CDR2_ Chotia

<400> SEQUENCE: 64
tatacatcca ctctggca                                                     18

<210> SEQ ID NO 65
<211> LENGTH: 18
<212> TYPE: DNA
<213> ORGANISM: Artificial sequence
<220> FEATURE:
<223> OTHER INFORMATION: Podo447_Vk_CDR2_ Kabat

<400> SEQUENCE: 65
tatacatcca ctctggca                                                     18

<210> SEQ ID NO 66
<211> LENGTH: 36
<212> TYPE: DNA
<213> ORGANISM: Artificial sequence
<220> FEATURE:
<223> OTHER INFORMATION: Podo447_Vk_CDR3_ IMGT

<400> SEQUENCE: 66
gcaggcgttt atgagggtag tagtgataat agggct                                 36

<210> SEQ ID NO 67
<211> LENGTH: 36
<212> TYPE: DNA
<213> ORGANISM: Artificial sequence
<220> FEATURE:
<223> OTHER INFORMATION: Podo447_Vk_CDR3_ Chotia

<400> SEQUENCE: 67
gcaggcgttt atgagggtag tagtgataat agggct                                 36

<210> SEQ ID NO 68
<211> LENGTH: 36
<212> TYPE: DNA
<213> ORGANISM: Artificial sequence
<220> FEATURE:
<223> OTHER INFORMATION: Podo447_Vk_CDR3_ Kabat

<400> SEQUENCE: 68
gcaggcgttt atgagggtag tagtgataat agggct                                 36

<210> SEQ ID NO 69
<211> LENGTH: 408
```

<212> TYPE: DNA
<213> ORGANISM: Artificial sequence
<220> FEATURE:
<223> OTHER INFORMATION: humanized_podo447VH

<400> SEQUENCE: 69

| | | | | | |
|---|---|---|---|---|---|
| atggaatttg | ggttgagttg | ggtattcctg | gtcgccatat | tgaagggcgt | gcaatgcgaa | 60 |
| gtacagcttg | tagaatctgg | gggggtctc | gttcaaccgg | gtaggagttt | gagactgagc | 120 |
| tgcacggcct | ctggcttcag | cttgtctgga | taccaaatga | actgggtgcg | acaagcgccc | 180 |
| ggcaagggtt | tggaatgggt | gggttacatc | tggagtgatg | gcggaacgga | ttacactgct | 240 |
| tccgtaaagg | gccgatttac | catttccagg | gacggtagca | aaagtatcgc | gtaccttcaa | 300 |
| atgaactccc | tcaagacaga | ggatacggct | gtgtactact | gcgcgaggga | aggatattgg | 360 |
| ctcggggcat | cgacccatg | gggtcaggga | acctcagtca | ccgtcagc | | 408 |

<210> SEQ ID NO 70
<211> LENGTH: 136
<212> TYPE: PRT
<213> ORGANISM: Artificial sequence
<220> FEATURE:
<223> OTHER INFORMATION: humanized_podo447VH

<400> SEQUENCE: 70

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Thr Ala Ser Gly Phe Ser Leu
        35                  40                  45

Ser Gly Tyr Gln Met Asn Trp Val Arg Gln Ala Pro Gly Lys Gly Leu
    50                  55                  60

Glu Trp Val Gly Tyr Ile Trp Ser Asp Gly Gly Thr Asp Tyr Thr Ala
65                  70                  75                  80

Ser Val Lys Gly Arg Phe Thr Ile Ser Arg Asp Gly Ser Lys Ser Ile
                85                  90                  95

Ala Tyr Leu Gln Met Asn Ser Leu Lys Thr Glu Asp Thr Ala Val Tyr
            100                 105                 110

Tyr Cys Ala Arg Glu Gly Tyr Trp Leu Gly Ala Phe Asp Pro Trp Gly
        115                 120                 125

Gln Gly Thr Ser Val Thr Val Ser
    130                 135

<210> SEQ ID NO 71
<211> LENGTH: 1401
<212> TYPE: DNA
<213> ORGANISM: Artificial sequence
<220> FEATURE:
<223> OTHER INFORMATION: humanized_podo447VH_hIgG1C

<400> SEQUENCE: 71

| | | | | | |
|---|---|---|---|---|---|
| atggaatttg | ggttgagttg | ggtattcctg | gtcgccatat | tgaagggcgt | gcaatgcgaa | 60 |
| gtacagcttg | tagaatctgg | gggggtctc | gttcaaccgg | gtaggagttt | gagactgagc | 120 |
| tgcacggcct | ctggcttcag | cttgtctgga | taccaaatga | actgggtgcg | acaagcgccc | 180 |
| ggcaagggtt | tggaatgggt | gggttacatc | tggagtgatg | gcggaacgga | ttacactgct | 240 |
| tccgtaaagg | gccgatttac | catttccagg | gacggtagca | aaagtatcgc | gtaccttcaa | 300 |
| atgaactccc | tcaagacaga | ggatacggct | gtgtactact | gcgcgaggga | aggatattgg | 360 |

```
ctcggggcat tcgacccatg gggtcaggga acctcagtca ccgtcagcgc tagcaccaag    420
ggcccatcgg tcttcccct ggcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggatgagct gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401

<210> SEQ ID NO 72
<211> LENGTH: 466
<212> TYPE: PRT
<213> ORGANISM: Artificial sequence
<220> FEATURE:
<223> OTHER INFORMATION: humanized_podo447VH_hIgG1C

<400> SEQUENCE: 72

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Thr Ala Ser Gly Phe Ser Leu
            35                  40                  45

Ser Gly Tyr Gln Met Asn Trp Val Arg Gln Ala Pro Gly Lys Gly Leu
        50                  55                  60

Glu Trp Val Gly Tyr Ile Trp Ser Asp Gly Gly Thr Asp Tyr Thr Ala
65                  70                  75                  80

Ser Val Lys Gly Arg Phe Thr Ile Ser Arg Asp Gly Ser Lys Ser Ile
                85                  90                  95

Ala Tyr Leu Gln Met Asn Ser Leu Lys Thr Glu Asp Thr Ala Val Tyr
            100                 105                 110

Tyr Cys Ala Arg Glu Gly Tyr Trp Leu Gly Ala Phe Asp Pro Trp Gly
        115                 120                 125

Gln Gly Thr Ser Val Thr Val Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175
```

```
Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
        450                 455                 460

Gly Lys
465

<210> SEQ ID NO 73
<211> LENGTH: 402
<212> TYPE: DNA
<213> ORGANISM: Artificial sequence
<220> FEATURE:
<223> OTHER INFORMATION: humanized_podo447VL6

<400> SEQUENCE: 73
atggacatgc gggttccagc gcagctcttg ggactcttgc tgttgtggtt gcccggtgcc     60
aggtgtgcgg cccagcttac acagagtccc tctcctttgt cagcttcagt tggtgatagg    120
gtgactataa cctgtcagag tagtcagtcc gttcaccaca gaacgacct cgcgtggtat    180 cagcagaagc ctggcaaagc gccgaaactg ctcatttact atacgtctac gttggcaagt    240
ggtgtcccct cacggttctc aggctccggt agcgggacag attttactct cacaatcagc    300
tcccttcagc ccgaagattt cgctacatat tattgtgctg ggtatatga ggggagttct    360
```
gataatcggg catttggggg cggcacgaag gtggagatta aa                402

```
<210> SEQ ID NO 74
<211> LENGTH: 134
<212> TYPE: PRT
<213> ORGANISM: Artificial sequence
<220> FEATURE:
<223> OTHER INFORMATION: humanized_podo447VL6
```

<400> SEQUENCE: 74

Met Asp Met Arg Val Pro Ala Gln Leu Leu Gly Leu Leu Leu Trp
1               5                   10                  15

Leu Pro Gly Ala Arg Cys Ala Ala Gln Leu Thr Gln Ser Pro Ser
            20                  25                  30

Leu Ser Ala Ser Val Gly Asp Arg Val Thr Ile Thr Cys Gln Ser Ser
        35                  40                  45

Gln Ser Val His His Lys Asn Asp Leu Ala Trp Tyr Gln Gln Lys Pro
    50                  55                  60

Gly Lys Ala Pro Lys Leu Leu Ile Tyr Tyr Thr Ser Thr Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Ala Gly Val Tyr Glu Gly Ser Ser Asp Asn Arg Ala Phe Gly Gly Gly
        115                 120                 125

Thr Lys Val Glu Ile Lys
    130

```
<210> SEQ ID NO 75
<211> LENGTH: 723
<212> TYPE: DNA
<213> ORGANISM: Artificial sequence
<220> FEATURE:
<223> OTHER INFORMATION: humanized_podo447VL6_hIgkC
```

<400> SEQUENCE: 75
atggacatgc gggttccagc gcagctcttg ggactcttgc tgttgtggtt gcccggtgcc    60
aggtgtgcgg cccagcttac acagagtccc tctcctttgt cagcttcagt tggtgatagg   120
gtgactataa cctgtcagag tagtcagtcc gttcaccaca gaacgacct cgcgtggtat    180
cagcagaagc ctggcaaagc gccgaaactg ctcatttact atacgtctac gttggcaagt   240
ggtgtcccct cacggttctc aggctccggt agcgggacag attttactct cacaatcagc   300
tcccttcagc ccgaagattt cgctacatat tattgtgctg ggtatatga ggggagttct    360
gataatcggg catttggggg cggcacgaag gtggagatta acgtacggt ggctgcacca    420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                 723

```
<210> SEQ ID NO 76
<211> LENGTH: 241
```

<212> TYPE: PRT
<213> ORGANISM: Artificial sequence
<220> FEATURE:
<223> OTHER INFORMATION: humanized_podo447VL6_hIgkC

<400> SEQUENCE: 76

```
Met Asp Met Arg Val Pro Ala Gln Leu Leu Gly Leu Leu Leu Leu Trp
1               5                   10                  15
Leu Pro Gly Ala Arg Cys Ala Ala Gln Leu Thr Gln Ser Pro Ser Pro
            20                  25                  30
Leu Ser Ala Ser Val Gly Asp Arg Val Thr Ile Thr Cys Gln Ser Ser
        35                  40                  45
Gln Ser Val His His Lys Asn Asp Leu Ala Trp Tyr Gln Gln Lys Pro
    50                  55                  60
Gly Lys Ala Pro Lys Leu Leu Ile Tyr Tyr Thr Ser Thr Leu Ala Ser
65                  70                  75                  80
Gly Val Pro Ser Arg Phe Ser Gly Ser Gly Ser Gly Thr Asp Phe Thr
                85                  90                  95
Leu Thr Ile Ser Ser Leu Gln Pro Glu Asp Phe Ala Thr Tyr Tyr Cys
            100                 105                 110
Ala Gly Val Tyr Glu Gly Ser Ser Asp Asn Arg Ala Phe Gly Gly Gly
        115                 120                 125
Thr Lys Val Glu Ile Lys Arg Thr Val Ala Ala Pro Ser Val Phe Ile
130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
Gln Asp Ser Lys Asp Ser Thr Tyr Ser Leu Ser Ser Thr Leu Thr Leu
        195                 200                 205
Ser Lys Ala Asp Tyr Glu Lys His Lys Val Tyr Ala Cys Glu Val Thr
    210                 215                 220
His Gln Gly Leu Ser Ser Pro Val Thr Lys Ser Phe Asn Arg Gly Glu
225                 230                 235                 240
Cys
```

<210> SEQ ID NO 77
<211> LENGTH: 789
<212> TYPE: DNA
<213> ORGANISM: Artificial sequence
<220> FEATURE:
<223> OTHER INFORMATION: humanized_scFv_podo447VH_GGGGS_VL6

<400> SEQUENCE: 77

```
atggaatttg ggttgagttg ggtattcctg gtcgccatat tgaagggcgt gcaatgcgaa      60
gtacagcttg tagaatctgg gggggtctc gttcaaccgg gtaggagttt gagactgagc     120
tgcacggcct ctggcttcag cttgtctgga taccaaatga actgggtgcg acaagcgccc    180
ggcaagggtt tggaatgggt gggttacatc tggagtgatg gcggaacgga ttacactgct    240
tccgtaaagg ggcgatttac catttccagg gacggtagca aaagtatcgc gtaccttcaa    300
atgaactccc tcaagacaga ggatacggct gtgtactact gcgcgaggga aggatattgg    360
ctcgggggcat tcgacccatg gggtcaggga acctcagtca ccgtcagcgg gggaggtggg    420
tccggcgggg gcggcagtgg aggcggcggg tctgcggccc agcttacaca gagtccctct    480
```

```
cctttgtcag cttcagttgg tgataggtg actataacct gtcagagtag tcagtccgtt      540
caccacaaga acgacctcgc gtggtatcag cagaagcctg gcaaagcgcc gaaactgctc      600
atttactata cgtctacgtt ggcaagtggt gtcccctcac ggttctcagg ctccggtagc      660
gggacagatt ttactctcac aatcagctcc cttcagcccg aagatttcgc tacatattat      720
tgtgctgggg tatatgaggg gagttctgat aatcgggcat tggggggcgg cacgaaggtg      780
gagattaaa                                                              789
```

```
<210> SEQ ID NO 78
<211> LENGTH: 263
<212> TYPE: PRT
<213> ORGANISM: Artificial sequence
<220> FEATURE:
<223> OTHER INFORMATION: humanized_scFv_podo447VH_GGGGS_VL6

<400> SEQUENCE: 78

Met Glu Phe Gly Leu Ser Trp Val Phe Leu Val Ala Ile Leu Lys Gly
 1               5                  10                  15

Val Gln Cys Glu Val Gln Leu Val Glu Ser Gly Gly Gly Leu Val Gln
            20                  25                  30

Pro Gly Arg Ser Leu Arg Leu Ser Cys Thr Ala Ser Gly Phe Ser Leu
        35                  40                  45

Ser Gly Tyr Gln Met Asn Trp Val Arg Gln Ala Pro Gly Lys Gly Leu
    50                  55                  60

Glu Trp Val Gly Tyr Ile Trp Ser Asp Gly Thr Asp Tyr Thr Ala
65                  70                  75                  80

Ser Val Lys Gly Arg Phe Thr Ile Ser Arg Asp Gly Ser Lys Ser Ile
                85                  90                  95

Ala Tyr Leu Gln Met Asn Ser Leu Lys Thr Glu Asp Thr Ala Val Tyr
            100                 105                 110

Tyr Cys Ala Arg Glu Gly Tyr Trp Leu Gly Ala Phe Asp Pro Trp Gly
        115                 120                 125

Gln Gly Thr Ser Val Thr Val Ser Gly Gly Gly Gly Ser Gly Gly Gly
    130                 135                 140

Gly Ser Gly Gly Gly Gly Ser Ala Ala Gln Leu Thr Gln Ser Pro Ser
145                 150                 155                 160

Pro Leu Ser Ala Ser Val Gly Asp Arg Val Thr Ile Thr Cys Gln Ser
                165                 170                 175

Ser Gln Ser Val His His Lys Asn Asp Leu Ala Trp Tyr Gln Gln Lys
            180                 185                 190

Pro Gly Lys Ala Pro Lys Leu Leu Ile Tyr Tyr Thr Ser Thr Leu Ala
        195                 200                 205

Ser Gly Val Pro Ser Arg Phe Ser Gly Ser Gly Ser Gly Thr Asp Phe
    210                 215                 220

Thr Leu Thr Ile Ser Ser Leu Gln Pro Glu Asp Phe Ala Thr Tyr Tyr
225                 230                 235                 240

Cys Ala Gly Val Tyr Glu Gly Ser Ser Asp Asn Arg Ala Phe Gly Gly
                245                 250                 255

Gly Thr Lys Val Glu Ile Lys
            260

<210> SEQ ID NO 79
<211> LENGTH: 1599
<212> TYPE: DNA
<213> ORGANISM: Artificial sequence
```

<220> FEATURE:
<223> OTHER INFORMATION: humanized_scFv_podo447VH_GGGGS_VL6_CAR

<400> SEQUENCE: 79

| | | | | | |
|---|---|---|---|---|---|
| atggaatttg | ggttgagttg | ggtattcctg | gtcgccatat | tgaagggcgt | gcaatgcgaa | 60 |
| gtacagcttg | tagaatctgg | gggggtctc | gttcaaccgg | gtaggagttt | gagactgagc | 120 |
| tgcacggcct | ctggcttcag | cttgtctgga | taccaaatga | actgggtgcg | acaagcgccc | 180 |
| ggcaaggggtt | tggaatgggt | gggttacatc | tggagtgatg | gcggaacgga | ttacactgct | 240 |
| tccgtaaagg | ggcgatttac | catttccagg | gacggtagca | aaagtatcgc | gtaccttcaa | 300 |
| atgaactccc | tcaagacaga | ggatacggct | gtgtactact | gcgcgaggga | aggatattgg | 360 |
| ctcggggcat | tcgacccatg | gggtcaggga | acctcagtca | ccgtcagcgg | gggaggtggg | 420 |
| tccggcgggg | gcggcagtgg | aggcggcggg | tctgcggccc | agcttacaca | gagtccctct | 480 |
| cctttgtcag | cttcagttgg | tgatagggtg | actataacct | gtcagagtag | tcagtccgtt | 540 |
| caccacaaga | acgacctcgc | gtggtatcag | cagaagcctg | gcaaagcgcc | gaaactgctc | 600 |
| atttactata | cgtctacgtt | ggcaagtggt | gtcccctcac | ggttctcagg | ctccggtagc | 660 |
| gggacagatt | ttactctcac | aatcagctcc | cttcagcccg | aagatttcgc | tacatattat | 720 |
| tgtgctgggg | tatatgaggg | gagttctgat | aatcgggcat | ttgggggcgg | cacgaaggtg | 780 |
| gagattaaag | agcagaagct | gatcagcgag | gaggacctga | accggatccg | tggggtcacc | 840 |
| gtctcttcag | cgctgagcaa | ctccatcatg | tacttcagcc | acttcgtgcc | ggtcttcctg | 900 |
| ccagcgaagc | ccaccacgac | gccagcgccg | cgaccaccaa | caccggcgcc | caccatcgcg | 960 |
| tcgcagcccc | tgtccctgcg | cccagaggcg | tgccggccag | cggcgggggg | cgcagtgcac | 1020 |
| acgagggggc | tggacccctt | tgggttttgg | gtgctggtgg | tggttggtgg | agtcctggct | 1080 |
| tgctatagct | tgctagtaac | agtggccttt | attattttct | gggtgaggag | taagaggagc | 1140 |
| aggctcctgc | acagtgacta | catgaacatg | actccccgcc | gccccgggcc | cacccgcaag | 1200 |
| cattaccagc | cctatgcccc | accacgcgac | ttcgcagcct | atcgctccct | cgagagagtg | 1260 |
| agagtgaagt | tcagcaggag | cgcagacgcc | cccgcgtacc | agcagggcca | gaaccagctc | 1320 |
| tataacgagc | tcaatctagg | acgaagagag | gagtacgatg | ttttggacaa | gagacgtggc | 1380 |
| cgggaccctg | agatgggggg | aaagccgaga | aggaagaacc | ctcaggaagg | cctgtacaat | 1440 |
| gaactgcaga | aagataagat | ggcggaggcc | tacagtgaga | ttgggatgaa | aggcgagcgc | 1500 |
| cggaggggca | aggggcacga | tggcctttac | cagggtctca | gtacagccac | caaggacacc | 1560 |
| tacgacgccc | ttcacatgca | ggccctgccc | cctcgctaa | | | 1599 |

<210> SEQ ID NO 80
<211> LENGTH: 532
<212> TYPE: PRT
<213> ORGANISM: Artificial sequence
<220> FEATURE:
<223> OTHER INFORMATION: humanized_scFv_podo447VH_GGGGS_VL6_CAR

<400> SEQUENCE: 80

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Thr Ala Ser Gly Phe Ser Leu
        35                  40                  45

Ser Gly Tyr Gln Met Asn Trp Val Arg Gln Ala Pro Gly Lys Gly Leu

```
            50                  55                  60
Glu Trp Val Gly Tyr Ile Trp Ser Asp Gly Thr Asp Tyr Thr Ala
 65                  70                  75                  80

Ser Val Lys Gly Arg Phe Thr Ile Ser Arg Asp Gly Ser Lys Ser Ile
                 85                  90                  95

Ala Tyr Leu Gln Met Asn Ser Leu Lys Thr Glu Asp Thr Ala Val Tyr
                100                 105                 110

Tyr Cys Ala Arg Glu Gly Tyr Trp Leu Gly Ala Phe Asp Pro Trp Gly
                115                 120                 125

Gln Gly Thr Ser Val Thr Val Ser Gly Gly Gly Ser Gly Gly Gly
        130                 135                 140

Gly Ser Gly Gly Gly Ser Ala Ala Gln Leu Thr Gln Ser Pro Ser
145                 150                 155                 160

Pro Leu Ser Ala Ser Val Gly Asp Arg Val Thr Ile Thr Cys Gln Ser
                165                 170                 175

Ser Gln Ser Val His His Lys Asn Asp Leu Ala Trp Tyr Gln Gln Lys
            180                 185                 190

Pro Gly Lys Ala Pro Lys Leu Leu Ile Tyr Tyr Thr Ser Thr Leu Ala
            195                 200                 205

Ser Gly Val Pro Ser Arg Phe Ser Gly Ser Gly Ser Gly Thr Asp Phe
210                 215                 220

Thr Leu Thr Ile Ser Ser Leu Gln Pro Glu Asp Phe Ala Thr Tyr Tyr
225                 230                 235                 240

Cys Ala Gly Val Tyr Glu Gly Ser Ser Asp Asn Arg Ala Phe Gly Gly
                245                 250                 255

Gly Thr Lys Val Glu Ile Lys Glu Gln Lys Leu Ile Ser Glu Glu Asp
                260                 265                 270

Leu Asn Arg Ile Arg Gly Val Thr Val Ser Ser Ala Leu Ser Asn Ser
            275                 280                 285

Ile Met Tyr Phe Ser His Phe Val Pro Val Phe Leu Pro Ala Lys Pro
            290                 295                 300

Thr Thr Thr Pro Ala Pro Arg Pro Pro Thr Pro Ala Pro Thr Ile Ala
305                 310                 315                 320

Ser Gln Pro Leu Ser Leu Arg Pro Glu Ala Cys Arg Pro Ala Ala Gly
                325                 330                 335

Gly Ala Val His Thr Arg Gly Leu Asp Pro Phe Gly Phe Trp Val Leu
                340                 345                 350

Val Val Val Gly Gly Val Leu Ala Cys Tyr Ser Leu Leu Val Thr Val
            355                 360                 365

Ala Phe Ile Ile Phe Trp Val Arg Ser Lys Arg Ser Arg Leu Leu His
370                 375                 380

Ser Asp Tyr Met Asn Met Thr Pro Arg Arg Pro Gly Pro Thr Arg Lys
385                 390                 395                 400

His Tyr Gln Pro Tyr Ala Pro Pro Arg Asp Phe Ala Ala Tyr Arg Ser
                405                 410                 415

Leu Glu Arg Val Arg Val Lys Phe Ser Arg Ser Ala Asp Ala Pro Ala
                420                 425                 430

Tyr Gln Gln Gly Gln Asn Gln Leu Tyr Asn Glu Leu Asn Leu Gly Arg
            435                 440                 445

Arg Glu Glu Tyr Asp Val Leu Asp Lys Arg Arg Gly Arg Asp Pro Glu
            450                 455                 460

Met Gly Gly Lys Pro Arg Arg Lys Asn Pro Gln Glu Gly Leu Tyr Asn
465                 470                 475                 480
```

Glu Leu Gln Lys Asp Lys Met Ala Glu Ala Tyr Ser Glu Ile Gly Met
            485                 490                 495

Lys Gly Glu Arg Arg Gly Lys Gly His Asp Gly Leu Tyr Gln Gly
        500                 505                 510

Leu Ser Thr Ala Thr Lys Asp Thr Tyr Asp Ala Leu His Met Gln Ala
        515                 520                 525

Leu Pro Pro Arg
    530

<210> SEQ ID NO 81
<211> LENGTH: 798
<212> TYPE: DNA
<213> ORGANISM: Artificial sequence
<220> FEATURE:
<223> OTHER INFORMATION: humanized_scFv_podo447VL6_GGGGS_VH

<400> SEQUENCE: 81

| | | | | | |
|---|---|---|---|---|---|
| atggacatgc | gggttccagc | gcagctcttg | ggactcttgc | tgttgtggtt | gcccggtgcc | 60 |
| aggtgtgcgg | cccagcttac | acagagtccc | tctcctttgt | cagcttcagt | tggtgatagg | 120 |
| gtgactataa | cctgtcagag | tagtcagtcc | gttcaccaca | agaacgacct | cgcgtggtat | 180 |
| cagcagaagc | ctggcaaagc | gccgaaactg | ctcatttact | atacgtctac | gttggcaagt | 240 |
| ggtgtcccct | cacggttctc | aggctccggt | agcgggacag | attttactct | cacaatcagc | 300 |
| tcccttcagc | ccgaagattt | cgctacatat | tattgtgctg | ggtatatga | ggggagttct | 360 |
| gataatcggg | catttggggg | cggcacgaag | gtggagatta | aggggggagg | tgggtccggc | 420 |
| gggggcggca | gtggaggcgg | cgggtctgaa | gtacagcttg | tagaatctgg | ggggggtctc | 480 |
| gttcaaccgg | gtaggagttt | gagactgagc | tgcacggcct | ctggcttcag | cttgtctgga | 540 |
| taccaaatga | actgggtgcg | acaagcgccc | ggcaagggtt | tggaatgggt | gggttacatc | 600 |
| tggagtgatg | gcggaacgga | ttacactgct | tccgtaaagg | ggcgatttac | catttccagg | 660 |
| gacggtagca | aaagtatcgc | gtaccttcaa | atgaactccc | tcaagacaga | ggatacggct | 720 |
| gtgtactact | gcgcgaggga | aggatattgg | ctcggggcat | cgacccatg | gggtcaggga | 780 |
| acctcagtca | ccgtcagc | | | | | 798 |

<210> SEQ ID NO 82
<211> LENGTH: 266
<212> TYPE: PRT
<213> ORGANISM: Artificial sequence
<220> FEATURE:
<223> OTHER INFORMATION: humanized_scFv_podo447VL6_GGGGS_VH

<400> SEQUENCE: 82

Met Asp Met Arg Val Pro Ala Gln Leu Leu Gly Leu Leu Leu Leu Trp
1               5                   10                  15

Leu Pro Gly Ala Arg Cys Ala Ala Gln Leu Thr Gln Ser Pro Ser Pro
            20                  25                  30

Leu Ser Ala Ser Val Gly Asp Arg Val Thr Ile Thr Cys Gln Ser Ser
        35                  40                  45

Gln Ser Val His His Lys Asn Asp Leu Ala Trp Tyr Gln Gln Lys Pro
    50                  55                  60

Gly Lys Ala Pro Lys Leu Leu Ile Tyr Tyr Thr Ser Thr Leu Ala Ser
65                  70                  75                  80

Gly Val Pro Ser Arg Phe Ser Gly Ser Gly Ser Gly Thr Asp Phe Thr
                85                  90                  95

```
Leu Thr Ile Ser Ser Leu Gln Pro Glu Asp Phe Ala Thr Tyr Tyr Cys
            100                 105                 110

Ala Gly Val Tyr Glu Gly Ser Ser Asp Asn Arg Ala Phe Gly Gly Gly
        115                 120                 125

Thr Lys Val Glu Ile Lys Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Arg Ser Leu Arg Leu Ser Cys Thr Ala Ser Gly Phe
                165                 170                 175

Ser Leu Ser Gly Tyr Gln Met Asn Trp Val Arg Gln Ala Pro Gly Lys
            180                 185                 190

Gly Leu Glu Trp Val Gly Tyr Ile Trp Ser Asp Gly Thr Asp Tyr
        195                 200                 205

Thr Ala Ser Val Lys Gly Arg Phe Thr Ile Ser Arg Asp Gly Ser Lys
    210                 215                 220

Ser Ile Ala Tyr Leu Gln Met Asn Ser Leu Lys Thr Glu Asp Thr Ala
225                 230                 235                 240

Val Tyr Tyr Cys Ala Arg Glu Gly Tyr Trp Leu Gly Ala Phe Asp Pro
                245                 250                 255

Trp Gly Gln Gly Thr Ser Val Thr Val Ser
            260                 265

<210> SEQ ID NO 83
<211> LENGTH: 1608
<212> TYPE: DNA
<213> ORGANISM: Artificial sequence
<220> FEATURE:
<223> OTHER INFORMATION: humanized_scFv_podo447VL6_GGGGS_VH_CAR

<400> SEQUENCE: 83
atggacatgc gggttccagc gcagctcttg gactcttgc tgttgtggtt gcccggtgcc     60
aggtgtgcgg cccagcttac acagagtccc tctcctttgt cagcttcagt tggtgatagg   120
gtgactataa cctgtcagag tagtcagtcc gttcaccaca gaacgacct cgcgtgtat    180
cagcagaagc ctggcaaagc gccgaaactg ctcattact atacgtctac gttggcaagt   240
ggtgtcccct cacggttctc aggctccggt agcgggacag attttactct cacaatcagc   300
tcccttcagc ccgaagattt cgctacatat tattgtgctg ggtatatga gggagttct    360
gataatcggg catttggggg cggcacgaag gtggagatta agggggagg tgggtccggc   420
ggggggcgga gtggaggcgg cgggtctgaa gtacagcttg tagaatctgg ggggggtctc   480
gttcaaccgg gtaggagttt gagactgagc tgcacggcct ctggcttcag cttgtctgga   540
taccaaatga actgggtgcg acaagcgccc ggcaagggtt tggaatgggt gggttacatc   600
tggagtgatg gcggaacgga ttacactgct tccgtaaagg gcgatttac catttccagg   660
gacggtagca aaagtatcgc gtaccttcaa atgaactccc tcaagacaga ggatacggct   720
gtgtactact gcgcgaggga aggatattgg ctcggggcat tcgacccatg gggtcaggga   780
acctcagtca ccgtcagcga gcagaagctg atcagcgagg aggacctgaa ccggatccgt   840
ggggtcaccg tctcttcagc gctgagcaac tccatcatgt acttcagcca cttcgtgccg   900
gtcttcctgc agcgaagcc caccacgacg ccagcgccgc gaccaccaac accggcgccc   960
accatcgcgt cgcagcccct gtccctgcgc cagaggcgc gccggccagc ggcggggggc  1020
gcagtgcaca cgagggggct ggacccctttt gggtttgggg tgctggtggt ggttggtgga  1080
```

```
gtcctggctt gctatagctt gctagtaaca gtggccttta ttattttctg ggtgaggagt    1140
aagaggagca ggctcctgca cagtgactac atgaacatga ctccccgccg ccccgggccc    1200
acccgcaagc attaccagcc ctatgcccca ccacgcgact cgcagccta tcgctccctc     1260 gagagagtga gagtgaagtt cagcaggagc cagacgcccc ccgcgtacca gcagggccag    1320
aaccagctct ataacgagct caatctagga cgaagagagg agtacgatgt tttggacaag    1380
agacgtggcc gggaccctga gatgggggga agccgagaa ggaagaaccc tcaggaaggc     1440
ctgtacaatg aactgcagaa agataagatg gcggaggcct acagtgagat tgggatgaaa    1500
ggcgagcgcc ggaggggcaa ggggcacgat ggcctttacc agggtctcag tacagccacc    1560
aaggacacct acgacgccct tcacatgcag gccctgcccc ctcgctaa                1608
```

<210> SEQ ID NO 84
<211> LENGTH: 535
<212> TYPE: PRT
<213> ORGANISM: Artificial sequence
<220> FEATURE:
<223> OTHER INFORMATION: humanized_scFv_podo447VL6_GGGGS_VH_CAR
<400> SEQUENCE: 84

```
Met Asp Met Arg Val Pro Ala Gln Leu Leu Gly Leu Leu Leu Leu Trp
1               5                   10                  15

Leu Pro Gly Ala Arg Cys Ala Ala Gln Leu Thr Gln Ser Pro Ser Pro
            20                  25                  30

Leu Ser Ala Ser Val Gly Asp Arg Val Thr Ile Thr Cys Gln Ser Ser
        35                  40                  45

Gln Ser Val His His Lys Asn Asp Leu Ala Trp Tyr Gln Gln Lys Pro
    50                  55                  60

Gly Lys Ala Pro Lys Leu Leu Ile Tyr Tyr Thr Ser Thr Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Ala Gly Val Tyr Glu Gly Ser Ser Asp Asn Arg Ala Phe Gly Gly Gly
        115                 120                 125

Thr Lys Val Glu Ile Lys Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Arg Ser Leu Arg Leu Ser Cys Thr Ala Ser Gly Phe
                165                 170                 175

Ser Leu Ser Gly Tyr Gln Met Asn Trp Val Arg Gln Ala Pro Gly Lys
            180                 185                 190

Gly Leu Glu Trp Val Gly Tyr Ile Trp Ser Asp Gly Thr Asp Tyr
        195                 200                 205

Thr Ala Ser Val Lys Gly Arg Phe Thr Ile Ser Arg Asp Gly Ser Lys
    210                 215                 220

Ser Ile Ala Tyr Leu Gln Met Asn Ser Leu Lys Thr Glu Asp Thr Ala
225                 230                 235                 240

Val Tyr Tyr Cys Ala Arg Glu Gly Tyr Trp Leu Gly Ala Phe Asp Pro
                245                 250                 255

Trp Gly Gln Gly Thr Ser Val Thr Val Ser Glu Gln Lys Leu Ile Ser
            260                 265                 270
```

-continued

```
Glu Glu Asp Leu Asn Arg Ile Arg Gly Val Thr Val Ser Ser Ala Leu
            275                 280                 285

Ser Asn Ser Ile Met Tyr Phe Ser His Phe Val Pro Val Phe Leu Pro
    290                 295                 300

Ala Lys Pro Thr Thr Thr Pro Ala Pro Arg Pro Pro Thr Pro Ala Pro
305                     310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Pro Phe Gly Phe
            340                 345                 350

Trp Val Leu Val Val Val Gly Gly Val Leu Ala Cys Tyr Ser Leu Leu
            355                 360                 365

Val Thr Val Ala Phe Ile Ile Phe Trp Val Arg Ser Lys Arg Ser Arg
    370                 375                 380

Leu Leu His Ser Asp Tyr Met Asn Met Thr Pro Arg Arg Pro Gly Pro
385                 390                 395                 400

Thr Arg Lys His Tyr Gln Pro Tyr Ala Pro Pro Arg Asp Phe Ala Ala
                405                 410                 415

Tyr Arg Ser Leu Glu Arg Val Arg Val Lys Phe Ser Arg Ser Ala Asp
            420                 425                 430

Ala Pro Ala Tyr Gln Gln Gly Gln Asn Gln Leu Tyr Asn Glu Leu Asn
            435                 440                 445

Leu Gly Arg Arg Glu Glu Tyr Asp Val Leu Asp Lys Arg Arg Gly Arg
            450                 455                 460

Asp Pro Glu Met Gly Gly Lys Pro Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Arg Gly Lys Gly His Asp Gly Leu
                500                 505                 510

Tyr Gln Gly Leu Ser Thr Ala Thr Lys Asp Thr Tyr Asp Ala Leu His
            515                 520                 525

Met Gln Ala Leu Pro Pro Arg
530                 535
```

ANTI-PODOCALYXIN ANTIBODIES AND METHODS OF USING THE SAME

REFERENCE TO RELATED APPLICATIONS

This application claims the benefit of U.S. Provisional Patent Application Ser. No. 62/236,130, filed 1 Oct. 2015, and U.S. Provisional Patent Application Ser. No. 62/244,644, filed 21 Oct. 2015, and U.S. Provisional Patent Application Ser. No. 62/291,262, filed 4 Feb. 2016, which are hereby incorporated by reference for all purposes as if fully set forth herein.

FIELD OF THE INVENTION

The present invention relates to the field of cancer, and to compositions and methods for the prevention, diagnosis and treatment of cancer.

BACKGROUND OF THE INVENTION

Podocalyxin, a sialoglycoprotein, is thought to be the major constituent of the glycocalyx of podocytes. It is a member of the CD34 family of transmembrane sialomucins (Nielsen J S, McNagny K M (2008). J of Cell Science 121 (Pt 22): 3682-3692). It coats the secondary foot processes of the podocytes. It is negatively charged and thus functions to keep adjacent foot processes separated, thereby keeping the urinary filtration barrier open. This function is further supported by knockout studies in mice, which reveal an essential role in podocyte morphogenesis (Doyonnas R. et al (2001). J Exp Med 194 (1): 13-27; Nielsen J S, McNagny K M (2009). J Am Soc Nephrol 20 (10): 1669-76). Podocalyxin is also upregulated in a number of cancers and is frequently associated with poor prognosis in numerous cancers including breast (Somasiri et al), ovarian, colorectal, bladder and renal cell carcinoma as well as glioblastoma (Nielsen J S, McNagny K M (2009). supra; Somasiri A et al. (2004). Cancer Res 64 (15): 5068-73; Huntsman et al. U.S. 20100061978A1); Binder et al., PLOS ONE, 8:10 e75945 (2013), Hsu et al., Am J Pathol 176(6):3050-61, Cipollone et al., Clin Exp Metasatasis 29(3): 239-252, Kaprio et al., BMC Cancer 14:493, Binder et al., PLoS One 8(10):e75945, Boman et al., Br J Cancer 108(11): 2321-8. In fact, overexpression of the anti-adhesin podocalyxin can be an independent predictor of breast cancer progression (Somasiri et al. Cancer Res. 2004 Aug. 1; 64(15):5068-73).

Sialylated, O-glycosylated glycoforms of podocalyxin expressed by colon carcinoma cells possess L-selectin and E-selectin binding activity, and appear to be associated with the metastasis of colon carcinoma cells (Thomas S N et al. (March 2009). Am J Physiol Cell Physiol 296 (3): C505-13; Konstantopoulos K et al. (2009). Annu Rev Biomed Eng 11: 177-202; Thomas S N et al. (2009). Biorheology 46 (3): 207-25). In addition, it has been reported that podocalyxin is a prognostic indicator of tumor metastasis (McNagny et al. U.S. Pat. No. 7,833,733), and may modulate cancer cell growth (Hunstman et al. U.S. 2010/0061978). As such, there is a need for antagonists of podocalyxin for the treatment of cancer.

SUMMARY OF THE INVENTION

In one aspect, the invention provides anti-podocalyxin antibodies, including fragments thereof, and methods of using the same, for example, for the prevention, diagnosis and treatment of cancer.

In one embodiment, anti-podocalyxin antibodies of the invention bind to the podocalyxin tumor epitope. The "podocalyxin tumor epitope", as used herein, refers to the epitope that is bound by an antibody comprising a heavy chain variable region comprising SEQ ID NO:27 and a light chain variable region comprising SEQ ID NO:29.

In one embodiment, the podocalyxin tumor epitope comprises a post-translational modification of a podocalyxin polypeptide. In one embodiment, the post-translational modification of the podocalyxin polypeptide comprises a sialylated O-glycosyl moiety. In one embodiment, the post-translational modification of the podocalyxin polypeptide comprises an O-linked glycan moiety that is linked to podocalyxin. In one embodiment, the post-translational modification of the podocalyxin polypeptide comprises a glycan moiety comprising beta-N-acetyl-galactosamine. In one embodiment, the beta-N-acetyl-galactosamine is a terminal beta-N-acetyl-galactosamine.

Accordingly, in one embodiment, an anti-podocalyxin antibody of the invention binds to a moiety that is a post-translational modification of podocalyxin. In one embodiment, an anti-podocalyxin antibody of the invention binds to a sialylated O-glycosyl moiety attached to podocalyxin. In one embodiment, an anti-podocalyxin antibody of the invention binds to an O-linked glycan moiety that is linked to podocalyxin. In one embodiment, an anti-podocalyxin antibody of the invention binds to a glycan moiety that is linked to podocalyxin, wherein the glycan moiety has at its terminus beta-N-acetyl-galactosamine.

In one embodiment, the invention provides an anti-podocalyxin antibody that competes with an antibody comprising a heavy chain variable region comprising SEQ ID NO:27 and a light chain variable region comprising SEQ ID NO:29 for binding to a podocalyxin epitope.

Anti-podocalyxin antibodies of the invention include, for example, monoclonal antibodies, antibody fragments, including Fab, Fab', F(ab')$_2$, and Fv fragments, diabodies, single domain antibodies, chimeric antibodies, humanized antibodies, single-chain antibodies and antibodies that competitively inhibit the binding of an antibody comprising a heavy chain variable region comprising SEQ ID NO:27 and a light chain variable region comprising SEQ ID NO:29 to the podocalyxin tumor epitope.

In one embodiment, an anti-podocalyxin antibody comprises a heavy chain variable region comprising an amino acid sequence selected from the group consisting of: GFSLSGYQ (SEQ ID NO:33); GFSLSGY (SEQ ID NO:34); and GYQMN (SEQ ID NO:35).

In one embodiment, an anti-podocalyxin antibody comprises a heavy chain variable region comprising an amino acid sequence selected from the group consisting of: IWSDGGT (SEQ ID NO:36); WSDGG (SEQ ID NO:37); and YIWSDGGTDYASWAKG (SEQ ID NO:38).

In one embodiment, an anti-podocalyxin antibody comprises a heavy chain variable region comprising an amino acid sequence selected from the group consisting of: AREGYWLGAFDP (SEQ ID NO:39) and EGYWLGAFDP (SEQ ID NO:40).

In one embodiment, an anti-podocalyxin antibody comprises a light chain variable region comprising an amino acid sequence selected from the group consisting of: QSVHHKND (SEQ ID NO:42) and QSVHHKNDLA (SEQ ID NO:43).

In one embodiment, an anti-podocalyxin antibody comprises a light chain variable region comprising an amino acid sequence selected from the group consisting of: YTS (SEQ ID NO:45) and YTSLAS (SEQ ID NO:46).

In one embodiment, an anti-podocalyxin antibody comprises a light chain variable region comprising the amino acid sequence AGVYEGSSDNRA (SEQ ID NO:48).

In one embodiment, an anti-podocalyxin antibody comprises a heavy chain variable region comprising a CDR1 selected from SEQ ID NOs: 33-35; a CDR2 selected from SEQ ID NOs: 36-38; and a CDR3 selected from SEQ ID NOs: 39-41.

In one embodiment, an anti-podocalyxin antibody comprises a light chain variable region comprising a CDR1 selected from SEQ ID NOs: 42-44; a CDR2 selected from SEQ ID NOs: 45 and 46; and a CDR3 set forth by SEQ ID NO:48.

In one embodiment, an anti-podocalyxin antibody comprises a heavy chain variable region comprising a CDR1 selected from SEQ ID NOs: 33-35; a CDR2 selected from SEQ ID NOs: 36-38; and a CDR3 selected from SEQ ID NOs: 39-41; and further comprises a light chain variable region comprising a CDR1 selected from SEQ ID NOs: 42-44; a CDR2 selected from SEQ ID NOs: 45 and 46; and a CDR3 set forth by SEQ ID NO: 48.

In one embodiment, an anti-podocalyxin antibody comprises a heavy chain variable region comprising a CDR1 set forth by SEQ ID NO:33, a CDR2 set forth by SEQ ID NO:36, and a CDR3 set forth by SEQ ID NO:39; and further comprises a light chain variable region comprising a CDR1 set forth by SEQ ID NO:42, a CDR2 set forth by SEQ ID NO:45, and a CDR3 set forth by SEQ ID NO:48.

In one embodiment, an anti-podocalyxin antibody comprises a heavy chain variable region comprising a CDR1 set forth by SEQ ID NO:34, a CDR2 set forth by SEQ ID NO:37, and a CDR3 set forth by SEQ ID NO:40; and further comprises a light chain variable region comprising a CDR1 set forth by SEQ ID NO:43, a CDR2 set forth by SEQ ID NO:46, and a CDR3 set forth by SEQ ID NO:48.

In one embodiment, an anti-podocalyxin antibody comprises a heavy chain variable region comprising a CDR1 set forth by SEQ ID NO:35, a CDR2 set forth by SEQ ID NO:38, and a CDR3 set forth by SEQ ID NO:41; and further comprises a light chain variable region comprising a CDR1 set forth by SEQ ID NO:43, a CDR2 set forth by SEQ ID NO:46, and a CDR3 set forth by SEQ ID NO:48.

In one embodiment, an anti-podocalyxin antibody comprises a heavy chain variable region comprising:

```
                                          (SEQ ID NO: 27)
METGLRWLLLVAVLKGVQCQSLEESGGRLVTPGTPLTLTCTASGFSLSGY

QMNWVRQAPGKGLEWIGYIWSDGGTDYASWAKGRFTISKTSSTTVDLKMT

SLTTEDTATYFCAREGYWLGAFDPWGPGTLVTVSS.
```

In one embodiment, an anti-podocalyxin antibody comprises a light chain variable region comprising:

```
                                          (SEQ ID NO: 29)
MDTRAPTQLLGLLLLWLPGATFAAVLTQTPSPVSAAVGATVSVSCQSSQS

VHHKNDLAWFQQKPGQPPKLLIYYTSTLASGVPSRFKGSGSGTQFTLTIS

DLECDDAATYYCAGVYEGSSDNRAFGGGTEVVVK.
```

In one embodiment, an anti-podocalyxin antibody comprises a heavy chain variable region comprising SEQ ID NO:27 and a light chain variable region comprising SEQ ID NO:29.

In one embodiment, an anti-podocalyxin antibody is a chimeric, humanized, or human antibody.

In one embodiment, an anti-podocalyxin antibody is a monoclonal antibody.

In one embodiment, an anti-podocalyxin antibody is an antibody fragment.

In one aspect, the invention provides a CAR modified immune cell, preferably a CAR-T or CAR-NK cell, comprising a chimeric antigen receptor capable of binding to the podocalyxin tumor epitope.

In one aspect, the invention provides a CAR modified immune cell, preferably a CAR-T or CAR-NK cell, comprising a chimeric antigen receptor, wherein the chimeric antigen receptor comprises a light chain variable region of an anti-podocalyxin antibody and a heavy chain variable region of an anti-podocalyxin antibody.

In one aspect, the invention provides a CAR modified immune cell, preferably a CAR-T or CAR-NK cell, comprising an anti-podocalyxin antibody. In one embodiment, the anti-podocalyxin antibody is an antibody fragment. In one embodiment, the anti-podocalyxin antibody is an scFv.

In one aspect, the invention provides a method of inhibiting the growth of a cell that displays the podocalyxin tumor epitope, comprising contacting the cell with an anti-podocalyxin antibody or CAR modified immune cell, preferably a CAR-T or CAR-NK cell, of the invention. In one embodiment, the anti-podocalyxin antibody is used in the form of an antibody-drug conjugate (ADC).

In one aspect, the invention provides a method of inhibiting the proliferation of a cell that displays the podocalyxin tumor epitope, comprising contacting the cell with an anti-podocalyxin antibody or CAR modified immune cell, preferably a CAR-T or CAR-NK cell, of the invention. In one embodiment, the anti-podocalyxin antibody is used in the form of an ADC.

In one aspect, the invention provides a method of inducing death of a cell that displays the podocalyxin tumor epitope, comprising contacting the cell with an anti-podocalyxin antibody or CAR modified immune cell, preferably a CAR-T or CAR-NK cell, of the invention. In one embodiment, the anti-podocalyxin antibody is used in the form of an ADC.

In one aspect, the invention provides a method of inhibiting delamination of a cell that displays the podocalyxin tumor epitope, comprising contacting the cell with an anti-podocalyxin antibody or CAR modified immune cell, preferably a CAR-T or CAR-NK cell, of the invention. In one embodiment, the anti-podocalyxin antibody is used in the form of an ADC.

In one aspect, the invention provides a method of inhibiting vascularization of a tumor comprising a cell that displays the podocalyxin tumor epitope, comprising contacting the cell with an anti-podocalyxin antibody or CAR modified immune cell, preferably a CAR-T or CAR-NK cell, of the invention. In one embodiment, the anti-podocalyxin antibody is used in the form of an ADC.

In preferred methods, the cell displaying the podocalyxin tumor epitope is a cancer cell.

In one aspect, the invention provides a method for treating a subject having cancer, comprising administering to the subject an effective amount of an anti-podoclayxin antibody or CAR modified immune cell, preferably a CAR-T or CAR-NK cell, of the invention. In one embodiment, the anti-podocalyxin antibody is used in the form of an ADC.

In one aspect, the invention provides a method of inhibiting tumor metastasis in a subject having cancer, comprising administering to the subject an effective amount of an anti-podoclayxin antibody or CAR modified immune cell, preferably a CAR-T or CAR-NK cell, of the invention. In one embodiment, the anti-podocalyxin antibody is used in the form of an ADC.

In one aspect, the invention provides a method of decreasing tumor size in a subject having cancer, comprising administering to the subject an effective amount of an anti-podocalyxin antibody or CAR modified immune cell, preferably a CAR-T or CAR-NK cell, of the invention. In one embodiment, the anti-podocalyxin antibody is used in the form of an ADC.

In one embodiment, the subject is a human subject. In one embodiment, the cancer is selected from the group consisting of breast cancer, ovarian cancer, melanoma, glioblastoma, AML, and ALL.

In one aspect, the invention provides a pharmaceutical composition, comprising an anti-podocalyxin antibody and a pharmaceutically acceptable carrier. In one aspect, the invention provides a pharmaceutical composition, comprising a CAR modified immune cell, preferably a CAR-T or CAR-NK cell, of the invention and a pharmaceutically acceptable carrier. In one embodiment, the anti-podocalyxin antibody is used in the form of an ADC.

In one aspect, the invention provides methods for making an anti-podocalyxin antibody. In one aspect, the invention provides methods for making a CAR modified immune cell disclosed herein. In one embodiment, the invention provides methods for making an ADC comprising an anti-podocalyxin antibody.

In one aspect, the invention provides a method for the preparation of a medicament for the treatment of cancer.

In one aspect, the invention provides a method of determining the presence of podocalyxin tumor epitope in a subject or in a biological sample from a subject. In one embodiment, the method comprises contacting a sample with an anti-podocalyxin antibody and determining binding of the anti-podocalyxin antibody to the sample, wherein binding of the anti-podocalyxin antibody to the sample is indicative of the presence of the podocalyxin tumor epitope in the sample.

In one aspect, the invention provides a method for diagnosing cancer in a subject, comprising detecting the presence of the podocalyxin tumor epitope in the subject or in a biological sample from the subject.

In one aspect, the invention provides a method for determining the prognosis for a subject diagnosed with cancer, comprising detecting the presence of the podocalyxin tumor epitope in a subject or in a biological sample from the subject. In one embodiment, the method involves detecting the presence of the podocalyxin tumor epitope in the subject or in a biological sample from the subject after the subject has received a therapeutic agent for the treatment of cancer.

Also provided herein are kits and methods of using the same.

BRIEF DESCRIPTION OF THE DRAWINGS

FIG. 1 shows the amino acid sequences of human podocalyxin isoforms 1 and 2—SEQ ID NOS: 31 and 32 (Accession Nos. NP 001018121.1 and NP 005388.2).

FIG. 2, Panels A and B show the nucleic acid sequence for the heavy chain variable region (SEQ ID NO: 12); the amino acid sequence for the heavy chain variable region (SEQ ID NO:27); the nucleic acid sequence for the light chain variable region (SEQ ID NO: 14); and the amino acid sequence for the light chain variable region (SEQ ID NO:29) of the anti-podocalyxin antibody anti-Podo (see Examples).

FIG. 3 is a set of tables that demonstrate the specificity of various anti-Podo antibodies against various prodocalyxin-expressing cell lines.

FIG. 4, Panels A is a graph that provide FACS profile data of anti-podocalyxin antibodies Podo447 and Podo83 in tumor and normal cell lines. Panel B is a graph showing the FACS binding of Podo 447 in THP1 cells in response to co-culture with bone marrow stroma or CoC12.

FIG. 5 is a table providing binding data for Podo83 and Podo447 antibodies.

FIG. 7 is a table that provides data relating to IHC staining from normal and malignant tissues.

FIG. 11 is a figure showing the FACS binding of PODO447 on OVCAR10 cells in response to co-culture with bone marrow stromal cells or CoC12.

FIG. 23 is a table summarizing the binding of PODO447 and PODO83 in tumor cell lines with and without knockdown of endogenous podocalyxin transcript.

DETAILED DESCRIPTION OF THE INVENTION

I. General Techniques

Figure 6:
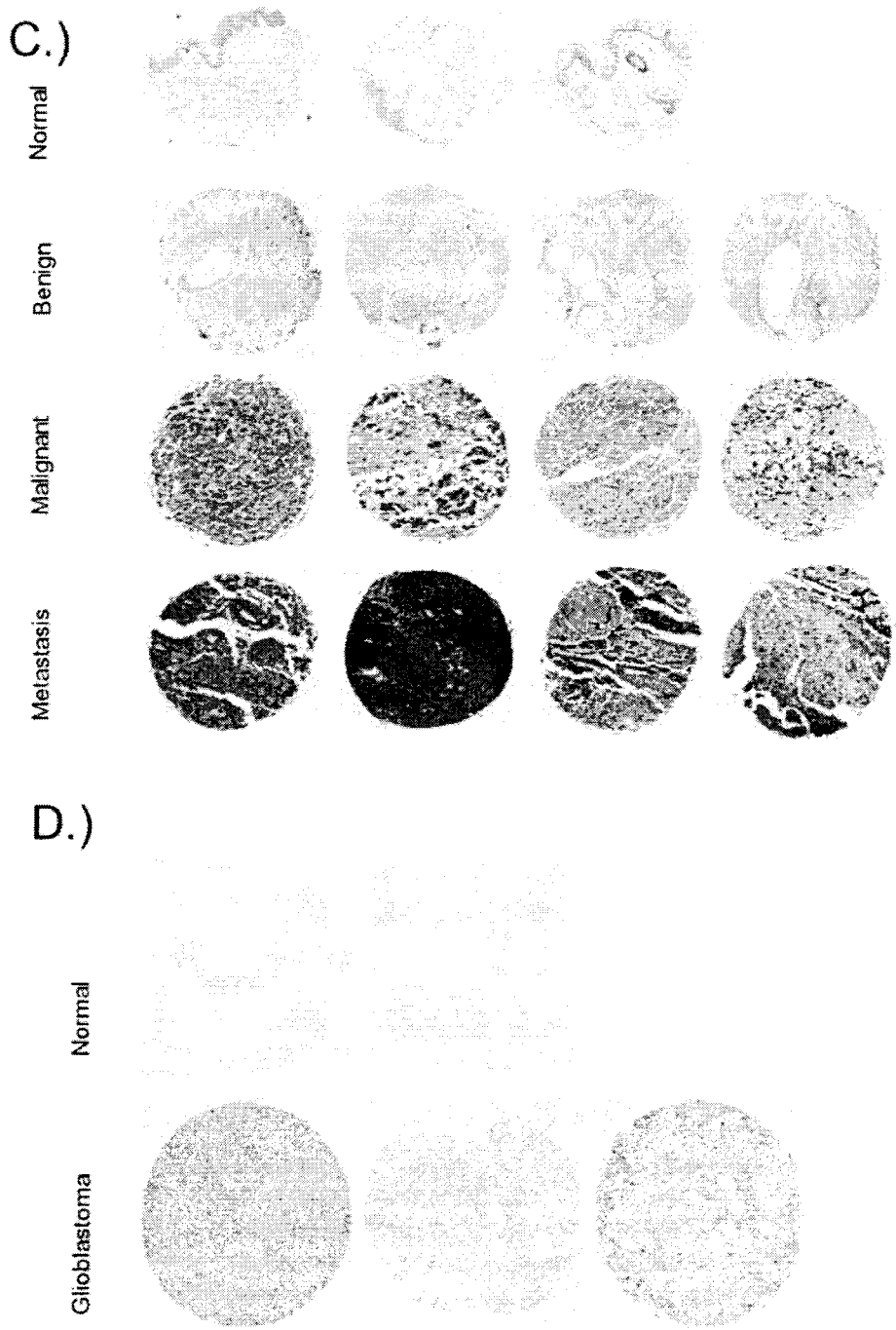
FIG. 6, Panels A-D show representative IHC staining from normal and malignant tissues.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

II. Definitions

For purposes of interpreting this specification, the following definitions will apply and whenever appropriate, terms used in the singular will also include the plural and vice versa. In the event that any definition set forth conflicts with any document incorporated herein by reference, the definition set forth below shall control.

The term "podocalyxin", as used herein, refers to any native podocalyxin from any vertebrate source, including mammals such as primates (e.g. humans, primates, and rodents (e.g., mice and rats), unless otherwise indicated. The podocalyxin molecule is also referred to as podocalyxin-like protein 1, PC, PCLP1, gp135, MEP21, and thrombomucin. Human podocalyxin is encoded by the nucleotide sequence corresponding to Accession Nos. NM_001018111.2 and NM_005397.3. Isoforms of podocalyxin include a 558 amino acid polypeptide (Accession: NP 001018121.1) and a 526 amino acid polypeptide (Accession No. NP_005388.2).

The term "podocalyxin" encompasses "full-length," unprocessed podocalyxin as well as any form of podocalyxin that results from processing in the cell. The term also encompasses naturally occurring variants of podocalyxin, e.g., splice variants, allelic variants and isoforms. The podocalyxin polypeptides described herein may be isolated from a variety of sources, such as from human tissue types or from another source, or prepared by recombinant or synthetic methods. The amino acid sequence of human podocalyxin includes sequences corresponding to SEQ ID NO: 31 or 32 (FIG. 1). A "native sequence podocalyxin polypeptide" comprises a polypeptide having the same amino acid sequence as the corresponding podocalyxin polypeptide derived from nature. Such native sequence podocalyxin polypeptides can be isolated from nature or can be produced by recombinant or synthetic means. The term "native sequence podocalyxin polypeptide" specifically encompasses naturally-occurring truncated or secreted forms of the specific podocalyxin polypeptide (e.g., an extracellular domain sequence), naturally-occurring variant forms (e.g., alternatively spliced forms) and naturally-occurring allelic variants of the polypeptide. In certain embodiments of the invention, the native sequence podocalyxin polypeptides disclosed herein are mature or full-length native sequence polypeptides comprising the full-length amino acid sequences shown in the accompanying figures. Although the podocalyxin polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the podocalyxin polypeptides.

The term "podocalyxin tumor epitope", also referred to interchangeably herein as the "podocalyxin epitope", as used herein refers to the epitope bound by an antibody comprising a heavy chain variable region comprising SEQ ID NO:27 and a light chain variable region comprising SEQ ID NO:29. One such antibody, referred to herein as the Podo447 antibody, has a binding profile illustrated herein, e.g., Example 3. The podocalyxin tumor epitope is displayed, for example, on the surface of A172 cells, a human glioblastoma cell line, as well as melanoma cells. The podocalyxin tumor epitope is found to be enriched in, or specific to, cancerous forms of certain cell types as compared to normal cells. The podocalyxin tumor epitope is found to correlate with stage of disease (for example, melanoma). Anti-podocalyxin antibodies of the invention may be identified by an ability to compete with an antibody comprising a heavy chain variable region comprising SEQ ID NO:27 and a light chain variable region comprising SEQ ID NO:29 for binding to the podocalyxin tumor epitope, for example, as discplayed on A172 cells.

In one embodiment, the podocalyxin tumor epitope comprises a post-translational modification of a podocalyxin polypeptide. In one embodiment, the post-translational modification of the podocalyxin polypeptide comprises a sialylated O-glycosyl moiety. In one embodiment, the post-translational modification of the podocalyxin polypeptide comprises an O-linked glycan moiety that is linked to podocalyxin. In one embodiment, the post-translational modification of the podocalyxin polypeptide comprises a glycan moiety comprising beta-N-acetyl-galactosamine. In one embodiment, the beta-N-acetyl-galactosamine is a terminal beta-N-acetyl-galactosamine.

Accordingly, in one embodiment, an anti-podocalyxin antibody of the invention binds to a moiety that is a post-translational modification ofpodocalyxin. In one embodiment, an anti-podocalyxin antibody of the invention binds to a sialylated O-glycosyl moiety attached to podocalyxin. In one embodiment, an anti-podocalyxin antibody of the invention binds to an O-linked glycan moiety that is linked to podocalyxin. In one embodiment, an anti-podocalyxin antibody of the invention binds to a glycan moiety that is linked to podocalyxin, wherein the glycan moiety has at its terminus beta-N-acetyl-galactosamine.

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution", or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

The term "antibody" is used in the broadest sense and specifically covers, for example, single anti-podocalyxin monoclonal antibodies (including agonist, antagonist, neutralizing antibodies, full length or intact monoclonal antibodies), anti-podocalyxin antibody compositions with polyepitopic specificity, polyclonal antibodies, multivalent antibodies, multispecific antibodies (e.g., bispecific antibodies so long as they exhibit the desired biological activity), formed from at least two intact antibodies, single chain anti-podocalyxin antibodies, and fragments of anti-podocalyxin antibodies (see below), including Fab, Fab', F(ab')2 and Fv fragments, diabodies, single domain antibodies (sd-Abs), as long as they exhibit the desired biological or immunological activity. Also included among anti-podocalyxin antibodies, and among fragments in particular, are portions of anti-podocalyxin antibodies (and combinations of portions of anti-podocalyxin antibodies, for example, scFv) that may be used as targeting arms, directed to podocalyxin tumor epitope, in chimeric antigenic receptors of CAR-T cells or CAR-NK cells. Such fragments are not necessarily proteolytic fragments but rather portions of polypeptide sequences that can confer affinity for target. The term "immunoglobulin" (Ig) is used interchangeably with antibody herein. An antibody can be, for example, human, humanized and/or affinity matured.

The terms "anti-podocalyxin antibody", "podocalyxin antibody", and "an antibody that binds to podocalyxin" are used interchangeably. Anti-podocalytxin antibodies are preferably capable of binding with sufficient affinity such that the antibody is useful as a diagnostic and/or therapeutic agent.

In one embodiment, podocalyxin antibody is used herein to specifically refer to an anti-podocalyxin monoclonal antibody that (i) comprises the heavy chain variable domain of SEQ ID NO: 27 (FIG. 2) and/or the light chain variable domain of SEQ ID NO: 29 (FIG. 2); or (ii) comprises one, two, three, four, five, or six of the CDRs shown in Table 3.

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or nonproteinaceous solutes.

The basic 4-chain antibody unit is a heterotetrameric glycoprotein composed of two identical light (L) chains and two identical heavy (H) chains. In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2.

The "variable region" or "variable domain" of an antibody refers to the amino-terminal domains of the heavy or light chain of the antibody. The variable domain of the heavy chain may be referred to as "VH" or "$V_H$" The variable domain of the light chain may be referred to as "VL" or "$V_L$". These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)).

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen. Also included among anti-podocalyxin antibody fragments are portions of anti-podocalyxin antibodies (and combinations of portions of anti-podocalyxin antibodies, for example, scFv) that may be used as targeting arms, directed to podocalyxin tumor epitope, in chimeric antigenic receptors of CAR-T cells or CAR-NK cells. Such fragments are not necessarily proeteolytic fragments but rather portions of polypeptide sequences that can confer affinity for target.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra. In one embodiment, an anti-podocalyxin antibody derived scFv is used as the targeting arm of a CAR-T cell or a CAR-NK cell disclosed herein.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32 ... 34 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H52-H56 | H47-H58 |
| H3 | H95-H102 | H95-H102 | H95-H102 | H93-H101 |

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system.

A "blocking" antibody or an "antagonist" antibody is one which inhibits or reduces biological activity of the antigen it binds. Preferred blocking antibodies or antagonist antibodies substantially or completely inhibit the biological activity of the antigen. In one embodiment, an anti-podocalyxin antibody is provided, which is an antagonist antibody.

An antibody that "binds" an antigen or epitope of interest is one that binds the antigen or epitope with sufficient affinity that is measurably different from a non-specific interaction. Specific binding can be measured, for example, by determining binding of a molecule compared to binding of a control molecule, which generally is a molecule of similar structure that does not have binding activity.

An antibody that inhibits the growth of tumor cells is one that results in measurable growth inhibition of cancer cells. In one embodiment, an anti-podoclayxin antibody is capable of inhibiting the growth of cancer cells displaying the podocalyxin tumor epitope. Preferred growth inhibitory anti-podocalyxin antibodies inhibit growth of podocalyxin-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody being tested.

Anti-podocalyxin antibodies may (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind.

The term "antagonist" is used in the broadest sense, and includes any molecule that partially or fully blocks, inhibits, or neutralizes a biological activity of antigen. Suitable antagonist molecules specifically include antagonist antibodies or antibody fragments, fragments or amino acid sequence variants of native podocalyxin polypeptides, peptides, antisense oligonucleotides, small organic molecules, etc. Methods for identifying antagonists of a podocalyxin polypeptide, may comprise contacting a podocalyxin polypeptide, with a candidate antagonist molecule and measuring a detectable change in one or more biological activities normally associated with the podocalyxin polypeptide.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), skin cancer, melanoma, lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer (e.g., pancreatic ductal adenocarcinoma), glioblastoma, cervical cancer, ovarian cancer (e.g., high grade serous ovarian carcinoma), liver cancer (e.g., hepatocellular carcinoma (HCC)), bladder cancer (e.g., urothelial bladder cancer), testicular (germ cell tumour) cancer, hepatoma, breast cancer, brain cancer (e.g., astrocytoma), colon cancer, rectal cancer, colorectal cancer, endometrial or uterine carcinoma, salivary gland carcinoma, kidney or renal cancer (e.g., renal cell carcinoma, nephroblastoma or Wilms' tumour), prostate cancer, vulval cancer, thyroid cancer, hepatic carcinoma, anal carcinoma, penile carcinoma, as well as head and neck cancer. Additional examples of cancer include, without limitation, retinoblastoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, and urinary tract carcinomas.

In a preferred embodiment, the cancer is melanoma. In another preferred embodiment, the cancer is glioblastoma. In another preferred embodiment, the cancer is acute myeloid leukemia (AML) or acute lymphoblastic leukemia (ALL). In another preferred embodiment, the cancer is ovarian cancer. In another preferred embodiment, the cancer is breast cancer.

The term "metastatic cancer" means the state of cancer where the cancer cells of a tissue of origin are transmitted from the original site to one or more sites elsewhere in the body, by the blood vessels or lymphatics, to form one or more secondary tumors in one or more organs besides the tissue of origin. A prominent example is metastatic breast cancer.

As used herein, a "podocalyxin-associated cancer" is a cancer that is associated with over-expression of a podocalyxin gene or gene product and/or is associated with display of the podocalyxin tumor epitope. Suitable control cells can be, for example, cells from an individual who is not affected with cancer or non-cancerous cells from the subject who has cancer.

The present methods include methods of treating a subject having cancer. Particularly cancer that is associated with expression of the podocalyxin tumor epitope. The present methods also include methods for modulating certain cell behaviours, particularly cancer cell behaviours, particularly cancer cells displaying the podocalyxin tumor epitope. In one embodiment, the podocalyxin tumor epitope comprises a post-translational modification of podocalyxin. In one embodiment, the podocalyxin tumor epitope comprises a sialylated O-glycosyl moiety attached to podocalyxin. In one embodiment, the podocalyxin tumor epitope comprises an O-linked glycan moiety that is linked to podocalyxin. In one embodiment, the podocalyxin tumor epitope comprises a glycan moiety that is linked to podocalyxin, wherein the glycan moiety has at its terminus beta-N-acetyl-galactosamine.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

The terms "predictive" and "prognostic" as used herein are also interchangeable. In one sense, the methods for prediction or prognostication are to allow the person practicing a predictive/prognostic method of the invention to select patients that are deemed (usually in advance of treatment, but not necessarily) more likely to respond to treatment with an anti-cancer agent, preferably an anti-podocalyxin antibody or a CAR-T cell or CAR-NK cell of the invention.

III. Compositions and Methods of the Invention

In one aspect, the invention provides anti-podocalyxin antibodies, including fragments thereof, compositions comprising the same, and methods of using the same for various purposes, including the treatment of cancer.

In one aspect, the invention provides an antibody that binds to the podocalyxin tumor epitope. In one aspect, an antibody competes for binding to, or binds substantially to, the podocalyxin tumor epitope. Optionally, the antibody is a monoclonal antibody, antibody fragment, including Fab, Fab', F(ab')$_2$, and Fv fragment, diabody, single domain antibody, chimeric antibody, humanized antibody, single-chain antibody or antibody that competitively inhibits the binding of an anti-podocalyxin epitope antibody to its respective antigenic epitope. The antibodies of the present invention may optionally be produced in CHO cells or bacterial cells or by other means. In one embodiment, an anti-podocalyxin antibody induces death of a cell to which it binds. For detection purposes, the anti-podocalyxin antibodies of the present invention may be detectably labeled, attached to a solid support, or the like.

In one aspect, a functional anti-podocalyxin antibody is provided, wherein the antibody has one or more of the following activities: (i) inhibits delamination; (ii) inhibits tumor metastasis in vivo; (iii) inhibits tumor growth in vivo; (iv) decreases tumor size in vivo; (v) inhibits tumor vascularization in vivo; (vi) exhibits cytotoxic activity on tumor cell expressing podocalyxin in vivo; or (vii) exhibits cytostatic activity on a tumor cell expressing podocalyxin in vivo.

In one aspect, an antibody that binds to podocalyxin is provided, wherein the antibody comprises a heavy chain variable region comprising:

(SEQ ID NO: 27)
METGLRWLLLVAVLKGVQCQSLEESGGRLVTPGTPLTLTCTASGFSLSGY

QMNWVRQAPGKGLEWIGYIWSDGGTDYASWAKGRFTISKTSSTTVDLKMT

SLTTEDTATYFCAREGYWLGAFDPWGPGTLVTVSS.

In one aspect, an antibody that binds to podocalyxin is provided, wherein the antibody comprises a light chain variable region comprising:

(SEQ ID NO: 29)
MDTRAPTQLLGLLLLWLPGATFAAVLTQTPSPVSAAVGATVSVSCQSSQS

VHHKNDLAWFQQKPGQPPKLLIYYTSTLASGVPSRFKGSGSGTQFTLTIS

DLECDDAATYYCAGVYEGSSDNRAFGGGTEVVVK.

In one aspect, an antibody that binds to podocalyxin is provided, wherein the antibody comprises a heavy chain variable region comprising SEQ ID NO:27 and a light chain variable region comprising SEQ ID NO:29.

In one aspect, an antibody that binds to podocalyxin is provided, wherein the antibody comprises a heavy chain variable region comprising a CDR1 comprising an amino acid sequence selected from the group consisting of: GFSLSGYQ (SEQ ID NO:33); GFSLSGY (SEQ ID NO:34); and GYQMN (SEQ ID NO:35).

In one aspect, an antibody that binds to podocalyxin is provided, wherein the antibody comprises a heavy chain variable region comprising a CDR2 comprising an amino acid sequence selected from the group consisting of: IWSDGGT (SEQ ID NO:36); WSDGG (SEQ ID NO:37); and YIWSDGGTDYASWAKG (SEQ ID NO:38).

In one aspect, an antibody that binds to podocalyxin is provided, wherein the antibody comprises a heavy chain variable region comprising a CDR3 comprising an amino acid sequence selected from the group consisting of: AREGYWLGAFDP (SEQ ID NO:39); EGYWLGAFDP (SEQ ID NO:40); and EGYWLGAFDP (SEQ ID NO:41).

In one aspect, an antibody that binds to podocalyxin is provided, wherein the antibody comprises a light chain variable region comprising a CDR1 comprising an amino acid sequence selected from the group consisting of: QSVHHKND (SEQ ID NO:42); QSSQSVHHKNDLA (SEQ ID NO:43); and QSSQSVHHKNDLA (SEQ ID NO:44).

In one aspect, an antibody that binds to podocalyxin is provided, wherein the antibody comprises a light chain variable region comprising a CDR2 comprising an amino acid sequence selected from the group consisting of: YTS (SEQ ID NO:45); YTSLAS (SEQ ID NO:46); and YTSLAS (SEQ ID NO:47).

In one aspect, an antibody that binds to podocalyxin is provided, wherein the antibody comprises a light chain variable region comprising a CDR3 comprising an amino acid sequence selected from the group consisting of: AGVYEGSSDNRA (SEQ ID NO:48); AGVYEGSSDNRA (SEQ ID NO:49); and AGVYEGSSDNRA (SEQ ID NO:50).

In one aspect, an antibody that binds to podocalyxin is provided, wherein the antibody comprises a heavy chain variable region comprising a CDR1 selected from SEQ ID NOs: 33-35; a CDR2 selected from SEQ ID NOs: 36-38; and a CDR3 selected from SEQ ID NOs: 39-41.

In one aspect, an antibody that binds to podocalyxin is provided, wherein the antibody comprises a light chain variable region comprising a CDR1 selected from SEQ ID NOs: 42-44; a CDR2 selected from SEQ ID NOs: 45-47; and a CDR3 selected from SEQ ID NOs: 48-50.

In one aspect, an antibody that binds to podocalyxin is provided, wherein the antibody comprises a heavy chain variable region comprising a CDR1 selected from SEQ ID NOs: 33-35; a CDR2 selected from SEQ ID NOs: 36-38; and a CDR3 selected from SEQ ID NOs: 39-41; and further comprises a light chain variable region comprising a CDR1 selected from SEQ ID NOs: 42-44; a CDR2 selected from SEQ ID NOs: 45-47; and a CDR3 selected from SEQ ID NOs: 48-50.

In one embodiment, an antibody of the invention comprising these sequences (in combination as described herein) is a humanized or human antibody.

In one aspect, the invention includes an anti-podocalyxin antibody comprising (i) a heavy chain variable domain comprising SEQ ID NO: 27; and/or (ii) a light chain variable domain comprising SEQ ID NO: 29.

In some embodiments, these antibodies further comprise a human subgroup III heavy chain framework consensus sequence. In one embodiments of these antibodies, these antibodies further comprise a human KI light chain framework consensus sequence.

In one aspect, an anti-podocalyxin antibody competes for binding to a tumor displayed podocalyxin (for example, as displayed on A172 cells) with an anti-podocalyxin antibody comprising a heavy chain variable region comprising SEQ ID NO: 69 and a light chain variable region comprising SEQ ID NO 74.

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-mouse antibody response (HAMA) at a substantially reduced level compared to an antibody comprising the sequence of SEQ ID NO: 27 and 29 in a host subject. In another example, the invention provides a humanized antibody that elicits and/or is expected to elicit minimal or no human anti-mouse antibody response (HAMA). In one example, an antibody of the invention elicits anti-mouse antibody response that is at or less than a clinically-acceptable level.

A humanized antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position.

As is known in the art, and as described in greater detail herein, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions. In one embodiment, these hypervariable positions include one or more positions 26-30, 33-35B, 47-49, 57-65, 93, 94 and 101-102 in a heavy chain variable domain. In one embodiment, these hybrid hypervariable positions include one or more of positions 24-29, 35-36, 46-49, 56 and 97 in a light chain variable domain. In one embodiment, an antibody of the invention comprises a human variant human subgroup consensus framework sequence modified at one or more hybrid hypervariable positions.

An antibody of the invention can comprise any suitable human or human consensus light chain framework sequences, provided the antibody exhibits the desired biological characteristics (e.g., a desired binding affinity). In one embodiment, an antibody of the invention comprises at least a portion (or all) of the framework sequence of human κ light chain. In one embodiment, an antibody of the invention comprises at least a portion (or all) of human κ subgroup I framework consensus sequence.

In some aspects, the invention provides vectors comprising DNA encoding any of the herein described anti-podocalyxin antibodies or portions thereof. Host cells comprising any such vector are also provided. By way of example, the host cells may be CHO cells, E. coli cells, or yeast cells. A process for producing any of the herein described polypeptides is further provided and comprises culturing host cells under conditions suitable for expression of the desired polypeptide and recovering the desired polypeptide from the cell culture.

The antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, inmmunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372, 907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Crosslinking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

In one aspect, an anti-podocalyxin antibody of the invention binds to the same epitope on podocalyxin bound by another podocalyxin antibody. In another embodiment, a podocalyxin antibody of the invention binds to the same epitope on podocalyxin bound by a fragment (e.g., a Fab fragment) of a monoclonal antibody comprising the variable domains of SEQ ID NO: 27 and SEQ ID NO: 29 (FIG. 2)

or a chimeric antibody comprising the variable domain of the monoclonal antibody comprising the sequences of SEQ ID NO: 27 and SEQ ID NO: 29 (FIG. 2) and constant domains from IgG1.

In one aspect, the invention provides compositions comprising one or more antibodies of the invention and a carrier. In one embodiment, the carrier is pharmaceutically acceptable.

In one aspect, the invention provides nucleic acids encoding a podocalyxin antibody (or portion(s) thereof) of the invention.

In one aspect, the invention provides vectors comprising a nucleic acid of the invention. In one embodiment, the vectors comprise SEQ ID NO: 12 and/or SEQ ID NO:14 (FIG. 2).

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, E. coli. In one embodiment, a host cell is a eukaryotic cell, for example a mammalian cell such as Chinese Hamster Ovary (CHO) cell.

In one aspect, the invention provides methods for making an antibody of the invention. For example, the invention provides a method of making a podocalyxin antibody (which, as defined herein includes full length and fragments thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more podocalyxin antibodies or CAR modified immune cell, preferably a CAR-T or CAR-NK cell, of the invention. In one embodiment, the composition comprises a nucleic acid of the invention. In one embodiment, a composition comprising an antibody or CAR modified immune cell, preferably a CAR-T or CAR-NK cell, further comprises a carrier, which in some embodiments is pharmaceutically acceptable. In one embodiment, an article of manufacture of the invention further comprises instructions for administering the composition (e.g., the antibody) to a subject.

In one aspect, the invention provides a kit comprising a first container comprising a composition comprising one or more podocalyxin antibodies or CAR modified immune cells, preferably a CAR-T or CAR-NK cells, of the invention; and a second container comprising a buffer. In one embodiment, the buffer is pharmaceutically acceptable. In one embodiment, a kit further comprises instructions for administering the composition (e.g., the antibody) to a subject.

In one aspect, the invention provides use of a podocalyxin antibody or CAR modified immune cells, preferably a CAR-T or CAR-NK cells, of the invention in the preparation of a medicament for the therapeutic and/or prophylactic treatment of a disease, such as a cancer, a tumor and/or a cell proliferative disorder.

In one aspect, the invention provides use of a nucleic acid of the invention in the preparation of a medicament for the therapeutic and/or prophylactic treatment of a disease, such as a cancer, a tumor and/or a cell proliferative disorder.

In one aspect, the invention provides use of an expression vector of the invention in the preparation of a medicament for the therapeutic and/or prophylactic treatment of a disease, such as a cancer, a tumor and/or a cell proliferative disorder.

In one aspect, the invention provides use of a host cell of the invention in the preparation of a medicament for the therapeutic and/or prophylactic treatment of a disease, such as a cancer, a tumor and/or a cell proliferative disorder.

In one aspect, the invention provides use of an article of manufacture of the invention in the preparation of a medicament for the therapeutic and/or prophylactic treatment of a disease, such as a cancer, a tumor and/or a cell proliferative disorder.

In one aspect, the invention provides use of a kit of the invention in the preparation of a medicament for the therapeutic and/or prophylactic treatment of a disease, such as a cancer, a tumor and/or a cell proliferative disorder.

In one aspect, the invention provides a method of inhibiting the growth of a cell that expresses podocalyxin, said method comprising contacting said cell with an antibody or CAR modified immune cells, preferably a CAR-T or CAR-NK cells of the invention thereby causing an inhibition of growth of said cell.

In one aspect, the invention provides a method of therapeutically treating a mammal having a cancerous tumor comprising a cell that expresses podocalyxin, said method comprising administering to said mammal a therapeutically effective amount of an antibody or CAR modified immune cells, preferably a CAR-T or CAR-NK cells of the invention, thereby effectively treating said mammal.

In one aspect, the invention provides use of a podocalyxin antibody of the invention in the preparation of a medicament for (i) inhibiting the vascularization of a tumor comprising cells expressing podocalyxin; (ii) inhibiting the delamination of cells expressing podocalyxin; (iii) inhibiting tumor metastasis in a patient having cancer; (iv) decreasing tumor size in a patient having cancer.

In one aspect, the invention provides a method for treating or preventing a cell proliferative disorder associated with increased expression of podocalyxin, said method comprising administering to a subject in need of such treatment an effective amount of an antibody or CAR modified immune cells, preferably a CAR-T or CAR-NK cells of the invention, thereby effectively treating or preventing said cell proliferative disorder. In one embodiment, said cell proliferative disorder is cancer.

In one aspect, the invention provides a method of determining the presence of podocalyxin in a sample suspected of containing podocalyxin, said method comprising exposing said sample to an antibody of the invention, and determining binding of said antibody to podocalyxin in said sample wherein binding of said antibody to podocalyxin in said sample is indicative of the presence of said protein in said sample. In one embodiment, the sample is a biological sample. In a further embodiment, the biological sample comprises breast cancer cells. In one embodiment, the biological sample is from a mammal experiencing or suspected of experiencing a breast cancer disorder and/or a breast cancer cell proliferative disorder. In a further embodiment, the biological sample comprises ovarian cancer cells. In one embodiment, the biological sample is from a mammal experiencing or suspected of experiencing an ovarian cancer disorder and/or an ovarian cancer cell proliferative disorder. In a further embodiment, the biological sample comprises melanoma cells. In one embodiment, the biological sample is from a mammal experiencing or suspected of experiencing a melanoma disorder and/or a melanoma cell proliferative disorder. In a further embodiment, the biological sample comprises glioblastoma cells. In one embodiment, the biological sample is from a mammal experiencing or suspected of experiencing a glioblastoma disorder and/or a glioblastoma cell proliferative disorder.

In one aspect, a method of diagnosing a cell proliferative disorder associated with (i) an increase in cells, such as, e.g., breast cancer cells, ovarian cancer cells, melanoma cells, or glioblastoma cells, expressing podocalyxin, or (ii) an increase in podocalyxin expression within a tumor, is provided. In one embodiment, the method comprises contacting a test cell in a biological sample with any of the above antibodies; determining the level of antibody bound to test cells in the sample by detecting binding of the antibody to podocalyxin; and comparing the level of antibody bound to cells in a control sample, wherein the level of antibody bound is normalized to the number of podocalyxin-expressing cells in the test and control samples, and wherein a higher level of antibody bound in the test sample as compared to the control sample indicates the presence of a cell proliferative disorder associated with cells expressing podocalyxin.

In one aspect, the invention provides a method of inhibiting the vascularization of a tumor comprising cells expressing podocalyxin, comprising administering to a patient an effective amount of an antibody or CAR modified immune cells, preferably a CAR-T or CAR-NK cells described herein, thereby effectively inhibiting vascularization of the tumor.

In one aspect, the invention provides a method of inhibiting the delamination of cells expressing podocalyxin, comprising administering to a patient an effective amount of an antibody or CAR modified immune cells, preferably a CAR-T or CAR-NK cells described herein, thereby effectively inhibiting delamination of the cells.

In one aspect, the invention provides a method of inhibiting tumor metastasis in a patient having cancer, comprising administering to a patient an effective amount of an antibody or CAR modified immune cells, preferably a CAR-T or CAR-NK cells described herein, thereby effectively inhibiting tumor metastasis.

In one aspect, the invention provides a method of decreasing tumor size, comprising administering to a patient an effective amount of an antibody or CAR modified immune cells, preferably a CAR-T or CAR-NK cells described herein, thereby effectively decreasing tumor size.

In one aspect, the invention provides a method for treating or preventing a cell proliferative disorder associated with increased expression of podocalyxin, said method comprising administering to a subject in need of such treatment an effective amount of an antibody or CAR modified immune cells, preferably a CAR-T or CAR-NK cells of the invention, thereby effectively treating or preventing said cell proliferative disorder. In one embodiment, said proliferative disorder is cancer.

In one aspect, the invention provides a method of binding an antibody of the invention to a cell that expresses podocalyxin, said method comprising contacting said cell with an antibody of the invention.

In other aspects of the present invention, the invention provides vectors comprising DNA encoding any of the herein described antibodies (or portion(s) thereof). Host cell comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

In a still further aspect, the invention concerns a composition of matter comprising an anti-podocalyxin antibody as described herein, in combination with a carrier. Optionally, the carrier is a pharmaceutically acceptable carrier. In a still further aspect, the invention concerns a composition of matter comprising an CAR modified immune cells, preferably a CAR-T or CAR-NK cells as described herein, in combination with a carrier. Optionally, the carrier is a pharmaceutically acceptable carrier.

Another aspect of the present invention is directed to the use of an anti-podocalyxin epitope antibody as described herein, for the preparation of a medicament useful in the treatment of a condition which is responsive to the anti-podocalyxin epitope antibody.

In another aspect, the invention provides immunoconjugates, or antibody-drug conjugates (ADC), comprising an anti-podocalyxin antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the immunoconjugates. In one aspect, an immunoconjugate comprises any of the above anti-podocalyxin antibodies covalently attached to a cytotoxic agent or a detectable agent.

A. Anti-Podocalyxin Antibodies

In one embodiment, the present invention provides anti-podocalyxin antibodies which may find use herein as therapeutic agents. Exemplary antibodies include polyclonal, monoclonal, chimeric, humanized, and human antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R'N=C=NR$, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

A monoclonal antibody (mAb) to an antigen-of-interest can be prepared by using any technique known in the art. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). The Selected Lymphocyte Antibody Method (SLAM) (Babcook, J. S., et al., A novel strategy for generating monoclonal antibodies from single, isolated lymphocytes producing antibodies of defined specificities. Proc Natl Acad Sci USA, 1996. 93 (15): p. 7843-8.) and (McLean G R, Olsen O A, Watt I N, Rathanaswami P, Leslie K B, Babcook J S, Schrader J W. Recognition of human cytomegalovirus by human primary immunoglobulins identifies an innate foundation to an adaptive immune response. J Immunol. 2005 Apr. 15; 174(8):4768-78. Such antibodies may be of any immunoglobulin class including IgG, IgM, IgE, IgA, and IgD and any subclass thereof. The hybridoma producing the mAbs of use in this invention may be cultivated in vitro or in vivo.

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal, e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and C0 sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Chimeric, Humanized, and Human Antibodies

In some embodiments, the anti-podocalyxin antibody is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

The anti-podocalyxin antibodies of the invention may further comprise humanized antibodies or human antibodies. Humanized forms of non-human (e.g., murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35B (H1), 50-65, 47-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

As described herein, hypervariable region-grafted variants may be generated by Kunkel mutagenesis of nucleic acid encoding the human acceptor sequences, using a separate oligonucleotide for each hypervariable region. Kunkel et al., Methods Enzymol. 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage(mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., Proteins, 8:309 (1990); Lowman and Wells, Methods: A Companion to Methods in Enzymology, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. Nos. 5,723,286, 5,432,018, 5,580,717, 5,427,908 and 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., Methods Enzymol. 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

| IUB Codes |
| --- |
| G Guanine |
| A Adenine |
| T Thymine |
| C Cytosine |
| R (A or G) |
| Y (C or T) |
| M (A or C) |
| K (G or T) |
| S (C or G) |
| W (A or T) |
| H (A or C or T) |
| B (C or G or T) |
| V (A or C or G) |
| D (A or G or T) H |
| N (A or C or G or T) |

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. Nucleic Acids Res. 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, 75:5765 (1978).

The DNA template is generated by those vectors that are either derived from bacteriophage M13 vectors (the commercially available M13 mp 18 and M13 mp 19 vectors are suitable), or those vectors that contain a single-stranded phage origin of replication as described by Viera et al., Meth. Enzymol., 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. Meth. Enzymol., 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, antigen binding may be restored during humanization of antibodies through the selection of repaired hypervariable regions (See application Ser. No. 11/061,841, filed Feb. 18, 2005). The method includes incorporating non-human hypervariable regions onto an acceptor framework and further introducing one or more amino acid substitutions in one or more hypervariable regions without modifying the acceptor framework sequence. Alternatively, the introduction of one or more amino acid substitutions may be accompanied by modifications in the acceptor framework sequence.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-podocalyxin antibody are contemplated. For example, the humanized antibody may be an antibody fragment, such as a Fab. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

In another embodiment, the antibodies of this disclosure are human monoclonal antibodies. Such human monoclonal antibodies directed against podocalyxin can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice."

The HuMAb Mouse™ (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or K, and in response to immunization, the introduced human heavy and light chain transgenes undergo class switching and somatic mutation to generate high affinity human IgGK monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse™, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al., (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchomosomes, such as a mouse that carries a human heavy chain transgene and a human light chain transchromosome. This mouse is referred to herein as a "KM Mouse™" and is described in detail in PCT Publication WO 02/43478 to Ishida et al.

Still further, alternative transgenic animal systems expressing human immunoglobulin genes are available in the art and can be used to raise anti-podocalyxin antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-podocalyxin antibodies of this disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise anti-podocalyxin antibodies of this disclosure.

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example.

In one embodiment, an anti-podocalyxin antibody derived scFv is used in a CAR modified immune cell, preferably a CAR-T or CAR-NK cell disclosed herein. Included among anti-podocalyxin antibody fragments are portions of anti-podocalyxin antibodies (and combinations of portions of anti-podocalyxin antibodies, for example, scFv) that may be used as targeting arms, directed to podocalyxin tumor epitope, in chimeric antigenic receptors of CAR-T or CAR-NK cells. Such fragments are not necessarily proeteolytic fragments but rather portions of polypeptide sequences that can confer affinity for target. 5. Bispecific Antibodies Bispecific antibodies are antibodies that have binding specificities for at least two different epitopes. Exemplary bispecific antibodies may bind to two different epitopes of a podocalyxin protein as described herein. Other such antibodies may combine a podocalyxin binding site with a binding site for another protein. Alternatively, an anti-podocalyxin arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the podocalyxin-expressing cell. Bispecific antibodies may also be used to localize cytotoxic agents to cells which express podocalyxin. These antibodies possess a podocalyxin-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

6. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

B. Certain Methods of Making Antibodies

1. Screening for Anti-Podocalyxin Antibodies with the Desired Properties

Techniques for generating antibodies that bind to podocalyxin polypeptides have been described above. One may further select antibodies with certain biological characteristics, as desired.

The growth inhibitory effects of an anti-podocalyxin antibody of the invention may be assessed by methods known in the art, e.g., using cells which express a podocalyxin polypeptide either endogenously or following transfection with the podocalyxin gene. For example, appropriate tumor cell lines and podocalyxin-transfected cells may be treated with an anti-podocalyxin monoclonal antibody of the invention at various concentrations for a few days (e.g., 2-7) days and stained with crystal violet or MTT or analyzed by some other colorimetric assay. Another method of measuring proliferation would be by comparing 3H-thymidine uptake by the cells treated in the presence or absence an anti-podocalyxin antibody of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a podocalyxin polypeptide. The anti-podocalyxin antibody will inhibit cell proliferation of a podocalyxin-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-podocalyxin antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-podocalyxin antibody which induces cell death, loss of membrane integrity as indicated by, e.g., propidium iodide (PI), trypan blue or 7AAD uptake may be assessed relative to control. A PI uptake assay can be performed in the absence of complement and immune effector cells. Podocalyxin polypeptide-expressing tumor cells are incubated with medium alone or medium containing the appropriate anti-podocalyxin antibody (e.g., at about 10 µg/ml). The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-podocalyxin antibodies that induce statistically significant levels of cell death as determined by PI uptake may be selected as cell death-inducing anti-podocalyxin antibodies.

To screen for antibodies which bind to an epitope on a podocalyxin polypeptide bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody binds the same site or epitope as a known anti-Podocalyxin antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a podocalyxin polypeptide can be used in competition assays with the test antibodies or with a test antibody and an antibody with a characterized or known epitope.

In addition, candidate antibodies may also be screened for function using one or more of the following: in vivo screening for inhibition of metastasis, inhibition of chemotaxis by an in vitro method (e.g., Huntsman et al. U.S. 2010/0061978, incorporated herein by reference in its entirety), inhibition of vascularization, inhibition of tumour growth, and decrease in tumor size.

2. Certain Library Screening Methods

Anti-podocalyxin antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. (2001) in Methods in Molecular Biology 178:1-37 (O'Brien et al., ed., Human Press, Totowa, N.J.), and in certain embodiments, in Lee et al. (2004) J. Mol. Biol. 340:1073-1093.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-podocalyxin antibodies of the invention can be obtained by designing a suitable antigen screening procedure to select for the phage clone of interest followed by construction of a full length anti-podocalyxin antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-podocalyxin clones is desired, the subject is immunized with podocalyxin to generate an antibody response, and spleen cells and/or circulating B cells other peripheral blood lymphocytes (PBLs) are recovered for library construction. In a preferred embodiment, a human antibody gene fragment library biased in favor of anti-podocalyxin clones is obtained by generating an anti-podocalyxin antibody response in transgenic mice carrying a functional human immunoglobulin gene array (and lacking a functional endogenous antibody production system) such that podocalyxin immunization gives rise to B cells producing human antibodies against Podocalyxin. The generation of human antibody-producing transgenic mice is described below.

Additional enrichment for anti-podocalyxin reactive cell populations can be obtained by using a suitable screening procedure to isolate B cells expressing podocalyxin-specific membrane bound antibody, e.g., by cell separation using podocalyxin affinity chromatography or adsorption of cells to fluorochrome-labeled podocalyxin followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which podocalyxin is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression.

The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about 1012 clones). Both vectors contain in vivo recombination signals so that the VH and VL genes are recombined onto a single replicon and are co-packaged into phage virions. These huge libraries provide large numbers of diverse antibodies of good affinity (Kd-1 of about 10-8 M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity (Kd-1 of about 106 to 107 M-1), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about 10-9 M or less.

Screening of the libraries can be accomplished by various techniques known in the art. For example, Podocalyxin can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized podocalyxin under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci USA, 88: 7978-7982 (1991), or by alkali, e.g. as described in Marks et al., J. Mol. Biol., 222: 581-597 (1991), or by Podocalyxin antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for podocalyxin. However, random mutation of a selected antibody (e.g. as performed in some affinity maturation techniques) is likely to give rise to many mutants, most binding to antigen, and a few with higher affinity. With limiting podocalyxin, rare high affinity phage could be competed out. To retain all higher affinity mutants, phages can be incubated with excess biotinylated podocalyxin, but with the biotinylated podocalyxin at a concentration of lower molarity than the target molar affinity constant for podocalyxin. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-podocalyxin clones may be selected based on activity. In certain embodiments, the invention provides anti-podocalyxin antibodies that bind to living cells that naturally express podocalyxin. In one embodiment, the invention provides anti-podocalyxin antibodies that block the binding between a podocalyxin ligand and podocalyxin, but do not block the binding between a podocalyxin ligand and a second protein. Fv clones corresponding to such anti-podocalyxin antibodies can be selected by (1) isolating anti-podocalyxin clones from a phage library as described above, and optionally amplifying the isolated population of phage clones by growing up the population in a suitable bacterial host; (2) selecting podocalyxin and a second protein against which blocking and non-blocking activity, respectively, is desired; (3) adsorbing the anti-podocalyxin phage clones to immobilized podocalyxin; (4) using an excess of the second protein to elute any undesired clones that recognize podocalyxin-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-podocalyxin antibody derived from a hybridoma can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

3. Generation of Antibodies Using CAR T-Cells

Anti-podocalyxin antibodies of the invention can be made by using CAR T-cell platforms to screen for antibodies with the desired activity or activities. Chimeric antigen receptors (CARs) are composed of an extracellular antigen recognition domain (usually a single-chain variable fragment (scFv) antibody) attached to transmembrane and cytoplasmic signaling domains. Alvarez-Vallina, L, *Curr Gene Ther* 1: 385-397 (2001). CAR-mediated recognition converts tumor-associated antigens (TAA) expressed on the cell surface into recruitment points of effector functions, addressing the goal of major histocompatibility complex-independent activation of effector cells. First-generation CARs were constructed through the fusion of a scFv-based TAA-binding domain to a cytoplasmic signaling domain typically derived either from the chain of the ζ cell receptor (TCR)/CD3 complex or from the γ chain associated with some Fc receptors. Gross, G. et al., *Proc Natl Acad Sci USA* 86: 10024-10028 (1989). Second-generation CARs (CARv2) comprising the signaling region of the TCR ζ in series with the signaling domain derived from the T-cell co-stimulatory receptors CD28, 4-1BB (CD137) or OX40 (CD134) have also been developed. Sanz, L. et al., *Trends Immunol* 25: 85-91 (2004).

Upon encountering antigen, the interaction of a genetically transferred CAR triggers effector functions and can mediate cytolysis of tumor cells. The utility and effectiveness of the CAR approach have been demonstrated in a variety of animal models, and ongoing clinical trials using CAR-based genetically engineered T lymphocytes for the treatment of cancer patients. Lipowska-Bhalla, G. et al., *Cancer Immunol Immunother* 61: 953-962 (2012). CARs enable targeting of effector cells toward any native extracellular antigen for which a suitable antibody exists. Engineered cells can be targeted not only to proteins but also to structures such as carbohydrate and glycolipid tumor antigens. Mezzanzanica, D. et al., *Cancer Gene Ther* 5: 401-407 (1998); Kershaw, M H. et al., *Nat Rev Immunol* 5: 928-940 (2005).

Current methods for the generation of recombinant antibodies are mainly based on the use of purified proteins. Hoogenboom, H. R. et al., *Nat Biotechnol* 23: 1105-1116 (2005). However, a mammalian cell-based antibody display platform has recently been described, which takes advantage of the functional capabilities of T lymphocytes. Alonso-Camino et al, *Molecular Therapy Nucleic Acids* (2013) 2, e93. The display of antibodies on the surface of T lymphocytes, as a part of a CAR-mediating signaling, may ideally link the antigen-antibody interaction to a demonstrable change in cell phenotype, due to the surface expression of activation markers. Alonso-Camino, V. et al., *PLoS ONE* 4: e7174 (2009). By using a scFv-based CAR that recognizes a TAA, it has been demonstrated that combining CAR-mediated activation with fluorescence-activated cell sorting (FACS) of CD69+ T cells makes it possible to isolate binders to surface TAA, with an enrichment factor of at least $10^3$-fold after two rounds, resulting in a homogeneous population of T cells expressing TAA-specific CAR. Alonso-Camino, V, et al., *PLoS ONE* 4: e7174 (2009).

D. Anti-Podocalyxin Antibody Variants and Modifications

1. Variants

In addition to the anti-podocalyxin antibodies described herein, it is contemplated that anti-podocalyxin antibody variants can be prepared. Anti-podocalyxin antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-podocalyxin antibody, such as changing the number or position of glycosylation sites or altering the membrane anchoring characteristics.

Variations in the anti-podocalyxin antibodies described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-podocalyxin antibody. Guidance in determining which amino acid residue may be inserted, substituted or deleted without adversely affecting the desired activity may be found by comparing the sequence of the anti-podocalyxin antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-podocalyxin antibody fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-podocalyxin antibody.

Anti-podocalyxin antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-podocalyxin antibody fragments share at least one biological and/or immunological activity with the native anti-podocalyxin antibody disclosed herein.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-podocalyxin antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the anti-podocalyxin antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Any cysteine residue not involved in maintaining the proper conformation of the anti-podocalyxin antibody also may be substituted, generally with serine, to improve the oxidative stability of the molecule and prevent aberrant crosslinking. Conversely, cysteine bond(s) may be added to the anti-podocalyxin antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and podocalyxin polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-podocalyxin antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-podocalyxin antibody.

2. Modifications

Covalent modifications of anti-podocalyxin antibodies are included within the scope of this invention. One type of covalent modification includes reacting targeted amino acid residues of an anti-podocalyxin antibody with an organic derivatizing agent that is capable of reacting with selected side chains or the N- or C-terminal residues of the anti-podocalyxin antibody. Derivatization with bifunctional agents is useful, for instance, for crosslinking anti-podocalyxin antibody to a water-insoluble support matrix or surface for use in the method for purifying anti-podocalyxin antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the anti-podocalyxin antibody included within the scope of this invention comprises altering the native glycosylation pattern of the antibody or polypeptide. "Altering the native glycosylation pattern" is intended for purposes herein to mean deleting one or more carbohydrate moieties found in native sequence anti-podocalyxin antibody (either by removing the underlying glycosylation site or by deleting the glycosylation by chemical and/or enzymatic means), and/or adding one or more glycosylation sites that are not present in the native sequence anti-podocalyxin antibody. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-podocalyxin antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-podocalyxin antibody (for O-linked glycosylation sites). The anti-podocalyxin antibody amino acid sequence may optionally be altered through changes at the DNA level, particularly by mutating the DNA encoding the anti-podocalyxin antibody at preselected bases such that codons are generated that will translate into the desired amino acids.

Another means of increasing the number of carbohydrate moieties on the anti-podocalyxin antibody is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the anti-podocalyxin antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

E. Preparation of Anti-Podocalyxin Antibodies

The description below relates primarily to production of anti-podocalyxin antibodies by culturing cells transformed or transfected with a vector containing anti-podocalyxin antibody-encoding nucleic acid. It is, of course, contemplated that alternative methods, which are well known in the art, may be employed to prepare anti-podocalyxin antibodies. For instance, the appropriate amino acid sequence, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-podocalyxin antibody may be chemically synthesized separately and combined using chemical or enzymatic methods to produce the desired anti-podocalyxin antibody.

1. Isolation of DNA Encoding Anti-Podocalyxin Antibody

DNA encoding anti-podocalyxin antibody may be obtained from a cDNA library prepared from tissue believed to possess the anti-podocalyxin antibody mRNA and to express it at a detectable level. Accordingly, human anti-podocalyxin antibody DNA can be conveniently obtained from a cDNA library prepared from human tissue. The anti-podocalyxin antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-Podocalyxin antibody is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as Gen- Bank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-podocalyxin antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation, which means introduction of DNA into the host so that the DNA is replicable, either as an extrachromosomal or by chromosomal integrant, are known to the ordinarily skilled artisan, for example, CaCl2, CaPO4, liposome-mediated, polyethylene-gycol/DMSO and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells.

a. Prokarvotic Host Cells

Suitable prokaryotes include but are not limited to archaebacteria and eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, *Rhizobia*, *Vitreoscilla*, *Paracoccus* and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 (Bachmann, Cellular and Molecular Biology, vol. 2 (Washington, D.C.: American Society for Microbiology, 1987), pp. 1190-1219; ATCC Deposit No. 27,325) may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kanr; *E. coli* W3110 strain 37D6, which has the complete genotype tonA ptr3 phoA E15 (argF-lac)169 degP ompT rbs7 ilvG kanr; *E. coli* W3110 strain 40B4, which is strain 37D6 with a non-kanamycin resistant degP deletion mutation; *E. coli* W3110 strain 33D3 having genotype W3110 ΔfhuA (ΔtonA) ptr3 lac Iq lacL8 ΔompTΔ(nmpc-fepE) degP41 kanR (U.S. Pat. No. 5,639,635) and an *E. coli* strain having mutant periplasmic protease disclosed in U.S. Pat. No. 4,946,783 issued 7 Aug. 1990. Other strains and derivatives thereof, such as *E. coli* 294 (ATCC 31,446), *E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC 177, or pKN410 are used to supply the replicon. Typically the host cell should secrete minimal amounts of proteolytic enzymes, and additional protease inhibitors may desirably be incorporated in the cell culture. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

b. Eukaryotic Host Cells

In addition to prokaryotes, eukaryotic microbes such as filamentous fungi or yeast are suitable cloning or expression hosts for anti-podocalyxin antibody-encoding vectors. *Sac-*

*charomyces cerevisiae* is a commonly used lower eukaryotic host microorganism. Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 [1988]); *Candida; Trichoderma* reesia (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated anti-podocalyxin antibody are derived from multicellular organisms. Examples of invertebrate cells include insect cells such as *Drosophila* S2 and *Spodoptera* Sf9, as well as plant cells, such as cell cultures of cotton, corn, potato, soybean, *petunia*, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-podocalyxin antibody production and cultured in conventional nutrient media modified as appropriate for inducing promoters, selecting transformants, or amplifying the genes encoding the desired sequences.

3. Selection and Use of a Replicable Vector

For recombinant production of an antibody of the invention, the nucleic acid (e.g., cDNA or genomic DNA) encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The podocalyxin may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-podocalyxin antibody-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

a. Prokarvotic Host Cells

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides.

In general, plasmid vectors containing replicon and control sequences which are derived from species compatible with the host cell are used in connection with these hosts. Both expression and cloning vectors contain a nucleic acid sequence that enables the vector to replicate in one or more selected host cells, as well as marking sequences which are capable of providing phenotypic selection in transformed cells. Such sequences are well known for a variety of bacteria, yeast, and viruses. The origin of replication from the plasmid pBR322, which contains genes encoding ampicillin (Amp) and tetracycline (Tet) resistance and thus provides easy means for identifying transformed cells, is suitable for most Gram-negative bacteria, the 2μ plasmid origin is suitable for yeast, and various viral origins (SV40, polyoma, adenovirus, VSV or BPV) are useful for cloning vectors in mammalian cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters recognized by a variety of potential host cells are well known. Promoters suitable for use with prokaryotic hosts include the PhoA promoter, the β-galactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776] and hybrid promoters such as the tac [deBoer et al., Proc. Natl. Acad. Sci. USA, 80:21-25 (1983)] or the trc promoter. Promoters for use in bacterial systems also will contain a Shine-Dalgarno (S.D.) sequence operably linked to the DNA encoding anti-podocalyxin antibody. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB− strains) provide cytoplasm conditions that are favorable for disulfide bond formation, thereby permitting proper folding and assembly of expressed protein subunits. Proba and Pluckthun Gene, 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

b. Eukaryotic Host Cells

The vector components generally include, but are not limited to, one or more of the following: a signal sequence, an origin of replication, one or more marker genes, an enhancer element, a promoter, and a transcription termination sequence.

(1) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of Replication

Generally, an origin of replication component is not needed for mammalian expression vectors. For example, the SV40 origin may typically be used only because it contains the early promoter.

(3) Selection Gene Component

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

An example of suitable selectable markers for mammalian cells are those that enable the identification of cells competent to take up the anti-Podocalyxin antibody-encoding nucleic acid, such as DHFR or thymidine kinase, metallothionein-I and -II, preferably primate metallothionein genes, adenosine deaminase, ornithine decarboxylase, etc. An appropriate host cell when wild-type DHFR is employed is the CHO cell line deficient in DHFR activity (e.g., ATCC CRL-9096), prepared and propagated as described by Urlaub et al., Proc. Natl. Acad. Sci. USA, 77:4216 (1980). For example, cells transformed with the DHFR selection gene are first identified by culturing all of the transformants in a culture medium that contains methotrexate (Mtx), a competitive antagonist of DHFR. Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trpl gene present in the yeast plasmid YRp7 [Stinchcomb et al., Nature, 282:39 (1979); Kingsman et al., Gene, 7:141 (1979); Tschemper et al., Gene, 10:157 (1980)]. The trpl gene provides a selection marker for a mutant strain of yeast lacking the ability to grow in tryptophan, for example, ATCC No. 44076 or PEP4-1 [Jones, Genetics, 85:12 (1977)].

(4) Promoter Component

Expression and cloning vectors usually contain a promoter operably linked to the anti-Podocalyxin antibody-encoding nucleic acid sequence to direct mRNA synthesis. Promoters recognized by a variety of potential host cells are well known.

Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-podocalyxin antibody transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of a DNA encoding the anti-podocalyxin antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-podocalyxin antibody coding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-Podocalyxin antibody. One useful transcription termination component is the bovine growth hormone polyadenylation region. See WO94/11026 and the expression vector disclosed therein.

Still other methods, vectors, and host cells suitable for adaptation to the synthesis of anti-podocalyxin antibody in recombinant vertebrate cell culture are described in Gething et al., Nature, 293:620-625 (1981); Mantei et al., Nature, 281:40-46 (1979); EP 117,060; and EP 117,058.

4. Culturing the Host Cells

The host cells used to produce the anti-Podocalyxin antibody of this invention may be cultured in a variety of media.

a. Prokaryotic Host Cells

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For E. coli growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For E. coli, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

b. Eukaryotic Host Cells

Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of a duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence podocalyxin polypeptide or against a synthetic peptide based on the DNA sequences provided herein or against exogenous sequence fused to Podocalyxin DNA and encoding a specific antibody epitope.

6. Purification of Anti-Podocalyxin Antibody

Forms of anti-podocalyxin antibody may be recovered from culture medium or from host cell lysates. If membrane-bound, it can be released from the membrane using a suitable detergent solution (e.g. Triton-X 100) or by enzymatic cleavage. Cells employed in expression of anti-Podocalyxin antibody can be disrupted by various physical or chemical means, such as freeze-thaw cycling, sonication, mechanical disruption, or cell lysing agents.

It may be desired to purify anti-podocalyxin antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-podocalyxin antibody. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular anti-podocalyxin antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth.

62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

F. Pharmaceutical Formulations

The antibodies of the invention may be administered by any route appropriate to the condition to be treated. The antibody will typically be administered parenterally, i.e. infusion, subcutaneous, intramuscular, intravenous, intradermal, intrathecal and epidural.

For treating these cancers, in one embodiment, the antibody is administered via intravenous infusion. The dosage administered via infusion is in the range of about 1 µg/m2 to about 10,000 µg/m$^2$ per dose, generally one dose per week for a total of one, two, three or four doses. Alternatively, the dosage range is of about 1 µg/m$^2$ to about 1000 µg/m$^2$, about 1 µg/m$^2$ to about 800 µg/m$^2$, about 1 µg/m$^2$ to about 600 µg/m$^2$, about 1 µg/m$^2$ to about 400 µg/m$^2$, about 10 µg/m$^2$ to about 500 µg/m$^2$, about 10 µg/m$^2$ to about 300 µg/m$^2$, about 10 µg/m$^2$ to about 200 µg/m$^2$, and about 1 µg/m$^2$ to about 200 µg/m$^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the cancer being treated. Administration may continue after remission or relief of symptoms is achieved where such remission or relief is prolonged by such continued administration.

The invention also provides a method of treating breast cancer comprising administering to a patient suffering from breast cancer, a therapeutically effective amount of a humanized podocalyxin antibody of any one of the preceding embodiments. The antibody will typically be administered in a dosage range of about 1 µg/m$^2$ to about 1000 mg/m$^2$.

In one aspect, the invention further provides pharmaceutical formulations comprising at least one anti-podocalyxin antibody of the invention. In some embodiments, a pharmaceutical formulation comprises (1) an antibody of the invention, and (2) a pharmaceutically acceptable carrier.

Therapeutic formulations comprising an anti-podocalyxin antibody used in accordance with the present invention are prepared for storage by mixing the antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). Pharmaceutical formulations to be used for in vivo administration are generally sterile. This is readily accomplished by filtration through sterile filtration membranes.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

An antibody may be formulated in any suitable form for delivery to a target cell/tissue. For example, antibodies may be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

The formulations to be used for in vivo administration must be sterile. This is readily accomplished by filtration through sterile filtration membranes.

G. Treatment with Anti-Podocalyxin Antibodies

To determine podocalyxin expression in a cancer, various detection assays are available. In one embodiment, podocalyxin polypeptide overexpression may be analyzed by immunohistochemistry (IHC). Parrafin embedded tissue sections from a tumor biopsy may be subjected to the IHC assay and accorded a podocalyxin protein staining intensity criteria. In a preferred embodiment, determining whether a cancer is amenable to treatment by methods disclosed herein involves detecting the presence of the podocalyxin tumor epitope in a subject or in a sample from a subject.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of podocalyxin overexpression in the tumor.

Podocalyxin overexpression or amplification may be evaluated using an in vivo detection assay, e.g., by administering a molecule (such as an antibody) which binds the molecule to be detected and is tagged with a detectable label (e.g., a radioactive isotope or a fluorescent label) and externally scanning the patient for localization of the label.

As described above, the anti-podocalyxin antibodies of the invention have various non-therapeutic applications. The anti-podocalyxin antibodies of the present invention can be useful for staging of podocalyxin epitope-expressing cancers (e.g., in radioimaging). The antibodies are also useful for purification or immunoprecipitation of podocalyxin epitope from cells, for detection and quantitation of podocalyxin epitope in vitro, e.g., in an ELISA or a Western blot, to kill and eliminate podocalyxin-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-podocalyxin antibody therapy may be especially desirable in elderly patients who do not tolerate the toxicity and side effects of chemotherapy well and in metastatic disease where radiation therapy has limited usefulness. The tumor targeting anti-podocalyxin antibodies of the invention are useful to alleviate podocalyxin-expressing cancers upon initial diagnosis of the disease or during relapse.

The anti-podocalyxin antibodies are administered to a human patient, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-podocalyxin antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

The anti-podocalyxin antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody (i) competes for binding to the same epitope, and/or (ii) binds substantially to the same epitope, as the antibodies of the invention. Antibodies having the biological characteristics of the present anti-podocalyxin antibodies of the invention are also contemplated, specifically including the in vivo tumor targeting and any cell proliferation inhibition or cytotoxic characteristics.

Methods of producing the above antibodies are described in detail herein.

The present anti-podocalyxin antibodies are useful for treating a podocalyxin-expressing cancer or alleviating one or more symptoms of the cancer in a mammal. The cancers encompass metastatic cancers of any of the cancers described herein. The antibody is able to bind to at least a portion of the cancer cells that express podocalyxin epitope in the mammal. In a preferred embodiment, the antibody is effective to destroy or kill podocalyxin-expressing tumor cells or inhibit the growth of such tumor cells, in vitro or in vivo, upon binding to podocalyxin epitope on the cell. In other preferred embodiments, the antibodies are effective to (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind.

The invention provides a composition comprising an anti-podocalyxin antibody of the invention, and a carrier. The invention also provides formulations comprising an anti-podocalyxin antibody of the invention, and a carrier. In one embodiment, the formulation is a therapeutic formulation comprising a pharmaceutically acceptable carrier.

Another aspect of the invention is isolated nucleic acids encoding the anti-podocalyxin antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a podocalyxin polypeptide-expressing cancer or alleviating one or more symptoms of the cancer in a mammal, comprising administering a therapeutically effective amount of an anti-podocalyxin antibody to the mammal. The antibody therapeutic compositions can be administered short term (acute) or chronic, or intermittent as directed by physician. Also provided are methods of inhibiting the growth of, and killing a podocalyxin polypeptide-expressing cell.

The invention also provides kits and articles of manufacture comprising at least one anti-podocalyxin antibody. Kits containing anti-podocalyxin antibodies find use, e.g., for podocalyxin cell killing assays, for purification or immunoprecipitation of podocalyxin polypeptide from cells. For example, for isolation and purification of podocalyxin, the kit can contain an anti-podocalyxin antibody coupled to beads (e.g., sepharose beads). Kits can be provided which contain the antibodies for detection and quantitation of podocalyxin in vitro, e.g., in an ELISA or a Western blot. Such antibody useful for detection may be provided with a label such as a fluorescent or radiolabel.

Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Immunoconjugates

The invention also pertains to immunoconjugates (interchangeably referred to as "antibody-drug conjugates," or "ADCs") comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

In certain embodiments, an immunoconjugate comprises an antibody and a chemotherapeutic agent or other toxin. Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleuritesfordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation ofradionucleotide to the antibody. See WO94/11026.

Conjugates of an antibody and one or more small molecule toxins, such as a calicheamicin, auristatin peptides, such as monomethylauristatin (MMAE) (synthetic analog of dolastatin), maytansinoids, such as DM1, a trichothene, and CC 1065, and the derivatives of these toxins that have toxin activity, are also contemplated herein. Additional non-limiting examples of toxins include those described in WO 2014144871, the disclosure of which is herein incorporated by reference in its entirety.

Exemplary Immunoconjugates—Antibody-Drug Conjugates

An immunoconjugate (or "antibody-drug conjugate" ("ADC")) of the invention may be of Formula I, below, wherein an antibody is conjugated (i.e., covalently attached) to one or more drug moieties (D) through an optional linker (L). ADCs may include thioMAb drug conjugates ("TDC").

Ab-(L-D)$_p$   I

Accordingly, the antibody may be conjugated to the drug either directly or via a linker. In Formula I, p is the average number of drug moieties per antibody, which can range, e.g., from about 1 to about 20 drug moieties per antibody, and in certain embodiments, from 1 to about 8 drug moieties per antibody. The invention includes a composition comprising a mixture of antibody-drug compounds of Formula I where the average drug loading per antibody is about 2 to about 5, or about 3 to about 4.

a. Exemplary Linkers

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), and those resulting from conjugation with linker reagents: N-Succinimidyl 4-(2-pyridylthio) pentanoate forming linker moiety 4-mercaptopentanoic acid ("SPP"), N-succinimidyl 4-(N-maleimidomethyl) cyclohexane-1 carboxylate forming linker moiety 4-((2,5-dioxopyrrolidin-1-yl)methyl)cyclohexanecarboxylic acid ("SMCC", also referred to herein as "MCC"), 2,5-dioxopyrrolidin-1-yl 4-(pyridin-2-yldisulfanyl) butanoate forming linker moiety 4-mercaptobutanoic acid ("SPDB"), N-Succinimidyl (4-iodo-acetyl) aminobenzoate ("SIAB"), ethyleneoxy —CH$_2$CH$_2$O— as one or more repeating units ("EO" or "PEO"). Additional linker components are known in the art and some are described herein. Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020) may be used.

In certain embodiments, a linker is as shown in the following Formula II:

-A$_a$-W$_w$—Y$_y$—   II wherein A is a stretcher unit, and a is an integer from 0 to 1; W is an amino acid unit, and w is an integer from 0 to 12; Y is a spacer unit, and y is 0, 1, or 2; and Ab, D, and p are defined as above for Formula I. Exemplary embodiments of such linkers are described in US 2005-0238649 A1, which is expressly incorporated herein by reference.

In some embodiments, a linker component may comprise a "stretcher unit" that links an antibody to another linker component or to a drug moiety. Exemplary stretcher units are shown below (wherein the wavy line indicates sites of covalent attachment to an antibody):

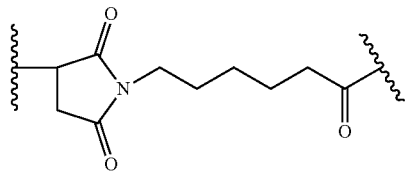
MC

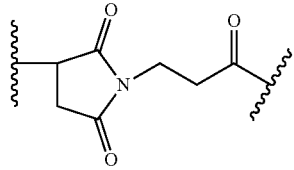
MP

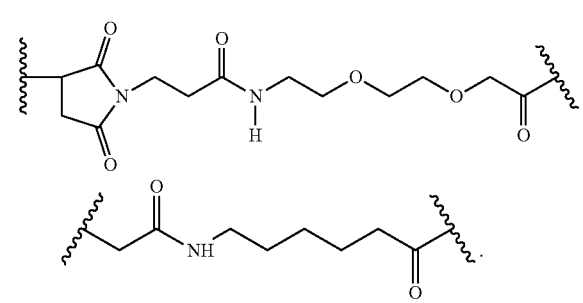
MPEG

In some embodiments, a linker component may comprise an amino acid unit. In one such embodiment, the amino acid unit allows for cleavage of the linker by a protease, thereby facilitating release of the drug from the immunoconjugate upon exposure to intracellular proteases, such as lysosomal enzymes. See, e.g., Doronina et al. (2003) Nat. Biotechnol. 21:778-784. Exemplary amino acid units include, but are not limited to, a dipeptide, a tripeptide, a tetrapeptide, and a pentapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, a linker component may comprise a "spacer" unit that links the antibody to a drug moiety, either directly or by way of a stretcher unit and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic) cleavage of the ADC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an ADC containing a glycine-glycine spacer unit by a tumor-cell associated protease would result in release of a glycine-glycine-drug moiety from the remainder of the ADC. In one such embodiment, the glycine-glycine-drug moiety is then subjected to a separate hydrolysis step in the tumor cell, thus cleaving the glycine-glycine spacer unit from the drug moiety.

A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. See, e.g., Hamann et al. (2005) *Expert Opin. Ther. Patents* (2005) 15:1087-1103. In one embodiment, the spacer unit is p-aminobenzyloxycarbonyl (PAB). In certain embodiments, the phenylene portion of a p-amino benzyl unit is substituted with Qm, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., US 2005/0256030 A1), such as 2-aminoimidazol-5-methanol derivatives (Hay et al. (1999) *Bioorg. Med. Chem. Lett.* 9:2237) and ortho- or para-aminobenzylacetals. Spacers can be used that undergo cyclization upon amide bond hydrolysis, such as substituted and unsubstituted 4-aminobutyric acid amides (Rodrigues et al., *Chemistry Biology*, 1995, 2, 223); appropriately substituted bicyclo[2.2.1] and bicyclo [2.2.2] ring systems (Storm, et al., *J. Amer. Chem. Soc.*, 1972, 94, 5815); and 2-aminophenylpropionic acid amides (Amsberry, et al., *J. Org. Chem.*, 1990, 55, 5867). Elimination of amine-containing drugs that are substituted at the a-position of glycine (Kingsbury, et al., *J. Med. Chem.*, 1984, 27, 1447) are also examples of self-immolative spacers useful in ADCs.

In one embodiment, a spacer unit is a branched bis (hydroxymethyl)styrene (BHMS) unit as depicted below, which can be used to incorporate and release multiple drugs.

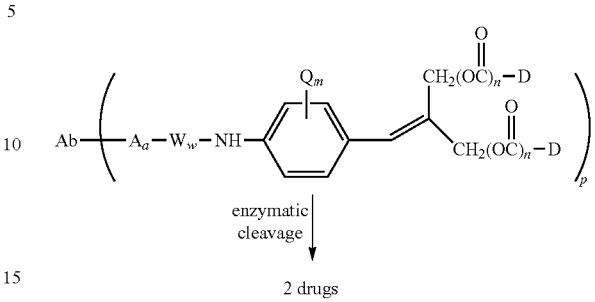

wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to about 20.

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Exemplary linker components and combinations thereof are shown below in the context of ADCs of Formula II:

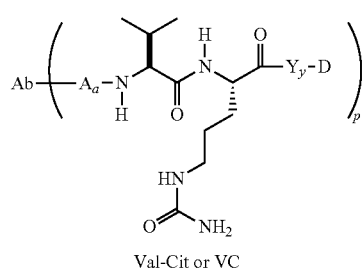

Val-Cit or VC

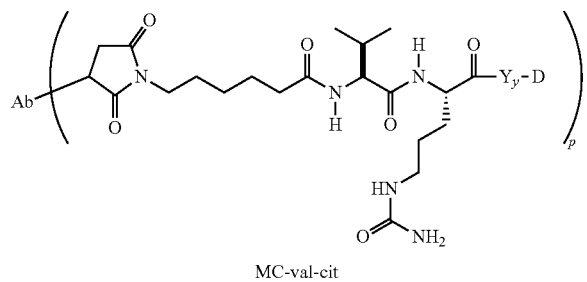

MC-val-cit

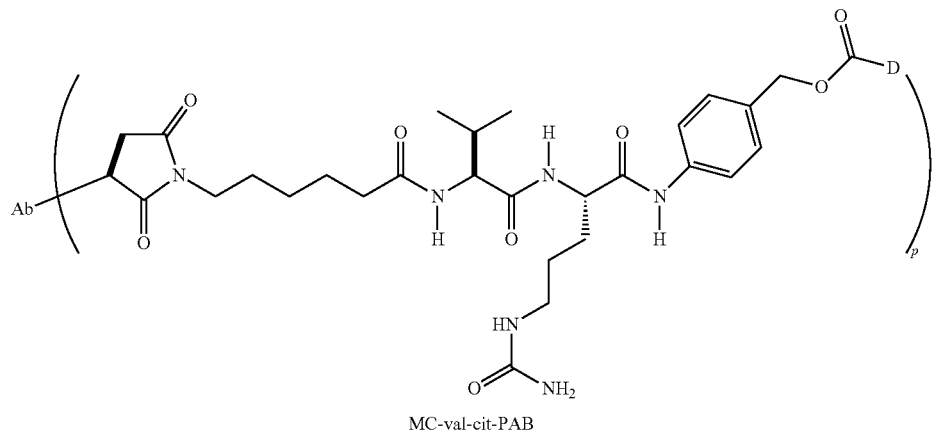

MC-val-cit-PAB

Linkers components, including stretcher, spacer, and amino acid units, may be synthesized by methods known in the art, such as those described in US 2005-0238649 A1.

Additional non-limiting examples of linkers include those described in WO 2015095953, the disclosure of which is herein incorporated by reference in its entirety.

b. Exemplary Drug Moieties (1) Maytansine and Maytansinoids

In some embodiments, an immunoconjugate comprises an antibody conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through disulfide and non-disulfide linkers to antibodies, (iii) stable in plasma, and (iv) effective against a variety of tumor cell lines.

Maytansine compounds suitable for use as maytansinoid drug moieties are well known in the art and can be isolated from natural sources according to known methods or produced using genetic engineering and fermentation techniques (U.S. Pat. No. 6,790,952; US 2005/0170475; Yu et al (2002) *PNAS* 99:7968-7973). Maytansinol and maytansinol analogues may also be prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions.

Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2$ OR)(U.S. Pat. No. 4,331,598); C-14-hydroxymethyl or acyloxymethyl ($CH_2OH$ or $CH_2OAc$) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable (U.S. Pat. No. 5,208,020; U.S. RE39151; U.S. Pat. Nos. 6,913,748; 7,368,565; US 2006/0167245; US 2007/0037972).

Maytansinoid drug moieties include those having the structure:

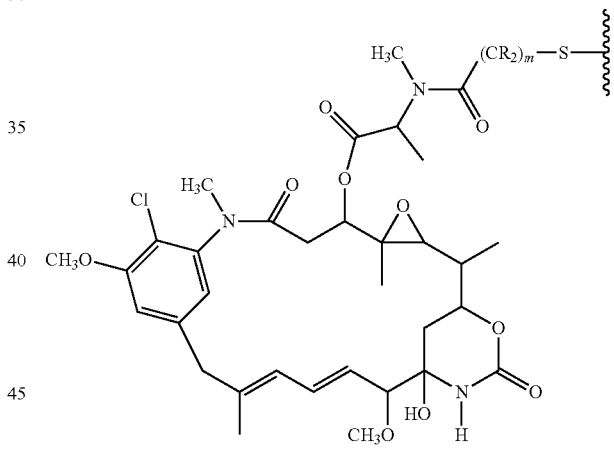

where the wavy line indicates the covalent attachment of the sulfur atom of the maytansinoid drug moiety to a linker of an ADC. R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. Nos. 633,410; 5,208,020; 7,276,497; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the compounds of the invention, i.e. any combination of R and S configurations at the chiral carbons of D. In one embodiment, the maytansinoid drug moiety will have the following stereochemistry:

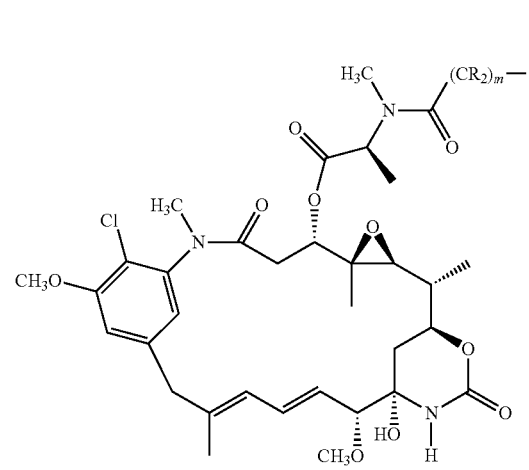

Exemplary embodiments of maytansinoid drug moieties include: DM1; DM3; and DM4, having the structures:

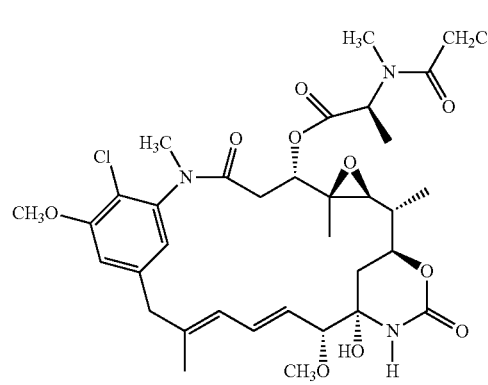

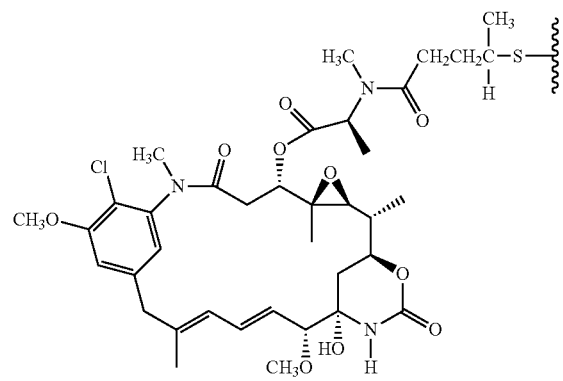

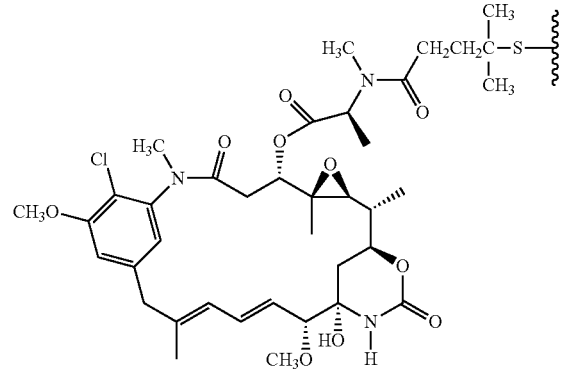

wherein the wavy line indicates the covalent attachment of the sulfur atom of the drug to a linker (L) of an antibody-drug conjugate. (WO 2005/037992; US 2005/0276812 A1).

Other exemplary maytansinoid antibody-drug conjugates have the following structures and abbreviations, (wherein Ab is antibody and p is 1 to about 8):

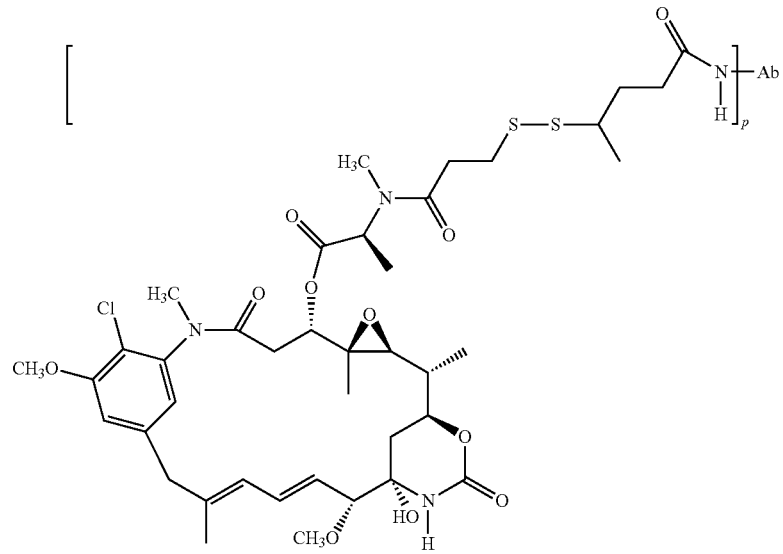

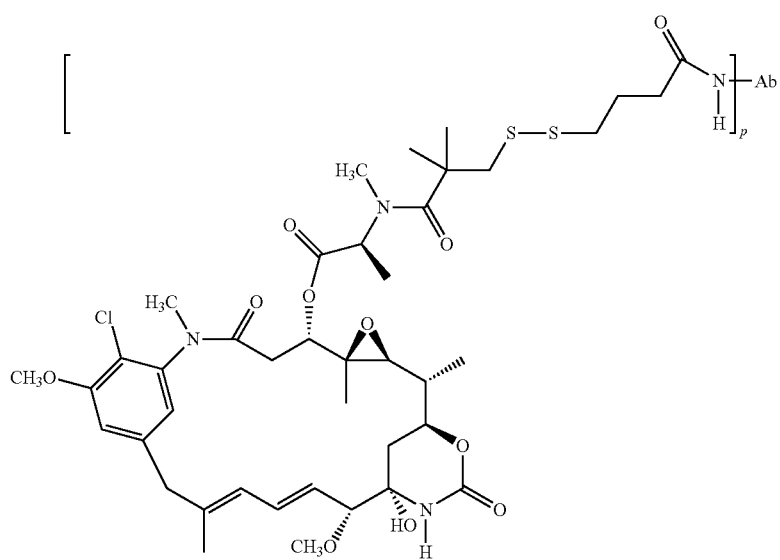
Ab-SPDB-DM4
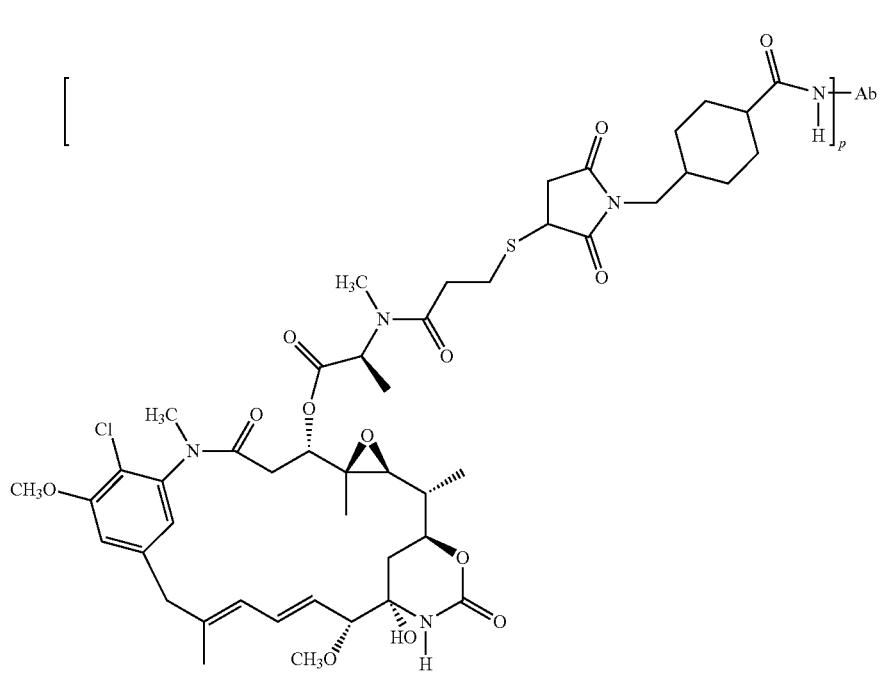
Ab-SMCC-DM1

In one embodiment, the antibody-drug conjugate is formed where DM4 is linked through an SPDB linker to a thiol group of the antibody (see U.S. Pat. Nos. 6,913,748 and 7,276,497 incorporated herein by reference in their entirety).

Exemplary antibody-drug conjugates where DM1 is linked through a BMPEO linker to a thiol group of the antibody have the structure and abbreviation:

ponent SMCC may be prepared as disclosed in US 2005/0276812 A1, "Antibody-drug conjugates and Methods." The linkers comprise disulfide groups, thioether groups, acid labile groups, photolabile groups, peptidase labile groups, or esterase labile groups, as disclosed in the above-identified patents. Additional linkers are described and exemplified herein.

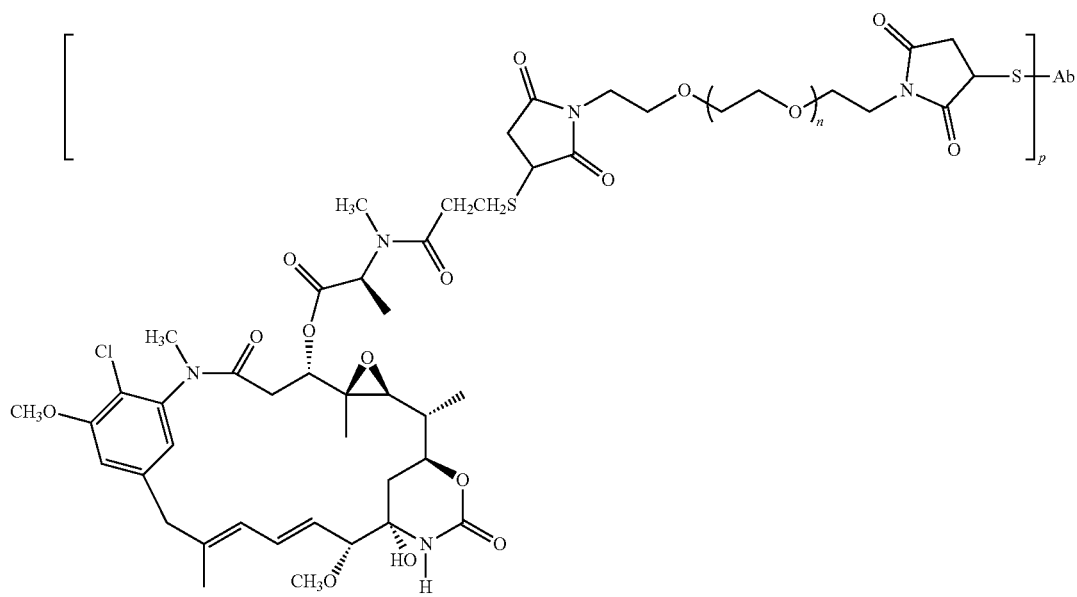

where Ab is antibody; n is 0, 1, or 2; and p is 1, 2, 3, or 4.

Immunoconjugates containing maytansinoids, methods of making the same, and their therapeutic use are disclosed, for example, in Erickson, et al (2006) *Cancer Res.* 66(8):4426-4433; U.S. Pat. Nos. 5,208,020, 5,416,064, US 2005/0276812 A1, and European Patent EP 0 425 235 B1, the disclosures of which are hereby expressly incorporated by reference.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). Maytansinoids can be synthesized by known techniques or isolated from natural sources. Suitable maytansinoids are disclosed, for example, in U.S. Pat. No. 5,208,020 and in the other patents and nonpatent publications referred to hereinabove, such as maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1; Chari et al. *Cancer Research* 52:127-131 (1992); and US 2005/016993 A1, the disclosures of which are hereby expressly incorporated by reference. Antibody-maytansinoid conjugates comprising the linker com- Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In certain embodiments, the coupling agent is N-succinimidyl-3-(2-pyridyldithio) propionate (SPDP) (Carlsson et al., *Biochem. J.* 173:723-737 (1978)) or N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

(2) Auristatins and Dolastatins

In some embodiments, an immunoconjugate comprises an antibody conjugated to dolastatin or a dolastatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (US 2005/0238649, disclosed in Senter et al, Proceedings of the American Association for Cancer Research, Volume 45, Abstract Number 623, presented Mar. 28, 2004, the disclosure of which is expressly incorporated by reference in its entirety).

A peptidic drug moiety may be selected from Formulas $D_E$ and $D_F$ below:

each $R^8$ is independently selected from H, OH, $C_1$-$C_8$ alkyl, $C_3$-$C_8$ carbocycle and O—($C_1$-$C_8$ alkyl);
$R^9$ is selected from H and $C_1$-$C_8$ alkyl;
$R^{10}$ is selected from aryl or $C_3$-$C_8$ heterocycle;
Z is O, S, NH, or $NR^{12}$, wherein $R^{12}$ is $C_1$-$C_8$ alkyl;
$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;
m is an integer ranging from 1-1000;
$R^{13}$ is $C_2$-$C_8$ alkyl;
$R^{14}$ is H or C1-C8 alkyl;
each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;
each occurrence of $R^{16}$ is independently H, $C_1$-$C_8$ alkyl, or —$(CH_2)_n$—COOH;
$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and
n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

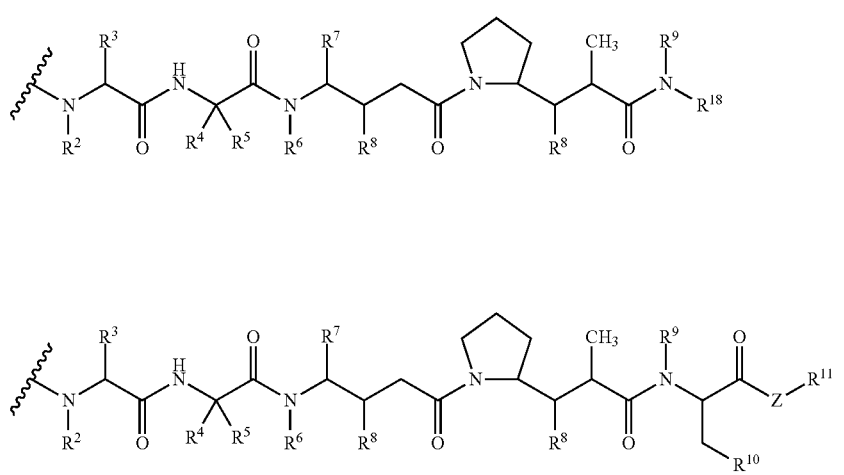

$D_E$ $D_F$ wherein the wavy line of $D_E$ and $D_F$ indicates the covalent attachment site to an antibody or antibody-linker component, and independently at each location:
$R^2$ is selected from H and C1-C8 alkyl;
$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
$R^5$ is selected from H and methyl;
or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;
$R^6$ is selected from H and $C_1$-$C_8$ alkyl;
$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

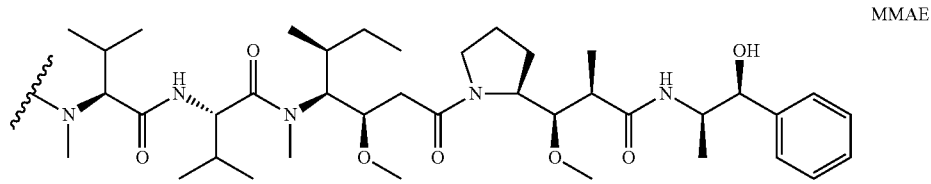 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula $D_F$ is MMAF, wherein the wavy line indicates the covalent attachment to a linker (L) of an antibody-drug conjugate (see US 2005/0238649 and Doronina et al. (2006) *Bioconjugate Chem.* 17:114-124):

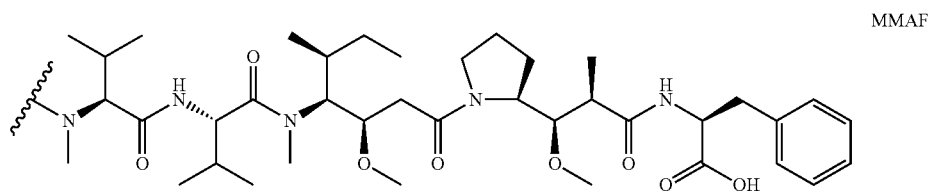 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a linker (L) of an antibody-drug conjugate:

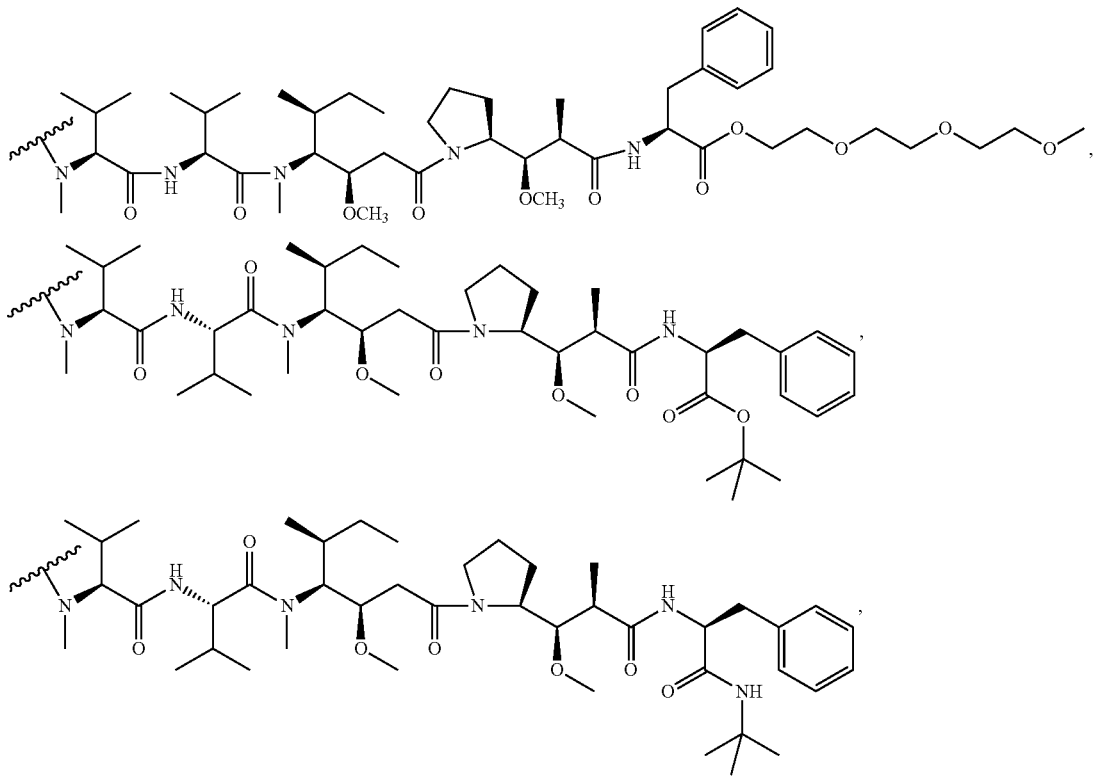

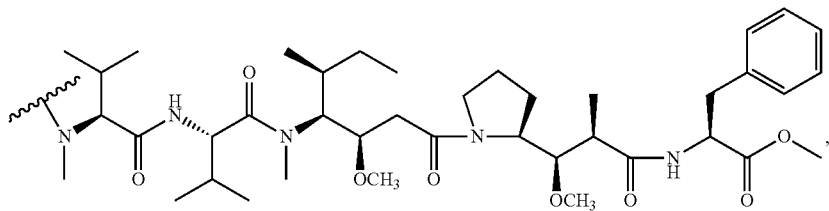
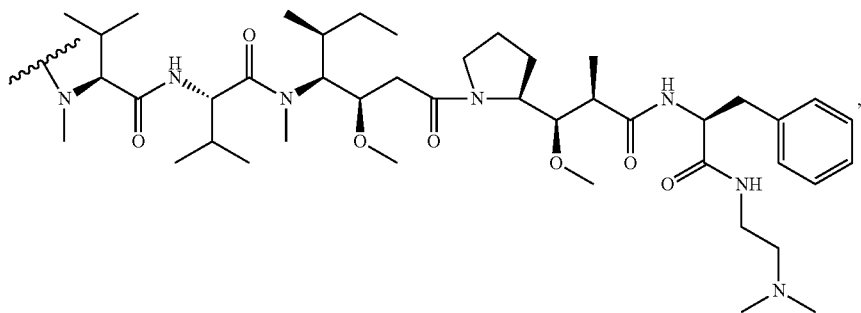
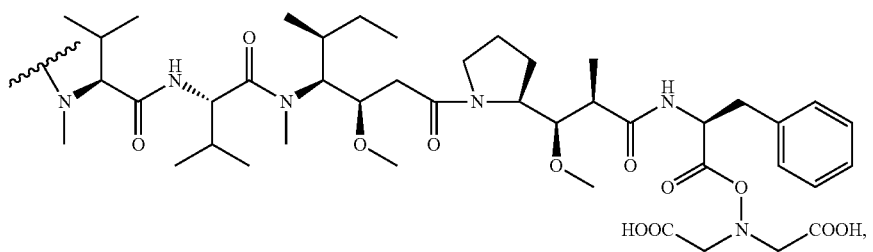
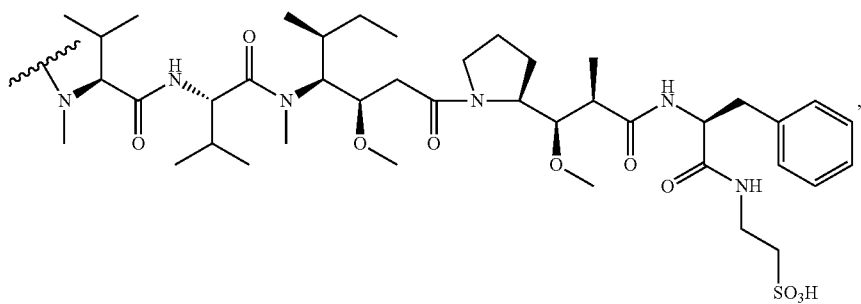
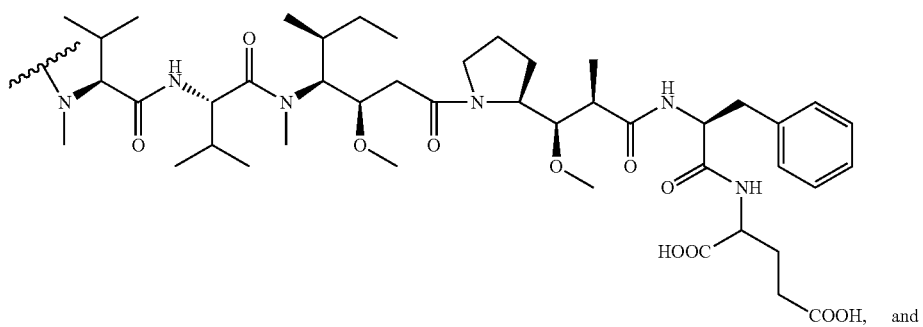

-continued

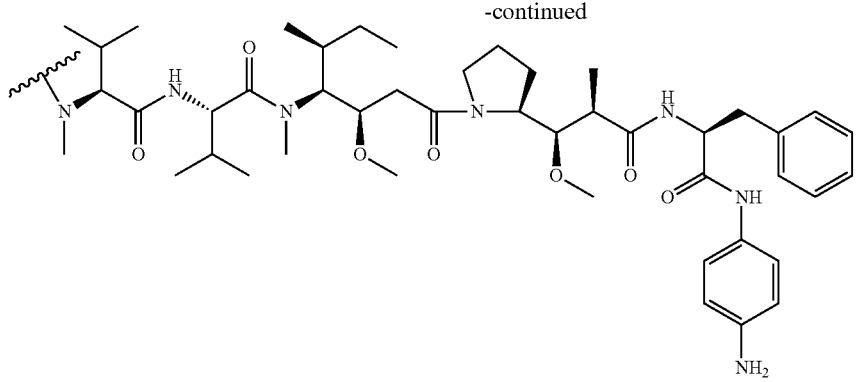

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Exemplary embodiments of ADCs of Formula I comprising an auristatin/dolastatin or derivative thereof are described in US 2005-0238649 and Doronina et al. (2006) *Bioconjugate Chem.* 17:114-124, which is expressly incorporated herein by reference. Exemplary embodiments of ADCs of Formula I comprising MMAE or MMAF and various linker components have the following structures and abbreviations (wherein "Ab" is an antibody; p is 1 to about 8, "Val-Cit" or "vc" is a valine-citrulline dipeptide; and "S" is a sulfur atom. It will be noted that in certain of the structural descriptions of sulfur linked ADC herein the antibody is represented as "Ab-S" merely to indicate the sulfur link feature and not to indicate that a particular sulfur atom bears multiple linker-drug moieties. The left parentheses of the following structures may also be placed to the left of the sulfur atom, between Ab and S, which would be an equivalent description of the ADC of the invention described throughout herein.

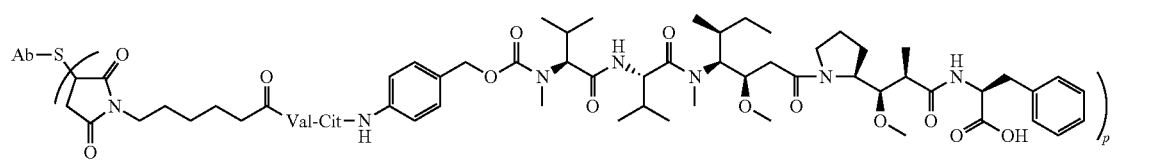

Ab-MC-vc-PAB-MMAF

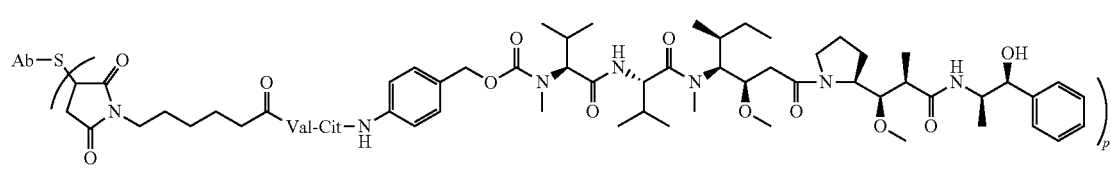

Ab-MC-vc-PAB-MMAE

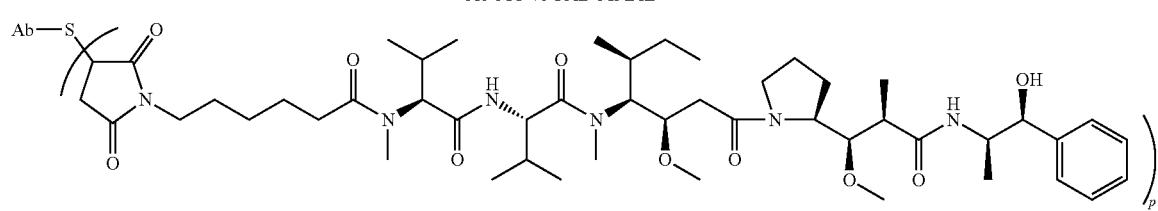

Ab-MC-MMAE

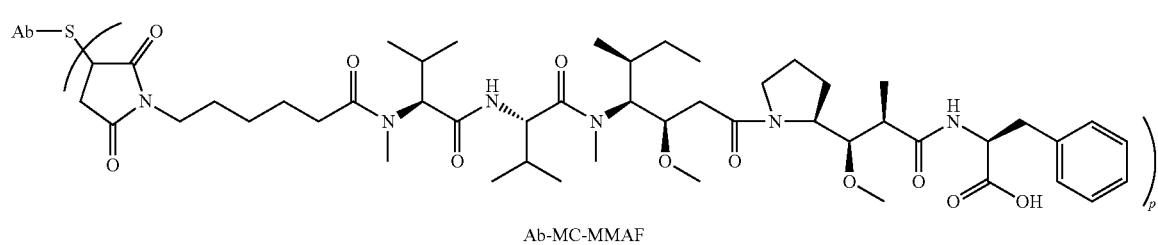

Ab-MC-MMAF

Exemplary embodiments of ADCs of Formula I comprising MMAF and various linker components further include Ab-MC-PAB-MMAF and Ab-PAB-MMAF. Interestingly, immunoconjugates comprising MMAF attached to an antibody by a linker that is not proteolytically cleavable have been shown to possess activity comparable to immunoconjugates comprising MMAF attached to an antibody by a proteolytically cleavable linker. See, Doronina et al. (2006) *Bioconjugate Chem.* 17:114-124. In such instances, drug release is believed to be effected by antibody degradation in the cell. Id.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. Auristatin/dolastatin drug moieties may be prepared according to the methods of: US 2005-0238649 A1; U.S. Pat. Nos. 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J. Chem. Soc. Perkin Trans.* 1 5:859-863; and Doronina (2003) *Nat. Biotechnol.* 21(7):778-784.

In particular, auristatin/dolastatin drug moieties of formula $D_F$, such as MMAF and derivatives thereof, may be prepared using methods described in US 2005-0238649 A1 and Doronina et al. (2006) *Bioconjugate Chem.* 17:114-124. Auristatin/dolastatin drug moieties of formula $D_E$, such as MMAE and derivatives thereof, may be prepared using methods described in Doronina et al. (2003) *Nat. Biotech.* 21:778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) *Nat. Biotech.* 21:778-784, and Patent Application Publication No. US 2005/0238649 A1, and then conjugated to an antibody of interest.

(3) Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998), and the aforementioned U.S. patents to American Cyanamid). Another anti-tumor drug to which the antibody can be conjugated is QFA, which is an antifolate. Both calicheamicin and QFA have intracellular sites of action and do not readily cross the plasma membrane. Therefore, cellular uptake of these agents through antibody-mediated internalization greatly enhances their cytotoxic effects.

c. Other Cytotoxic Agents

Other antitumor agents that can be conjugated to an antibody include BCNU, streptozocin, vincristine and 5-fluorouracil, the family of agents known collectively as the LL-E33288 complex, described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the immunoconjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes other methods in detail.

In certain embodiments, an immunoconjugate may comprise an antibody conjugated to a prodrug-activating enzyme that converts a prodrug (e.g., a peptidyl chemotherapeutic agent, see WO 81/01145) to an active drug, such as an anti-cancer drug. Such immunoconjugates are useful in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. Enzymes may be covalently bound to d. Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis. Pharmaceutical formulations of Formula I antibody-drug conjugates may thus be a heterogeneous mixture of such conjugates with antibodies linked to 1, 2, 3, 4, or more drug moieties.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; or from about 3 to about 5. Indeed, it has been shown that for certain ADCs, the optimal ratio of drug moieties per antibody may be less than 8, and may be about 2 to about 5. See US 2005-0238649 A1.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

Treatment with CAR Modified Immune Cells

In certain embodiments, the invention relates to compositions and methods for treating cancer including but not limited to hematologic malignancies and solid tumors. In certain embodiments, CAR modified immune cells are used. CAR-T cells can be used therapeutically for patients suffering from non-hematological tumors such as solid tumors arising from breast, CNS, and skin malignancies. In certain embodiments, CAR-NK cells can be used therapeutically for patients suffering from any one of a number of malignancies.

In certain embodiments, the present invention relates to a strategy of adoptive cell transfer of T cells or NK cells transduced to express a chimeric antigen receptor (CAR). CARs are molecules that combine antibody-based specificity for a desired antigen (e.g., tumor antigen) with, for example, a T cell receptor-activating intracellular domain to generate a chimeric protein that exhibits a specific anti-tumor cellular immune activity.

In one aspect, the present invention relates to the use of NK cells genetically modified to stably express a desired CAR. NK cells expressing a CAR are referred to herein as CAR-NK cells or CAR modified NK cells. Preferably, the cell can be genetically modified to stably express an antibody binding domain on its surface, conferring novel antigen specificity. Methods for generating CAR-NK cells are known in the art. For example, see Glienke et al., *Advantages and applications of CAR-expressing natural killer cells*, Front Pharmacol. 2015; 6: 21. Services for generating CAR-NK cells are commercially avaibale. See for example Creative Biolabs Inc., 45-1 Ramsey Road, Shirley, N.Y. 11967, USA.

In one aspect, the present invention relates to the use of T cells genetically modified to stably express a desired CAR. T cells expressing a CAR are referred to herein as CAR-T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one embodiment, the transmembrane domain is the CD8a hinge domain.

With respect to the cytoplasmic domain, the CAR of the invention can be designed to comprise the CD28 and/or 4-1BB signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof. Accordingly, the invention provides CAR T cells and methods of their use for adoptive therapy.

In one embodiment, the CAR T cells of the invention can be generated by introducing a lentiviral vector comprising a desired CAR, for example a CAR comprising anti-podocalyxin, CD8a hinge and transmembrane domain, and human 4-1BB and CD3zeta signaling domains, into the cells. The CAR T cells of the invention are able to replicate in vivo resulting in long-term persistence that can lead to sustained tumor control.

In one embodiment, the anti-podocalyxin domain comprises a heavy chain variable region comprising:

(SEQ ID NO: 27)
METGLRWLLLVAVLKGVQCQSLEESGGRLVTPGTPLTLTCTASGFSLSGY

QMNWVRQAPGKGLEWIGYIWSDGGTDYASWAKGRFTISKTSSTTVDLKMT

SLTTEDTATYFCAREGYWLGAFDPWGPGTLVTVSS.

In one embodiment, the anti-podocalyxin domain comprises a light chain variable region comprising:

(SEQ ID NO: 29)
MDTRAPTQLLGLLLLWLPGATFAAVLTQTPSPVSAAVGATVSVSCQSSQS

VHHKNDLAWFQQKPGQPPKLLIYYTSTLASGVPSRFKGSGSGTQFTLTIS

DLECDDAATYYCAGVYEGSSDNRAFGGGTEVVVK.

In one embodiment, the anti-podocalyxin domain comprises SEQ ID NO:27 and SEQ ID NO:29.

In one embodiment, the anti-podocalyxin domain comprises an amino acid sequence selected from the group consisting of: GFSLSGYQ (SEQ ID NO:33); GFSLSGY (SEQ ID NO:34); and GYQMN (SEQ ID NO:35).

In one embodiment, the anti-podocalyxin domain comprises an amino acid sequence selected from the group consisting of: IWSDGGT (SEQ ID NO:36); WSDGG (SEQ ID NO:37); and YIWSDGGTDYASWAKG (SEQ ID NO:38).

In one embodiment, the anti-podocalyxin domain comprises an amino acid sequence selected from the group consisting of: AREGYWLGAFDP (SEQ ID NO:39); EGYWLGAFDP (SEQ ID NO:40); and EGYWLGAFDP (SEQ ID NO:41).

In one embodiment, the anti-podocalyxin domain comprises an amino acid sequence selected from the group consisting of: QSVHHKND (SEQ ID NO:42); QSSQSVHHKNDLA (SEQ ID NO:43); and QSSQSVHHKNDLA (SEQ ID NO:44).

In one embodiment, the anti-podocalyxin domain comprises an amino acid sequence selected from the group consisting of: YTS (SEQ ID NO:45); YTSLAS (SEQ ID NO:46); and YTSLAS (SEQ ID NO:47).

In one embodiment, the anti-podocalyxin domain comprises an amino acid sequence selected from the group consisting of: AGVYEGSSDNRA (SEQ ID NO:48); AGVYEGSSDNRA (SEQ ID NO:49); and AGVYEGSSDNRA (SEQ ID NO:50).

In one embodiment, the anti-podocalyxin domain comprises an amino acid sequence selected from the group consisting of: SEQ ID NOs: 33-35; and further comprises an amino acid sequence selected from the group consisting of SEQ ID NOs: 36-38; and further comprises an amino acid sequence selected from the group consisting of SEQ ID NOs: 39-41.

In one embodiment, the anti-podocalyxin domain comprises an amino acid sequence selected from the group consisting of: SEQ ID NOs: 42-44; and further comprises an amino acid sequence selected from the group consisting of SEQ ID NOs: 45-47; and further comprises an amino acid sequence selected from the group consisting of SEQ ID NOs: 48-50.

In one embodiment, the anti-podocalyxin domain comprises an amino acid sequence selected from the group consisting of: SEQ ID NOs: 33-35; and further comprises an amino acid sequence selected from the group consisting of SEQ ID NOs: 36-38; and further comprises an amino acid sequence selected from the group consisting of SEQ ID NOs: 39-41; and further comprises an amino acid sequence selected from the group consisting of SEQ ID NOs: 42-44; and further comprises an amino acid sequence selected from the group consisting of SEQ ID NOs: 45-47; and further comprises an amino acid sequence selected from the group consisting of SEQ ID NOs: 48-50.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

The invention also includes treating a malignancy or an autoimmune disease in which chemotherapy and/or immunotherapy in a patient results in significant immunosuppression in the patient, thereby increasing the risk of the patient of developing a malignancy (e.g., CLL).

The invention includes using T cells expressing an anti-podocalyxin antibody derived CAR including both CD3-zeta and either the 4-1BB or CD28 costimulatory domain (also referred to as CARTPODO T cells). The CARTPODO T cells of the invention can undergo robust in vivo T cell expansion and can establish memory cells specific for cells displaying podocalyxin tumor epitope, which memory cells persist at high levels for an extended amount of time in blood and bone marrow.

The present invention provides chimeric antigen receptor (CAR) comprising an extracellular and intracellular domain. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the CAR of the invention comprises a target-specific binding element otherwise referred to as an antigen binding moiety, or targeting arm. Antigen binding moieties used in the present invention are capable of binding the podocalyxin tumor epitope. As such, the antigen binding moiety is chosen to recognize a ligand that acts as a cell surface marker on target cells associated with a particular disease state.

A CAR of the invention is engineered to target a cell displaying the podocalyxin tumor epitope by way of engineering an appropriate antigen binding moiety that specifically binds to the podocalyxin tumor epitope.

Preferably, the antigen binding moiety portion in the CAR of the invention is scFV, or scFab wherein the nucleic acid sequence of the scFV comprises the nucleic acid sequence(s) of one or more light chain CDRs and one or more heavy chain CDRs disclosed herein for anti-podocalyxin antibodies, and wherein the nucleic acid sequence of the scFab comprises the nucleic acid sequence(s) of one or more light chain CDRs and one or more heavy chain CDRs disclosed herein for anti-podocalyxin antibodies.

Preferably, the antigen binding moiety portion in the CAR of the invention is an scFV, or scFab comprising an amino acid sequence selected from the group consisting of: GFSLSGYQ (SEQ ID NO:33); GFSLSGY (SEQ ID NO:34); and GYQMN (SEQ ID NO:35).

Preferably, the antigen binding moiety portion in the CAR of the invention is an scFV, or scFab comprising an amino acid sequence selected from the group consisting of: IWSDGGT (SEQ ID NO:36); WSDGG (SEQ ID NO:37); and YIWSDGGTDYASWAKG (SEQ ID NO:38).

Preferably, the antigen binding moiety portion in the CAR of the invention is an scFV, or scFab comprising an amino acid sequence selected from the group consisting of: AREGYWLGAFDP (SEQ ID NO:39); EGYWLGAFDP (SEQ ID NO:40); and EGYWLGAFDP (SEQ ID NO:41).

Preferably, the antigen binding moiety portion in the CAR of the invention is an scFV, or scFab comprising an amino acid sequence selected from the group consisting of: QSVHHKND (SEQ ID NO:42); QSSQSVHHKNDLA (SEQ ID NO:43); and QSSQSVHHKNDLA (SEQ ID NO:44).

Preferably, the antigen binding moiety portion in the CAR of the invention is an scFV, or scFab comprising an amino acid sequence selected from the group consisting of: YTS (SEQ ID NO:45); YTSLAS (SEQ ID NO:46); and YTSLAS (SEQ ID NO:47).

Preferably, the antigen binding moiety portion in the CAR of the invention is an scFV, or scFab comprising an amino acid sequence selected from the group consisting of: AGVYEGSSDNRA (SEQ ID NO:48); AGVYEGSSDNRA (SEQ ID NO:49); and AGVYEGSSDNRA (SEQ ID NO:50).

Preferably, the antigen binding moiety portion in the CAR of the invention is an scFV, or scFab comprising an amino acid sequence selected from the group consisting of: SEQ ID NOs: 33-35; and further comprises an amino acid sequence selected from the group consisting of SEQ ID NOs: 36-38; and further comprises an amino acid sequence selected from the group consisting of SEQ ID NOs: 39-41.

Preferably, the antigen binding moiety portion in the CAR of the invention is an scFV, or scFab comprising an amino acid sequence selected from the group consisting of: SEQ ID NOs: 42-44; and further comprises an amino acid sequence selected from the group consisting of SEQ ID NOs: 45-47; and further comprises an amino acid sequence selected from the group consisting of SEQ ID NOs: 48-50.

Preferably, the antigen binding moiety portion in the CAR of the invention is an scFV, or scFab comprising an amino acid sequence selected from the group consisting of: SEQ ID NOs: 33-35; and further comprises an amino acid sequence selected from the group consisting of SEQ ID NOs: 36-38; and further comprises an amino acid sequence selected from the group consisting of SEQ ID NOs: 39-41; and further comprises an amino acid sequence selected from the group consisting of SEQ ID NOs: 42-44; and further comprises an amino acid sequence selected from the group consisting of SEQ ID NOs: 45-47; and further comprises an amino acid sequence selected from the group consisting of SEQ ID NOs: 48-50.

In one embodiment, the antigen binding moiety portion in the CAR of the invention is an scFV, or scFab comprising an amino acid sequence having about 80%, 85%, 90%, or 95% identity to the SEQ ID NOs recited above.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Preferably, the transmembrane domain in the CAR of the invention is the CD8 transmembrane domain. In one embodiment, the CD8 transmembrane domain comprises the nucleic acid sequence of SEQ ID NO: 16 of U.S. Pat. No. 9,102,760. In one embodiment, the CD8 transmembrane domain comprises the nucleic acid sequence that encodes the amino acid sequence of SEQ ID NO: 22 of U.S. Pat. No. 9,102,760. In another embodiment, the CD8 transmembrane domain comprises the amino acid sequence of SEQ ID NO: 22 of U.S. Pat. No. 9,102,760. In another embodiment, sequences disclosed herein in Table 2 are used.

In some instances, the transmembrane domain of the CAR of the invention comprises the CD8a hinge domain. In one embodiment, the CD8 hinge domain comprises the nucleic acid sequence of SEQ ID NO: 15 of U.S. Pat. No. 9,102,760. In one embodiment, the CD8 hinge domain comprises the nucleic acid sequence that encodes the amino acid sequence of SEQ ID NO: 21 of U.S. Pat. No. 9,102,760. In another embodiment, the CD8 hinge domain comprises the amino acid sequence of SEQ ID NO: 21 of U.S. Pat. No. 9,102,760. In another embodiment, sequences disclosed herein in Table 2 are used.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence set forth in SEQ ID NO: 17 of U.S. Pat. No. 9,102,760 and the signaling domain of CD3-zeta comprises the nucleic acid sequence set forth in SEQ ID NO: 18 of U.S. Pat. No. 9,102,760. In another embodiment, sequences disclosed herein in Table 2 are used.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence that encodes the amino acid sequence of SEQ ID NO: 23 of U.S. Pat. No. 9,102,760 and the signaling domain of CD3-zeta comprises the nucleic acid sequence that encodes the amino acid sequence of SEQ ID NO: 24 of U.S. Pat. No. 9,102,760. In another embodiment, sequences disclosed herein in Table 2 are used.

In one embodiment, the cytoplasmic domain in the CAR of the invention is designed to comprise the signaling domain of 4-1BB and the signaling domain of CD3-zeta, wherein the signaling domain of 4-1BB comprises the amino acid sequence set forth in SEQ ID NO: 23 of U.S. Pat. No. 9,102,760 and the signaling domain of CD3-zeta comprises the amino acid sequence set forth in SEQ ID NO: 24 of U.S. Pat. No. 9,102,760. In another embodiment, sequences disclosed herein in Table 2 are used.

Vectors

The present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises an anti=podocalyxin antibody derived scFv, human CD8 hinge and transmembrane domain, and human 4-1BB and CD3zeta signaling domains.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

In addition to the methods described above, the following methods may be used.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20.degree. C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+T$ cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used.

For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (TH, $CD4^+$) that is greater than the cytotoxic or suppressor T cell population (Tc, $CD8^+$). Ex vivo expansion of T cells by stimulating CD3 and CD28 receptors produces a population of T cells that prior to about days 8-9 consists predominately of TH cells, while after about days 8-9, the population of T cells comprises an increasingly greater population of Tc cells. Accordingly, depending on the purpose of treatment, infusing a subject with a T cell population comprising predominately of TH cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) transduced with a lentiviral vector (LV). For example, the LV encodes a CAR that combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. In certain embodiments, CAR T cells can be used therapeutically for patients suffering from non-hematological tumors such as solid tumors arising from breast, CNS, and skin malignancies.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one aspect, CAR T cells may be used for ex vivo immunization. With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. In certain embodiments, 1 to 10 mg per day is used. In other embodiments, larger doses of up to 40 mg per day may be used (for example as described in U.S. Pat. No. 6,120,766).

H. Articles of Manufacture and Kits

Another embodiment of the invention is an article of manufacture containing materials useful for the treatment, prevention and/or diagnosis of podocalyxin-expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosing the cancer condition and may have a sterile access port (for example the container may be an intravenous solution bag or a vial having a stopper pierceable by a hypodermic injection needle). At least one active agent in the composition is an anti-podocalyxin antibody of the invention. The label or package insert indicates that the composition is used for treating cancer. The label or package insert will further comprise instructions for administering the antibody composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for podocalyxin-expressing cell killing assays, for purification or immunoprecipitation of podocalyxin polypeptide from cells. For isolation and purification of podocalyxin polypeptide, the kit can contain an anti-podocalyxin antibody coupled to beads (e.g., sepharose beads). Kits can be provided which contain the antibodies for detection and quantitation of podocalyxin polypeptide in vitro, e.g., in an ELISA or a Western blot. As with the article of manufacture, the kit comprises a container and a label or package insert on or associated with the container. The container holds a composition comprising at least one anti-podocalyxin antibody of the invention. Additional containers may be included that contain, e.g., diluents and buffers, control antibodies. The label or package insert may provide a description of the composition as well as instructions for the intended in vitro or detection use.

I. Method of Screening

Yet another embodiment of the present invention is directed to a method of determining the presence of a podocalyxin polypeptide in a sample suspected of containing the podocalyxin polypeptide, wherein the method comprises exposing the sample to an antibody that binds to the podocalyxin polypeptide and determining binding of the antibody to the podocalyxin polypeptide in the sample, wherein the presence of such binding is indicative of the presence of the podocalyxin polypeptide in the sample. Optionally, the sample may contain cells (which may be cancer cells) suspected of expressing the podocalyxin polypeptide. The antibody employed in the method may optionally be detectably labeled, attached to a solid support, or the like.

Another embodiment of the present invention is directed to a method of diagnosing the presence of a tumor in a mammal, wherein the method comprises (a) contacting a test sample comprising tissue cells obtained from the mammal with an antibody that binds to a podocalyxin polypeptide and (b) detecting the formation of a complex between the antibody and the podocalyxin polypeptide in the test sample, wherein the formation of a complex is indicative of the presence of a tumor in the mammal. Optionally, the antibody is detectably labeled, attached to a solid support, or the like, and/or the test sample of tissue cells is obtained from an individual suspected of having a cancerous tumor. Antibody detection can be achieved via different techniques as described herein, e.g., IHC and PET imaging.

IV. Further Methods of Using Anti-Podocalyxin Antibodies

A. Therapeutic Methods

An antibody of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-podocalyxin antibody under conditions permissive for binding of the antibody to podocalyxin. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In certain embodiments, the cell is a B cell. In certain embodiments, the cell is a xenograft, e.g., as exemplified herein. The antibodies may also (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind.

In one aspect, an antibody of the invention is used to treat or prevent a cell proliferative disorder. In certain embodiments, the cell proliferative disorder is associated with increased expression and/or activity of podocalyxin. For example, in certain embodiments, the cell proliferative disorder is associated with increased expression of podocalyxin on the surface of a cell. In certain embodiments, the cell proliferative disorder is a tumor or a cancer.

In one aspect, the invention provides methods for treating a cell proliferative disorder comprising administering to an individual an effective amount of an anti-podocalyxin antibody.

In one embodiment, an anti-podocalyxin antibody can be used in a method for binding podocalyxin in an individual suffering from a disorder associated with increased podocalyxin expression and/or activity, the method comprising administering to the individual the antibody such that podocalyxin in the individual is bound. In one embodiment, the podocalyxin is human podocalyxin, and the individual is a human individual. An anti-podocalyxin antibody can be administered to a human for therapeutic purposes. Moreover, an anti-podocalyxin antibody can be administered to a non-human mammal expressing podocalyxin with which the antibody cross-reacts (e.g., a primate, pig, rat, or mouse) for veterinary purposes or as an animal model of human disease. Regarding the latter, such animal models may be useful for evaluating the therapeutic efficacy of antibodies of the invention (e.g., testing of dosages and time courses of administration).

An antibody of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

B. Activity Assays

Anti-podocalyxin antibodies of the invention may be characterized for their physical/chemical properties and/or biological activities by various assays known in the art.

1. Activity Assays

In one aspect, assays are provided for identifying anti-podocalyxin antibodies thereof having biological activity. Biological activity may include, e.g., the ability to inhibit cell growth or proliferation (e.g., "cell killing" activity), or the ability to induce cell death, including programmed cell death (apoptosis). Antibodies having such biological activity in vivo and/or in vitro are also provided.

In certain embodiments, an anti-podocalyxin antibody is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602,677. The assay may be conducted in 96- or 384-well format, making it amenable to automated high-throughput screening (HTS). See Cree et al (1995) AntiCancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

In one aspect, an anti-podocalyxin antibody is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) Cytotechnology, 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of 3×106 per dish in 100×20 mm dishes and allowed to attach overnight. The medium is removed and replaced with fresh medium alone or medium containing various concentrations of the antibody. The cells are incubated for a 3-day time period. Following treatment, monolayers are washed with PBS and detached by trypsinization. Cells are then centrifuged at 1200 rpm for 5 minutes at 4° C., the pellet resuspended in 3 ml cold Ca2+ binding buffer (10 mM Hepes, pH 7.4, 140 mM NaCl, 2.5 mM CaCl2) and aliquoted into 35 mm strainer-capped 12×75 mm tubes (1 ml per tube, 3 tubes per treatment group) for removal of cell clumps. Tubes then receive PI (10 µg/ml). Samples are analyzed using a FACSCAN™ flow cytometer and FACSCONVERT™ CellQuest software (Becton Dickinson). Antibodies which induce statistically significant levels of cell death as determined by PI uptake are thus identified.

In one aspect, an anti-podocalyxin antibody is tested for its ability to induce apoptosis (programmed cell death) in vitro. An exemplary assay for antibodies that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 µg/ml of the antibody. Following a three-day incubation period, monolayers are washed with PBS and detached by trypsinization. Cells are then centrifuged, resuspended in Ca2+ binding buffer, and aliquoted into tubes as discussed in the preceding paragraph. Tubes then receive labeled annexin (e.g. annexin V-FITC) (1 µg/ml). Samples are analyzed using a FACSCAN™ flow cytometer and FACSCONVERT™ CellQuest software (BD Biosciences). Antibodies that induce statistically significant levels of annexin binding relative to control are thus identified. Another exemplary assay for antibodies that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express podocalyxin or that have been engineered to express podocalyxin. Such cells include tumor cells that overexpress podocalyxin relative to normal cells of the same tissue origin. Such cells also include cell lines (including tumor cell lines) that express podocalyxin and cell lines that do not normally express podocalyxin but have been transfected with nucleic acid encoding podocalyxin.

In one aspect, an anti-podocalyxin antibody thereof is tested for its ability to inhibit cell growth or proliferation in vivo. In certain embodiments, an anti-podocalyxin antibody thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., a SCID mouse. An antibody of the invention is administered to the animal. The ability of the antibody to inhibit or decrease tumor growth is measured. In certain embodiments of the above xenograft system, the human tumor cells are tumor cells from a human patient. In certain embodiments, the human tumor cells are introduced into a suitably immunocompromised non-human animal by subcutaneous injection or by transplantation into a suitable site, such as a mammary fat pad.

2. Binding Assays and Other Assays

In one aspect, an anti-podocalyxin antibody is tested for its antigen binding activity. For example, in certain embodiments, an anti-podocalyxin antibody is tested for its ability to bind to podocalyxin expressed on the surface of a cell. A FACS assay may be used for such testing.

In one aspect, competition assays may be used to identify a monoclonal antibody that competes with a monoclonal antibody comprising the variable domains of SEQ ID NO: 27 and SEQ ID NO: 29 (FIG. 2) or a chimeric antibody comprising the variable domain of the monoclonal antibody comprising the sequences of SEQ ID NO: 27 and SEQ ID NO: 29 (FIG. 2) and constant domains from IgG1 for binding to podocalyxin. In certain embodiments, such a competing antibody binds to the same epitope (e.g., a linear or a conformational epitope) that is bound by a monoclonal antibody comprising the variable domains of SEQ ID NO: 27 and SEQ ID NO: 29 (FIG. 2) or a chimeric antibody comprising the variable domain of the monoclonal antibody comprising the sequences of SEQ ID NO: 27 and SEQ ID NO: 29 (FIG. 2) and constant domains from IgG1. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In an exemplary competition assay, immobilized podocalyxin is incubated in a solution comprising a first labeled antibody that binds to podocalyxin (e.g., a monoclonal antibody comprising the variable domains of SEQ ID NO: 27 and SEQ ID NO: 29 (FIG. 2) or a chimeric antibody comprising the variable domain of the monoclonal antibody comprising the sequences of SEQ ID NO: 27 and SEQ ID NO: 29 (FIG. 2) and constant domains from IgG1) and a second unlabeled antibody that is being tested for its ability to compete with the first antibody for binding to podocalyxin. The second antibody may be present in a hybridoma supernatant. As a control, immobilized podocalyxin is incubated in a solution comprising the first labeled antibody but not the second unlabeled antibody. After incubation under conditions permissive for binding of the first antibody to podocalyxin, excess unbound antibody is removed, and the amount of label associated with immobilized podocalyxin is measured. If the amount of label associated with immobilized podocalyxin is substantially reduced in the test sample relative to the control sample, then that indicates that the second antibody is competing with the first antibody for binding to podocalyxin. In certain embodiments, immobilized podocalyxin is present on the surface of a cell or in a membrane preparation obtained from a cell expressing podocalyxin on its surface.

In one aspect, purified anti-podocalyxin antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

The following examples are offered for illustrative purposes only, and are not intended to limit the scope of the present invention in any way.

All patent, patent application, and literature references cited in the present specification are hereby incorporated by reference in their entirety.

EXAMPLES

Antibody Production.

High-affinity, monoclonal antibodies (mAbs) were generated that specifically bind podocalyxin. The anti-podocalyxin antibody Podo-447, as well as others, were selected for further study.

FIG. 1 provides the amino acid sequence of human podocalyxin isoforms 1 and 2 (Accession Nos. NM_001018111.2 and NP_001018121.1). FIG. 2 provides the nucleic acid sequence for the heavy chain variable region (SEQ ID NO:12); the amino acid sequence for the heavy chain variable region (SEQ ID NO:27); the nucleic acid sequence for the light chain variable region (SEQ ID NO: 14); and the amino acid sequence for the light chain variable region (SEQ ID NO:29) of an anti-podocalyxin antibody (Podo447).

Tumour Cell Line Selectivity Panel Staining.

HUVEC cells were purchased from Pascal Bernatchez at St. Pauls Hospital and were grown at CDRD in Millipore EndoGro-VEGF (Cat# SCME002). T47D, MCF-7, and MDA-MB-231 human breast carcinoma cell lines and Ovarian carcinoma-derived CaOV-3, OVCAR-3, OVCAR-8, and OVCAR-10 cells were obtained from the Lab of Dr. Roskelly where they were grown in T75 Tissue culture flasks (BD Falcon#353136). The breast carcinoma cells were routinely maintained in DMEM/F12 medium (Sigma, St. Louis, Mo. cat# D6421) supplemented with 5% fetal bovine serum (FBS, Invitrogen, Carlsbad, Calif.) and insulin (5 μg/ml; Sigma, St. Louis, Mo. cat#19278). The Ovarian carcinoma-derived cells were routinely cultured in a 199/105 medium (Sigma, St. Louis, Mo. cat#s M4530/M6395) supplemented with 5% fetal bovine serum (FBS, invitrogen, Carlsbad, Calif.). A-172 (purchased from ATCC® CRL-1620™) were grown in T175 tissue culture flasks (BD Falcon 353112 at CDRD using DMEM (Gibco#10313-021)+10% Fetal Bovine Serum (FBS, Gibco#26140-079). 293 cells (293-6E, purchased from NCR-BRI) were grown in suspension (shaker flasks, Corning #431145) using FreeStyle™ 293 Expression Medium (Gibco#12338-018)+Pluronic (Gibco #24040-032). Adherent cells first had their medium aspirated, and then were washed using 5 mL sterile PBS (Gibco#100-10-049). The PBS wash was discarded and replaced by 3 mL of cell dissociation buffer (Sigma Cat # C5914). The cells were incubated at 37° C./5% $CO_2$ for 30 minutes. 7 mL DMEM+10% FBS was used to disperse the cells and the resulting 10 mL cell suspensions were transferred to 15 mL conical tubes (BD Falcon #352096). 293 cells were taken directly from their culture flask and were transferred to a 15 mL conical tube. The cell suspensions were counted using the ViCell (Beckman Coulter) and 15-50000 cells/well were seeded into V-bottom 96-well plates (Sarstedt#82.1583.001). Cells were pelleted by centrifugation at 400 g for 3 minutes. The supernatants were discarded. The cell pellets were then resuspended using 15 uL of 5 ug/mL protein G (GE: Protein G HP, 1 mL #17-0404-03) purified Anti-PODO (chimeric Rabbit/Human IgG1) diluted in PBS+1% FBS (FACS buffer). Cells and antibody were incubated on ice for 1 hour. Wash Procedure: 200 uL ice cold FACS buffer added to each well, centrifuge the plate at 400 g for 3 minutes (4° C.) to pellet cells, discard the diluted primary antibody, resuspend the cell pellets in 200 uL FACS buffer, ensuring pellet is disrupted, centrifuge plate at 400 g for 3 minutes to pellet cells, discard the supernatant. To detect cell-bound primary antibody, the cells were then resuspended in 25 uL/well fluorescently-labelled secondary antibody (5 ug/mL, Goat anti-Human IgG-Fc-Alexa Fluor® 647; Jackson ImmunoResearch #109-605-098) plus a viability dye (2 ug/mL, 7-actinomycin-D; Sigma # A9400) which were diluted together in FACS buffer. Incubate plates on ice for 0.5 hours. Repeat the same wash procedure as above. Resuspend each well in 100 uL FACS buffer and analyse by flow cytometry (IntelliCyt High-throughput Flow Cytometer, 3 second sip, 1.5 second up, 15 RPM pump speed). Results were analysed using IntelliCyt Hyperview Software. 7-actinomycin-D positive events (dead cells) were excluded from the analysis. The results are expressed as geometric mean fluorescence units.

Glycoepitope Mapping (for Podo83 and Podo447 Anti-Podo Antibody Comparison)

Enzyme Treatment SKOV3 ovarian carcinoma cells were removed from adherent culture and a single cell suspension was generated using enzyme-free cell dissociation buffer. The cell suspension was then spun down and washed with buffer ($Ca^{2+}$-free DMEM/F12 base media+2 mM $CaCl_2$+ 0.1% BSA). $5 \times 10^5$ cells were treated in suspension for 45 min at 37° C. (in microfuge tube in the incubator; flicked tube every 10 min) in 100 ul buffer (Ca-free media+2 mM $CaCl_2$+0.1% BSA) with either 1000 U/mL neuraminidase (New England Biolabs) or 0.2 mg/ml endopeptidase (O-sialoglycoprotein endopeptidase; Cedarlane) or buffer alone as control. Cells were washed with buffer and spun down to collect. Cells were either lysed in 30 ul RIPA or stained with antibodies for flow cytometry analysis. Regarding Podo83, see WO2015058301.

Flow Cytometry

Cells were incubated with antibodies in PBS+1% BSA. 3D3 was used at 1/50 dilution. 83 and 447 were used at 10 ug/ml. Secondary antibodies (anti-mouse-biotin for 3D3 or anti-human-biotin for 83 and 447) were used at 10 ug/ml. Cells were then incubated with streptavidin-APC. All incubations were for 30 min at 4° C. and were followed by 2 washes with PBS/BSA. For wheat germ agglutinin-647 staining, cells were incubated on ice in PBS for 15 min, followed by 3 washes.

WesternBlotting 20 ug of protein was run per lane on polyacrylamide gels. Transfer to PVDF membrane was performed in a wet transfer system at room temperature for 1.5 hours at 100V. Membranes were blocked with TBS-T/5% milk for 1 hour and then incubated with primary antibodies overnight at 4° C. 3D3 was used at a 1/10 dilution. 447 was used at 2 ug/ml and 83 was used at 1 ug/ml. Secondary antibodies (anti-mouse-HRP for 3D3 or anti-human-HRP for 447, 83) were used at 1/15,000.

Example 1—Development of Therapeutic Antibodies Against Podocalyxin

Antibodies that have the ability to bind podocalyxin, particularly podocalyxin present on tumor cells, have been developed. The antibodies have been observed to have favorable binding profiles based on flow cytometry screening of tumor cell lines known to express podocalyxin to varying degrees (A172, HUVEC, HEK 293, MDA-MB-231, MCF7, T47-D, CaOV3, OVCAR3, OVCAR10 and SKOV3) (FIG. 3). Based on the reactivity of the antibodies to podocalyxin by flow cytometry, certain candidate antibodies were selected for further analysis. Anti-podocalyxin antibodies were also evaluated in various in-vitro diagnostic assays to determine their ability to bind to tumor cells expressing podocalyxin.

Example 2—Podo447 and Podo83 FACS Profile in Tumor and Normal Cell Lines, and in Response to Hypoxia and Stroma A panel of cancer and normal cell lines from Breast, Prostate, Ovarian, Colon, Brain, Lung and Pancreas were tested for Podo83 and Podo447 reactivity (FIG. 4, Panel A). THP-1 cells were labeled with 5 µM CT670 and incubated overnight alone (FIG. 4, Panel B, solid line), with 150 µM Co2C12 (FIG. 4, Panel B, dashed line), or in co culture with M2-10B4 murinee bone marrow/stroma cells (10:1 target to stroma) (FIG. 4, Panel B, dotted line). The binding characteristics of certain anti-podocalyxin antibodies are summarized in the table provided in FIG. 5. Regarding Podo83, see also WO2015058301.

Example 3—Podo447 Staining of Normal and Malignant Tissue

Normal human and macaque kidney were stained with Podo83 and Podo447 at 1:1000 and 1:25 dilutions respectively (FIG. 6, Panel A). Normal Skin, Liver, Colon, Cerebum staining with Podo447 (FIG. 6, Panel B). Normal and malignant melanoma tissue microarray sections stained with Podo447 (FIG. 6, Panel C). Normal cerebellum and malignant glioblastoma tissue microarray staining with podo-447 (FIG. 6, Panel D). All tissues were formalin fixed, Podo447 dilution in Panels B, C, and D is at 1:700. The results demonstrate that Podo447 stains primary malignant tissues in glioblastoma, melanoma, and ovarian tumors and the intensity of staining correlates with the stage of disease. Accordingly, espression of the Podo447 epitope correlates with disease progression. Additional data is provided in FIG. 7 in table format.

Example 4—Identification of a Novel Posttranslational Modification of Podocalyxin Involved in Malignant Disease Anti-podocalyxin antibody Podo447 binds tumor-associated Podocalyxin with exceptionally high affinity, and does not appear to recognize WT Podocalyxin, at least in certain contexts, by IHC (FIG. 6, FIG. 7) or FACS (FIG. 4, Panel A). The epitope recognized by Podo447 is referred to herein as the "podocalyxin tumor epitope". Staining intensity of Podo447 in melanoma and glioblastoma tissue microarrays correlates with disease progression and is strongest in metastatic lesions (FIG. 6, FIG. 7). In breast cancers, Podocalyxin is implicated in escape of cancerous cells from the tumor bed into circulation and studies with patient derived glioblastoma cell lines have shown that podocalyxin expression is associated with clonogenic potential in tumor-sphere forming assays. Taken together these data suggest podocalyxin plays a role in escape of tumor initiating cells from primary lesions and may be a marker of cancer stem cells.

SKOV3 ovarian carcinoma cells were removed from adherent culture and a single cell suspension was generated using enzyme-free cell dissociation buffer. The cell suspension was then spun down and washed with buffer ($Ca^{2+}$-free DMEM/F12 base media+2 mM $CaCl_2$+0.1% BSA). $5 \times 10^5$ cells were treated in suspension for 45 min at 37° C. (in microfuge tube in the incubator; flicked tube every 10 min) in 100 ul buffer (Ca-free media+2 mM $CaCl_2$+0.1% BSA) with either 1000 U/mL neuraminidase (New England Biolabs) or 0.2 mg/ml endopeptidase (O-sialoglycoprotein endopeptidase; Cedarlane) or buffer alone as control. Cells were washed with buffer and spun down to collect. Cells were either lysed in 30 ul RIPA or stained with antibodies for flow cytometry analysis.

For glycoepitope mapping using flow cytometry, cells were incubated with antibodies in PBS+1% BSA. 3D3 (Abcam Catalogue # ab178566) was used at 1/50 dilution. Podo83 (sometimes referred to herein as "83"), and Podo447 (sometimes referred to herein as "447") were used at 10 ug/ml. Secondary antibodies (anti-mouse-biotin for 3D3 or anti-human-biotin for 83, and 447) were used at 10 ug/ml. Cells were then incubated with streptavidin-APC. All incubations were for 30 min at 4° C. and were followed by 2 washes with PBS/BSA. For wheat germ agglutinin-647 staining, cells were incubated on ice in PBS for 15 min, followed by 3 washes.

For glycoepitope mapping using western blotting, 20 ug of protein was run per lane on polyacrylamide gels. Transfer to PVDF membrane was performed in a wet transfer system at room temperature for 1.5 hours at 100V. Membranes were blocked with TBS-T/5% milk for 1 hour and then incubated with primary antibodies overnight at 4° C. 3D3 was used at a 1/10 dilution. 447 was used at 2 ug/ml and 83 was used at 1 ug/ml. Secondary antibodies (anti-mouse-HRP for 3D3 or anti-human-HRP for 447, 83) were used at 1/15,000.

Figure 8:
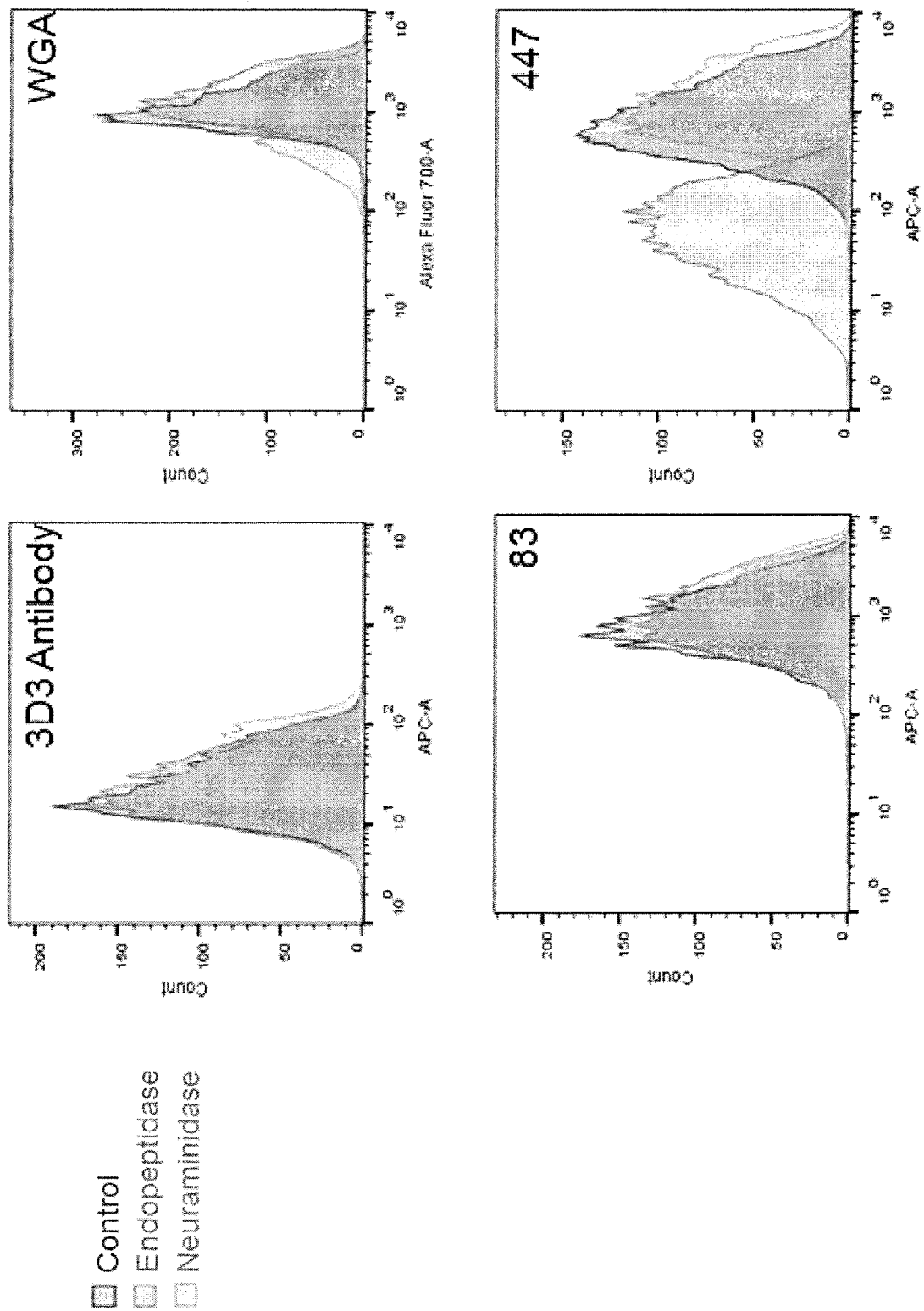
FIG. 8 is a set of graphs showing glycoepitope mapping for the 83 and 447 anti-Podo antibodies using flow cytometry.
Figure 9:
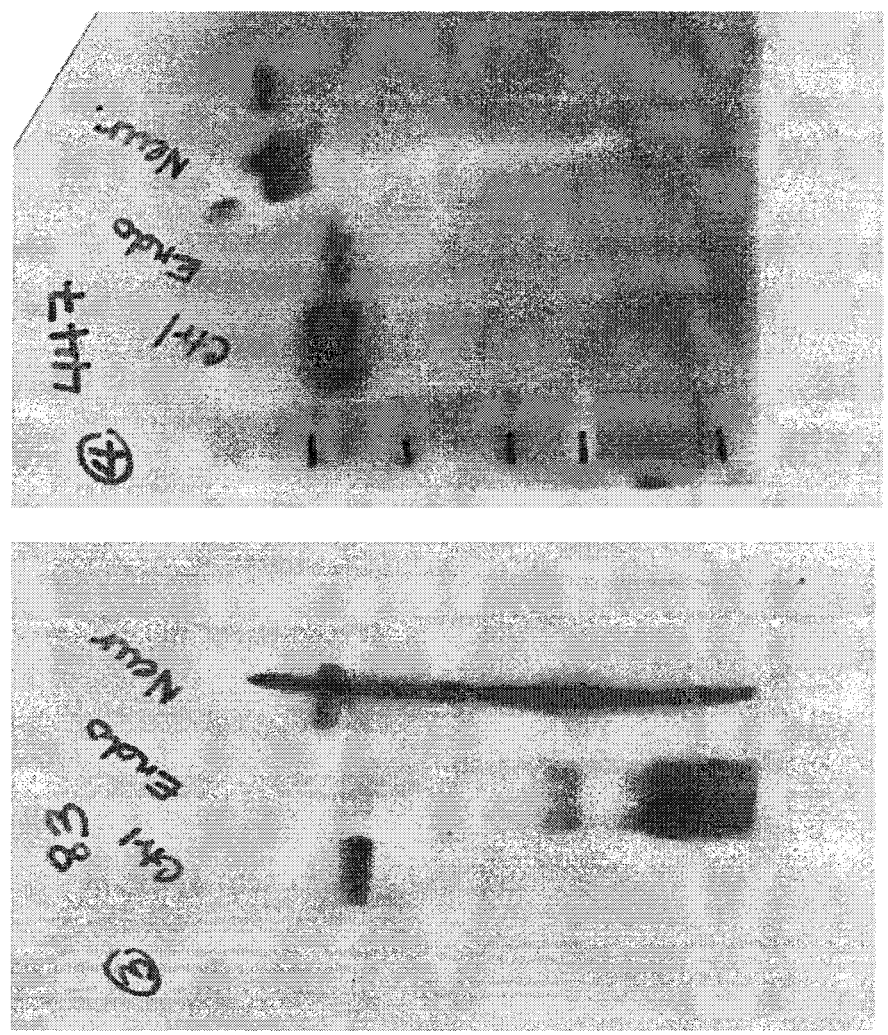
FIG. 9 is a set of images showing glycoepitope mapping for the 83 and 447 anti-Podo antibodies using Western blotting.

The flow cytometry and western blot analyses provide consistent results (FIGS. 8 and 9, respectively), demonstrating that the 3D3 and 83 antibodies bind regardless of endopeptidase or neuraminidase treatment while 447 antibodies still bind following neuraminidase treatment but do not bind following endopeptidase treatment. Thus, the PODO-447 epitope appears to rely on posttranslational modification of podocalyxin. Regarding Podo83 and Podo3D3, see WO2015058301. Note that Podo83 and Podo3D3 competitively bind podocalyxin, while neither competes with binding of Podo447 to podocalyxin. Hence, Podo83 and Podo3D3 do not bind the "podocalyxin tumor epitope" as defined herein.

FIG. 32: To further confirm that 447 binds a tumor displayed glycoepitope on podocalyxin and to begin characterizing this glycoepitope, we treated A172 glioblastoma cells with glycolyitic enzymes under live and denaturing conditions and then assessed the ability of 447 antibody to bind the modified forms of podocalyxin as compared to 3D3 antibody, which recognizes core pododocalyxin protein.

Specifically, for live cell treatments, cells were suspended in DMEM/F12 base medium (Sigma D9785) supplemented with 2 mM $CaCl_2$ and 0.1% bovine serum albumin at $5 \times 10^6$ cells/ml. Enzymes used and dilution: 1/10 O-sialoglycoprotein endopeptidase (Cedarlane cat# CLE100), 1/50 neuraminidase (NEB cat# P0720), 1/30 PNGaseF (N-glycanase; NEB cat# P0704), 1/15 O-glycosidase (NEB cat#P0733). The cells were incubated with enzymes for 1h45m at 37° C., followed by 2 washes, and then lysis in RIPA buffer. For denaturing conditions, cells were resuspended in 20 ul Glycoprotein denaturing buffer (NEB) and boiled for 10 min. To this, 4 ul of 10% NP-40, 4 ul of G7 reaction buffer (NEB), and $dH_2O$ was added to give a final reaction volume of 40 ul. Enzymes were added and incubated with denatured protein for 1 h at 37° C. Samples were separated by SDS-PAGE and blotted with either anti-human podocalyxin 3D3 antibody (1/10) or anti-human podocalyxin 447 (1/2500).

The data demonstrate that the enzymatic treatments had effects on the mobility of tumor displayed (A172-derived) podocalyxin. The major lower molecular weight form of endopeptidase-treated podocalyxin generated in live cells (as recognized by 3d3 antibody) was not recognized by the 447 antibody, which supports that the 447 antibody recognizes a glycoepitope. In addition, the data suggest that neuraminidase may increase the binding of the 447 antibody to A172-derived podocalyxin slightly. These results, in combination with the examples and findings infra, support that 447 recognizes a post-translational modification of tumor displayed podocalyxin polypeptide, which post-translational modification includes a beta-GalNAc that may be a terminal beta-GalNAc, and that the presence of sialic acid as a post-translational modification of tumor displayed podocalyxin polypeptide slightly reduces 447 binding, possibly as a sialic acid cap (under normal conditions) component of the post-translational modification of tumor displayed podocalyxin to which 447 binds.

FIG. 33: To begin to further characterize the glycoepitope on tumor-displayed podocalyxin recognized by the 447 antibody, podocalyxin from A172 glioblastoma cell lysates was first purified by immunoprecipitation and were then treated under denaturing condition with glycosidases and subjected to Western blotting.

Specifically, A172 cells were lysed in IP lysis buffer (20 mM Tris-HCl pH 7.5, 137 mM NaCl, 2 mM EDTA, 1% NP-40) with protease inhibitor cocktail (Roche). 500 ug of total protein in 500 ul IP lysis buffer was incubated with 10 ug of rabbit anti-human podocalyxin 447 at 4° C. overnight. Protein G agarose beads (Thermo) were added and incubated for 4h at 4° C. The beads were washed 3 times with IP lysis buffer. Protein was eluted from the beads by incubation with 0.2M glycine pH 2.6. Elution solution was neutralized with the addition of 1M Tris pH 8.3. 18 ul of the elution was added to 2 ul of 10× glycoprotein denaturing buffer (NEB) and samples were boiled for 10 min. To this, 4 ul of 10% NP-40, 4 ul of 10× G7 reaction buffer (NEB), and $dH_2O$ was added to give a final reaction volume of 40 ul. Enzymes were added and incubated with denatured protein for 1 h at 37° C. Enzymes used: 2 ul PNGaseF (N-glycanase; NEB cat# P0704), 2 ul neuraminidase (NEB cat# P0720), 2 ul O-glycosidase (NEB cat#P0733). Samples were separated by SDS-PAGE and blotted for either anti-human podocalyxin 3D3 antibody (1/10) or anti-human podocalyxin 447 (1/2500).

The data confirm that neuramininidase treatment slightly increases 447 binding to tumor displayed podocalyxin. In addition PNGase F (N-glycanase) treatment did not extinguish 447 binding to tumor displayed podocalyxin, supporting that the 447 epitope is not an N-linked glycan. The data also support that the 447 epitope of tumor displayed podocalyxin may include an O-glycanase resistant O-linked glycosylation.

Figure 10:
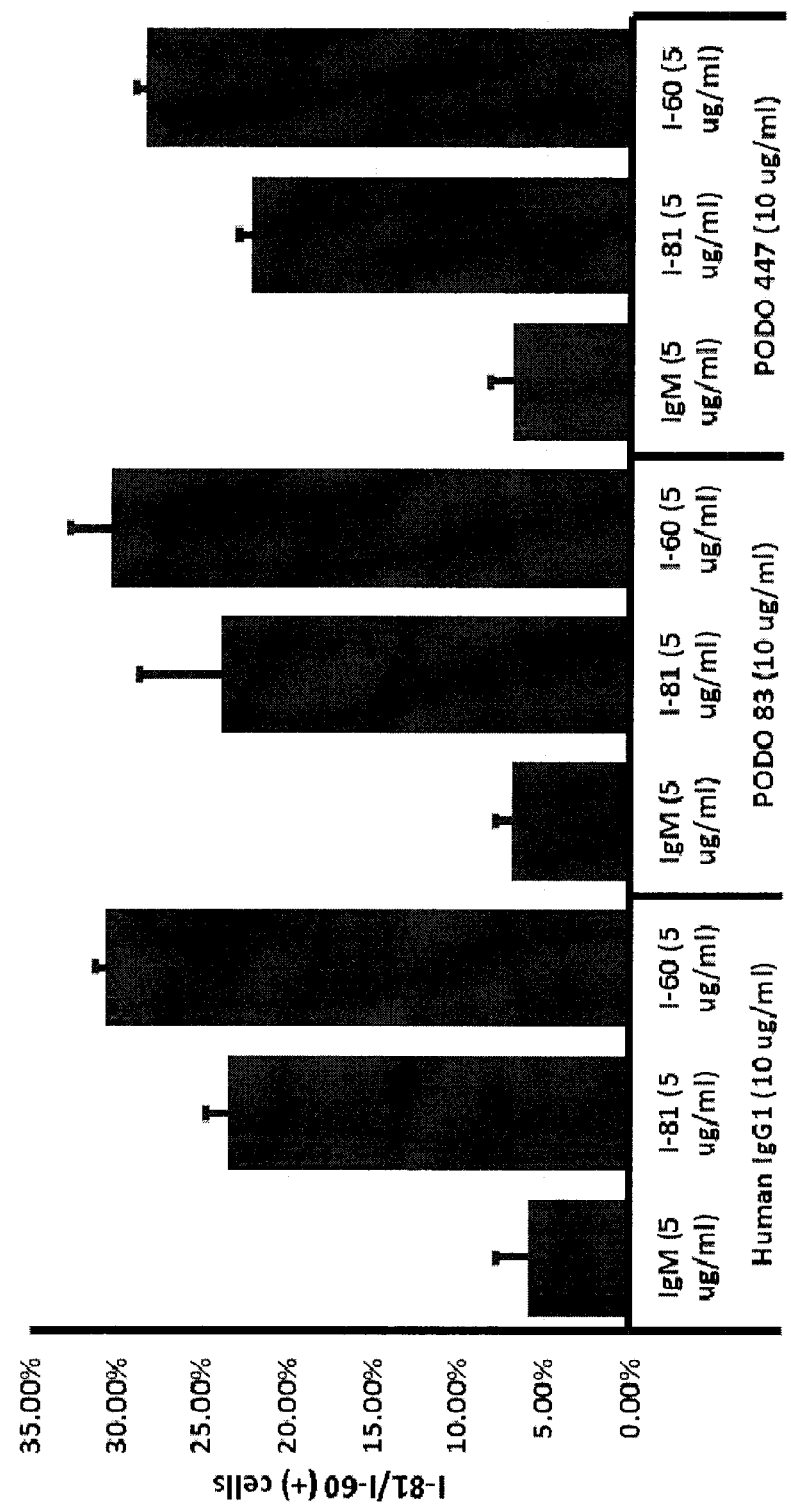
FIG. 10 is a graph of the competition assays used to establish that the Podo447 antibody recognizes a novel posttranslational modification of podocalyxin.

FIG. 10: To further assess the novelty of the the Podo447 epitope, competition assays were peformed against the human stem cell-defining antigens TRA-1-60 and TRA-1-81. A172 cells were incubated with Podo83 or Podo447 first (human IgG1 as control), followed by anti TRA 1-60 or anti-TRA 1-81 (murine IgM as control), washed, and stained with goat-anti-mouse IgM Cy5 conjugate. All incubations were done on ice until the FACS. As demonstrated in FIG. 10, Podo447 does not compete for Tra 1-60 or Tra 1-81 epitopes. Thus, the Podo447 antibody recognizes a novel posttranslational modification ofpodocalyxin involved in malignant disease. This epitope is referred to herein as the "podocalyxin tumor epitope".

Example 5—Tumor Microenvironment Effect on Podo447 Binding

Bone marrow stroma, as well as hypoxia, have been implicated as critical mediators of disease progression and chemotherapy resistance in acute myeloid leukemia. FIG. 11 shows FACS binding of PODO447 on OVCAR10 cells in response to co-culture with bone marrow stromal cells or CoC12. FIG. 11 supports that stromal co-culture upregulates tumor displayed podocalyxin recognized by Podo447.

Figure 13:
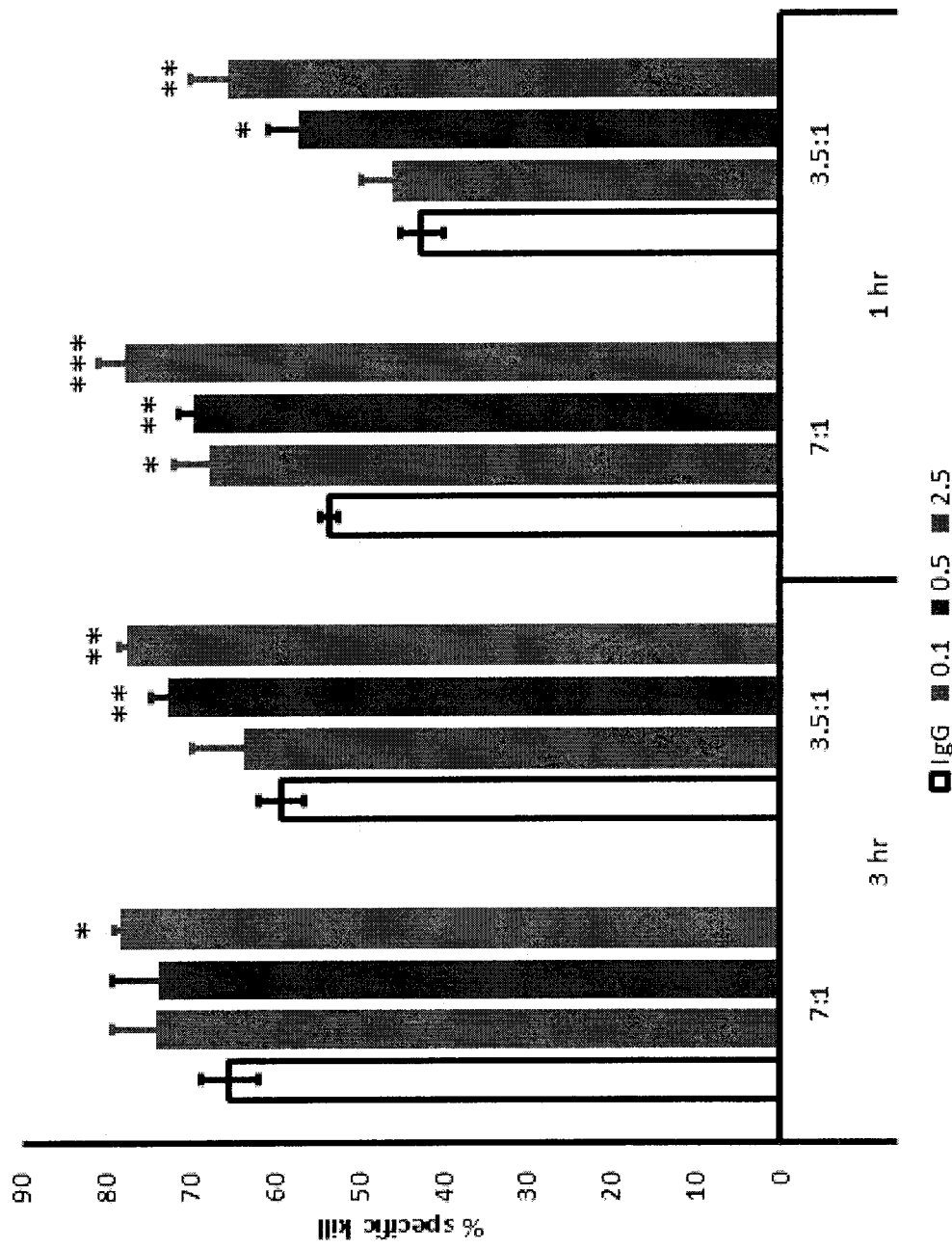
FIG. 13 is a graph that provides data from a human IgG1 chimeric Podo447 antibody that promotes antibody dependent cytotoxicity (ADCC).

Example 6—Podo447 Promotes Antibody Dependent Cytotoxicity (ADCC) and is Effective as an ADC Fluorescently labeled A172 cells were incubated with control human IgG1 (2.5 µg/ml), or increasing doses (0.1, 0.5, 2.5 µg/ml) of human IgG1 chimeric Podo447, followed by addition of human peripheral blood mononuclear cells at 7:1 or 3.5:1 effector:target ratios, for 1 hr or 3 hr. Killed A172 cells were quantitated by flow cytometry, and results are shown in FIG. 13, expressed as % specific kill. *=$p<0.05$; =$p<0.005$; *=$p<0.0005$ vs IgG control.

Figure 12:
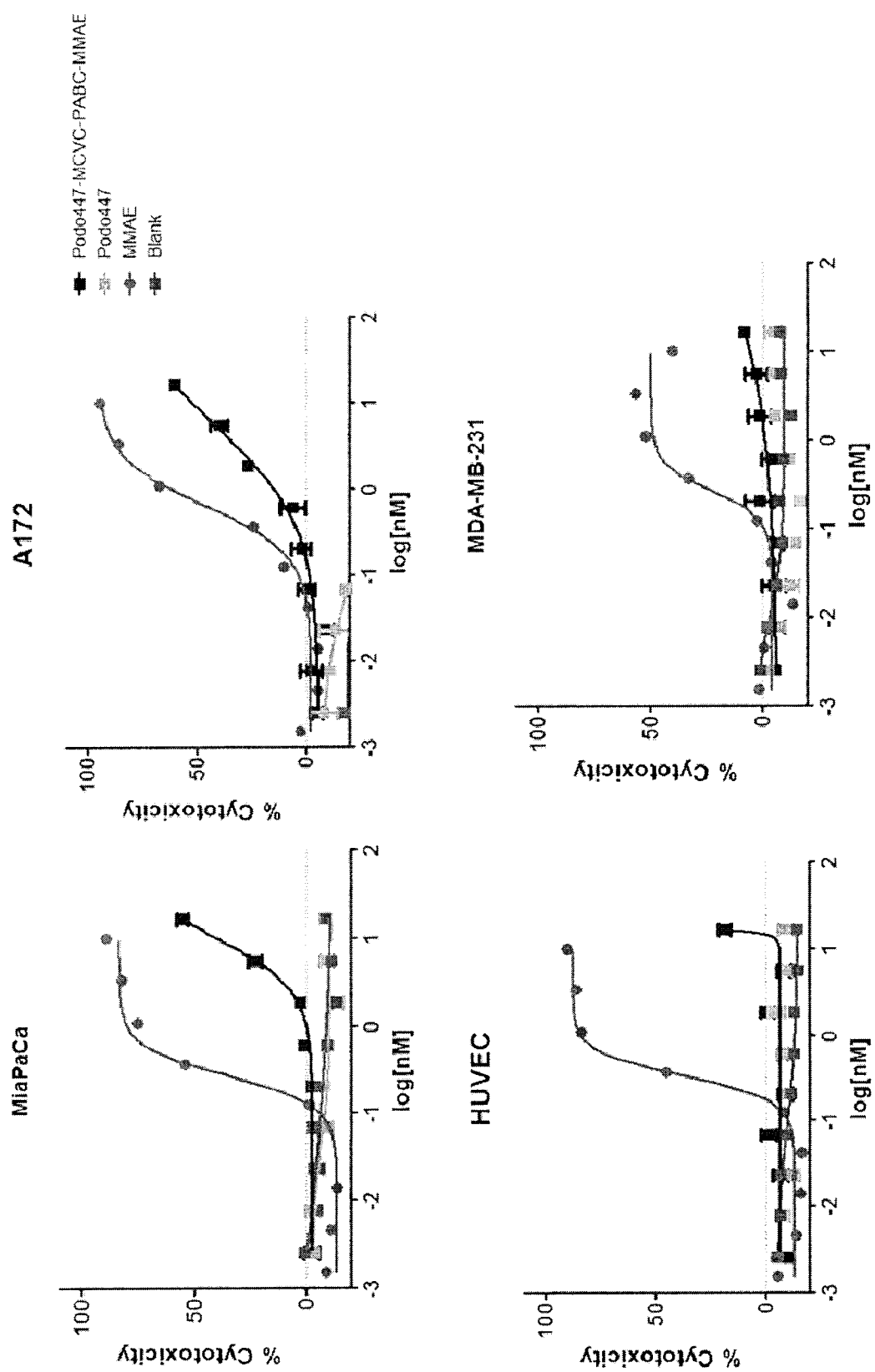
FIG. 12 is a set of graphs that provide cytolytic activity data of a Podo447 antibody drug conjugate on pancreatic (MiaPaCa), glioblastoma (A172), breast (MDA-MB231) and normal endothelial (HUVEC) cells.
Figure 14:
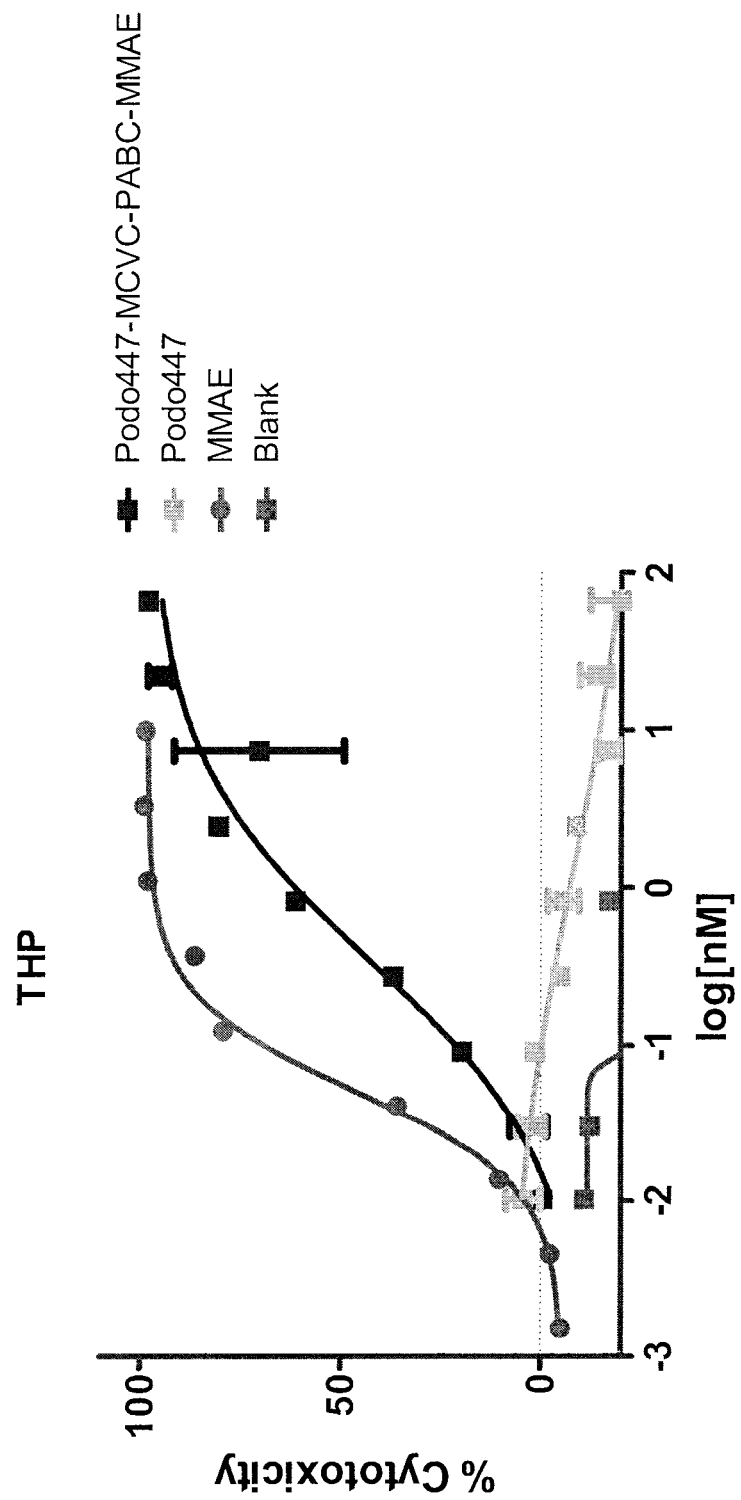
FIG. 14 is a graph that demonstrates a Podo447 conjugate is efficiently internalized and kills a THP-1 AML cell line.
Figure 15:
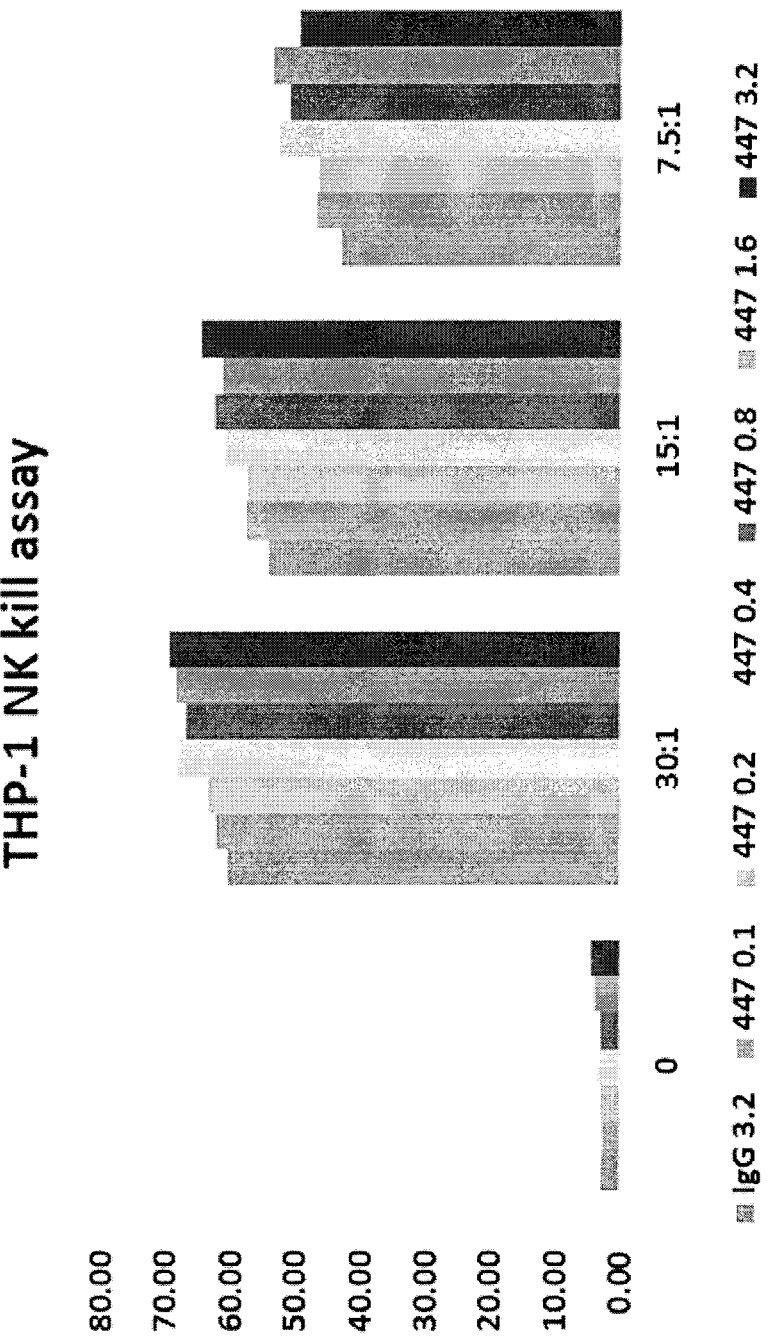
FIG. 15 is a graph that provides quantitation of enhancement of NK cytolytic activity by Podo447 at specific effector to target ratios.
Figure 16:
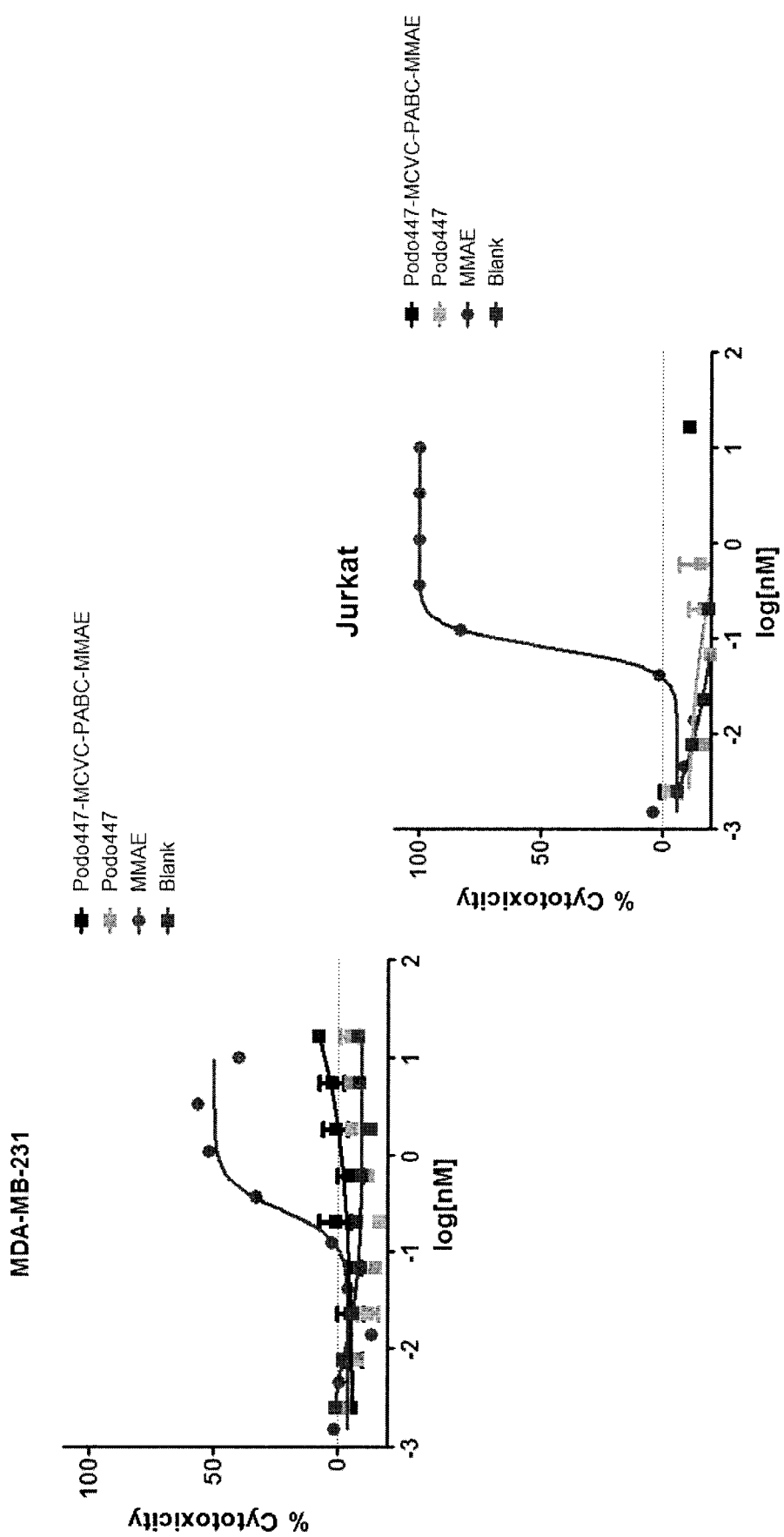
FIG. 16 is a graph that demonstrates Podo447 does not kill MDA-MB231 or Jurkat Cells.
Figure 17:
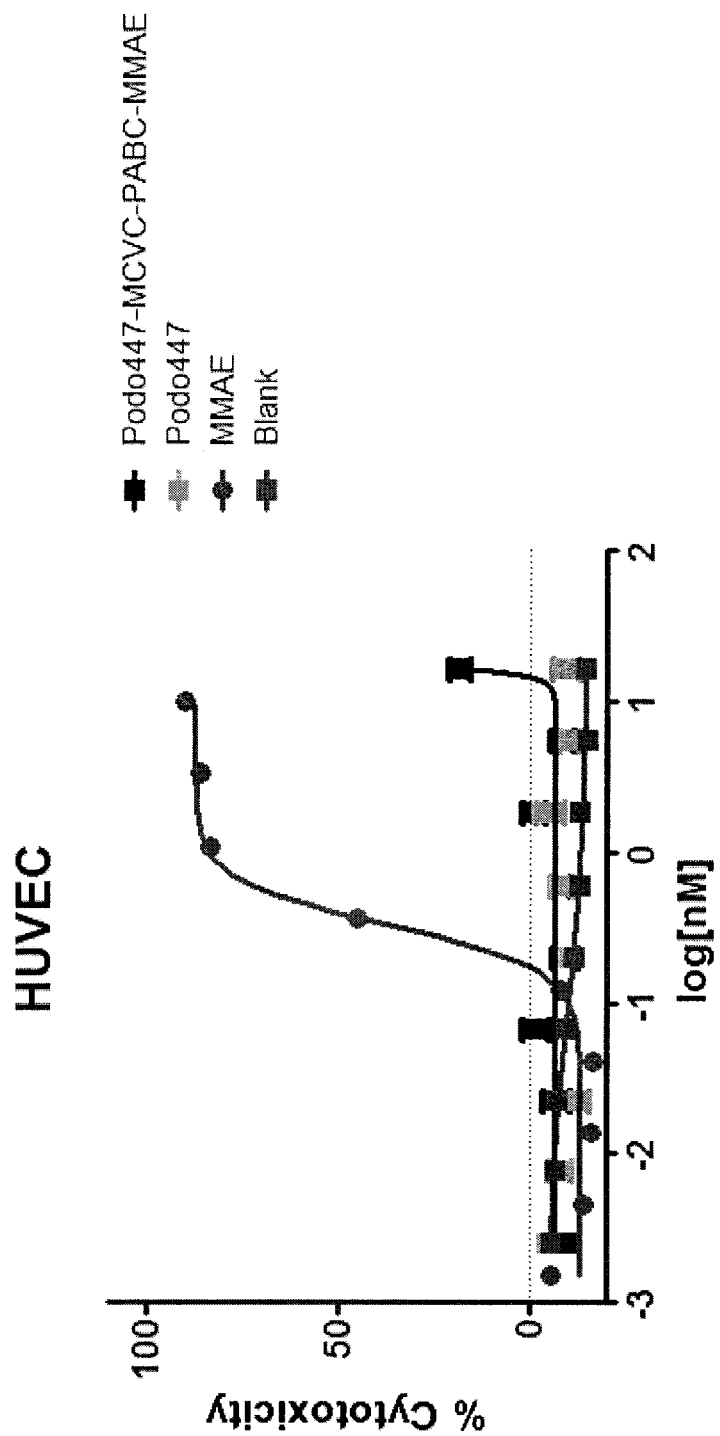
FIG. 17 is a graph that demonstrates Podo447 does not kill normal HUVEC cells.

As demonstrated in FIG. 12, Podo447 is efficiently internalized as an ADC and kills MiaPaCa and A172 cells. Additional data is provided in FIG. 13 demonstrating the effector:target ratios effective for Podo447 to kill A172 cells via antibody dependent cellular cytotoxicity (ADCC). FIG. 14 further demonstrates that Podo447 is efficiently internalized and kills a THP-1 AML cell line. However, Podo 447 was shown not to kill MDA-MB231 or Jurkat Cells (FIG. 16) or normal HUVEC cells (FIG. 17). Figure. 15 provides a quantitative depiction of the enhancement of NK cytolytic activity by Podo447 at specific effector to target ratios in the THP-1 assay.

Example 7—Use of Antibodies Specific to Podocalyzin Epitope for the Treatment of Multiple Tumor Types Using Podo447 conjugated with a microtubulin inhibitor, potent, dose-dependent cell killing in A172 glioblastoma and MiaPaCa pancreatic cancer cell lines has been demonstrated (FIG. 12). Importantly, no antibody dependent cytotoxicity in control HUVEC cells was observed. This potent tumor-specific killing is in vitro validation of the therapeutic potential of Podo447 as an antibody therapeutic.

Example 8—Humanization of the Podo447 Rabbit V-Gene Sequences

The Podo447 antibody is a recombinant rabbit human chimera utilizing the rabbit V genes and a human IgG1 constant region. In order to minimize potential immune response to the Podo447 CAR constructs rabbit V genes are replaced with human V-gene homologs. A series of V gene variants is generated based on sequence homology and CDR's grafted onto the framework scaffolds. These variants are then expressed as soluble scFv fragments or scFab fragments. Each construct is evaluated for binding affinity against recombinant podocalxin purified from A172 cells known to display the glyco-epitope of interest. Counter screening for specificity against WT podocalyxin expressed on HUVEC cells is also conducted. Constructs which retain affinity and specificity are evaluated for suitable physical and chemical properties including; stability, potential for aggregation, and likely post-translational modifications. Candidate scFv's are reformatted in the $2^{nd}$ and $3^{rd}$ generation CAR constructs and checked for expression in lymphocytes. Suitable human V-gene sequences are identified, which will support grafting of the rabbit CDR sequences without severely impacting the affinity and specificity of the parental construct. In the course of humanization, a small number of framework residues are identified which will impact binding affinity and which will be included in the final construct.

Figure 18:
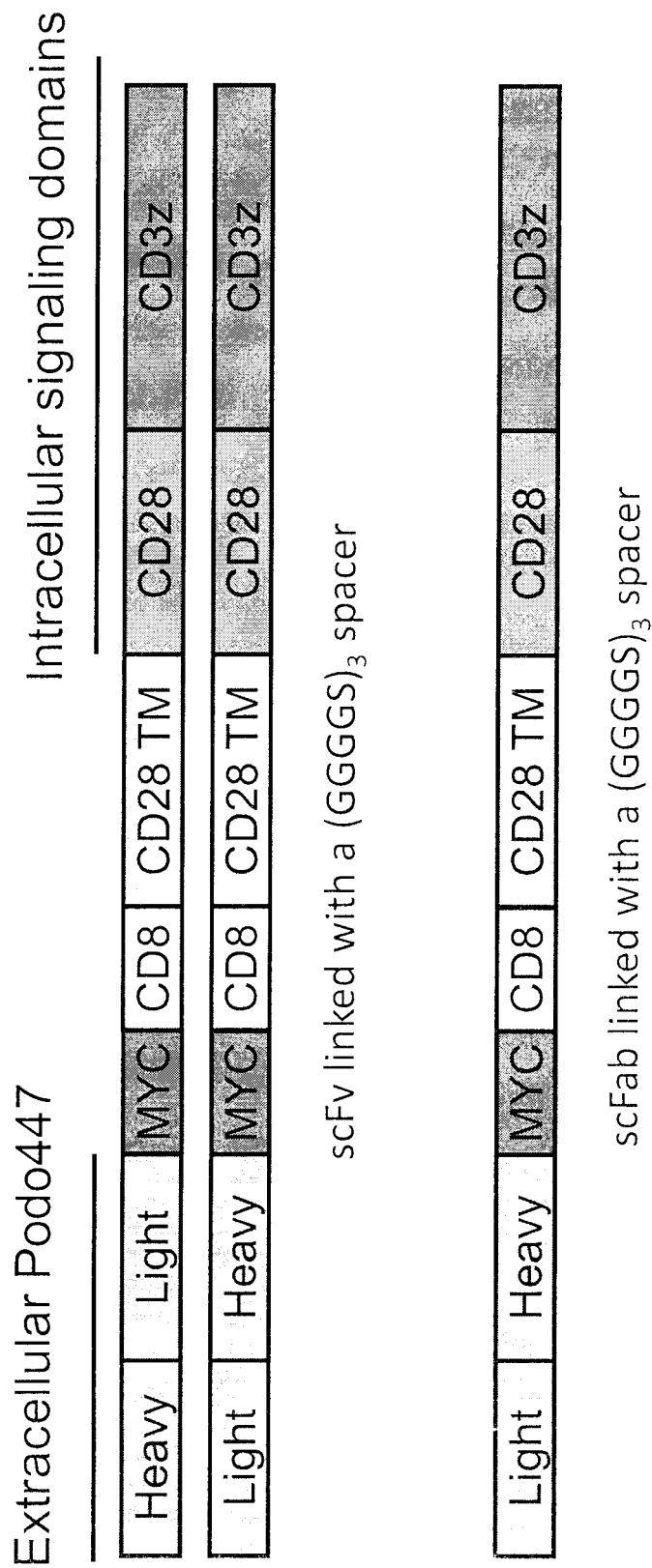
FIG. 18 is a schematic illustration of two different CAR T-cell constructs that comprise heavy and light chain binding domains of Podo447.
Figure 19:
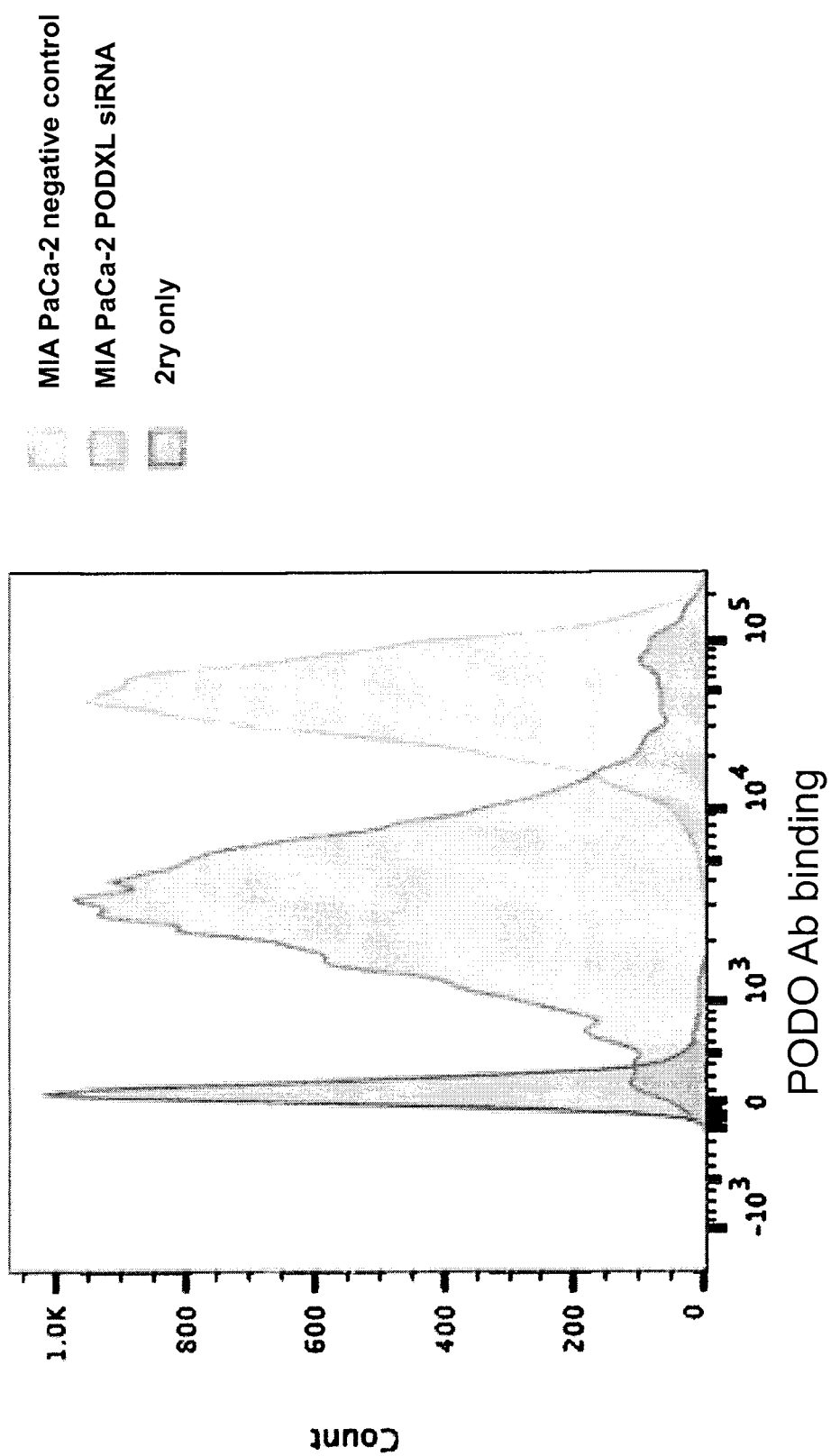
FIG. 19 is a graph showing loss of PODO 447 specific binding in MIA PaCa cells in which the PODXL gene expression has been knocked down with siRNA.
Figure 20:
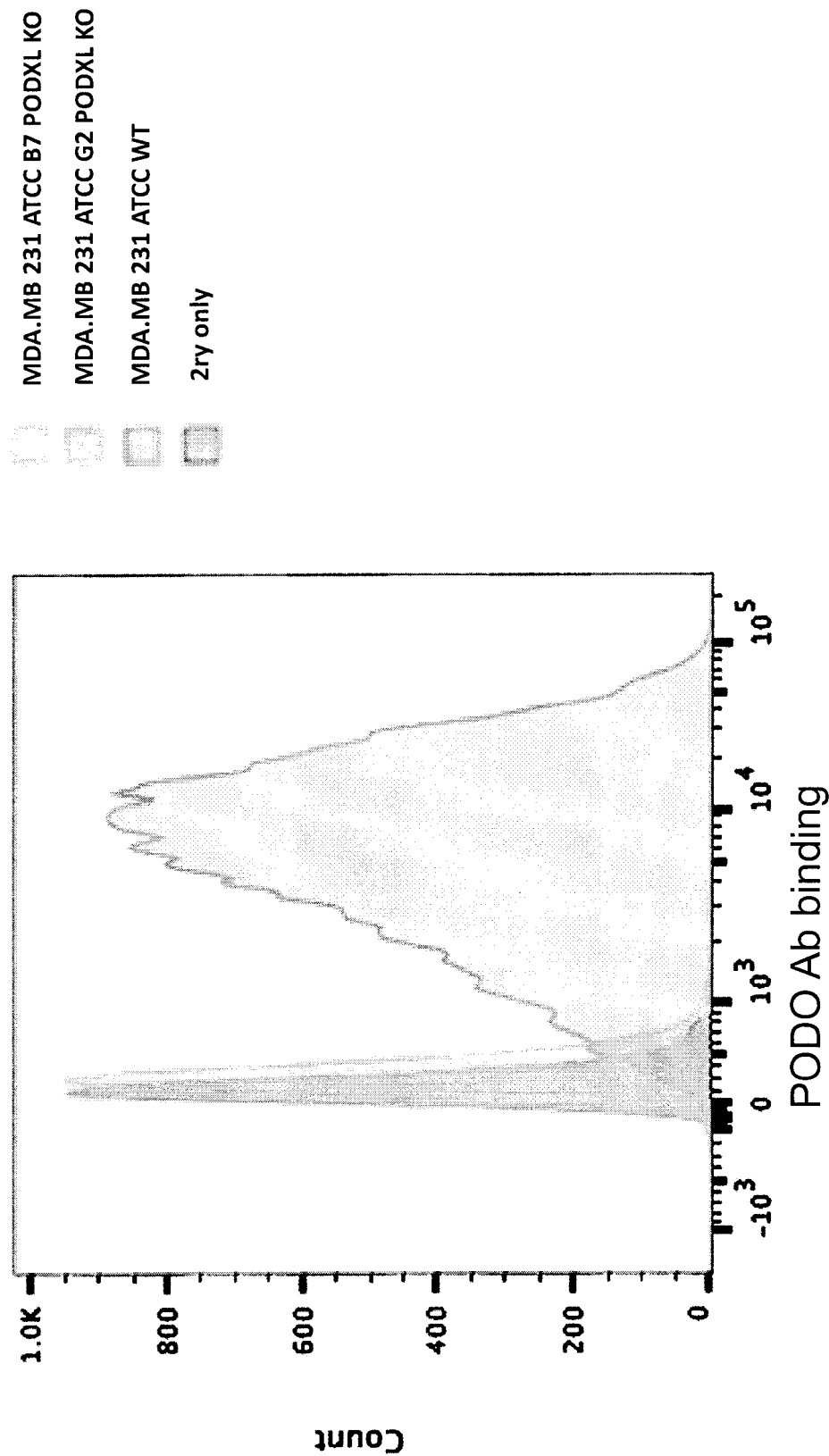
FIG. 20 is a graph showing loss of the PODO447 specific binding in MDA-MB231 breast cancer cells in which the PODXL gene expression has been knocked down by shRNA.
Figure 21:
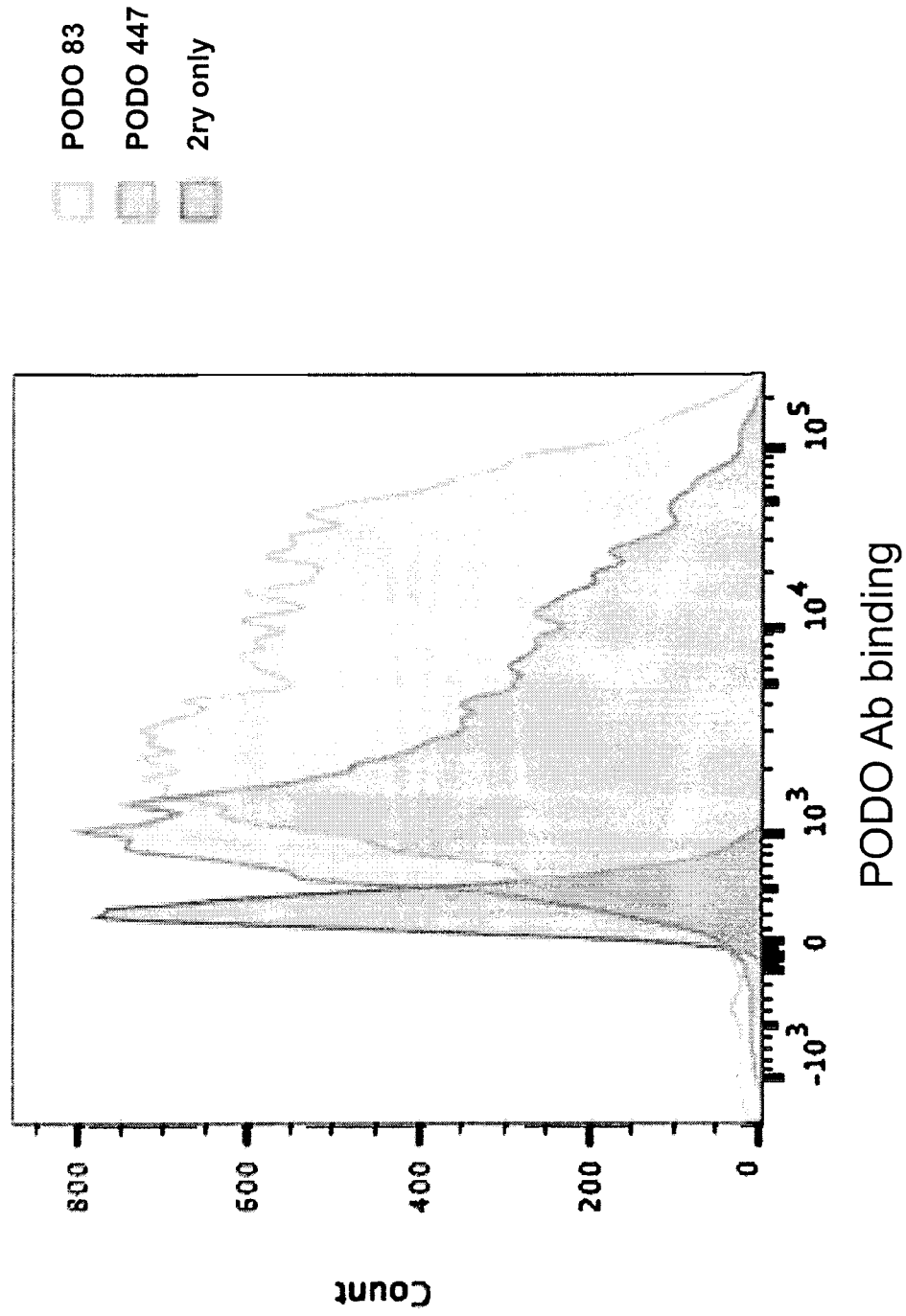
FIG. 21 is a figure showing the FACS binding profile of PODO447 and PODO83 antibodies on PANC-1 pancreatic cancer cells.
Figure 22:
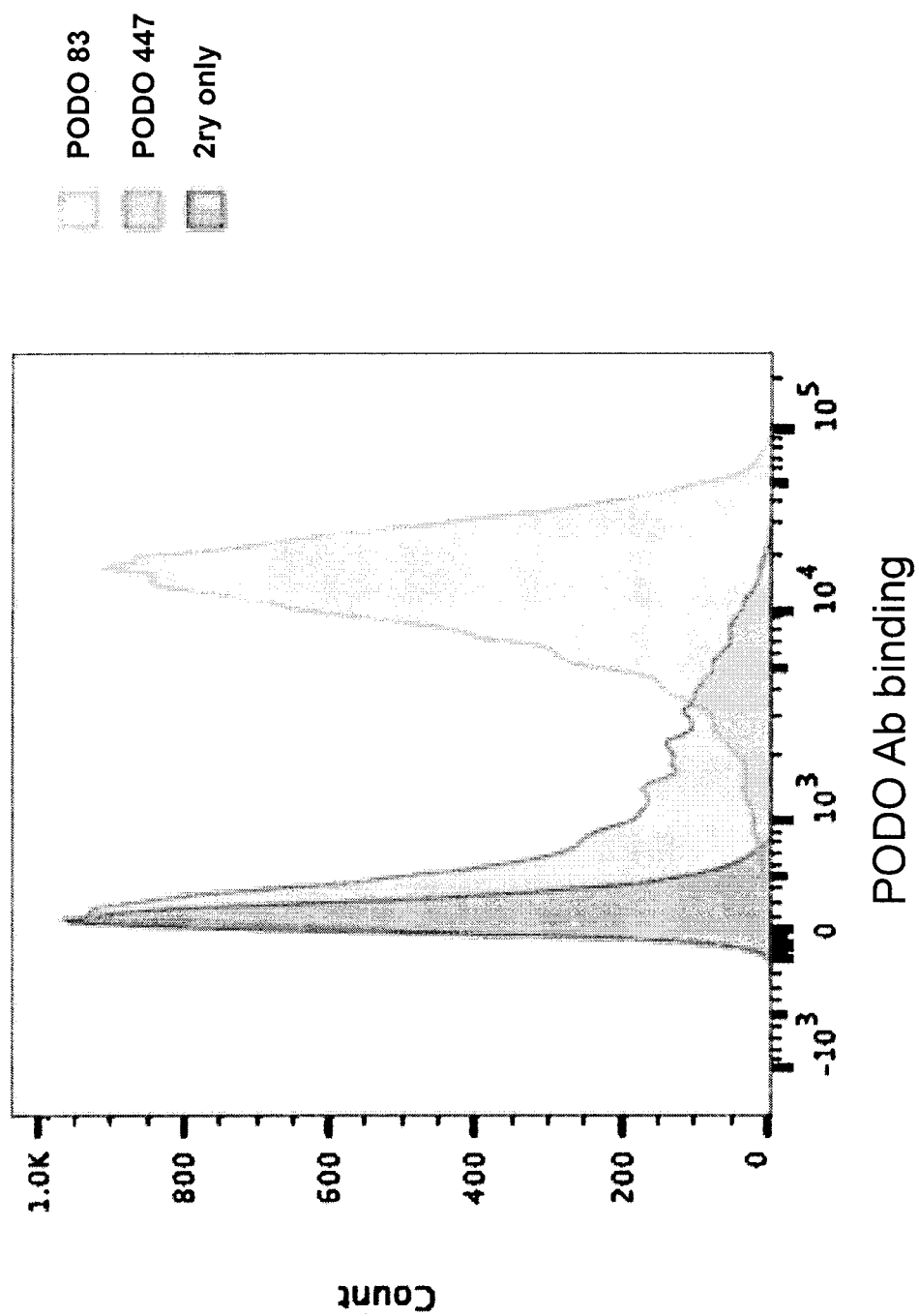
FIG. 22 is a figure showing the FACS binding profile of PODO447 and PODO83 antibodies on CFPAC-1 pancreatic cancer cells.

Example 9—Podo447 Single Chain Fv Incorporated into $2^{nd}$ and/or $3^{rd}$ Generation CAR Constructs Enables T Cells and NK Cells to Destroy Tumor Targets In Vitro and In Vivo Chimeric antigen receptor constructs for Podo447 were generated by cloning the humanized VH and VL sequences as either a scFV or scFAB into CD28-CD3 ($2^{nd}$ generation) and CD28-CD3-41BB ($3^{rd}$ generation) chimeric antigen receptor constructs. Lentivirus of the Podo447 enabled CAR constructs were generated and used to transduce CD3 or CD56-positive lymphocytes. The nucleotide sequences of the construct corresponding to Podo447 specific chimeric antigen receptor (CAR) and corresponding amino acid sequences are listed in Tables 2 and 3. An outline of the CAR construct is shown in FIG. 18. Synthetic genes were ordered as synthetic gBlocks® gene fragments from IDT® (Integrated DNA Technologies) and assembled using Gibson assembly (New England Biolabs, catalogue #E5510S) into the pLVX-EF1a-IRES-ZsGreenl vector (Clonetech, catalogue #631982).

Example 10-PODO447 and PODO83 Binding is Abolished by Knockdown of PODXL Gene Transcript MDA.MB-231 cells were fluorescently labeled with GFP or RFP by infecting with retrovirus vectors pLNCX2-GFP or pLNCX2-RFP, respectively. All cell lines used were obtained from pooled cultures. Human PODXL was silenced ('knocked down') in MDA.MB-231 breast tumor cells by lentiviral infection using pLKO.1 with either a scrambled shRNA construct (Scr-ctrl) or shRNA targeting the PODXL gene (PODXL-KD). Cells were cultured under continuous antibiotic selection with puromycin (4 µg/ml; Invitrogen, Burlington, ON) and G418 (lmg/ml; Calbiochem, Darmstadt, Germany). shRNA constructs were generously provided by Dr. John Wilkins (University of Manitoba, Winnipeg, MB) and the infections were performed by Michelle Turvey and Dr. Shaun McColl (University of Adelaide, Australia). $2.5\times10^5$ MIA PaCa-2 cells were seeded per well in a 6-well TC-Treated plate (Costar, cat#3516). After incubation overnight, cells were transfected with 10 nM siRNA following the guidelines of the Oligofectamine protocol (cat#12252-011, Invitrogen, Burlington, ON). Pre-Design and validated siRNA (PODXL siRNA, cat# s10770; Negative control No. 1 siRNA, cat#4390843) were obtained from Ambion (Thermo Fisher Scientific, Burlington, ON). Knock-downs were assessed by flow cytometry two days after transfection.

Sub-confluent cell lines were washed once with $Ca^{2+}$ and $Mg^{2+}$ free HBSS (Invitrogen, Carlsbad, Calif.) harvested with 0.25% Trypsin/EDTA (Invitrogen, Carlsbad, Calif.). Cells were quenched with normal growth media and centrifuged at 300×g for 5 minutes. Cells were washed once with FACS buffer (2% FBS, 2 mM EDTA, PBS, 0.05% NaAzide). Cells were blocked for 20 minutes at 4° C. in Blocking Buffer (2% rat serum, 2 µg/ml dilution of 2.4G2 (anti-CD16/CD32)) in a 96 well 'v' bottom plate. Cells were spun at 453×g for 4 minutes and primary antibodies were incubated for 20 minutes at 4° C. Rabbit/human-anti-human podocalyxin 447 and 83 (10 µg/ml; CDRD) were used for the detection of human podocalyxin by flow cytometry. Cells stained with secondary antibody only were used as negative control. After primary incubation with primary antibodies, cells were washed three times in FACS buffer. Cells were then incubated with goat-anti-human IgG AlexaFluor (AF) 647-coupled secondary antibody (2 µg/ml; Jackson ImmunoResearch, West Grove, Pa.) for 20 minutes at 4° C. Cells were washed three times with FACS buffer and transferred to bullet tubes for flow cytometry. A LSRII flow cytometry machine (BD Biosciences, Mississauga, ON) was used for all flow cytometric experiments. FlowJo™ software was used to analyze all flow cytometry data (FlowJo, Treestar Inc., Ashland, Oreg.).

Example 11—PODO447 Kills AML, Glioblastoma and Pancreatic Cancer Cell Lines as an Antibody Drug Conjugate (ADC)

Samples of Podo447 mAb in PBS was reduced by mixing the antibody, 2-10 molar equivalents of Tris(2-carboxyethyl) phosphine hydrochloride (TCEP-HCl) (Thermo Scientific, catalogue #20490) and 1 mM final concentration of Diethylenetriaminepentaacetic dianhydride (DTPA) (Sigma Aldrich, catalogue #284025). The mixture was incubated at 37° C. for 120 minutes. After cooling on wet ice, 10-15 molar equivalents maleimide toxin (MC-vc-PABC-MonoMethyl Auristatin E) was added from a 10 mM DMSO stock solution. The conjugation reaction was allowed to proceed for 30 minutes on ice before purification and buffer exchange through a Zeba™ spin columns (Pierce, catalogue #87767) preconditioned with PBS, pH 7.4 according to the manufacturer's instructions. The eluates were assayed using a bicinchoninic acid assay (BCA) (Pierce, #23225) using Herceptin as a standard to establish protein concentration.

The antibody drug conjugates described above were tested at varying concentrations against various cell lines expressing or not expressing the podo447 epitope. On the day prior to adding compounds, the adherent cell lines MiaPaCa, A172 and HUVEC (100 uL) were added to opaque-walled clear-bottomed 96-well tissue culture-treated microtiter plates using complete growth medium at a density of 2500 cells/100 µL of medium. The cells were incubated for one night at 37° C./5% $CO_2$ to allow the cells to attach to the microtiter plate surface. On the day of the adding the compounds the suspension cell lines Jurkat and THP were added to the opaque-walled clear-bottomed 96-well tissue culture-treated microtiter plates at the same density as described above. Antibody drug conjugates were diluted in complete growth medium at five-times the final concentration maximum concentration desired and compounds were then titrated 1:3 in the same medium, eight steps. A control with no compound (growth medium alone) was included on each microtiter plate in sextuplicate. The prepared compounds titrations were added (twenty-five µL/well) in triplicate to the cells. The cells and compound titrations were incubated at 37° C./5% $CO_2$ for three or five nights. After the incubation, cell viability was measured using CellTiter-Glo® 2.0 reagent (Promega, catalogue #G9242) by adding 25 µL of reagent to each assay well. The mixture was incubated for a minimum of twenty minutes prior to measurement of luminescence using a microplate luminometer (500 ms integration time). The collected relative luminescence units (RLU) are converted to % cytotoxicity using the growth medium alone control mentioned above (% Cytotoxicity=1−[Well RLU/average medium alone control RLU]). Data were fit to curves using non-linear regression methods available with Prism Graph Pad software. A graph showing the data from this study is provided in FIGS. 12, and 14.

Example 12 Isolation of Antibodies Recognizing PODXL

Podo 447 was raised in New Zealand White Rabbits by sequential semi-monthly subcutaneous immunization with A—172 cells (20 million 1st injection, 10 million for subsequent injections—mixed with Aluminum Hydroxide (5 mg/injection)+CpG (ODN 1826) 20 ug/injection)—Cedarlane® Burlington, ON. Four days following the 11th injection, the rabbit was euthanized and the spleen was harvested (Cedarlane). B cells were cultured and isolated as per Babcook et al, PNAS, 1996, Jul. 23; 93(15):7843-8. A-172 (purchased from ATCC® CRL-1620™).

Podo 447 was identified by screening the B Cell supernatants for binding to MDA-MB-231 and 293 cells by FACS. Secondary screening was done on hPodo-MDA-MB-231 transients by FACS and soluble MDA-expressed Podo-Fc, MDA-expressed Podo-His, and HEK-293-expressed Podo-Fc by ELISA. Podo 447 was also back-screened on HUVEC cells. In order to clone the antibody from cultured B cells, the frozen cells were thawed into a fluorescent plaque assay using AlexaFluor488 F(ab)'2 Gt-anti-Rabbit IgG Fc to identify B cells that recognized A172 cells. These single cells were picked using a micromanipulator and then lysed. Antibody V-genes were amplified by RT-PCR. PCR products corresponding to matched antibody heavy and light chains were then cloned into human IgG1 constant region and IgK constant region constructs (pTT5/IgG1, pTT5/Igk). To produce recombinant Podo 447, Podo 447 VH and VL chain plasmids were transfected into 293-6E cells using 293fectin. After 96 hours of secretion, the antibody-containing supernatant was cleared of cells by centrifugation and sterile filtration (0.22 um). Podo 447 was purified using HiTrap Protein G HP (GE healthcare).

Example 13—Determination of Affinity of PODO447 and PODO83 for Cellular PODXL Antigens by Kinetic Exclusion Assay The concentration dependence of free anti-podo antibody as a function of A172 cell number was determined using a Sapidyne KinExA 3200. Briefly, A172 cells, which express endogenous Podocalyxin, were titrated 1:2 from $10 \times 10^6$ cells/mL down 12 steps, and incubated with a fixed concentration of Podo 447 antibody. A172 cells and cell bound antibodies were then isolated by centrifugation. Supernatant containing free, unbound antibody was then transferred to a new tube. In the KinExA, a new column of PMMA beads coated with a Gt anti-IgG-Fc capture antibody is packed for each sample assayed. The supernatant containing free unbound antibody is passed over the column. The amount of free antibody captured on the PMMA beads was then measured using a Gt anti-IgG-Fc-A647. The concentration of free antibody over the entire 12 step dilution series was then used to determine the antibody Kd's using the standard Kd template in the KineExA Pro Software.

Example 14—Design and Cloning of PODO447 Chimeric Antigen Receptors

The nucleotide sequences of the construct corresponding to Podo447 specific chimeric antigen receptor (CAR) and corresponding amino acid sequences are listed in Table 2.

An outline of the CAR construct is shown in FIG. 18. Synthetic genes were ordered as synthetic gBlocks® gene fragments from IDT® (Integrated DNA Technologies) and assembled using Gibson assembly (New England Biolabs, catalogue #E5510S) into the pLVX-EF1a-IRES-ZsGreen1 vector (Clonetech, catalogue #631982). The construct contains the following segments.

The Kozak consensus sequence according to Kozak, *Nucl. Acids Res.* 15:8125, 1987, was added to initiate translation (GCCACC). This was follows by a signal sequence derived from Podo447. Three different binding domains were created with different structure and binding domain orientations. Two different scFvs were generated where the Podo447 VH and Podo447 VL were linked with a (GGGGS)3 sequence. SEQ ID NO: 5 (Table 2) was designed with a VL-linker-VH orientation, and SEQ ID NO:4 (Table 2) was designed with a VH-linker-VL orientation. In addition SEQ ID NO:6 (Table 2) was designed as a scFab with a VL-CL-linker-VH-CH1 orientation. All of the constructs were cloned in frame with a MYC tag followed by a CD8 hinge region, CD28 transmembrane region, CD28 intracellular signaling domain and CD3z signaling domain.

Briefly, 1 µg of the pLVX-EF1a-IRES-ZsGreen1 vector (Clonetech, catalogue #631982) was digested using EcoRI-HF (New England Biolabs, catalogue # R3101S) and BamHI-HF (New England Biolabs, catalogue # R3101S). The digested plasmid was separated on a 1% agarose gel and the digested plasmid was extracted from the gel using QIAquick extraction kit (Qiagen, catalogue #28704). 50 ng of the plasmid was incubated with 3 molar excess of the synthetic gBlocks® gene fragments coding the binding domains and the intracellular signaling domains. 10 µl of Gibson assembly master mix (New England Biolabs, catalogue # E5510S) was added to the reaction and the mix was incubated at 50° C. for 1 hour. Competent DH5α E-*coli* (New England Biolabs, catalogue # E5510S) were transformed with 2 µl of the Gibson assembly mix according to manufacturer's protocol. 100 µl was spread on ampicillin selective LB-agar plates and single-cell colonies were grown at 37° C. overnight. To isolate the plasmids, single cells colonies were inoculated into liquid LB-ampicillin media, grown overnight at 37° C., 225 RPM, and plasmids were isolated using Qiagen® QIAprep® spin miniprep kit (Qiagen Catalogue #27104). The clones were screened by digesting the isolated plasmids, and verified by sequence analysis using Geneious sequence alignment, assembly and analysis software from Biomatters.

TABLE 2

| Seq name | SEQ ID | NT |
|---|---|---|
| scFv_VH_GGGGS_VL CAR | 1 | ATGGAGACGGGACTCAGGTGGCTGCTTCTTGTCGCCGTCC<br>TGAAGGGGTGCAGTGCCAGAGCCTTGAAGAAAGCGGCGG<br>AAGACTGGTCACGCCTGGGACTCCGCTGACACTGACTTGC<br>ACGGCTTCCGGATTTTCACTCAGTGGATACCAAATGAACT<br>GGGTTAGGCAAGCCCCAGGGAAGGGTCTCGAATGGATCGG<br>CTATATATGGAGTGATGGAGGCACCGATTATGCCTCCTGG<br>GCTAAGGGACGCTTCACTATATCCAAGACCTCCAGTACTA<br>CAGTGGACTTGAAAATGACATCTCTTACGACAGAGGACAC<br>CGCCACCTACTTCTGCGCAAGAGAGGGGTACTGGCTGGGC<br>GCCTTTGACCCATGGGGCCCCGGGACCCTTGTGACCGTGA<br>GTTCCGGGGAGGTGGGTCCGGCGGGGGCGGCAGTGGAGG<br>CGGCGGGTCTGCCGTCCTTACTCAAACACCAAGCCCCGTG<br>TCCGCCGCAGTTGGCGCTACTGTTAGCGTCAGCTGCCAGA<br>GTTCCCAGTCAGTGCATCACAAGAACGACCTTGCATGGTT<br>TCAGCAGAAGCCCGGGCAACCACCCAAGCTCCTCATTTAT<br>TATACAAGTACTCTGGCCAGTGGGGTGCCATCCCGCTTCA<br>AGGGGTCAGGGTCTGGGACCCAATTTACACTCACTATTAG<br>CGACCTCGAGTGTGACGACGCCGCCACGTATTATTGCGCC<br>GGAGTGTACGAAGGCAGCTCTGATAACCGCGCCTTCGGCG<br>GTGGGACTGAAGTGGTTGTTAAAGAGCAGAAGCTGATCAG<br>CGAGGAGGACCTGAACCGGATCCGTGGGGTCACCGTCTCT<br>TCAGCGCTGAGCAACTCCATCATGTACTTCAGCCACTTCG<br>TGCCGGTCTTCCTGCCAGCGAAGCCCACCACGACGCCAGC<br>GCCGCGACCACCAACACCGGCGCCCACCATCGCGTCGCAG<br>CCCCTGTCCCTGCGCCCAGAGGCGTGCCGGCCAGCGGCGG<br>GGGGCGCAGTGCACACGAGGGGGCTGGACCCCTTTGGGTT<br>TTGGGTGCTGGTGGTGGTTGGTGGAGTCCTGGCTTGCTAT<br>AGCTTGCTAGTAACAGTGGCCTTTATTATTTTCTGGGTGA<br>GGAGTAAGAGGAGCAGGCTCCTGCACAGTGACTACATGAA<br>CATGACTCCCCGCCGCCCGGGCCCACCCGCAAGCATTAC<br>CAGCCCTATGCCCCACCACGCGACTTCGCAGCCTATCGCT<br>CCCTCGAGAGAGTGAGAGTGAAGTTCAGCAGGAGCGCAGA<br>CGCCCCCGCGTACCAGCAGGGCCAGAACCAGCTCTATAAC<br>GAGCTCAATCTAGGACGAAGAGAGGAGTACGATGTTTTGG<br>ACAAGAGACGTGGCCGGGACCCTGAGATGGGGGAAAGCC<br>GAGAAGGAAGAACCCTCAGGAAGGCCTGTACAATGAACTG<br>CAGAAAGATAAGATGGCGGAGGCCTACAGTGAGATTGGGA<br>TGAAAGGCGAGCGCCGGAGGGGCAAGGGGCACGATGGCCT<br>TTACCAGGGTCTCAGTACAGCCACCAAGGACACCTACGAC<br>GCCCTTCACATGCAGGCCCTGCCCCCTCGCTAA |
| scFv_VL_GGGGS_VH CAR | 2 | ATGGATACCCGCGCACCCACTCAACTGCTCGGGCTGCTCC<br>TGCTGTGGCTCCCTGGGGCAACATTTGCTGCCGTCCTTAC<br>TCAAACACCAAGCCCCGTGTCCGCCGCAGTTGGCGCTACT<br>GTTAGCGTCAGCTGCCAGAGTTCCCAGTCAGTGCATCACA<br>AGAACGACCTTGCATGGTTTCAGCAGAAGCCCGGGCAACC<br>ACCCAAGCTCCTCATTTATTATACAAGTACTCTGGCCAGT |

TABLE 2-continued

| | | |
|---|---|---|
| | | GGGGTGCCATCCCGCTTCAAGGGGTCAGGGTCTGGGACCC |
| | | AATTTACACTCACTATTAGCGACCTCGAGTGTGACGACGC |
| | | CGCCACGTATTATTGCGCCGGAGTGTACGAAGGCAGCTCT |
| | | GATAACCGCGCCTTCGGCGGTGGGACTGAAGTGGTTGTTA |
| | | AAGGGGGAGGTGGGTCCGGCGGGGCGGCAGTGGAGGCGG |
| | | CGGGTCTCAGTCCCTTGAGGAGTCTGGGGGTAGACTTGTG |
| | | ACCCCGGGAACACCACTGACTCTGACGTGTACCGCGTCTG |
| | | GCTTCTCCCTGAGTGGCTACCAAATGAACTGGGTGAGGCA |
| | | GGCTCCTGGAAAAGGACTCGAGTGGATTGGCTATATCTGG |
| | | TCCGACGGTGGCACCGACTATGCCAGCTGGGCTAAGGGAA |
| | | GATTTACAATCTCAAAAACCAGCAGCACCACAGTGGACCT |
| | | CAAAATGACCAGCCTCACTACAGAAGATACCGCCACGTAT |
| | | TTCTGTGCCAGAGAGGGATATTGGCTTGGGGCTTTTGACC |
| | | CATGGGGGCCTGGGACCCTCGTCACCGTGAGTTCAGAGCA |
| | | GAAGCTGATCAGCGAGGAGGACCTGAACCGGATCCGTGGG |
| | | GTCACCGTCTCTTCAGCGCTGAGCAACTCCATCATGTACT |
| | | TCAGCCACTTCGTGCCGGTCTTCCTGCCAGCGAAGCCCAC |
| | | CACGACGCCAGCGCCGCGACCACCAACACCGGCGCCCACC |
| | | ATCGCGTCGCAGCCCCTGTCCCTGCGCCCAGAGGCGTGCC |
| | | GGCCAGCGGCGGGGGGCGCAGTGCACACGAGGGGGCTGGA |
| | | CCCCTTTGGGTTTTGGGTGCTGGTGGTGGTTGGTGGAGTC |
| | | CTGGCTTGCTATAGCTTGCTAGTAACAGTGGCCTTTATTA |
| | | TTTTCTGGGTGAGGAGTAAGAGGAGCAGGCTCCTGCACAG |
| | | TGACTACATGAACATGACTCCCCGCCGCCCCGGGCCCACC |
| | | CGCAAGCATTACCAGCCCTATGCCCCACCACGCGACTTCG |
| | | CAGCCTATCGCTCCCTCGAGAGAGTGAGAGTGAAGTTCAG |
| | | CAGGAGCGCAGACGCCCCCGCGTACCAGCAGGGCCAGAAC |
| | | CAGCTCTATAACGAGCTCAATCTAGGACGAAGAGAGGAGT |
| | | ACGATGTTTTGGACAAGAGACGTGGCCGGGACCCTGAGAT |
| | | GGGGGGAAAGCCGAGAAGGAAGAACCCTCAGGAAGGCCTG |
| | | TACAATGAACTGCAGAAAGATAAGATGGCGGAGGCCTACA |
| | | GTGAGATTGGGATGAAAGGCGAGCGCCGGAGGGGCAAGGG |
| | | GCACGATGGCCTTTACCAGGGTCTCAGTACAGCCACCAAG |
| | | GACACCTACGACGCCCTTCACATGCAGGCCCTGCCCCCTC |
| | | GCTAA |
| scFab_VL_CL_GGGGSVH_CH1 CAR | 3 | ATGGATACCCGCGCACCCACTCAACTGCTCGGGCTGCTCC |
| | | TGCTGTGGCTCCCTGGGGCAACATTTGCTGCCGTCCTTAC |
| | | TCAAACACCAAGCCCCGTGTCCGCCGCAGTTGGCGCTACT |
| | | GTTAGCGTCAGCTGCCAGAGTTCCCAGTCAGTGCATCACA |
| | | AGAACGACCTTGCATGGTTTCAGCAGAAGCCCGGGCAACC |
| | | ACCCAAGCTCCTCATTTATTATACAAGTACTCTGGCCAGT |
| | | GGGGTGCCATCCCGCTTCAAGGGGTCAGGGTCTGGGACCC |
| | | AATTTACACTCACTATTAGCGACCTCGAGTGTGACGACGC |
| | | CGCCACGTATTATTGCGCCGGAGTGTACGAAGGCAGCTCT |
| | | GATAACCGCGCCTTCGGCGGTGGGACTGAAGTGGTTGTTA |
| | | AACGCACAGTCGCAGCCCCCTCCGTGTTTATCTTCCCTCC |
| | | TAGCGACGAACAACTGAAGAGCGGAACAGCCAGCGTCGTA |
| | | TGTTTGCTCAATAACTTCTATCCAAGGGAAGCCAAAGTGC |
| | | AGTGGAAAGTCGATAATGCACTCCAGAGCGGCAATAGCCA |
| | | GGAAAGTGTAACTGAGCAGGACAGCAAAGATAGCACCTAT |
| | | AGCCTGAGCTCAACCCTGACACTGTCAAAAGCAGATTACG |
| | | AGAAACACAAGGTTTACGCGTGCGAAGTGACTCATCAAGG |
| | | GTTGTCCAGTCCCGTGACAAAAAGCTTCAATCGAGGCGAG |
| | | TGTGGCGGGGCGGTAGCGGCGGAGGTGGCAGTGGTGGTG |
| | | GCGGCTCACAGTCTCTGGAGGAAAGCGGAGGCAGGCTGGT |
| | | GACCCCAGGTACACCCCTGACCCTCACCTGTACCGCCAGC |
| | | GGCTTTAGCCTTTCTGGGTACCAGATGAATTGGGTACGAC |
| | | AGGCCCCTGGGAAGGGTCTGGAGTGGATAGGTTATATCTG |
| | | GTCTGATGGGGGCACCGATTACGCAAGCTGGGCGAAGGGC |
| | | AGATTCACTATCAGCAAAACTTCCAGCACCACCGTAGATC |
| | | TGAAAATGACCAGTCTGACAACAGAAGATACTGCCACTTA |
| | | TTTTTGCGCCAGGGAAGGATACTGGCTGGGCGCCTTCGAT |
| | | CCTTGGGGCCCCGGTACGCTGGTAACTGTCTCATCCGCAT |
| | | CCACGAAGGGACCTTCTGTGTTCCCTTTGGCTCCAAGCTC |
| | | CAAAAGCACAAGCGGAGGAACCGCAGCGCTTGGCTGTTTG |
| | | GTTAAGGATTACTTCCCCGAACCTGTGACTGTGTCATGGA |
| | | ACTCTGGGGCGCTTACCAGCGGCGTCCACACATTTCCAGC |
| | | AGTTCTGCAGTCTAGTGGGCTTTACAGTCTGTCATCTGTA |
| | | GTGACTGTGCCTTCTTCCAGCCTCGGGACCCAGACCTACA |
| | | TCTGCAATGTCAATCACAAGCCATCCAACACTAAAGTGGA |
| | | TAAGAGAGTGGAGCAGAAGCTGATCAGCGAGGAGGACCTG |
| | | AACCGGATCCGTGGGGTCACCGTCTCTTCAGCGCTGAGCA |
| | | ACTCCATCATGTACTTCAGCCACTTCGTGCCGGTCTTCCT |
| | | GCCAGCGAAGCCCACCACGACGCCAGCGCCGCGACCACCA |
| | | ACACCGGCGCCCACCATCGCGTCGCAGCCCCTGTCCCTGC |
| | | GCCCAGAGGCGTGCCGGCCAGCGGCGGGGGGCGCAGTGCA |
| | | CACGAGGGGCTGGACCCCTTTGGGTTTTGGGTGCTGGTG |
| | | GTGGTTGGTGGAGTCCTGGCTTGCTATAGCTTGCTAGTAA |
| | | CAGTGGCCTTTATTATTTTCTGGGTGAGGAGTAAGAGGAG |

TABLE 2-continued

| | | |
|---|---|---|
| | | CAGGCTCCTGCACAGTGACTACATGAACATGACTCCCCGC
CGCCCCGGGCCCACCCGCAAGCATTACCAGCCCTATGCCC
CACCCACGCGACTTCGCAGCCTATCGCTCCCTCGAGAGAGT
GAGAGTGAAGTTCAGCAGGAGCGCAGACGCCCCCGCGTAC
CAGCAGGGCCAGAACCAGCTCTATAACGAGCTCAATCTAG
GACGAAGAGAGGGAGTACGATGTTTTGGACAAGAGACGTGG
CCGGGACCCTGAGATGGGGGGAAAGCCGAGAAGGAAGAAC
CCTCAGGAAGGCCTGTACAATGAACTGCAGAAAGATAAGA
TGGCGGAGGCCTACAGTGAGATTGGGATGAAAGGCGAGCG
CCCGGAGGGGCAAGGGGCACGATGGCCTTTACCAGGGTCTC
AGTACAGCCACCAAGGACACCTACGACGCCCTTCACATGC
AGGCCCTGCCCCCTCGCTAA |
| Podo447
scFv_VH_GGGGS_VL | 4 | ATGGAGACGGGACTCAGGTGGCTGCTTCTTGTCGCCGTCC
TGAAGGGGGTGCAGTGCCAGAGCCTTGAAGAAAGCGGCGG
AAGACTGGTCACGCCTGGGACTCCGCTGACACTGACTTGC
ACGGCTTCCGGATTTTCACTCAGTGGATACCAAATGAACT
GGGTTAGGCAAGCCCCAGGGAAGGGTCTCGAATGGATCGG
CTATATATGGAGTGATGGAGGCACCGATTATGCCTCCTGG
GCTAAGGGACGCTTCACTATATCCAAGACCTCCAGTACTA
CAGTGGACTTGAAAATGACATCTCTTACGACAGAGGACAC
CGCCACCTACTTCTGCGCAAGAGAGGGGTACTGGCTGGGC
GCCTTTGACCCATGGGGCCCCGGGACCCTTGTGACCGTGA
GTTCCGGGGAGGTGGGTCCGGCGGGGCGGCAGTGGAGG
CGGCGGGTCTGCCGTCCTTACTCAAACACCAAGCCCCGTG
TCCGCCGCAGTTGGCGCTACTGTTAGCGTCAGCTGCCAGA
GTTCCCAGTCAGTGCATCACAAGAACGACCTTGCATGGTT
TCAGCAGAAGCCCGGGCAACCACCCAAGCTCCTCATTTAT
TATACAAGTACTCTGGCCAGTGGGGTGCCATCCCGCTTCA
AGGGGTCAGGGTCTGGGACCCAATTTACACTCACTATTAG
CGACCTCGAGTGTGACGACGCCGCCACGTATTATTGCGCC
GGAGTGTACGAAGGCAGCTCTGATAACCGCGCCTTCGGCG
GTGGGACTGAAGTGGTTGTTAAA |
| Podo 447
scFv_VL_GGGGS_VH | 5 | ATGGATACCCGCGCACCCACTCAACTGCTCGGGCTGCTCC
TGCTGTGGCTCCCTGGGGCAACATTTGCTGCCGTCCTTAC
TCAAACACCAAGCCCCGTGTCCGCCGCAGTTGGCGCTACT
GTTAGCGTCAGCTGCCAGAGTTCCCAGTCAGTGCATCACA
AGAACGACCTTGCATGGTTTCAGCAGAAGCCCGGGCAACC
ACCCAAGCTCCTCATTTATTATACAAGTACTCTGGCCAGT
GGGGTGCCATCCCGCTTCAAGGGGTCAGGGTCTGGGACCC
AATTTACACTCACTATTAGCGACCTCGAGTGTGACGACGC
CGCCACGTATTATTGCGCCGGAGTGTACGAAGGCAGCTCT
GATAACCGCGCCTTCGGCGGTGGGACTGAAGTGGTTGTTA
AAGGGGGAGGTGGGTCCGGCGGGGCGGCAGTGGAGGCGG
CGGGTCTCAGTCCCTTGAGGAGTCTGGGGGTAGACTTGTG
ACCCCGGGAACACCACTGACTCTGACGTGTACCGCGTCTG
GCTTCTCCCTGAGTGGCTACCAAATGAACTGGGTGAGGCA
GGCTCCTGGAAAAGGACTCGAGTGGATTGGCTATATCTGG
TCCGACGGTGGCACCGACTATGCCAGCTGGGCTAAGGGAA
GATTTACAATCTCAAAAACCAGCAGCACCACAGTGGACCT
CAAAATGACCAGCCTCACTACAGAAGATACCGCCACGTAT
TTCTGTGCCAGAGAGGGATATTGGCTTGGGGCTTTTGACC
CATGGGGGCCTGGGACCCTCGTCACCGTGAGTTCA |
| Podo447
scFab_VL_CL_GGGGS_VH_CH1 | 6 | ATGGATACCCGCGCACCCACTCAACTGCTCGGGCTGCTCC
TGCTGTGGCTCCCTGGGGCAACATTTGCTGCCGTCCTTAC
TCAAACACCAAGCCCCGTGTCCGCCGCAGTTGGCGCTACT
GTTAGCGTCAGCTGCCAGAGTTCCCAGTCAGTGCATCACA
AGAACGACCTTGCATGGTTTCAGCAGAAGCCCGGGCAACC
ACCCAAGCTCCTCATTTATTATACAAGTACTCTGGCCAGT
GGGGTGCCATCCCGCTTCAAGGGGTCAGGGTCTGGGACCC
AATTTACACTCACTATTAGCGACCTCGAGTGTGACGACGC
CGCCACGTATTATTGCGCCGGAGTGTACGAAGGCAGCTCT
GATAACCGCGCCTTCGGCGGTGGGACTGAAGTGGTTGTTA
AACGCACAGTCGCAGCCCCCTCCGTGTTTATCTTCCCTCC
TAGCGACGAACAACTGAAGAGCGGAACAGCCAGCGTCGTA
TGTTTGCTCAATAACTTCTATCCAAGGGAAGCCAAAGTGC
AGTGGAAAGTCGATAATGCACTCCAGAGCGGCAATAGCCA
GGAAAGTGTAACTGAGCAGGACAGCAAAGATAGCACCTAT
AGCCTGAGCTCAACCCTGACACTGTCAAAAGCAGATTACG
AGAAACACAAGGTTTACGCGTGCGAAGTGACTCATCAAGG
GTTGTCCAGTCCCGTGACAAAAAGCTTCAATGAGGCGAG
TGTGGCGGGGCGGTAGCGGCGGAGGTGGCAGTGGTGGTG
GCGGCTCACAGTCTCTGGAGGAAAGCGGAGGCAGGCTGGT
GACCCCAGGTACACCCCTGACCCTCACCTGTACCGCCAGC
GGCTTTAGCCTTTCTGGGTACCAGATGAATTGGGTACGAC
AGGCCCCTGGGAAGGGTCTGGAGTGGATAGGTTATATCTG
GTCTGATGGGGGCACCGATTACGCAAGCTGGGCGAAGGGC
AGATTCACTATCAGCAAAACTTCCAGCACCACCGTAGATC |

TABLE 2-continued

| | | |
|---|---|---|
| | | TGAAAATGACCAGTCTGACAACAGAAGATACTGCCACTTA<br>TTTTTGCGCCAGGGAAGGATACTGGCTGGGCGCCTTCGAT<br>CCTTGGGGCCCCGGTACGCTGGTAACTGTCTCATCCGCAT<br>CCACGAAGGGACCTTCTGTGTTCCCTTTGGCTCCAAGCTC<br>CAAAAGCACAAGCGGAGGAACCGCAGCGCTTGGCTGTTTG<br>GTTAAGGATTACTTCCCCGAACCTGTGACTGTGTCATGGA<br>ACTCTGGGGCGCTTACCAGCGGCGTCCACACATTTCCAGC<br>AGTTCTGCAGTCTAGTGGGCTTTACAGTCTGTCATCTGTA<br>GTGACTGTGCCTTCTTCCAGCCTCGGGACCCAGACCTACA<br>TCTGCAATGTCAATCACAAGCCATCCAACACTAAAGTGGA<br>TAAGAGAGTG |
| MYC tag | 7 | GAGCAGAAGCTGATCAGCGAGGAGGACCTG |
| CD8 hinge | 8 | TCAGCGCTGAGCAACTCCATCATGTACTTCAGCCACTTCG<br>TGCCGGTCTTCCTGCCAGCGAAGCCCACCACGACGCCAGC<br>GCCGCGACCACCAACACCGGCGCCCACCATCGCGTCGCAG<br>CCCCTGTCCCTGCGCCCAGAGGCGTGCCGGCCAGCGGCGG<br>GGGGCGCAGTGCACACGAGGGGGCTGGAC |
| CD28 TM | 9 | TTTTGGGTGCTGGTGGTGGTTGGTGGAGTCCTGGCTTGCT<br>ATAGCTTGCTAGTAACAGTGGCCTTTATTATTTTCTGGGT<br>G |
| CD28 IC | 10 | AGGAGTAAGAGGAGCAGGCTCCTGCACAGTGACTACATGA<br>ACATGACTCCCCGCCGCCCCGGGCCCACCCGCAAGCATTA<br>CCAGCCCTATGCCCCACCACGCGACTTCGCAGCCTATCGC<br>TCC |
| CD3z | 11 | AGAGTGAAGTTCAGCAGGAGCGCAGACGCCCCCGCGTACC<br>AGCAGGGCCAGAACCAGCTCTATAACGAGCTCAATCTAGG<br>ACGAAGAGAGGAGTACGATGTTTTGGACAAGAGACGTGGC<br>CGGGACCCTGAGATGGGGGAAAGCCGAGAAGGAAGAACC<br>CTCAGGAAGGCCTGTACAATGAACTGCAGAAAGATAAGAT<br>GGCGGAGGCCTACAGTGAGATTGGGATGAAAGGCGAGCGC<br>CGGAGGGGCAAGGGGCACGATGGCCTTTACCAGGGTCTCA<br>GTACAGCCACCAAGGACACCTACGACGCCCTTCACATGCA<br>GGCCCTGCCCCCTCGCTAA |
| podo447VH | 12 | ATGGAGACTGGGCTGCGCTGGCTTCTCCTGGTCGCTGTGC<br>TCAAAGGTGTCCAGTGTCAGTCGCTGGAGGAGTCCGGGGG<br>TCGCCTGGTCACGCCTGGGACACCCCTGACACTCACCTGC<br>ACAGCCTCTGGATTCTCCCTCAGTGGCTACCAGATGAACT<br>GGGTCCGCCAGGCTCCAGGGAAGGGGCTGGAGTGGATCGG<br>ATATATTTGGAGTGATGGTGGTACAGACTACGCGAGCTGG<br>GCGAAAGGCCGATTCACCATCTCCAAAACCTCGTCGACCA<br>CGGTGGATCTGAAAATGACCAGTCTGACAACCGAGGACAC<br>GGCCACCTATTTCTGTGCCAGGGAGGGATACTGGCTTGGT<br>GCTTTTGATCCCTGGGGCCCAGGCACCCTGGTCACCGTCT<br>CTTCAGCTAGCACCAAGGGCCCATCGGTCTTCCCCCTGGC<br>ACCCTCCTCCAAGAGCACCTCTGGGGGCACAGCGGCCCTG<br>GGCTGCCTGGTCAAGGACTACTTCCCCGAACCGGTGACGG<br>TGTCGTGGAACTCAGGCGCCCTGACCAGCGGCGTGCACAC<br>CTTCCCGGCTGTCCTACAGTCCTCAGGACTCTACTCCCTC<br>AGCAGCGTGGTGACCGTGCCCTCCAGCAGCTTGGGCACCC<br>AGACCTACATCTGCAACGTGAATCACAAGCCCAGCAACAC<br>CAAGGTGGACAAGAGAGTTGAGCCCAAATCTTGTGACAAA<br>ACTCACACATGCCCACCGTGCCCAGCACCTGAACTCCTGG<br>GGGGACCGTCAGTCTTCCTCTTCCCCCCAAAACCCAAGGA<br>CACCCTCATGATCTCCCGGACCCCTGAGGTCACATGCGTG<br>GTGGTGGACGTGAGCCACGAAGACCCTGAGGTCAAGTTCA<br>ACTGGTACGTGGACGGCGTGGAGGTGCATAATGCCAAGAC<br>AAAGCCGCGGGAGGAGCAGTACAACAGCACGTACCGTGTG<br>GTCAGCGTCCTCACCGTCCTGCACCAGGACTGGCTGAATG<br>GCAAGGAGTACAAGTGCAAGGTCTCCAACAAAGCCCTCCC<br>AGCCCCCATCGAGAAAACCATCTCCAAAGCCAAAGGGCAG<br>CCCCGAGAACCACAGGTGTACACCCTGCCCCCATCCCGGG<br>ATGAGCTGACCAAGAACCAGGTCAGCCTGACCTGCCTGGT<br>CAAAGGCTTCTATCCCAGCGACATCGCCGTGGAGTGGGAG<br>AGCAATGGGCAGCCGGAGAACAACTACAAGACCACGCCTC<br>CCGTGCTGGACTCCGACGGCTCCTTCTTCCTCTACAGCAA<br>GCTCACCGTGGACAAGAGCAGGTGGCAGCAGGGGAACGTC<br>TTCTCATGCTCCGTGATGCATGAGGCTCTGCACAACCACT<br>ACACGCAGAAGAGCCTCTCCCTGTCTCCGGGTAAA |
| podo447VH_hIgG1C_chimeric | 13 | ATGGAGACTGGGCTGCGCTGGCTTCTCCTGGTCGCTGTGC<br>TCAAAGGTGTCCAGTGTCAGTCGCTGGAGGAGTCCGGGGG<br>TCGCCTGGTCACGCCTGGGACACCCCTGACACTCACCTGC<br>ACAGCCTCTGGATTCTCCCTCAGTGGCTACCAGATGAACT<br>GGGTCCGCCAGGCTCCAGGGAAGGGGCTGGAGTGGATCGG |

TABLE 2-continued

|   |   |   |
|---|---|---|
| | | ATATATTTGGAGTGATGGTGGTACAGACTACGCGAGCTGG<br>GCGAAAGGCCGATTCACCATCTCCAAAACCTCGTCGACCA<br>CGGTGGATCTGAAAATGACCAGTCTGACAACCGAGGACAC<br>GGCCACCTATTTCTGTGCCAGGGAGGGATACTGGCTTGGT<br>GCTTTTGATCCCTGGGGCCCAGGCACCCTGGTCACCGTCT<br>CTTCAGCTAGCACCAAGGGCCCATCGGTCTTCCCCCTGGC<br>ACCCTCCTCCAAGAGCACCTCTGGGGGCACAGCGGCCCTG<br>GGCTGCCTGGTCAAGGACTACTTCCCCGAACCGGTGACGG<br>TGTCGTGGAACTCAGGCGCCCTGACCAGCGGCGTGCACAC<br>CTTCCCGGCTGTCCTACAGTCCTCAGGACTCTACTCCCTC<br>AGCAGCGTGGTGACCGTGCCCTCCAGCAGCTTGGGCACCC<br>AGACCTACATCTGCAACGTGAATCACAAGCCCAGCAACAC<br>CAAGGTGGACAAGAGAGTTGAGCCCAAATCTTGTGACAAA<br>ACTCACACATGCCCACCGTGCCCAGCACCTGAACTCCTGG<br>GGGGACCGTCAGTCTTCCTCTTCCCCCCAAAACCCAAGGA<br>CACCCTCATGATCTCCCGGACCCCTGAGGTCACATGCGTG<br>GTGGTGGACGTGAGCCACGAAGACCCTGAGGTCAAGTTCA<br>ACTGGTACGTGGACGGCGTGGAGGTGCATAATGCCAAGAC<br>AAAGCCGCGGGAGGAGCAGTACAACAGCACGTACCGTGTG<br>GTCAGCGTCCTCACCGTCCTGCACCAGGACTGGCTGAATG<br>GCAAGGAGTACAAGTGCAAGGTCTCCAACAAAGCCCTCCC<br>AGCCCCCATCGAGAAAACCATCTCCAAAGCCAAAGGGCAG<br>CCCCGAGAACCACAGGTGTACACCCTGCCCCCATCCCGGG<br>ATGAGCTGACCAAGAACCAGGTCAGCCTGACCTGCCTGGT<br>CAAAGGCTTCTATCCCAGCGACATCGCCGTGGAGTGGGAG<br>AGCAATGGGCAGCCGGAGAACAACTACAAGACCACGCCTC<br>CCGTGCTGGACTCCGACGGCTCCTTCTTCCTCTACAGCAA<br>GCTCACCGTGGACAAGAGCAGGTGGCAGCAGGGGAACGTC<br>TTCTCATGCTCCGTGATGCATGAGGCTCTGCACAACCACT<br>ACACGCAGAAGAGCCTCTCCCTGTCTCCGGGTAAAGCTAG<br>CACCAAGGGCCCATCGGTCTTCCCCCTGGCACCCTCCTCC<br>AAGAGCACCTCTGGGGGCACAGCGGCCCTGGGCTGCCTGG<br>TCAAGGACTACTTCCCCGAACCGGTGACGGTGTCGTGGAA<br>CTCAGGCGCCCTGACCAGCGGCGTGCACACCTTCCCGGCT<br>GTCCTACAGTCCTCAGGACTCTACTCCCTCAGCAGCGTGG<br>TGACCGTGCCCTCCAGCAGCTTGGGCACCCAGACCTACAT<br>CTGCAACGTGAATCACAAGCCCAGCAACACCAAGGTGGAC<br>AAGAGAGTTGAGCCCAAATCTTGTGACAAAACTCACACAT<br>GCCCACCGTGCCCAGCACCTGAACTCCTGGGGGGACCGTC<br>AGTCTTCCTCTTCCCCCCAAAACCCAAGGACACCCTCATG<br>ATCTCCCGGACCCCTGAGGTCACATGCGTGGTGGTGGACG<br>TGAGCCACGAAGACCCTGAGGTCAAGTTCAACTGGTACGT<br>GGACGGCGTGGAGGTGCATAATGCCAAGACAAAGCCGCGG<br>GAGGAGCAGTACAACAGCACGTACCGTGTGGTCAGCGTCC<br>TCACCGTCCTGCACCAGGACTGGCTGAATGGCAAGGAGTA<br>CAAGTGCAAGGTCTCCAACAAAGCCCTCCCAGCCCCCATC<br>GAGAAAACCATCTCCAAAGCCAAAGGGCAGCCCCGAGAAC<br>CACAGGTGTACACCCTGCCCCCATCCCGGGATGAGCTGAC<br>CAAGAACCAGGTCAGCCTGACCTGCCTGGTCAAAGGCTTC<br>TATCCCAGCGACATCGCCGTGGAGTGGGAGAGCAATGGGC<br>AGCCGGAGAACAACTACAAGACCACGCCTCCCGTGCTGGA<br>CTCCGACGGCTCCTTCTTCCTCTACAGCAAGCTCACCGTG<br>GACAAGAGCAGGTGGCAGCAGGGGAACGTCTTCTCATGCT<br>CCGTGATGCATGAGGCTCTGCACAACCACTACACGCAGAA<br>GAGCCTCTCCCTGTCTCCGGGTAAATGA |
| podo447VL | 14 | ATGGACACGAGGGCCCCCACTCAGCTGCTGGGGCTCCTGC<br>TGCTCTGGCTCCCAGGTGCCACATTTGCCGCCGTGCTGAC<br>CCAGACTCCATCTCCCGTGTCTGCAGCTGTGGGAGCCACA<br>GTCAGCGTCAGTTGCCAGTCCAGTCAGAGTGTCCATCATA<br>AGAACGACTTAGCCTGGTTTCAGCAGAAACCAGGTCAGCC<br>TCCCAAGCTCCTGATCTATTATACATCCACTCTGGCATCT<br>GGGGTCCCATCACGGTTCAAGGGCAGTGGATCTGGGACAC<br>AGTTCACTCTCACCATCAGCGACCTGGAGTGTGACGATGC<br>TGCCACTTACTACTGTCAGGCGTTTATGAGGGTAGTAGT<br>GATAATAGGGCTTTCGGCGGAGGGACCGAGGTGGTGGTCA<br>AA |
| podo447VL_hIgkC_chimeric | 15 | ATGGACACGAGGGCCCCCACTCAGCTGCTGGGGCTCCTGC<br>TGCTCTGGCTCCCAGGTGCCACATTTGCCGCCGTGCTGAC<br>CCAGACTCCATCTCCCGTGTCTGCAGCTGTGGGAGCCACA<br>GTCAGCGTCAGTTGCCAGTCCAGTCAGAGTGTCCATCATA<br>AGAACGACTTAGCCTGGTTTCAGCAGAAACCAGGTCAGCC<br>TCCCAAGCTCCTGATCTATTATACATCCACTCTGGCATCT<br>GGGGTCCCATCACGGTTCAAGGGCAGTGGATCTGGGACAC<br>AGTTCACTCTCACCATCAGCGACCTGGAGTGTGACGATGC<br>TGCCACTTACTACTGTCAGGCGTTTATGAGGGTAGTAGT<br>GATAATAGGGCTTTCGGCGGAGGGACCGAGGTGGTGGTCA<br>AACGTACGGTGGCTGCACCATCTGTCTTCATCTTCCCGCC<br>ATCTGATGAGCAGTTGAAATCTGGAACTGCCTCTGTTGTG |

TABLE 2-continued

```
TGCCTGCTGAATAACTTCTATCCCAGAGAGGCCAAAGTAC
AGTGGAAGGTGGATAACGCCCTCCAATCGGGTAACTCCCA
GGAGAGTGTCACAGAGCAGGACAGCAAGGACAGCACCTAC
AGCCTCAGCAGCACCCTGACGCTGAGCAAAGCAGACTACG
AGAAACACAAAGTCTACGCCTGCGAAGTCACCCATCAGGG
CCTGAGCTCGCCCGTCACAAAGAGCTTCAACAGGGGAGAG
TGTTAG
```

| Seq name | SEQ ID | AA |
|---|---|---|
| scFv_VH_GGGGS_VL CAR | 16 | METGLRWLLLVAVLKGVQCQSLEESGGRLVTPGTPLTLTC TASGFSLSGYQMNWVRQAPGKGLEWIGYIWSDGGTDYASW AKGRFTISKTSSTTVDLKMTSLTTEDTATYFCAREGYWLG AFDPWGPGTLVTVSSGGGGSGGGGSGGGGSAVLTQTPSPV SAAVGATVSVSCQSSQSVHHKNDLAWFQQKPGQPPKLLIY YTSTLASGVPSRFKGSGSGTQFTLTISDLECDDAATYYCA GVYEGSSDNRAFGGGTEVVVKEQKLISEEDLNRIRGVTVS SALSNSIMYFSHFVPVFLPAKPTTTPAPRPPTPAPTIASQ PLSLRPEACRPAAGGAVHTRGLDPFGFWVLVVVGGVLACY SLLVTVAFIIFWVRSKRSRLLHSDYMNMTPRRPGPTRKHY QPYAPPRDFAAYRSLERVRVKFSRSADAPAYQQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR |
| scFv_VL_GGGGS_VH CAR | 17 | MDTRAPTQLLGLLLLWLPGATFAAVLTQTPSPVSAAVGAT VSVSCQSSQSVHHKNDLAWFQQKPGQPPKLLIYYTSTLAS GVPSRFKGSGSGTQFTLTISDLECDDAATYYCAGVYEGSS DNRAFGGGTEVVVKGGGGSGGGGSGGGGSQSLEESGGRLV TPGTPLTLTCTASGFSLSGYQMNWVRQAPGKGLEWIGYIW SDGGTDYASWAKGRFTISKTSSTTVDLKMTSLTTEDTATY FCAREGYWLGAFDPWGPGTLVTVSSEQKLISEEDLNRIRG VTVSSALSNSIMYFSHFVPVFLPAKPTTTPAPRPPTPAPT IASQPLSLRPEACRPAAGGAVHTRGLDPFGFWVLVVVGGV LACYSLLVTVAFIIFWVRSKRSRLLHSDYMNMTPRRPGPT RKHYQPYAPPRDFAAYRSLERVRVKFSRSADAPAYQQGQN QLYNELNLGRREEYDVLDKRRGRDPEMGGKPRRKNPQEGL YNELQKDKMAEAYSEIGMKGERRRGKGHDGLYQGLSTATK DTYDALHMQALPPR |
| scFab_VL_CL_GGGGS_VH_CH1 CAR | 18 | MDTRAPTQLLGLLLLWLPGATFAAVLTQTPSPVSAAVGAT VSVSCQSSQSVHHKNDLAWFQQKPGQPPKLLIYYTSTLAS GVPSRFKGSGSGTQFTLTISDLECDDAATYYCAGVYEGSS DNRAFGGGTEVVVKRTVAAPSVFIFPPSDEQLKSGTASVV CLLNNFYPREAKVQWKVDNALQSGNSQESVTEQDSKDSTY SLSSTLTLSKADYEKHKVYACEVTHQGLSSPVTKSFNRGE CGGGGSGGGGSGGGGSQSLEESGGRLVTPGTPLTLTCTAS GFSLSGYQMNWVRQAPGKGLEWIGYIWSDGGTDYASWAKG RFTISKTSSTTVDLKMTSLTTEDTATYFCAREGYWLGAFD PWGPGTLVTVSSASTKGPSVFPLAPSSKSTSGGTAALGCL VKDYFPEPVTVSWNSGALTSGVHTFPAVLQSSGLYSLSSV VTVPSSSLGTQTYICNVNHKPSNTKVDKRVEQKLISEEDL NRIRGVTVSSALSNSIMYFSHFVPVFLPAKPTTTPAPRPP TPAPTIASQPLSLRPEACRPAAGGAVHTRGLDPFGFWVLV VVGGVLACYSLLVTVAFIIFWVRSKRSRLLHSDYMNMTPR RPGPTRKHYQPYAPPRDFAAYRSLERVRVKFSRSADAPAY QQGQNQLYNELNLGRREEYDVLDKRRGRDPEMGGKPRRKN PQEGLYNELQKDKMAEAYSEIGMKGERRRGKGHDGLYQGL STATKDTYDALHMQALPPR |
| Podo447 scFv_VH_GGGGS_VL | 19 | METGLRWLLLVAVLKGVQCQSLEESGGRLVTPGTPLTLTC TASGFSLSGYQMNWVRQAPGKGLEWIGYIWSDGGTDYASW AKGRFTISKTSSTTVDLKMTSLTTEDTATYFCAREGYWLG AFDPWGPGTLVTVSSGGGGSGGGGSGGGGSAVLTQTPSPV SAAVGATVSVSCQSSQSVHHKNDLAWFQQKPGQPPKLLIY YTSTLASGVPSRFKGSGSGTQFTLTISDLECDDAATYYCA GVYEGSSDNRAFGGGTEVVVK |
| Podo 447 scFv_VL_GGGGS_VH | 20 | MDTRAPTQLLGLLLLWLPGATFAAVLTQTPSPVSAAVGAT VSVSCQSSQSVHHKNDLAWFQQKPGQPPKLLIYYTSTLAS GVPSRFKGSGSGTQFTLTISDLECDDAATYYCAGVYEGSS DNRAFGGGTEVVVKGGGGSGGGGSGGGGSQSLEESGGRLV TPGTPLTLTCTASGFSLSGYQMNWVRQAPGKGLEWIGYIW SDGGTDYASWAKGRFTISKTSSTTVDLKMTSLTTEDTATY FCAREGYWLGAFDPWGPGTLVTVSS |
| Podo447 scFab_VL_CL_GGGGS_VH_CH1 | 21 | MDTRAPTQLLGLLLLWLPGATFAAVLTQTPSPVSAAVGAT VSVSCQSSQSVHHKNDLAWFQQKPGQPPKLLIYYTSTLAS GVPSRFKGSGSGTQFTLTISDLECDDAATYYCAGVYEGSS DNRAFGGGTEVVVKRTVAAPSVFIFPPSDEQLKSGTASVV |

TABLE 2-continued

| | | |
|---|---|---|
| | | CLLNNFYPREAKVQWKVDNALQSGNSQESVTEQDSKDSTY<br>SLSSTLTLSKADYEKHKVYACEVTHQGLSSPVTKSFNRGE<br>CGGGGSGGGGSGGGGSQSLEESGGRLVTPGTPLTLTCTAS<br>GFSLSGYQMNWVRQAPGKGLEWIGYIWSDGGTDYASWAKG<br>RFTISKTSSTTVDLKMTSLTTEDTATYFCAREGYWLGAFD<br>PWGPGTLVTVSSASTKGPSVFPLAPSSKSTSGGTAALGCL<br>VKDYFPEPVTVSWNSGALTSGVHTFPAVLQSSGLYSLSSV<br>VTVPSSSLGTQTYICNVNHKPSNTKVDKRV |
| MYC tag | 22 | EQKLISEEDL |
| CD8 hinge | 23 | SALSNSIMYFSHFVPVFLPAKPTTTPAPRPPTPAPTIASQ<br>PLSLRPEACRPAAGGAVHTRGLD |
| CD28 TM | 24 | FWVLVVVGGVLACYSLLVTVAFIIFWV |
| CD28 IC | 25 | RSKRSRLLHSDYMNMTPRRPGPTRKHYQPYAPPRDFAAYR<br>S |
| CD3z | 26 | RVKFSRSADAPAYQQGQNQLYNELNLGRREEYDVLDKRRG<br>RDPEMGGKPRRKNPQEGLYNELQKDKMAEAYSEIGMKGER<br>RRGKGHDGLYQGLSTATKDTYDALHMQALPPR |
| podo447VH | 27 | METGLRWLLLVAVLKGVQCQSLEESGGRLVTPGTPLTLTC<br>TASGFSLSGYQMNWVRQAPGKGLEWIGYIWSDGGTDYASW<br>AKGRFTISKTSSTTVDLKMTSLTTEDTATYFCAREGYWLG<br>AFDPWGPGTLVTVSS |
| podo447VH_hIgG1C_chimeric | 28 | METGLRWLLLVAVLKGVQCQSLEESGGRLVTPGTPLTLTC<br>TASGFSLSGYQMNWVRQAPGKGLEWIGYIWSDGGTDYASW<br>AKGRFTISKTSSTTVDLKMTSLTTEDTATYFCAREGYWLG<br>AFDPWGPGTLVTVSSASTKGPSVFPLAPSSKSTSGGTAAL<br>GCLVKDYFPEPVTVSWNSGALTSGVHTFPAVLQSSGLYSL<br>SSVVTVPSSSLGTQTYICNVNHKPSNTKVDKRVEPKSCDK<br>THTCPPCPAPELLGGPSVFLFPPKPKDTLMISRTPEVTCV<br>VVDVSHEDPEVKFNWYVDGVEVHNAKTKPREEQYNSTYRV<br>VSVLTVLHQDWLNGKEYKCKVSNKALPAPIEKTISKAKGQ<br>PREPQVYTLPPSRDELTKNQVSLTCLVKGFYPSDIAVEWE<br>SNGQPENNYKTTPPVLDSDGSFFLYSKLTVDKSRWQQGNV<br>FSCSVMHEALHNHYTQKSLSLSPGK |
| podo447VL | 29 | MDTRAPTQLLGLLLLWLPGATFAAVLTQTPSPVSAAVGAT<br>VSVSCQSSQSVHHKNDLAWFQQKPGQPPKLLIYYTSTLAS<br>GVPSRFKGSGSGTQFTLTISDLECDDAATYYCAGVYEGSS<br>DNRAFGGGTEVVVK |
| podo447VL_hIgkC_chimeric | 30 | MDTRAPTQLLGLLLLWLPGATFAAVLTQTPSPVSAAVGAT<br>VSVSCQSSQSVHHKNDLAWFQQKPGQPPKLLIYYTSTLAS<br>GVPSRFKGSGSGTQFTLTISDLECDDAATYYCAGVYEGSS<br>DNRAFGGGTEVVVKRTVAAPSVFIFPPSDEQLKSGTASVV<br>CLLNNFYPREAKVQWKVDNALQSGNSQESVTEQDSKDSTY<br>SLSSTLTLSKADYEKHKVYACEVTHQGLSSPVTKSFNRGE<br>C |

TABLE 3

| | Podo447 | | |
|---|---|---|---|
| | IMGT | Chotia | Kabat |
| VH CDR1 | GFSLSGYQ (SEQ ID NO: 33) | GFSLSGY (SEQ ID NO: 34) | GYQMN (SEQ ID NO: 35) |
| VH CDR2 | IWSDGGT (SEQ ID NO: 36) | WSDGG (SEQ ID NO: 37) | YIWSDGGTDYASWAKG (SEQ ID NO: 38) |
| VH CDR3 | AREGYWLGAFDP (SEQ ID NO: 39) | EGYWLGAFDP (SEQ ID NO: 40) | EGYWLGAFDP (SEQ ID NO: 41) |
| Vk CDR1 | QSVHHKND (SEQ ID NO: 42) | QSSQSVHHKNDLA (SEQ ID NO: 43) | QSSQSVHHKNDLA (SEQ ID NO: 44) |
| Vk CDR2 | YTS (SEQ ID NO: 45) | YTSLAS (SEQ ID NO: 46) | YTSLAS (SEQ ID NO: 47) |

TABLE 3-continued

Podo447

| | | | |
|---|---|---|---|
| Vk CDR3 | AGVYEGSSDNRA (SEQ ID NO: 48) | AGVYEGSSDNRA (SEQ ID NO: 49) | AGVYEGSSDNRA (SEQ ID NO: 50) |

| | IMGT | Chotia |
|---|---|---|
| VH CDR1 | GGATTCTCCCTCAGTGGCTAC CAG (SEQ ID NO: 51) | GGATTCTCCCTCAGTGGCTAC (SEQ ID NO: 52) |
| VH CDR2 | ATTTGGAGTGATGGTGGTAC A (SEQ ID NO: 54) | TGGAGTGATGGTGGT (SEQ ID NO: 55) |
| VH CDR3 | GCCAGGGAGGGATACTGGCT TGGTGCTTTTGATCCC (SEQ ID NO: 57) | GAGGGATACTGGCTTGGTGCT TTTGATCCC (SEQ ID NO: 58) |
| Vk CDR1 | CAGAGTGTCCATCATAAGAA CGAC (SEQ ID NO:60) | CAGTCCAGTCAGAGTGTCCAT CATAAGAACGACTTAGCC (SEQ ID NO:61) |
| Vk CDR2 | TATACATCC (SEQ ID NO:63) | TATACATCCACTCTGGCA 9SEQ ID NO:64) |
| Vk CDR3 | GCAGGCGTTTATGAGGGTAG TAGTGATAATAGGGCT (SEQ ID NO:66) | GCAGGCGTTTATGAGGGTAGT AGTGATAATAGGGCT (SEQ ID NO:67) |

| | Kabat |
|---|---|
| VH CDR1 | GGCTACCAG (SEQ ID NO: 53) |
| VH CDR2 | TATATTTGGAGTGATGGTGGTACAGACTACGCGAGCTGGGCGAAAGGC (SEQ ID NO: 56) |
| VH CDR3 | GAGGGATACTGGCTTGGTGCTTTTGATCCC (SEQ ID NO: 59) |
| Vk CDR1 | CAGTCCAGTCAGAGTGTCCATCATAAGAACGACTTAGCC (SEQ ID NO: 62) |
| Vk CDR2 | TATACATCCACTCTGGCA (SEQ ID NO: 65) |
| Vk CDR3 | GCAGGCGTTTATGAGGGTAGTAGTGATAATAGGGCT (SEQ ID NO: 68) |

Example 15: Activity of CAR-T and CAR-NK Cells

The Podo447 positive population is sorted and co-cultured with cancer cell lines and patient derived xenograft (PDX) lines known to express the Podo447 epitope at various ratios of effector:target. Activity of the Podo447 engineered T-cells is measured by titrating the ratio of the CAR-T effector cells to the target cells. % target killing, degranulation (CD107a externalization), and intracellular IFN-γ and TNFα content are monitored simultaneously by multicolor flow cytometry. Additionally, the efficacy of 447 CAR-T and NK cells is determined under hypoxic conditions and stromal cocultures. The best performing ($2^{nd}$ vs $3^{rd}$ generation, scFV vs scFAB) CAR constructs in T and NK cells are selected for in vivo efficacy testing.

In vivo efficacy of Podo447-CAR modified T and NK cells is determined in murine models of AML and GBM. Persistence of CAR-modified T cells is determined by flow cytometry in peripheral blood and bone marrow (AML) or peripheral blood and CSF (GBM) at the time of sacrifice. Renal, hepatic, and brain toxicity are determined by an animal pathologist post-mortem. In both models, animals will be implanted with $1\times10^6$ Podo447-CAR-T cells, $1\times10^6$ Podo447-CAR-NK cells, $1\times10^6$ lentiviral control infected T cells, and $1\times10^6$ lentiviral control infected NK cells. Animals are sacrificed when exhibiting signs of morbidity. Weight and temperature are monitored daily, and survival is determined by Kaplan-Meier analysis.

Third generation Podo447 CAR T and NK cells demonstrate increased efficacy and persistence in vivo. Poodo CAR-NK cells demonstrate superior survival benefit when compared to their T cell counterparts, in large part due to reduced graft-vs-host effects.

Figure 24:
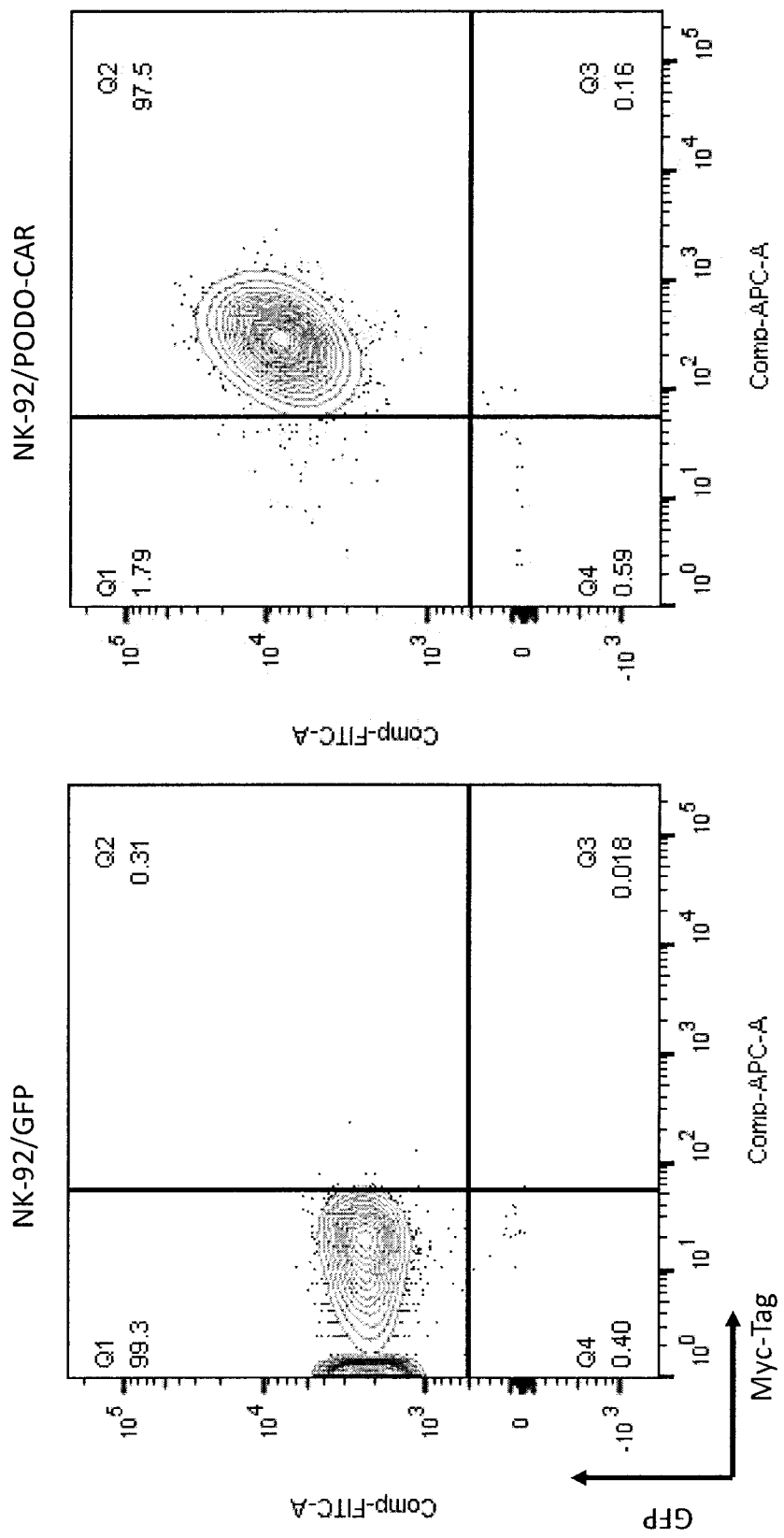
FIG. 24 Lentiviral transduction of NK-92 with PODO-CAR. Briefly, 100,000 NK-92 cells were cultured with 100 IU/ml of IL-2 and 8 μg/ml of polybrene in alpha minimal essential medium supplemented with 12.5% fetal calf serum and 12.5% horse serum. Empty vector control or PODO-CAR containing lentiviral vectors were added to the culture at a multiplicity of infection of 5:1. Cultures were spin-infected at 1,000×g for 99 minutes, and cultured for 72 h before FACS-sorting GFP positive cells. Surface expression of PODO447 targeting arm was verified in live NK-92 cells by flow cytometry using an anti-mycTag antibody (1:100 dilution) 7 days post-FACSsort.
Figure 25:
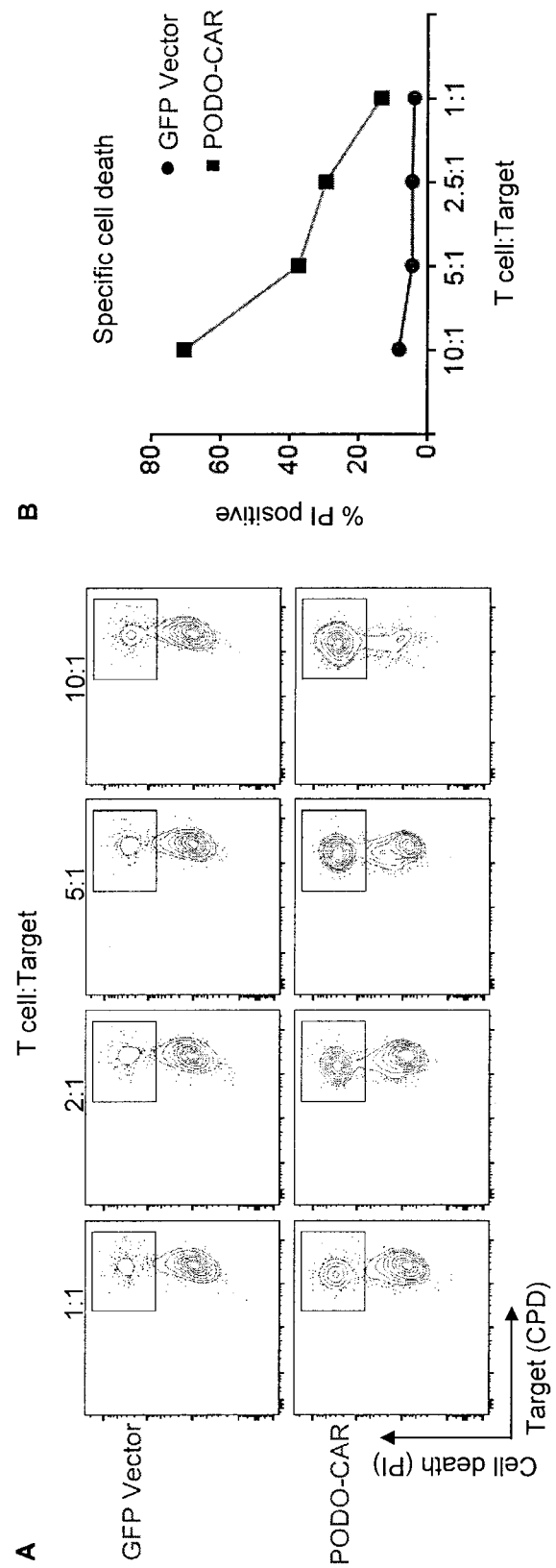
FIG. 25 PODO-CAR results in cytotoxic activity. GFP vector and PODO-CAR CD4$^+$ T cells were co-cultured with PODO 447$^+$ A-172 cells, which were labeled with cell proliferation dye eFluor 670 (CPD), at the indicated ratios for 24 hours. A) Shows representative plots of propidium iodide (PI) staining (gated on CPD$^+$GFP$^-$ cells) and B) shows specific cell death.

Example 16: Lentiviral Transduction of NK-92 with PODO-CAR and PODO-CAR Cytotoxic Activity (FIGS. 24 and 25)

SEQ ID NO:2 (encoding SEQ ID NO: 17) was the CAR sequence used to generate the PODO-CAR comprising the Podo-447 targeting arm (the binding scFv). The polynucleotide sequence encoding the binding scFv is provided by SEQ ID NO:5 (encoding SEQ ID NO:20).

Briefly, 100,000 NK-92 cells were cultured with 100 IU/ml of IL-2 and 8 µg/ml of polybrene in alpha minimal essential medium supplemented with 12.5% fetal calf serum and 12.5% horse serum. Empty vector control or PODO- CAR containing lentiviral vectors were added to the culture at a multiplicity of infection of 5:1. Cultures were spin-infected at 1,000×g for 99 minutes, and cultured for 72 h before FACS-sorting GFP positive cells. Surface expression of PODO447 targeting arm was verified in live NK-92 cells by flow cytometry using an anti-mycTag antibody (1:100 dilution) 7 days post-FACSsort.

GFP vector and PODO-CAR CD4$^+$ T cells were co-cultured with PODO 447$^+$ A-172 cells, which were labeled with cell proliferation dye eFluor 670 (CPD), at the indicated ratios for 24 hours. FIG. 25 (A) shows representative plots of propidium iodide (PI) staining (gated on CPD$^+$GFP$^-$ cells) and (B) shows specific cell death.

T Cell Isolation, Transduction, and Expansion.

CD3$^+$ and CD4$^+$ T cells were isolated from human peripheral blood mononuclear cells via EasySep (Stemcell) and stimulated with Dynabeads® Human T-Activator CD3/CD28 (Invitrogen) at a 1:1 bead to cell ratio in RPMI supplemented with 10% FCS and 50 U/ml IL-2. One day later, cells were transduced with GFP or PODO-CAR lentivirus (5 transducing units to 1 T cell) by centrifuging at room temp for 99 min at 1000 g in the presence of 8 µg/ml polybrene. At day 6, live GFP$^+$ cells were sorted with a FACSAria II (BD Biosciences) and expanded for an additional 7 days. Cells were then used for phenotypic and functional assays.

Lentivirus Preparation.

Briefly, Lenti-X-293 cells (Clontech) were cultured under subconfluent conditions (<80%) in DMEM medium supplemented with tetracycline-free fetal bovine serum (10%) and 1 mmole/L sodium pyruvate. 24 hours prior to transfection of packaging plasmids and expression vectors, Lenti-X-293 cells were seeded in 10 cm culture dishes (~4×10$^6$ cells per dish) in 8 mls of culture medium. The day of transfection, 7 µg of vector (empty vector control or VL6 PODO-CAR vector) plasmid was added to 600 µl of sterile water, and this solution was added to a single shot packaging tube (Clontech) and vortexed for 10 seconds per the manufacturer's instructions. 10 minutes after mixing, the contents of the single shot packaging tube were added dropwise to Lenti-X-293 cells cultured in a 10 cm dish while swirling. 16 hours after addition of single shot contents, cultures were supplemented with 6 mls of culture medium supplemented with 4.3 mmoles/L of sodium butyrate and cultured for an additional 48 h. Viral supernatants were harvested, cleared by centrifugation (1000×g for 10 minutes), and mixed with Lenti-X-concentrator solution (Clontech) per the manufacturers instructions. Viral particles were precipitated by centrifugation (1,500×g for 45 minutes at 4° C.), resuspended in RPMI-1640 medium, and frozen in aliquots. Viral titers were determined by infection of Lenti-X-293 cells.

Cytotoxicity Assays.

A-172 cells were labeled with CPDeFluor670 (eBiosciences) and co-cultured with PODO-CAR expressing cells at the indicated ratios for 24 hours in a 96-well U-bottom plate (1×10$^4$ A-172 cells/well). Adherent cells were trypsinized from plate and combined with supernatants containing non-adherent cells. Cell death in CPD$^+$GFP$^-$ A-172 cells was determined by adding 1 µg/ml propidium iodide (PI) prior to flow cytometry analysis on a LSRFortessa (BD Biosciences). Percent specific cell death was calculated by subtracting the percentage of dead A-172 cells in cultures with no T cells (% PI$^+$ in test sample−% PI$^+$ in target cells alone).

Figure 26:
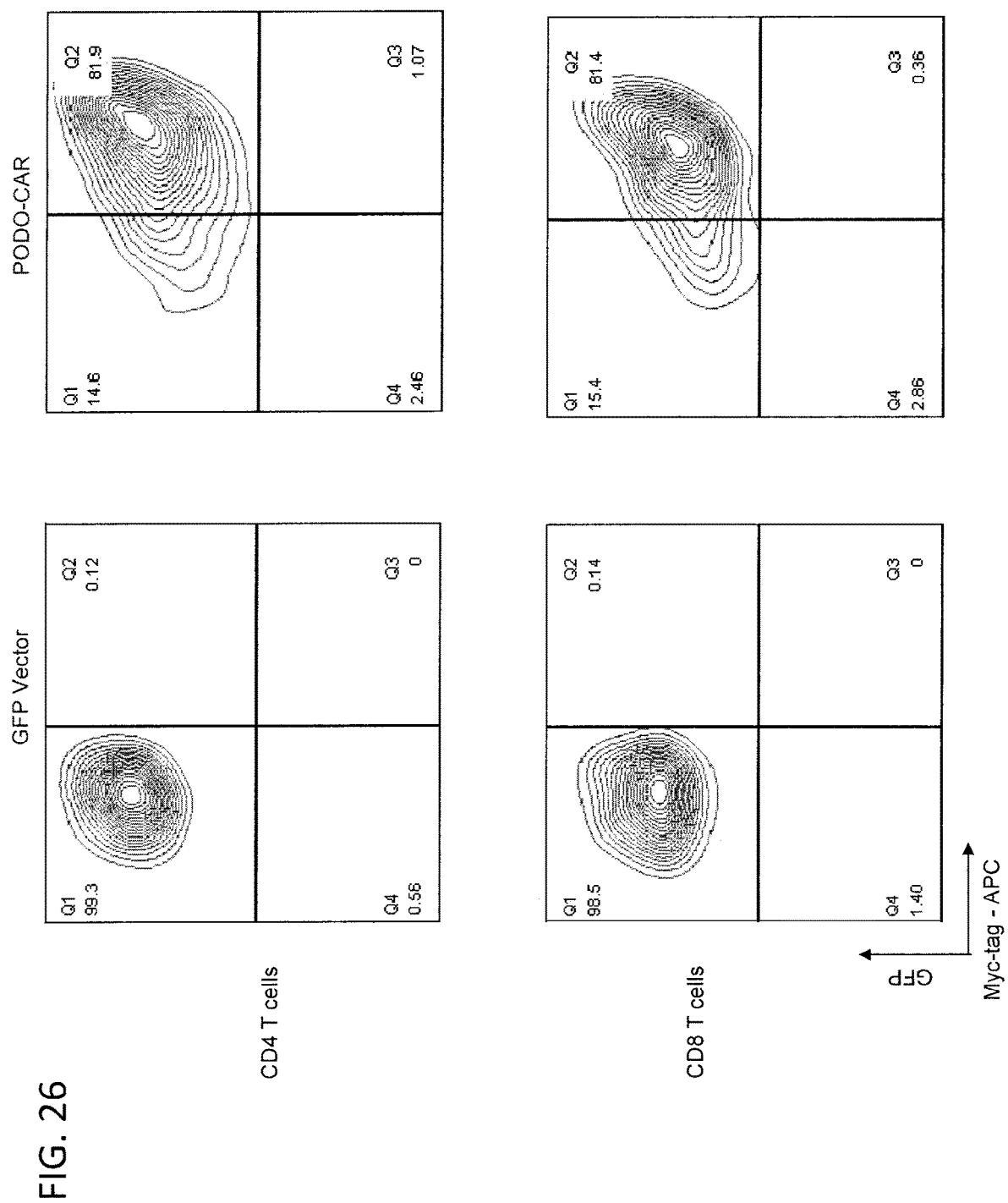
FIG. 26 PODO-CAR Expresses on the surface of CD4 and CD8 T cells. GFP vector and PODO-CAR CD3$^+$ T cells were stained with anti-CD4 (OKT4)-BV241, anti-CD8 (SKi) APCCy7, anti-Myc-Tag-Alexa-647, and PI for 15 minutes in the dark. Surface expression was determined by flow cytometric analysis on a BD-LSR Fortessa. Plots show surface expression 2.5 weeks post transduction gated on live (PI negative) cells.
Figure 27:
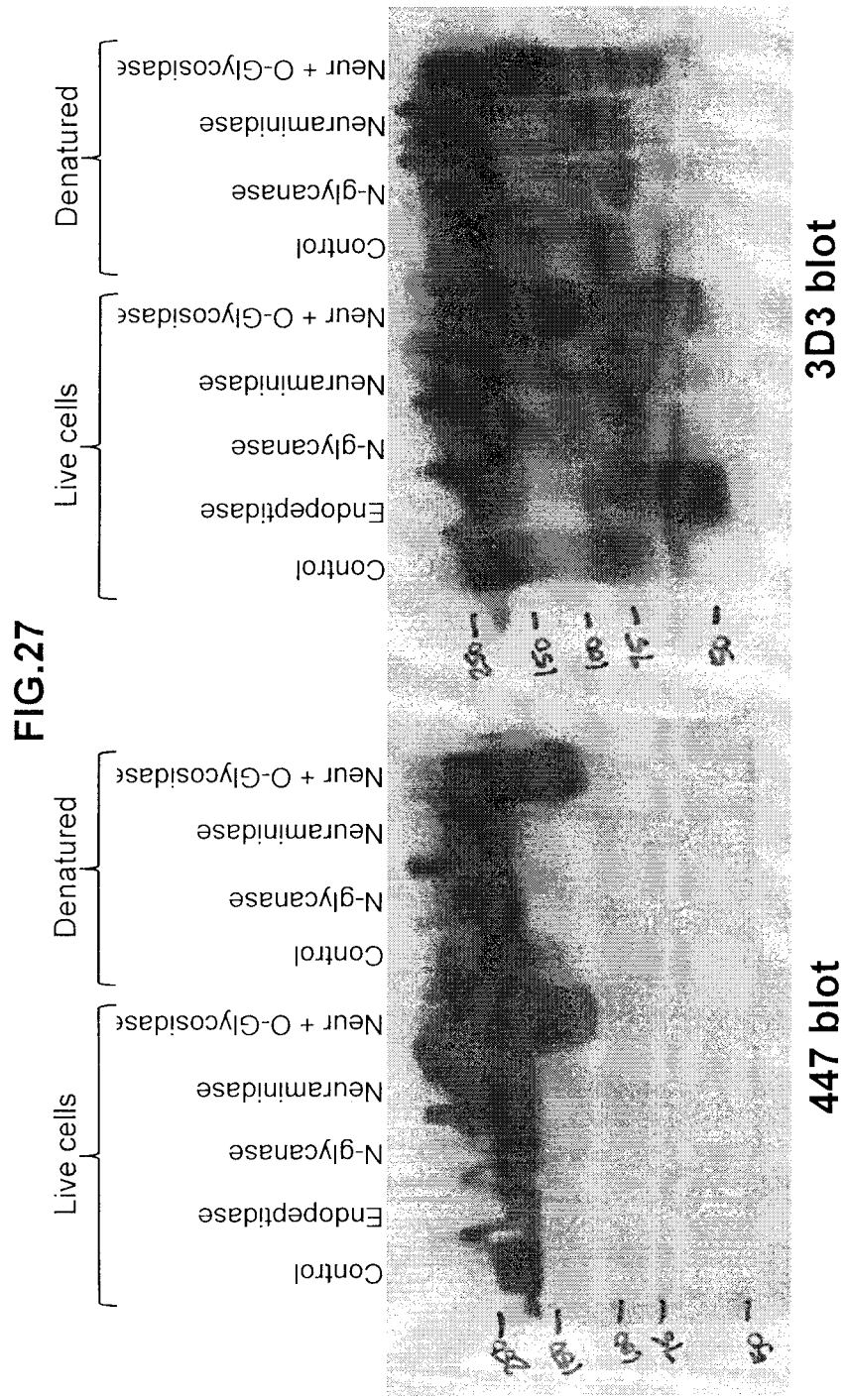
FIG. 27 A172 cells treated with enzyme (live cells) or lysates (denatured) treated with enzymes.
Figure 28:
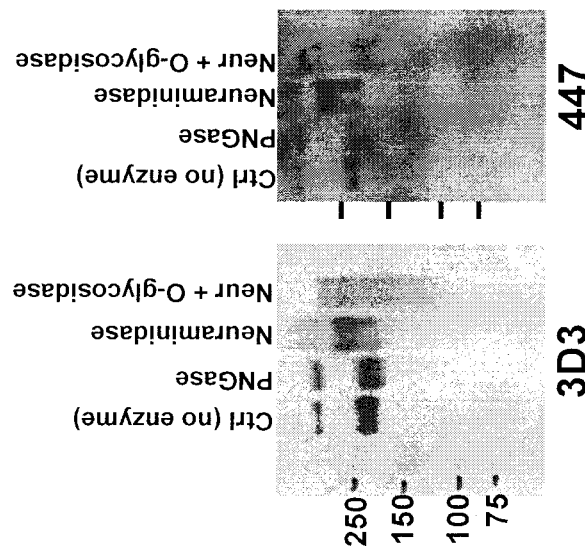
FIG. 28 A172 cells. 1. Pull down podocalyxin with podo447 antibody. 2. Treat podocalyxin with enzymes under denaturing conditions. 3. Run on gel and blot with (a) 3d3 podocalyxin antibody (an antibody that does not compete with podo447 antibody), (b) podo447 antibody.
Figure 29:
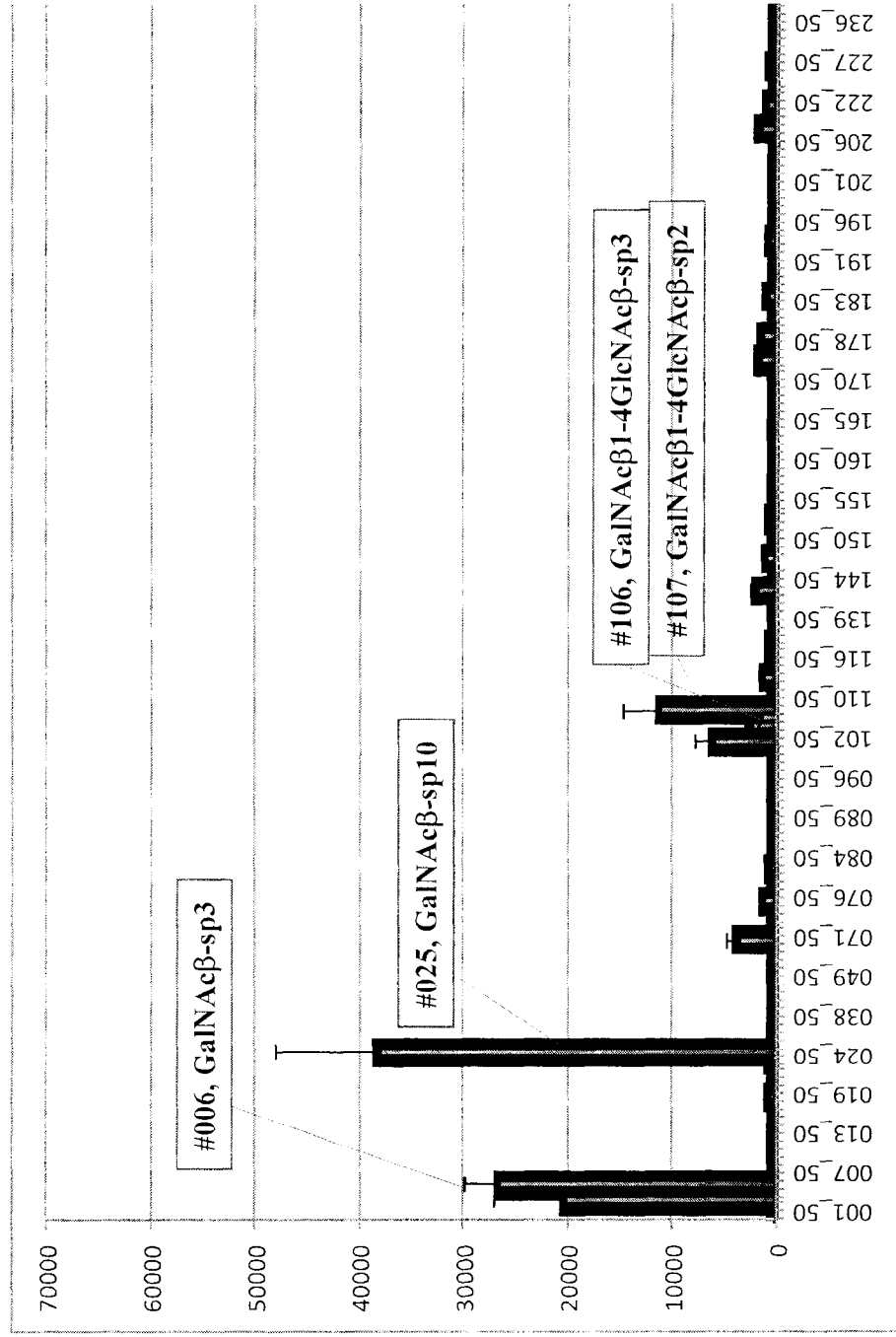
FIG. 29 Glycoepitope mapping. Glycan microarray (v3.1) analysis of Podo447 (A) and control antibody IgGlkappa (B). Podo447 bound positively to terminal GalNAc mono and oligosaccharides #006, #025, #106, #107, #263 and #389. Sp2: 2 amino-ethyl; spe: amino-propyl; sp10:PEG2 linker; DD: unknown conjugate.
Figure 29:
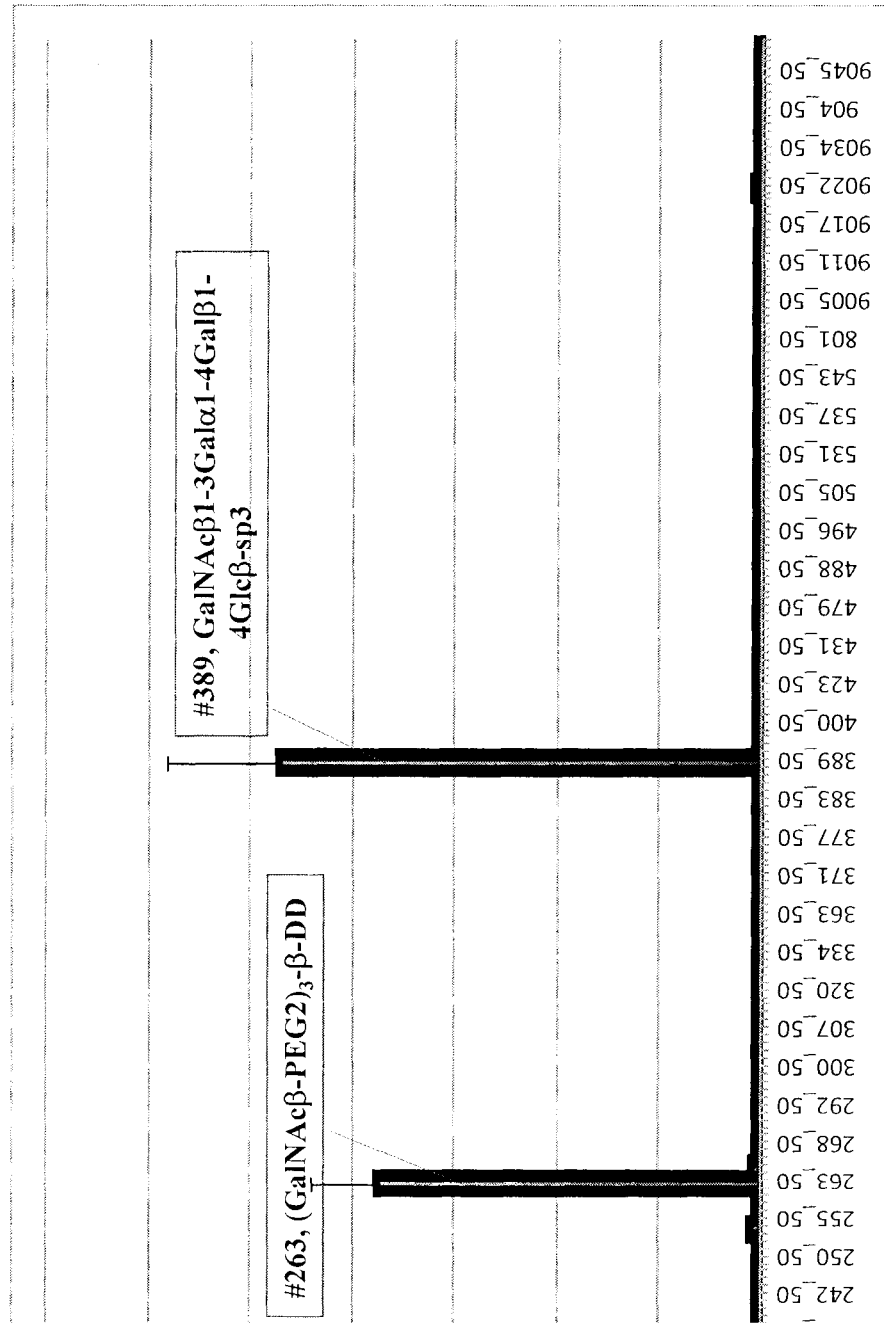
Figure 29:
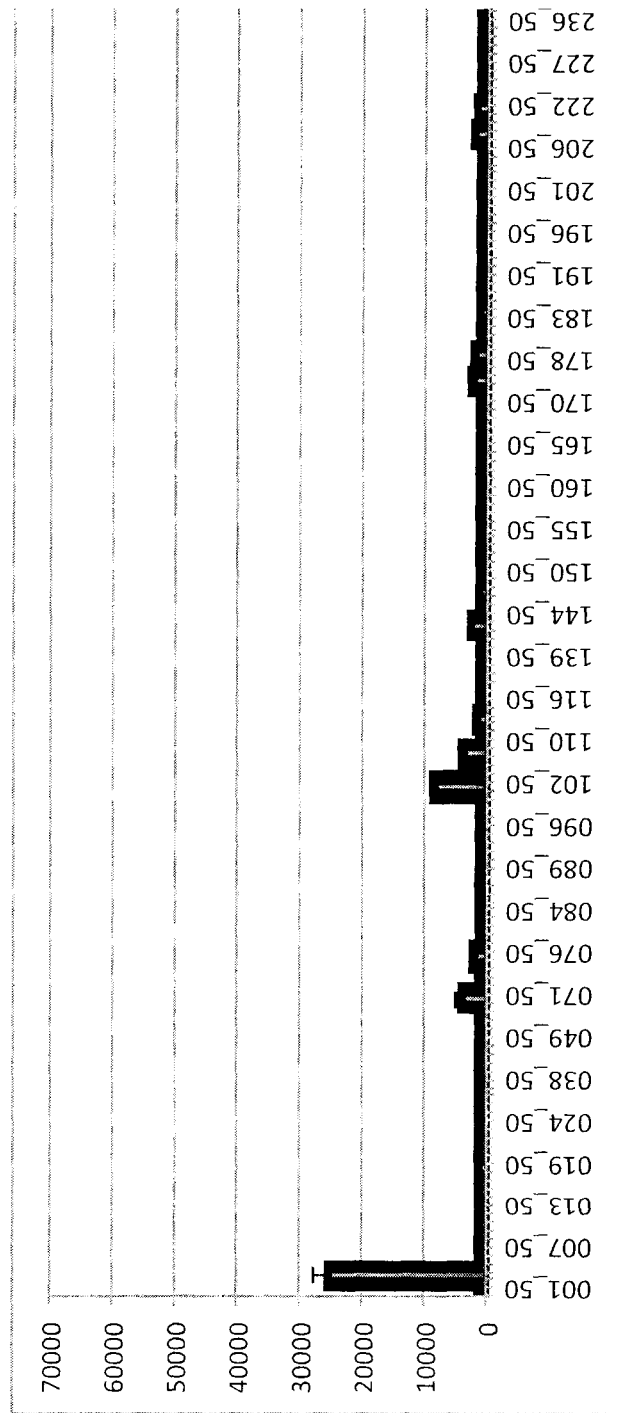

Example 17: PODO-CAR Expresses on the Surface of CD4 and CD8 T Cells. (FIG. 26)

SEQ ID No:2 (encoding SEQ ID NO:17) was the CAR sequence used to generate the PODO-CAR comprising the Podo-447 targeting arm (the binding scFv). The polynucleotide sequence encoding the binding scFv is provided by SEQ ID NO:5 (encoding SEQ ID NO:20).

Isolated and transduced CD3+ T cells were plated in 96-well U-bottom plate (2E4 cells/well), washed, and stained with anti-CD4 (OKT4)-BV241 (BioLegend), anti-CD8 (SKi)–APCCy7 (BioLegend), anti-Myc-Tag-Alexa-647 (Cell signaling), and PI for 15 minutes in the dark. Surface expression of PODO-CAR was determined by flow cytometric analysis on a BD-LSR Fortessa.

Example 18: Podo447 Binds to GBM Patient-Derived Xenograft in Murine Brain

Frozen GBM PDX samples were stained with rabbit or humanized Podo447 (1:100 and 1:500 dilutions). An tumor implant was introduced into one hemisphere. Rabbit and humanized Podo447 similarly recognized patient-derived GBM cells in the implanted hemisphere, but did not recognize cells in the other hemisphere. For implantations, see for example Vergenelli et al., *Nature Communications*, 4:2956 (2013). The number of implanted cells ranges from 2500 to 25000. Huamized Podo447 was generated by transfecting plasmids containing humanized_podo447VL6_hIgkC and humanized_podo447VH_hIgG1C. (data not shown)

Example 19: Podo447 Purification

Podo447 antibodies were expressed and secreted from HEK293 cells. HEK293 cells were transfected using 293-Free transfection reagent according to manufacture protocol (Novagen, Cat#: 72181). Cells were grown at 37° C. and 5% $CO_2$ while shaking at 120 rpm for 120 hours. Antibodies in media were obtained by pelleting the cells at 2500 xg for 15 minutes at 4° C. The media was then filtered through Nalgene® Rapid-Flow™ Filter Units (Thermo Scientific, Cat#: 73520-984) and stored at 4° C. until purification.

Podo447 (rabbit or humanized) was purified using AKTA Pure FPLC system (GE Healthcare Life Sciences). The filtered media was passed through the HiTrap Mab Select SuRe column (GE Healthcare Life Sciences, Cat#: 11-0034-94). The column was then washed with 10 column volume (CV) of PBS, pH 7.4 and followed by elution with 20 CV gradient of 0.1 M glycine, pH 3.0. Each eluted fractions (1-mL) were mixed with 40 µL of 1 M Tris, pH 11. The eluted antibodies were concentrated and buffer-exchanged into PBS by Amicon Ultra-15 Centrifugal Filters with 30 k MWCO (Millipore, Cat#: UFC803024). The final product was filtered with a Costar Spin-X Centrifuge Tube, 0.22 µm Pore CA Membrane (Corning, Cat#: 8160) and its concentration was determined by A280 absorbance using the predicted extinction coefficient. The purity of the antibody was tested by SDS-PAGE, UPLC-SEC, and LC-MS.

Example 20: Profiling Podo447 Binding to Human Tissue

Humanized Podo447 (generated by transfecting plasmids containing humanized_podo447VL6_hIgkC and humanized_podo447VH_hIgG1C) was used in Example 20. In order to detect binding, the biotinylated test article, designated Podo447-Bio, was applied to cryosections of normal human tissues (1 donor per tissue) at two concentrations (20 and 2 µg/mL). In addition, the test article was substituted with a human monoclonal antibody which has a different antigenic specificity from that of the test article, designated HuIgG1-Bio (control article). Other controls were produced by omission of the test or control articles from the assay (assay control). The results are summarized in Table 4.

TABLE 4

Cross Reactivity of Podo447-Bio with Normal Human Tissues

| Tissue | Source | Run | Test Article (Podo447-Bio) 20 µg/mL | Test Article (Podo447-Bio) 2 µg/mL | Control Article (HuIgG1-Bio) 20 µg/mL | Control Article (HuIgG1-Bio) 2 µg/mL | Assay Control | Tissue Validation (Tissue Staining) Control | Tissue Comments/Nonspecific Findings |
|---|---|---|---|---|---|---|---|---|---|
| Positive Control Material Cryosections of A-172 cells | CM0760-1 | 1 | 3-4+ (freq) | 3-4+ (freq) | Neg | Neg | Neg | NS | Strong to intense membrane and cytoplasmic staining of frequent positive control A-172 cells with both concentrations of Podo447-Bio. No staining of positive control cells with either concentration of HuIgG1-Bio or in the assay control slide. |
| Negative Control Material Cryosections of MDA-MB-231 (clone B5) cells | CM0761-1 | 1 | Neg | Neg | Neg | Neg | Neg | NS | No staining of negative control MDA-MB-231 (clone B5) cells with either concentration of Podo447-Bio or HuIgG1-Bio or in the assay control slide. |
| Ancillary Control Material Cryosections of human fetal kidney (fetal kidney cells) | HT204 | 1 | 1-3+ (rare to occas) | 1-2+ (rare) | Neg | Neg | Neg | NS | Weak to strong primarily cytoplasmic staining of rare to occasional fetal kidney cells with 20 µg/mL of Podo447-Bio. Staining intensity and frequency reduced to weak to moderate and rare at 2 µg/mL of Podo447-Bio. No staining of any tissue elements in cryosections of human fetal kidney with either concentration of HuIgG1-Bio or in the assay control slide. General Comments: All tissue specimens judged adequate for interpretation unless otherwise specified. Background staining due to incompletely quenched endogenous myeloperoxidase or endogenous/exogenous pigments described for individual tissues. Slides were numbered according to the following scheme: Slide 1 (Podo447-Bio, 20 µg/mL), Slide 2 (Podo447-Bio, 2 µg/mL), Slide 3 (HuIgG1-Bio, 20 µg/mL), Slide 4 (HuIgG1-Bio, 2 µg/mL), Slide 5 (Assay Control [omit primary antibody]), Slide 6 (Anti-$\beta_2$-microglobulin [tissue staining control]). |
| Blood Vessels (endothelium) | All tissues | 1, 2 | Detailed Under Individual Tissues | | | | | Pos | |
| Brain - cerebellum | HT1799-1 | 1, 2 | Neg | Neg | Neg | Neg | Neg | Pos | Endogenous lipofuscin pigment. Very minor nonspecific staining of rare glial cells in slides 1 and 3; did not preclude interpretation. |
| Brain - cerebral cortex | HT476-6 | 1, 2 | Neg | Neg | Neg | Neg | Neg | Pos | Endogenous lipofuscin pigment. |
| Breast | HT2094-1 | 1, 2 | Neg | Neg | Neg | Neg | Neg | Pos | No tissue comments. |
| Colon (large intestine) | HT2029-1 | 1, 2 | Neg | Neg | Neg | Neg | Neg | Pos | Pigmented macrophages present in sections. |
| Fallopian Tube | HT1923-1 | 1, 2 | | | | | | Pos | Exogenous pigment from tissue marking ink. |
| Epithelium, mucosa (cytoplasm, apical cytoplasm) | | | 1-3+ (rare to occas) | 1-2+ (rare) | Neg | Neg | Neg | | |
| Other elements | | | Neg | Neg | Neg | Neg | Neg | | |
| GI Tract - esophagus | HT1917-2 | 1, 2 | Neg | Neg | Neg | Neg | Neg | Pos | Minor nonspecific staining of mucus in multiple slides; did not preclude interpretation. Residual endogenous peroxidase (resident leukocytes). |
| GI Tract - small intestine | HT1913-2 | 1, 2 | | | | | | Pos | Residual endogenous peroxidase (resident leukocytes). |
| Epithelium, mucosa (cytoplasm, apical cytoplasm) | | | 1-3+ (rare to occas) | 1-2+ (rare) | Neg | Neg | Neg | | |
| Other elements | | | Neg | Neg | Neg | Neg | Neg | | |
| GI Tract - stomach | HT1906-2 | 1, 2 | Neg | Neg | Neg | Neg | Neg | Pos | Residual endogenous peroxidase (resident leukocytes). |
| Heart | HT1382-3 | 1, 2 | Neg | Neg | Neg | Neg | Neg | Pos | Endogenous lipofuscin pigment. |
| Kidney | HT1916-1 | 1, 2 | | | | | | Pos | No tissue comments. |

TABLE 4-continued

Cross Reactivity of Podo447-Bio with Normal Human Tissues

| Tissue | Source | Run | Test Article (Podo447-Bio) 20 µg/mL | Test Article (Podo447-Bio) 2 µg/mL | Control Article (HuIgG1-Bio) 20 µg/mL | Control Article (HuIgG1-Bio) 2 µg/mL | Assay Control | Tissue Validation (Tissue Staining) Control | Tissue Comments/Nonspecific Findings |
|---|---|---|---|---|---|---|---|---|---|
| Podocytes (cytoplasm > membrane) | | | 2-3+ (very rare) | 2-3+ (very rare) | Neg | Neg | Neg | | Cytoplasmic staining more prominent than membrane staining. |
| Other elements | | | Neg | Neg | Neg | Neg | Neg | | |
| Liver | HT1247-5 | 1, 2 | Neg | Neg | Neg | Neg | Neg | Pos | Endogenous bile and bilirubin pigment. |
| Ovary | HT2017-1 | 1, 2 | Neg | Neg | Neg | Neg | Neg | Pos | Pigmented macrophages present in sections. |
| Skin | HT548-12B | 1, 2 | | | | | | Pos | Endogenous melanin pigment. |
| Epithelium, sweat gland (apical cytoplasm) | | | 1+ (rare) | 1+ (very rare) | Neg | Neg | Neg | | |
| Other elements | | | Neg | Neg | Neg | Neg | Neg | | |

± = equivocal, 1+ = weak, 2+ = moderate, 3+ = strong, 4+ = intense, Neg = Negative, M = Missing, NE = Not Evaluated, freq = frequent, occas = occasional. Frequency modifiers were included to provide the approximate percentage staining of expected numbers of that cell type or tissue element at that location. The frequency of cells with staining was identified as follows: very rare (<1% of cells of a particular cell type); rare (1-5% of cells of a particular cell type); rare to occasional (>5-25% of cells of a particular cell type); occasional (>25-50% of cells of a particular type); occasional to frequent (>50-75% of cells of a particular cell type); frequent (>75-100% of cells of a particular cell type)

Materials and Methods: Method development experiments were conducted to determine the optimal test and control article concentrations, as well as other variable parameters of the immunohistochemistry methodology, for binding of Podo447-Bio with the control materials and in test tissue sections. During these methods development experiments, multiple concentrations between 1 and 20 µg/mL of Podo447-Bio were evaluated. Podo447-Bio stained the positive control material at all concentrations examined, with no reduction in frequency and/or intensity in staining at any concentration. In the ancillary control material, fetal kidney cells were stained at all concentrations of Podo447-Bio with a marked reduction in staining at concentrations below 2 µg/mL. Therefore, the optimal concentration determined for the study (i.e., the lowest concentration of test article that produced the maximum [plateau] binding to the target antigens) was 2 µg/mL. The second concentration of Podo447-Bio determined for the study was selected as 10× over the optimal concentration, i.e., 20 µg/mL, as this was the highest concentration examined in the methods development experiments that did not yield nonspecific staining of control samples and/or test tissues.

A direct immunoperoxidase procedure was performed. Acetone/formalin-fixed cryosections were rinsed twice with phosphate-buffered saline, 0.15M NaCl, pH 7.2 (PBS). Endogenous peroxidase was then quenched by incubation of the slides with Biocare peroxidase block for 5 minutes. Next, the slides were rinsed twice with PBS, incubated with the avidin solution for 15 minutes, rinsed once with PBS, incubated with the biotin solution for 15 minutes, and rinsed once with PBS. The slides were then treated with a protein block designed to reduce nonspecific binding for 20 minutes. The protein block was prepared as follows: PBS+1% bovine serum albumin (BSA); 0.5% casein; and 1.5% human gamma globulins (HGG). Following the protein block, the biotinylated primary antibodies (test article, control article, or none [buffer alone as the assay control]) were applied to the slides at concentrations of 20 and 2 µg/mL for 1 hour. Next, the slides were rinsed twice with PBS, treated with the ABC Elite reagent for 30 minutes, rinsed twice with PBS, and then treated with DAB+ solution (prepared by adding one drop of DAB+ chromogen per 1 mL of DAB+ substrate buffer) for 4 minutes as a substrate for the peroxidase reaction. All slides were rinsed with tap water, counterstained, dehydrated, and mounted.

PBS+1% BSA served as the diluent for all antibodies and the ABC Elite reagent.

Example 21: Podo447 Binding to Glycan Arrays

Humanized Podo447 (generated by transfecting plasmids containing humanized_podo447VL6_hIgkC and humanized_podo447VH_hIgG1C) and control antibody were exposed to glycan micriarray with standard PBS conditions 50 ug/mL (100 uL or 1.0 mL) 2 hr at RT (gentle agitation). Detected with Cy3-Strept (1 ug/mL). On the glycan array, strong and significant signals that were all related to GalNAc-beta structures were detected. Thus, it appears that Podo447 binds to a terminal beta GalNAc structure present on podocalyxin in certain contexts, particularly tumor contexts. FIG. 32 shows Glycan microarray (v3.1) analysis of Podo447 (A) and control antibody IgG1kappa (B). Podo447 bound positively to terminal GalNAc mono and oligosaccharides #006, #025, #106, #107, #263 and #389. Sp2: 2 amino-ethyl; spe: amino-propyl; sp10:PEG2 linker; DD: unknown conjugate.

MATERIALS for Example 21: Deionized water, to be used in all solutions; Blocking buffer (50 mM Ethanolamine buffer, pH 8.5); Phosphate-buffered saline (PBS; 0.5M Na2H PO$_4$, 0.15M NaCl, 0.3M KCl, 0.5M KH$_2$PO$_4$, pH 7.4); PBS-Tween (PBS-T; 0.5M Na$_2$HPO4, 0.15M NaCl, 0.3M KCl, 0.5M KH$_2$PO$_4$, 0.05% Tween 20, pH 7.4); PLI-P (0.0065M Na$_2$HPO4, 0.5M NaCl, 0.003M KCl, 0.0015M KH$_2$PO$_4$, 1% BSA, 1% Triton-x-100, pH 7.4; Bovine serum albumin (BSA), 96-98% grade (Sigma); Secondary Cy3 labeled anti-human-IgG antibody (Sigma C2571); Secondary biotinylated anti-human-IgG antibody (Sigma B1140); Streptavidin-Alexa Fluor 488 (Molecular Probes, Cat. No. S-32354); Human serum/mAb. Equipment: Covalently printed glycopeptides on amino reactive N-hydroxysuccinimide (NHS) glass slides (Nexterion H slides MPX16, SCHOTT Nexterion, Elmsford, N.Y.); 16- or 2 pad FAST frame hybridization chamber (Whatman, Schleicher & Schuell, Brentford, UK); Slide spinner model Galaxy Mini; ProScanArray HT slide scanner with Autoloader (Perkin Elmer, Wellesley, Mass.); ImaGene 6.1 software (Biodiscovery, Inc., El Segundo, Calif.); Perkin Elmer ScanArray Software; NOTE: All equipment and software are provided as examples. Other appropriate equipment and software can be used. This method is compatible with any standard microarray facility set-up that is capable of generating and reading array slides.

Antibody preparation: TIMING 10 min. Podo447 and control ab was diluted in PBS to final concentration 50 ug/mL and used immediately. Streptavidin preparation: Cy3-Strept duluted to working concentrationlug/mL. Preparation of slides: Slides merged into blocking buffer for 1 hour at room temperature gently rotation. Slides rinsed with PBS buffer 3× and deionized water 1× to clean the surface. Slides briefly spun until teflon area (or glass) is dry (30 sec). Serum/mAb suspension (100 uL for 16-pad or 500 uL for 2-pad) applied within the well. Onto shaker for gentle rotation (200 rpm) for 1 hr. Slides are kept in a sealed moisturized environment during the incubation preventing drying. Slides merged in wash buffer to immediately dilute samples, then wash sequence (300 mL) containing: (i) PBS-T 5 min), (ii) PBS, Idip), spun shortly. Slides immediately used for next step. The secondary antibody was applied as described above through sequence 3-4. The Streptavidin-Cy3 was applied as described above through sequence 5-6. A final wash step in de-ionized water (2 dips) was incorporated. The slides were dried by centrifugation (30 sec). Alternative for step 8-9: The Secondary Cy3 labeled anti-human-IgG antibody is applied as described above through sequence 5-6. A final wash step in de-ionized water (2 dips) is incorporated. The slides are dried by centrifugation (30 sec).

Scanning Instrument Setup: Scanner has 3 different lasers that excite at the following wavelengths: Laser 1: 633 nm, Laser 3: 543 nm, Laser 4: 488 nm. The ProScanArray software is used in conjunction with this instrument. Laser 4 (488 nm) is used for Alexa488. Using the ProScanArray software turn on Laser 4 at least 5 min prior to scanning. Laser 2 (543 nm) is used for Cy3. It takes 10 min to warm up the laser. Scanning: The Laser Power is usually set to a value between 70% to 100%. Every scan batch has been evaluated according to signal intensities and background. After this initial evaluation the exact Laser Power was set. Set the Laser Power by going to Configure/Application Settings/Scanning. Alexa Fluor 488 is selected for the fluorophore, as well as 70% PMT gain. After scan is finished image is saved as a TIF file. Software analysis: Loaded image, grid and GeneID. Aligned metagrid with scanned image by aligning the upper left hand subgrid. Checked if Individual subgrids needed to be aligned individually. Ensured entire metagrid was selected for the following steps: Deselected the "Grid Constraints" by going to File/Settings/Spot Finding. Auto adjusted spots by going to Auto/Auto Adjust Spots. Re-selected the "Grid Constraints" by going back to File/Settings/Spot Finding. Wrangled by going to Auto/Wrangle. Checked entire metagrid and ensured that all spots are encircled by a grid circle. Quantifed the scan by going to Measure/Make measurements (Quantify).

Example 22: Radioimmunoconjuuate of Podo447 is Useful for Imaging of Podocalyxin (Podxl) Expression on Tumour Cells In Vivo A radioimmunoconjugate comprising Podo447 (chimeric Rabbit/Human IgG1) was tested in a pancreatic tumour model with MIAPACA-2 tumor-bearing mice. Podo447 was conjugated with the DFO at a ratio of 3:1 (DFO:antibody) and efficiently radiolabeled with $^{89}$Zr with a radiochemical purity greater than 99% after purification and satisfying specific activities. Radioimmunoconjugates were injected in mice and showed high tumour uptake of 12% ID/g 5 days after injection. (data not shown)

Figure 30:
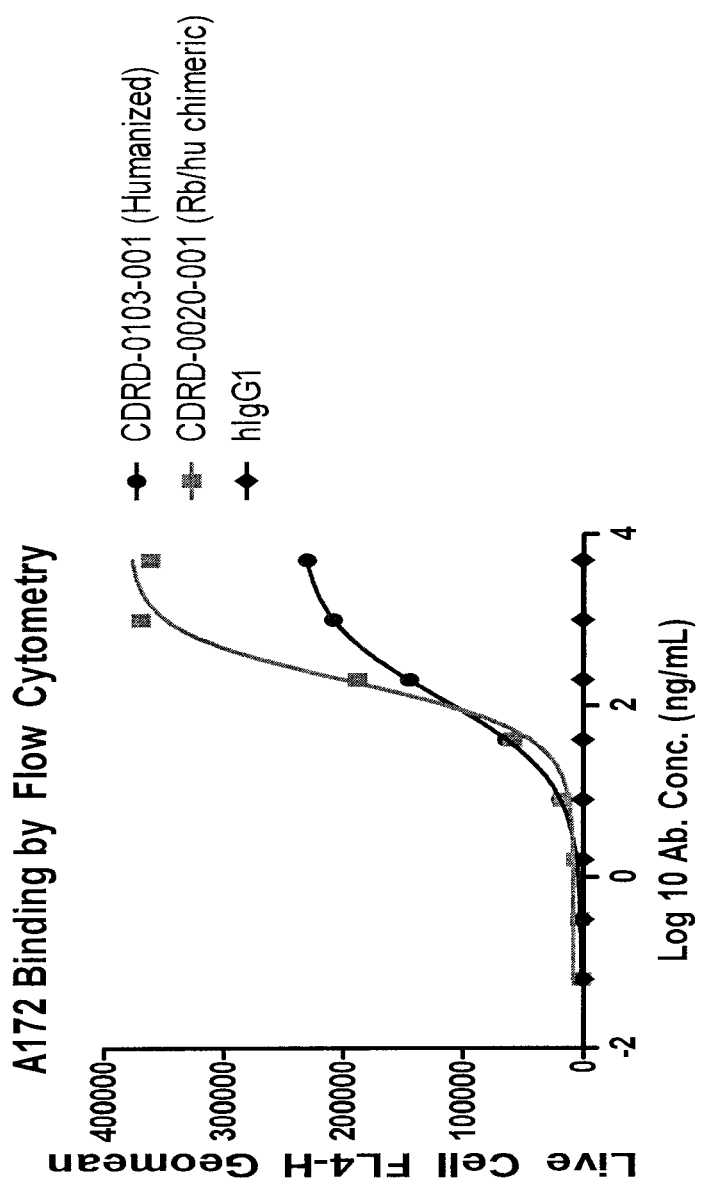
FIG. 30 A172 binding by flow cytometry. Humanized and rabbit/human chimeric Podo 447 antibody binding to A172 cells endogenously expressing Podocalyxin.

Example 23: Binding of Humanized Podo447 to A172 Cells (FIG. 30)

Humanized and rabbit/human chimeric Podo 447 antibody binding to A172 cells endogenously expressing Podocalyxin. Briefly, A172 cells were detached using cell dissociation solution (Sigma-C5914) and incubated with titrated purified antibodies in 96-well V-bottom plates. Antibody binding was detected using a goat anti-human IgG-Fc-Alexa 647 secondary antibody (Jackson 109-605-098) and the cells were analyzed on the Intellicyt high throughput flow cytometer (HTFC).

| log(inhibitor) vs. response - Variable slope (four parameters) | CDRD-0103-001 (Humanized) | CDRD-0020-001 (Rb/hu chimeric) |
|---|---|---|
| Best-fit values | | |
| Bottom | 1941 | 8626 |
| Top | 238392 | 379974 |
| LogIC50 | 2.094 | 2.284 |
| HillSlope | 0.9195 | 1.432 |
| IC50 | 124.3 | 192.1 |
| Span | 236451 | 371348 |
| Std. Error | | |
| Bottom | 381.6 | 8715 |
| Top | 805.6 | 17414 |
| LogIC50 | 0.005879 | 0.06467 |
| HillSlope | 0.01005 | 0.3146 |
| Span | 979.9 | 20868 |
| 95% Confidence Intervals | | |
| Bottom | 881.4 to 3000 | −15566 to 32818 |
| Top | 236155 to 240628 | 331634 to 428314 |
| LogIC50 | 2.078 to 2.111 | 2.104 to 2.463 |
| HillSlope | 0.8916 to 0.9474 | 0.5587 to 2.305 |
| IC50 | 119.7 to 129.1 | 127.1 to 290.5 |
| Span | 233731 to 239171 | 313418 to 429277 |
| Goodness of Fit | | |
| Degrees of Freedom | 4 | 4 |
| R square | 1 | 0.9937 |
| Absolute Sum of Squares | 1477000 | 1125000000 |
| Sy.x | 607.6 | 16772 |
| Number of points | | |
| Analyzed | 8 | 8 |

Table immediately above: Statistical data using Graphpad Prism analysis software representing the data presented above. Values were calculated using a variable slope (four parameters) non-linear regression analysis.

| Program | Antibody | Antigen | Kd | Kd Low | Kd High | Epitopes/Cell |
|---|---|---|---|---|---|---|
| Rb Podo.2 | R0943_A046 (Humanized) | A172 Cells | 14.39 pM | 4.59 pM | 45.94 pM | ~233000 |
| Rb Podo.2 | Podo 447 Rb/hIgG1 Chimeric | A172 Cells | 7.57 pM | 2.30 pM | 24.88 pM | ~420,000 |

Table immediately above: Kinetic exclusion assay (KinExA) affinity determination of humanized and rabbit/human chimeric antibodies to Podocalyxin endogenously expressed on A172 cells. A172 cells were titrated and incubated with constant antibody concentrations and allowed to reach equilibrium with a 16 hour incubation. Free, unbound antibody in the supernatant was then captured on the KinExA 3200 using poly(methyl methacrylate) (PMMA) beads coated with goat anti-human IgG-Fc capture antibodies and detected with goat anti-human IgG-Fc-alexa 647 label.

Example 24: Humanization of Podo447

The human immunoglobulin sequences obtained from the international ImMunoGeneTics information System® (IMGT®) database were first aligned to the rabbit sequences described in FIG. 2 using the IgBLAST tool available from the National Center for Biotechnology Information (NCBI). The V-gene delimitation system was set to the Kabat sequences to obtain the Kabat defined CDRs. In addition, the VH CDR1 defined by AbM was identified since a number of differences were observed in that region that may be important for maintaining the structure. IGKV1D-13*01 was chosen for the light chain variable region and the IGHV3-66*01 was chosen for the heavy chain variable region because the CDR2 appeared to be the same length as the rabbit CDR2, whereas the other sequences contained an extra amino acid. The human CDRs (Kabat numbering) were replaced with the counterpart CDRs from FIG. 2. For the heavy chain, the longer CDR3 defined by AbM was used because there were many differences and structurally important amino acids in that region. The humanized genes were codon optimized using the codon optimizer from IDT DNA (on the world wide web at idtdna.com/CodonOpt) using the settings for *Homo sapiens*. gBlocks® Gene Fragments were ordered from Integrated DNA Technologies (Coralville, Iowa) such that the 5' region of the VH contained a Kozak sequence, EcoRI site and a 21 bp overlap with a pTT5 plasmid containing a hIgG heavy chain constant region sequence (pTT5-hIgHC) digested with EcoRI. The 3' region contained a NheI restriction site followed by a 21 bp overlap with the pTT5-hIgGHC plasmid digested with NheI. The light chain was designed in a similar way with a 5' kozak sequence, and EcoRI site and an 18 bp overlap with a pTT5 plasmid containing a hIgk constant region sequence (pTT5-hIgkC) digested with EcoRI. At the 3' end, the sequence contained a BsiWI site followed by a 20 bp overlap with the pTT5-hIgkC plasmid digested with BsiWI. The pTT5-hIgGHC plasmid was digested with EcoRI and NheI and purified from an agarose gel. Similarly, the pTT5-hIgkC plasmid was digested with EcoRI and BsiWI and also purified from an agarose gel. The gBlocks® were resuspended in 20 µl Ultrapure distilled $H_2O$ (Gibco, Invitrogen), to a concentration of 10 ng/µl. The following were incubated at 50° C. for 1 hour: 50 ng linearized vector; 20 ng gBlocks®; 6 µl Ultrapure distilled $H_2O$; 10 µl Gibson Assembly Master Mix (2X) (New England Biolabs). The hIgkC was incubated with the light chain gBlock and the hIgGHC was incubated with the heavy chain gBlock. Dh5 competent bacteria supplied with the Gibson cloning kit were transformed with 2 µl of the mixture and spread onto ampicillin containing agar plates and incubated at 37° C. overnight. Two colonies were picked from each transformation and incubated at 37° C. at 250 rpm in 2 ml LB media containing 100 µg/ml ampicillin overnight. Plasmids were isolated using the Qiagen AIA prep Miniprep kit (Qiagen) according to the manufacturer's instructions. Purification of antibodies. As described above, two humanized VH constructs (1:1 and 2: 1) and one humanized Vk construct were made. HEK293 cells were grown to a concentration of $1 \times 10^6$ cells/ml (96.3% viable) at 37° C., 5% $CO_2$ in 90 ml Freestyle 293 expression media (Gibco), supplemented with 0.1% Pluronic F68 solution. 75 µg of each of the 1:1 and 2:1 VH constructs were mixed with the humanized Vk plasmid DNAs and diluted in 5 ml of Optimem I medium. 130 µl of 293fectin (Invitrogen) was diluted in another tube of 5 ml Optemem I medium. Both tubes were vortexed to mix the contents for 1 second and incubated for 5 min at room temperature. The DNAs were combined with the 293fectin solution and incubated for 20 minutes at room temperature. 10 ml of DNA/293 fectin solution was added dropwise to 90 ml of cells and the flask was swirled to mix the solutions. The cells were incubated for 96 hrs at 37° C., 5% $CO_2$. 96 hours post transfection, supernatants were collected, filter sterilized and stored at 4° C. Antibodies were purified from supernatants using the AKTAxpress (GE Healthcare) and Mab Select SuRe (GE Healthcare) columns according to the manufacturer's instructions. The eluate was spun through an Amicon Ultra-15 centrifugal filter device with 30 kDa MWCO at 3200×g for 20 min. The concentrated antibodies were resuspended in 15 ml PBS to exchange the buffer and was repeated three times. The final concentrated antibody solution was collected. The concentrated antibody solution was quantified by A280 using the Nanodrop (Thermo Fisher Scientific, Inc). Table 5 shows humanized antibodies. Regarding humanization, see also see WO2015058301.

TABLE 5

```
humanized_podo447VH (SEQ ID NO: 69)
ATGGAATTTGGGTTGAGTTGGGTATTCCTGGTCGCCATATTGAAGGGCGT
GCAATGCGAAGTACAGCTTGTAGAATCTGGGGGGGGTCTCGTTCAACCGG
GTAGGAGTTTGAGACTGAGCTGCACGGCCTCTGGCTTCAGCTTGTCTGGA
TACCAAATGAACTGGGTGCGACAAGCGCCCGGCAAGGGTTTGGAATGGGT
GGGTTACATCTGGAGTGATGGCGGAACGGATTACACTGCTTCCGTAAAGG
GGCGATTTACCATTTCCAGGGACGGTAGCAAAAGTATCGCGTACCTTCAA
ATGAACTCCCTCAAGACAGAGGATACGGCTGTGTACTACTGCGCGAGGGA
AGGATATTGGCTCGGGGCATTCGACCCATGGGGTCAGGGAACCTCAGTCA
CCGTCAGC >humanized_podo447VH (SEQ ID NO: 70)
MEFGLSWVFLVAILKGVQCEVQLVESGGGLVQPGRSLRLSCTASGFSLSG
YQMNWVRQAPGKGLEWVGYIWSDGGTDYTASVKGRFTISRDGSKSIAYLQ
MNSLKTEDTAVYYCAREGYWLGAFDPWGQGTSVTVS >humanized_podo447VH_hIgG1C (SEQ ID NO: 71)
ATGGAATTTGGGTTGAGTTGGGTATTCCTGGTCGCCATATTGAAGGGCGT
GCAATGCGAAGTACAGCTTGTAGAATCTGGGGGGGGTCTCGTTCAACCGG
GTAGGAGTTTGAGACTGAGCTGCACGGCCTCTGGCTTCAGCTTGTCTGGA
TACCAAATGAACTGGGTGCGACAAGCGCCCGGCAAGGGTTTGGAATGGGT
GGGTTACATCTGGAGTGATGGCGGAACGGATTACACTGCTTCCGTAAAGG
```

TABLE 5-continued

```
GGCGATTTACCATTTCCAGGGACGGTAGCAAAAGTATCGCGTACCTTCAA
ATGAACTCCCTCAAGACAGAGGATACGGCTGTGTACTACTGCGCGAGGGA
AGGATATTGGCTCGGGGCATTCGACCCATGGGGTCAGGGAACCTCAGTCA
CCGTCAGCGCTAGCACCAAGGGCCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACGGTGTCGTGGAACTCAGGCGCCCTGACCA
GCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTACACCCTGCCCCCATCCCGGGATGAGCTGACCAAGAACCAGGTCAGCC
TGACCTGCCTGGTCAAAGGCTTCTATCCCAGCGACATCGCCGTGGAGTGG
GAGAGCAATGGGCAGCCGGAGAACAACTACAAGACCACGCCTCCCGTGCT
GGACTCCGACGGCTCCTTCTTCCTCTACAGCAAGCTCACCGTGGACAAGA
GCAGGTGGCAGCAGGGGAACGTCTTCTCATGCTCCGTGATGCATGAGGCT
CTGCACAACCACTACACGCAGAAGAGCCTCTCCCTGTCTCCGGGTAAATG
A
```

>humanized_podo447VH_hIgG1C (SEQ ID NO: 72)
MEFGLSWVFLVAILKGVQCEVQLVESGGGLVQPGRSLRLSCTASGFSLSG
YQMNWVRQAPGKGLEWVGYIWSDGGTDYTASVKGRFTISRDGSKSIAYLQ
MNSLKTEDTAVYYCAREGYWLGAFDPWGQGTSVTVSSASTKGPSVFPLAPS
SKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK >humanized_podo447VL6 (SEQ ID NO: 73)
ATGGACATGCGGGTTCCAGCGCAGCTCTTGGGACTCTTGCTGTTGTGGTT
GCCCGGTGCCAGGTGTGCGGCCCAGCTTACACAGAGTCCCTCTCCTTTGT
CAGCTTCAGTTGGTGATAGGGTGACTATAACCTGTCAGAGTAGTCAGTCC
GTTCACCACAAGAACGACCTCGCGTGGTATCAGCAGAAGCCTGGCAAAGC
GCCGAAACTGCTCATTTACTATACGTCTACGTTGGCAAGTGGTGTCCCCT
CACGGTTCTCAGGCTCCGGTAGCGGGACAGATTTTACTCTCACAATCAGC
TCCCTTCAGCCCGAAGATTTCGCTACATATTATTGTGCTGGGGTATATGA
GGGGAGTTCTGATAATCGGGCATTTGGGGGCGGCACGAAGGTGGAGATTA
AA >humanized_podo447VL6 (SEQ ID NO: 74)
MDMRVPAQLLGLLLLWLPGARCAAQLTQSPSPLSASVGDRVTITCQSSQS
VHHKNDLAWYQQKPGKAPKLLIYYTSTLASGVPSRFSGSGSGTDFTLTIS
SLQPEDFATYYCAGVYEGSSDNRAFGGGTKVEIK >humanized_podo447VL6_hIgkC (SEQ ID NO: 75)
ATGGACATGCGGGTTCCAGCGCAGCTCTTGGGACTCTTGCTGTTGTGGTT
GCCCGGTGCCAGGTGTGCGGCCCAGCTTACACAGAGTCCCTCTCCTTTGT
CAGCTTCAGTTGGTGATAGGGTGACTATAACCTGTCAGAGTAGTCAGTCC
GTTCACCACAAGAACGACCTCGCGTGGTATCAGCAGAAGCCTGGCAAAGC
GCCGAAACTGCTCATTTACTATACGTCTACGTTGGCAAGTGGTGTCCCCT
CACGGTTCTCAGGCTCCGGTAGCGGGACAGATTTTACTCTCACAATCAGC
TCCCTTCAGCCCGAAGATTTCGCTACATATTATTGTGCTGGGGTATATGA
GGGGAGTTCTGATAATCGGGCATTTGGGGGCGGCACGAAGGTGGAGATTA
AACGTACGGTGGCTGCACCATCTGTCTTCATCTTCCCGCCATCTGATGAG
CAGTTGAAATCTGGAACTGCCTCTGTTGTGTGCCTGCTGAATAACTTCTA
TCCCAGAGAGGCCAAAGTACAGTGGAAGGTGGATAACGCCCTCCAATCGG
GTAACTCCCAGGAGAGTGTCACAGAGCAGGACAGCAAGGACAGCACCTAC
AGCCTCAGCAGCACCCTGACGCTGAGCAAAGCAGACTACGAGAAACACAA
AGTCTACGCCTGCGAAGTCACCCATCAGGGCCTGAGCTCGCCCGTCACAA
AGAGCTTCAACAGGGGAGAGTGT >humanized_podo447VL6_hIgkC (SEQ ID NO: 76)
MDMRVPAQLLGLLLLWLPGARCAAQLTQSPSPLSASVGDRVTITCQSSQS
VHHKNDLAWYQQKPGKAPKLLIYYTSTLASGVPSRFSGSGSGTDFTLTIS
SLQPEDFATYYCAGVYEGSSDNRAFGGGTKVEIKRTVAAPSVFIFPPSDE
QLKSGTASVVCLLNNFYPREAKVQWKVDNALQSGNSQESVTEQDSKDSTY
SLSSTLTLSKADYEKHKVYACEVTHQGLSSPVTKSFNRGEC >humanized_scFv_podo447VH_GGGGS_VL6 (SEQ ID NO: 77)
ATGGAATTTGGGTTGAGTTGGGTATTCCTGGTCGCCATATTGAAGGGCGT
GCAATGCGAAGTACAGCTTGTAGAATCTGGGGGGGGTCTCGTTCAACCGG
GTAGGAGTTTGAGACTGAGCTGCACGGCCTCTGGCTTCAGCTTGTCTGGA
TACCAAATGAACTGGGTGCGACAAGCGCCCGGCAAGGGTTTGGAATGGGT
GGGTTACATCTGGAGTGATGGCGGAACGGATTACACTGCTTCCGTAAAGG
GGCGATTTACCATTTCCAGGGACGGTAGCAAAAGTATCGCGTACCTTCAA
ATGAACTCCCTCAAGACAGAGGATACGGCTGTGTACTACTGCGCGAGGGA
AGGATATTGGCTCGGGGCATTCGACCCATGGGGTCAGGGAACCTCAGTCA
CCGTCAGCGGGGGAGGTGGGTCCGGCGGGGGCGGCAGTGGAGGCGGCAGG
TCTGCGGCCCAGCTTACACAGAGTCCCTCTCCTTTGTCAGCTTCAGTTGG
TGATAGGGTGACTATAACCTGTCAGAGTAGTCAGTCCGTTCACCACAAGA
ACGACCTCGCGTGGTATCAGCAGAAGCCTGGCAAAGCGCCGAAACTGCTC
ATTTACTATACGTCTACGTTGGCAAGTGGTGTCCCCTCACGGTTCTCAGG
CTCCGGTAGCGGGACAGATTTTACTCTCACAATCAGCTCCCTTCAGCCCG
AAGATTTCGCTACATATTATTGTGCTGGGGTATATGAGGGGAGTTCTGAT
AATCGGGCATTTGGGGCGGCACGAAGGTGGAGATTAAA >humanized_scFv_podo447VH_GGGGS_VL6 (SEQ ID NO: 78)
MEFGLSWVFLVAILKGVQCEVQLVESGGGLVQPGRSLRLSCTASGFSLSG
YQMNWVRQAPGKGLEWVGYIWSDGGTDYTASVKGRFTISRDGSKSIAYLQ
MNSLKTEDTAVYYCAREGYWLGAFDPWGQGTSVTVSGGGGSGGGGSGGGG
SAAQLTQSPSPLSASVGDRVTITCQSSQSVHHKNDLAWYQQKPGKAPKLL
IYYTSTLASGVPSRFSGSGSGTDFTLTISSLQPEDFATYYCAGVYEGSSD
NRAFGGGTKVEIK >humanized_scFv_podo447VH_GGGGS_VL6_CAR (SEQ ID NO: 79)
ATGGAATTTGGGTTGAGTTGGGTATTCCTGGTCGCCATATTGAAGGGCGT
GCAATGCGAAGTACAGCTTGTAGAATCTGGGGGGGGTCTCGTTCAACCGG
GTAGGAGTTTGAGACTGAGCTGCACGGCCTCTGGCTTCAGCTTGTCTGGA
TACCAAATGAACTGGGTGCGACAAGCGCCCGGCAAGGGTTTGGAATGGGT
GGGTTACATCTGGAGTGATGGCGGAACGGATTACACTGCTTCCGTAAAGG
GGCGATTTACCATTTCCAGGGACGGTAGCAAAAGTATCGCGTACCTTCAA
ATGAACTCCCTCAAGACAGAGGATACGGCTGTGTACTACTGCGCGAGGGA
AGGATATTGGCTCGGGGCATTCGACCCATGGGGTCAGGGAACCTCAGTCA
CCGTCAGCGGGGGAGGTGGGTCCGGCGGGGGCGGCAGTGGAGGCGGCAGG
TCTGCGGCCCAGCTTACACAGAGTCCCTCTCCTTTGTCAGCTTCAGTTGG
TGATAGGGTGACTATAACCTGTCAGAGTAGTCAGTCCGTTCACCACAAGA
ACGACCTCGCGTGGTATCAGCAGAAGCCTGGCAAAGCGCCGAAACTGCTC
ATTTACTATACGTCTACGTTGGCAAGTGGTGTCCCCTCACGGTTCTCAGG
CTCCGGTAGCGGGACAGATTTTACTCTCACAATCAGCTCCCTTCAGCCCG
AAGATTTCGCTACATATTATTGTGCTGGGGTATATGAGGGGAGTTCTGAT
AATCGGGCATTTGGGGCGGCACGAAGGTGGAGATTAAAGAGCAGAAGCT
GATCAGCGAGGAGGACCTGAACCGGATCCGTGGGGTCACCGTCTCTTCAG
CGCTGAGCAACTCCATCATGTACTTCAGCCACTTCGTGCCGGTCTTCCTG
CCAGCGAAGCCCACCACGACGCCAGCGCCGCGACCACCAACACCGGCGCC
CACCATCGCGTCGCAGCCCCTGTCCCTGCGCCCCGAGGCCTGCCGGCCAG
CGGCGGGGGGCGCAGTGCACACGAGGGGGCTGGACCCCTTTGGGTTTTGG
GTGCTGGTGGTGGTTGGTGGAGTCCTGGCTTGCTATAGCTTGCTAGTAAC
AGTGGCCTTTATTATTTTCTGGGTGAGGAGTAAGAGGAGCAGGCTCCTGC
ACAGTGACTACATGAACATGACTCCCCGCCGCCCCGGGCCCACCCGCAAG
CATTACCAGCCCTATGCCCCACCACGCGACTTCGCCGCCTATCGCTCCCT
CGAGAGAGTGAGAGTGAAGTTCAGCAGGAGCGCAGACGCCCCCGCGTACC
AGCAGGGCCAGAACCAGCTCTATAACGAGCTCAATCTAGGACGAAGAGAG
GAGTACGATGTTTTGGACAAGAGACGTGGCCGGGACCCTGAGATGGGGGG
AAAGCCGAGAAGGAAGAACCCTCAGGAAGGCCTGTACAATGAACTGCAGA
AAGATAAGATGGCGGAAGCCTACAGTGAGATTGGGATGAAAGGCGAGCGC
CGGAGGGGCAAGGGGCACGATGGCCTTTACCAGGGTCTCAGTACAGCCAC
CAAGGACACCTACGACGCCCTTCACATGCAGGCCCTGCCCCCTCGCTAA >humanized_scFv_podo447VH_GGGGS_VL6_CAR (SEQ ID NO: 80)
MEFGLSWVFLVAILKGVQCEVQLVESGGGLVQPGRSLRLSCTASGFSLSG
YQMNWVRQAPGKGLEWVGYIWSDGGTDYTASVKGRFTISRDGSKSIAYLQ
MNSLKTEDTAVYYCAREGYWLGAFDPWGQGTSVTVSGGGGSGGGGSGGGG
SAAQLTQSPSPLSASVGDRVTITCQSSQSVHHKNDLAWYQQKPGKAPKLL
IYYTSTLASGVPSRFSGSGSGTDFTLTISSLQPEDFATYYCAGVYEGSSD
NRAFGGGTKVEIKEQKLISEEDLNRIRGVTVSSALSNSIMYFSHFVPVFL
PAKPTTTPAPRPPTPAPTIASQPLSLRPEACRPAAGGAVHTRGLDFGFW
VLVVVGGVLACYSLLVTVAFIIFWVRSKRSLLHSDYMNMTPRRPGPTRK
HYQPYAPPRDFAAYRSLERVRVKFSRSADAPAYQQGQNQLYNELNLGRRE
EYDVLDKRRGRDPEMGGKPRRKNPQEGLYNELQKDKMAEAYSEIGMKGER
RRGKGHDGLYQGLSTATKDTYDALHMQALPPR TABLE 5-continued >humanized_scFv_podo447VL6_GGGGS_VH (SEQ ID NO: 81)
ATGGACATGCGGGTTCCAGCGCAGCTCTTGGGACTCTTGCTGTTGTGGTT
GCCCGGTGCCAGGTGTGCGGCCCAGCTTACACAGAGTCCCTCTCCTTTGT
CAGCTTCAGTTGGTGATAGGGTGACTATAACCTGTCAGAGTAGTCAGTCC
GTTCACCACAAGAACGACCTCGCGTGGTATCAGCAGAAGCCTGGCAAAGC
GCCGAAACTGCTCATTTACTATACGTCTACGTTGGCAAGTGGTGTCCCCT
CACGGTTCTCAGGCTCCGGTAGCGGGACAGATTTTACTCTCACAATCAGC
TCCCTTCAGCCCGAAGATTTCGCTACATATTATTGTGCTGGGGTATATGA
GGGGAGTTCTGATAATCGGGCATTTGGGGGCGGCACGAAGGTGGAGATTA
AAGGGGGAGGTGGGTCCGGCGGGGGCGGCAGTGGAGGCGGCGGGTCTGAA
GTACAGCTTGTAGAATCTGGGGGGGGTCTCGTTCAACCGGGTAGGAGTTT
GAGACTGAGCTGCACGGCCTCTGGCTTCAGCTTGTCTGGATACCAAATGA
ACTGGGTGCGACAAGCGCCCGGCAAGGGTTTGGAATGGGTGGGTTACATC
TGGAGTGATGGCGGAACGGATTACACTGCTTCCGTAAAGGGGCGATTTAC
CATTTCCAGGGACGGTAGCAAAAGTATCGCGTACCTTCAAATGAACTCCC
TCAAGACAGAGGATACGGCTGTGTACTACTGCGCGAGGGAAGGATATTGG
CTCGGGGCATTCGACCCATGGGGTCAGGGAACCTCAGTCACCGTCAGC >humanized_scFv_podo447VL6_GGGGS_VH (SEQ ID NO: 82)
MDMRVPAQLLGLLLLWLPGARCAAQLTQSPSPLSASVGDRVTITCQSSQS
VHHKNDLAWYQQKPGKAPKLLIYYTSTLASGVPSRFSGSGSGTDFTLTIS
SLQPEDFATYYCAGVYEGSSDNRAFGGGTKVEIKGGGGSGGGGSGGGGSE
VQLVESGGGLVQPGRSLRLSCTASGFSLSGYQMNWVRQAPGKGLEWVGYI
WSDGGTDYTASVKGRFTISRDGSKSIAYLQMNSLKTEDTAVYYCAREGYW
LGAFDPWGQGTSVTVS >humanized_scFv_podo447VL6_GGGGS_VH_CAR (SEQ ID NO: 83)
ATGGACATGCGGGTTCCAGCGCAGCTCTTGGGACTCTTGCTGTTGTGGTT
GCCCGGTGCCAGGTGTGCGGCCCAGCTTACACAGAGTCCCTCTCCTTTGT
CAGCTTCAGTTGGTGATAGGGTGACTATAACCTGTCAGAGTAGTCAGTCC
GTTCACCACAAGAACGACCTCGCGTGGTATCAGCAGAAGCCTGGCAAAGC
GCCGAAACTGCTCATTTACTATACGTCTACGTTGGCAAGTGGTGTCCCCT
CACGGTTCTCAGGCTCCGGTAGCGGGACAGATTTTACTCTCACAATCAGC
TCCCTTCAGCCCGAAGATTTCGCTACATATTATTGTGCTGGGGTATATGA
GGGGAGTTCTGATAATCGGGCATTTGGGGGCGGCACGAAGGTGGAGATTA
AAGGGGGAGGTGGGTCCGGCGGGGGCGGCAGTGGAGGCGGCGGGTCTGAA
GTACAGCTTGTAGAATCTGGGGGGGGTCTCGTTCAACCGGGTAGGAGTTT
GAGACTGAGCTGCACGGCCTCTGGCTTCAGCTTGTCTGGATACCAAATGA
ACTGGGTGCGACAAGCGCCCGGCAAGGGTTTGGAATGGGTGGGTTACATC
TGGAGTGATGGCGGAACGGATTACACTGCTTCCGTAAAGGGGCGATTTAC
CATTTCCAGGGACGGTAGCAAAAGTATCGCGTACCTTCAAATGAACTCCC
TCAAGACAGAGGATACGGCTGTGTACTACTGCGCGAGGGAAGGATATTGG
CTCGGGGCATTCGACCCATGGGGTCAGGGAACCTCAGTCACCGTCAGCGA GCAGAAGCTGATCAGCGAGGAGGACCTGAACCGGATCCGTGGGGTCACCG
TCTCTTCAGCGCTGAGCAACTCCATCATGTACTTCAGCCACTTCGTGCCG
GTCTTCCTGCCAGCGAAGCCCACCACGACGCCAGCGCCGCGACCACCAAC
ACCGGCGCCCACCATCGCGTCGCAGCCCCTGTCCCTGCGCCCAGAGGCGT
GCCGGCCAGCGGCGGGGGGCGCAGTGCACACGAGGGGGCTGGACCCCTTT
GGGTTTTGGGTGCTGGTGGTGGTTGGTGGAGTCCTGGCTTGCTATAGCTT
GCTAGTAACAGTGGCCTTTATTATTTTCTGGGTGAGGAGTAAGAGGAGCA
GGCTCCTGCACAGTGACTACATGAACATGACTCCCCGCCGCCCCGGGCCC
ACCCGCAAGCATTACCAGCCCTATGCCCCACCACGCGACTTCGCAGCCTA
TCGCTCCCTCGAGAGAGTGAGAGTGAAGTTCAGCAGGAGCGCAGACGCCC
CCGCGTACCAGCAGGGCCAGAACCAGCTCTATAACGAGCTCAATCTAGGA
CGAAGAGAGGAGTACGATGTTTTGGACAAGAGACGTGGCCGGGACCCTGA
GATGGGGGGAAAGCCGAGAAGGAAGAACCCTCAGGAAGGCCTGTACAATG
AACTGCAGAAAGATAAGATGGCGGAGGCCTACAGTGAGATTGGGATGAAA
GGCGAGCGCCGGAGGGGCAAGGGGCACGATGGCCTTTACCAGGGTCTCAG
TACAGCCACCAAGGACACCTACGACGCCCTTCACATGCAGGCCCTGCCCC
CTCGCTAA >humanized_scFv_podo447VL6_GGGGS_VH_CAR (SEQ ID NO: 84)
MDMRVPAQLLGLLLLWLPGARCAAQLTQSPSPLSASVGDRVTITCQSSQS
VHHKNDLAWYQQKPGKAPKLLIYYTSTLASGVPSRFSGSGSGTDFTLTIS
SLQPEDFATYYCAGVYEGSSDNRAFGGGTKVEIKGGGGSGGGGSGGGGSE
VQLVESGGGLVQPGRSLRLSCTASGFSLSGYQMNWVRQAPGKGLEWVGYI
WSDGGTDYTASVKGRFTISRDGSKSIAYLQMNSLKTEDTAVYYCAREGYW
LGAFDPWGQGTSVTVSEQKLISEEDLNRIRGVTVSSALSNSIMYFSHFVP
VFLPAKPTTTPAPRPPTPAPTIASQPLSLRPEACRPAAGGAVHTRGLDPF
GFWVLVVVGGVLACYSLLVTVAFIIFWVRSKRSRLLHSDYMNMTPRRPGP
TRKHYQPYAPPRDFAAYRSLERVRVKFSRSADAPAYQQGQNQLYNELNLG
RREEYDVLDKRRGRDPEMGGKPRRKNPQEGLYNELQKDKMAEAYSEIGMK
GERRRGKGHDGLYQGLSTATKDTYDALHMQALPPR While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An anti-podocalyxin antibody that binds to a podocalyxin tumor epitope, wherein said anti-podocalyxin antibody comprises:
   a) a VHCDR1 having an amino acid sequence set forth in SEQ ID NO:33;
   a VHCDR2 having an amino acid sequence set forth in SEQ ID NO:36;
   a VHCDR3 having an amino acid sequence set forth in SEQ ID NO:39;
   a VLCDR1 having an amino acid sequence set forth in SEQ ID NO:42;
   a VLCDR2 having an amino acid sequence set forth in SEQ ID NO:45; and
   a VLCDR3 having an amino acid sequence set forth in SEQ ID NO:48;
   b) a VHCDR1 having an amino acid sequence set forth in SEQ ID NO:34;
   a VHCDR2 having an amino acid sequence set forth in SEQ ID NO:37;
   a VHCDR3 having an amino acid sequence set forth in SEQ ID NO:40;
   a VLCDR1 having an amino acid sequence set forth in SEQ ID NO:43;
   a VLCDR2 having an amino acid sequence set forth in SEQ ID NO:46; and
   a VLCDR3 having an amino acid sequence set forth in SEQ ID NO:49; or
   c) a VHCDR1 having an amino acid sequence set forth in SEQ ID NO:35;
   a VHCDR2 having an amino acid sequence set forth in SEQ ID NO:38;
   a VHCDR3 having an amino acid sequence set forth in SEQ ID NO:41;
   a VLCDR1 having an amino acid sequence set forth in SEQ ID NO:44;
   a VLCDR2 having an amino acid sequence set forth in SEQ ID NO:47; and
   a VLCDR3 having an amino acid sequence set forth in SEQ ID NO:50.

2. The anti-podocalyxin antibody according to claim 1, wherein said podocalyxin tumor epitope comprises a post-translational modification of a podocalyxin polypeptide.

3. The anti-podocalyxin antibody according to claim 2, wherein said post-translational modification of said podocalyxin polypeptide comprises an O-linked glycan moiety that is linked to said podocalyxin polypeptide.

4. The anti-podocalyxin antibody according to claim 2, wherein said post-translational modification of said podocalyxin polypeptide comprises a glycan moiety that is linked to said podocalyxin polypeptide, wherein said glycan moiety comprises a beta-N-acetyl-galactosamine.

5. The anti-podocalyxin antibody according to claim 4, wherein said beta-N-acetyl-galactosamine is a terminal beta-N-acetyl-galactosamine.

6. The anti-podocalyxin antibody according to claim 1, comprising a heavy chain variable region comprising SEQ ID NO: 27.

7. The anti-podocalyxin antibody according to claim 1, comprising a light chain variable region comprising SEQ ID NO: 29.

8. The anti-podocalyxin antibody according to claim 1, comprising a heavy chain variable region comprising SEQ ID NO:27 and a light chain variable region comprising SEQ ID NO:29.

9. The anti-podocalyxin antibody according to claim 1, wherein the anti-podocalyxin antibody is a chimeric, humanized, or human antibody.

10. The anti-podocalyxin antibody according to claim 1, wherein the anti-podocalyxin antibody is a monoclonal antibody, and/or an antibody fragment.

11. The anti-podocalyxin antibody according to claim 1, wherein the anti-podocalyxin antibody is an antibody fragment.

12. A modified immune cell, comprising a chimeric antigen receptor (CAR), wherein said CAR comprises the anti-podocalyxin antibody according to claim 11.

13. The modified immune cell according to claim 12, wherein said modified immune cell is a modified T cell or a modified NK cell.

14. An antibody-drug conjugate (ADC), comprising the antibody according to claim 1.

15. A method of inhibiting the growth of a cell that displays a podocalyxin tumor epitope, comprising contacting said cell with the anti-podocalyxin antibody according to claim 1, the modified immune cell according to claim 12, or the ADC according to claim 14.

16. A method of treating a subject having a cancer which expresses a podocalyxin tumor epitope, comprising administering to said subject the anti-podocalyxin antibody according to claim 1, the modified immune cell according to claim 12, or the ADC according to claim 14.

17. A pharmaceutical composition comprising an antibody according to claim 1, and a pharmaceutically acceptable carrier.

18. A pharmaceutical composition comprising the modified immune cell according to claim 12, and a pharmaceutically acceptable carrier.

* * * * *